US009181182B2

(12) United States Patent
Grobelny et al.

(10) Patent No.: US 9,181,182 B2
(45) Date of Patent: Nov. 10, 2015

(54) S1P RECEPTORS MODULATORS

(75) Inventors: Damian W. Grobelny, Watsonia North (AU); Gurmit S. Gill, Craigieburn (AU)

(73) Assignee: Akaal Pharma PTY LTD, Bundoora (AU)

( * ) Notice: Subject to any disclaimer, the term of this patent is extended or adjusted under 35 U.S.C. 154(b) by 813 days.

(21) Appl. No.: 13/124,543

(22) PCT Filed: Oct. 16, 2009

(86) PCT No.: PCT/AU2009/001368
§ 371 (c)(1),
(2), (4) Date: Oct. 25, 2011

(87) PCT Pub. No.: WO2010/042998
PCT Pub. Date: Apr. 22, 2010

(65) Prior Publication Data
US 2012/0034270 A1 Feb. 9, 2012

(30) Foreign Application Priority Data

Oct. 17, 2008 (AU) ................. 2008905356
Jun. 4, 2009 (AU) ................. 2009902561

(51) Int. Cl.
| | |
|---|---|
| *A61K 31/136* | (2006.01) |
| *C07D 209/44* | (2006.01) |
| *C07D 215/06* | (2006.01) |
| *C07D 209/08* | (2006.01) |
| *C07C 215/18* | (2006.01) |
| *C07C 217/72* | (2006.01) |
| *C07C 225/16* | (2006.01) |
| *C07C 311/16* | (2006.01) |
| *C07D 209/12* | (2006.01) |
| *C07D 209/38* | (2006.01) |
| *C07D 215/20* | (2006.01) |
| *C07D 217/04* | (2006.01) |
| *C07D 223/16* | (2006.01) |
| *C07D 405/12* | (2006.01) |
| *C07D 413/10* | (2006.01) |
| *C07D 413/14* | (2006.01) |

(52) U.S. Cl.
CPC ............ *C07D 209/08* (2013.01); *C07C 215/18* (2013.01); *C07C 217/72* (2013.01); *C07C 225/16* (2013.01); *C07C 311/16* (2013.01); *C07D 209/12* (2013.01); *C07D 209/38* (2013.01); *C07D 209/44* (2013.01); *C07D 215/06* (2013.01); *C07D 215/20* (2013.01); *C07D 217/04* (2013.01); *C07D 223/16* (2013.01); *C07D 405/12* (2013.01); *C07D 413/10* (2013.01); *C07D 413/14* (2013.01); *C07C 2103/70* (2013.01); *C07C 2103/74* (2013.01)

(58) Field of Classification Search
CPC ........................... C07D 209/44; C07D 215/06
USPC .......................................... 546/152; 548/469
See application file for complete search history.

(56) References Cited

U.S. PATENT DOCUMENTS

| | | | |
|---|---|---|---|
| 2,550,646 A | 4/1951 | Murray | |
| 3,945,998 A * | 3/1976 | Anderson et al. .......... 546/271.4 |
| 5,643,932 A | 7/1997 | Chihiro et al. | |
| 5,719,176 A * | 2/1998 | Fujita et al. ................... 514/440 |
| 5,798,354 A | 8/1998 | Bernardon et al. | |
| 5,817,652 A * | 10/1998 | Brieaddy et al. ......... 514/211.09 |
| 5,877,342 A | 3/1999 | Bernardon et al. | |
| 5,883,106 A | 3/1999 | Stevens et al. | |
| 6,221,865 B1 | 4/2001 | Sebti et al. | |
| 6,228,868 B1 | 5/2001 | Gwaltney, II et al. | |
| 6,258,811 B1 | 7/2001 | Yamauchi et al. | |
| 6,376,491 B1 | 4/2002 | Aoki et al. | |
| 2002/0103234 A1 | 8/2002 | Kikuchi et al. | |
| 2006/0223866 A1* | 10/2006 | Evindar et al. ................ 514/365 |
| 2007/0149561 A1 | 6/2007 | Dhanak et al. | |
| 2008/0176874 A1 | 7/2008 | Bourrie et al. | |
| 2008/0200535 A1 | 8/2008 | Ohmori et al. | |

(Continued)

FOREIGN PATENT DOCUMENTS

| | | | |
|---|---|---|---|
| EP | 1661881 A2 | 5/2006 | |
| EP | 1864980 A1 | 12/2007 | |
| JP | 2007169194 A | 7/2007 | |

(Continued)

OTHER PUBLICATIONS

Anderson et al. "The Process of Structure-Based Drug Design." *Chem. Biol.* 10(2003):787-797.

(Continued)

*Primary Examiner* — Barbara P Badio
*Assistant Examiner* — Sara E Townsley
(74) *Attorney, Agent, or Firm* — Cooley LLP; Heidi A. Erlacher; Lian Ouyang

(57) ABSTRACT

The invention relates to novel compounds that have S1P receptor modulating activity and, preferably, apoptotic activity and/or anti proliferative activity against cancer cells and other cell types. Further, the invention relates to a pharmaceutical comprising at least one compound of the invention for the treatment of diseases and/or conditions caused by or associated with inappropriate S1P receptor modulating activity or expression, for example, cancer. A further aspect of the invention relates to the use of a pharmaceutical comprising at least one compound of the invention for the manufacture of a medicament for the treatment of diseases and/or conditions caused by or associated with inappropriate S1P receptor modulating activity or expression such as cancer.

3 Claims, 1 Drawing Sheet

(56) References Cited

U.S. PATENT DOCUMENTS

| | | | |
|---|---|---|---|
| 2009/0118349 A1 | 5/2009 | Szekely et al. | |
| 2011/0318388 A1 | 12/2011 | Gill et al. | |

FOREIGN PATENT DOCUMENTS

| | | |
|---|---|---|
| WO | WO-9509159 A1 | 4/1995 |
| WO | WO-0144223 A1 | 6/2001 |
| WO | WO-02074758 A2 | 9/2002 |
| WO | WO-03050098 A1 | 6/2003 |
| WO | WO-2004011418 A1 | 2/2004 |
| WO | WO-2004047724 A2 | 6/2004 |
| WO | WO-2004058762 A1 | 7/2004 |
| WO | WO-2005032471 A2 | 4/2005 |
| WO | WO-2005082089 A2 | 9/2005 |
| WO | WO-2005123673 A1 | 12/2005 |
| WO | WO-2006022442 A1 | 3/2006 |
| WO | WO-2006055625 A2 | 5/2006 |
| WO | WO-2007024922 A1 | 3/2007 |
| WO | WO-2007076055 A2 | 7/2007 |
| WO | WO-2007092638 A1 | 8/2007 |
| WO | WO-2007127183 A1 | 11/2007 |
| WO | WO-2008021532 A2 | 2/2008 |
| WO | WO-2008064320 A2 | 5/2008 |
| WO | WO-2008070740 A1 | 6/2008 |
| WO | WO-2008073785 A2 | 6/2008 |
| WO | WO-2008073942 A2 | 6/2008 |
| WO | WO-2008079382 A1 | 7/2008 |
| WO | WO-2008098857 A1 | 8/2008 |
| WO | WO-2008099781 A1 | 8/2008 |
| WO | WO-2008152149 A1 | 12/2008 |
| WO | WO-2009153307 A1 | 12/2009 |
| WO | WO-2010065760 A1 | 6/2010 |
| WO | WO-2010069949 A1 | 6/2010 |

OTHER PUBLICATIONS

Cowart et al. "Achievement of Behavioral Efficacy and Improved Potency in New Heterocyclic Analogs of Bezofuran H3 Antagonists." *Inflamm. Res.* 54.S1(2005):S25-S26.

Dawson et al. "An Adamantyl-Substituted Retinoid-Derived Molecule That Inhibits Cancer Cell Growth and Angiogenesis by Inducing Apoptosis and Binds to Small Heterodimer Partner Nuclear Receptor: Effects of Modifying Its Carboxylate Group on Apoptosis, Proliferation, and Protein-Tyrosine Phosphatase Activity." *J. Med. Chem.* 50(2007):2622-2639.

Fancelli et al. "Solid Phase Synthesis of 2-Substituted Benzofurans via the Palladium-catalysed Heteroannulation of Acetylenes." *Tetrahed. Lett.* 38.13(1997):2311-2314.

Li et al. "Synthesis and Biological Evaluation of 2-Indolyloxazolines as a New Class of Tubulin Polymerization Inhibitors." *Bioorg. Med. Chem. Lett.* 12(2002):465-469.

Thiel. "Structure-Aided Drug Design's Next Generation." *Nat. Biotechnol.* 2(2004):513-519.

Trofimov et al. "Synthesis of Isotryptamines and Tetrahydro-γ-Carbolines from 2-Indolylacetic Acid Derivatives." *Chemistry of Heterocyclic Compounds.* (1979):63-65.

Clemens et al. "Synthesis of 4(5)-phenylimidazole-Based Analogues of Sphingosine-1-Phosphate and FTY720: Discovery of Potent S1P1 Receptor Agonists." *Bioorg. Med. Chem. Lett.* 15.15(2005):3568-3572.

de Mauny, "Some Aminonitro Alcohols and Polyamino Alcohols", *Bulletin de la Societe Chimique de France*, 11: 281-283 (1944).

Villanueva et al., "A Trapped Intermediate in the Copper(II)-Mediated Template Synthesis of an Amino Acid-Containing Ligand", *Inorg. Chem.*, 36: 4585-4592 (1997).

\* cited by examiner

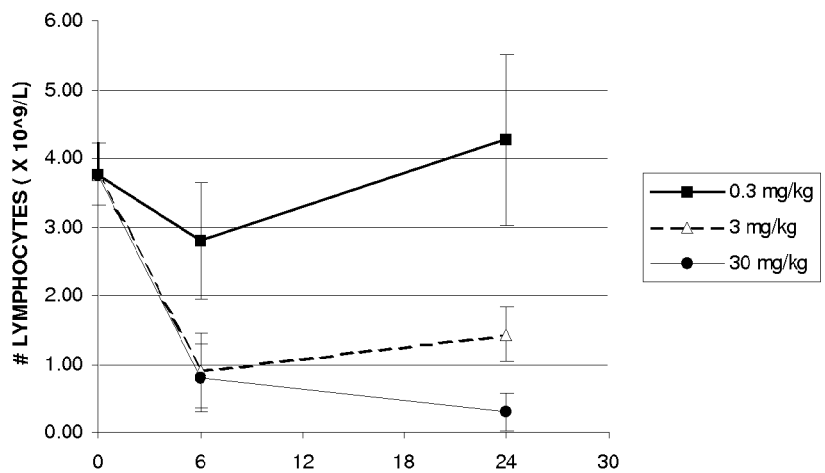
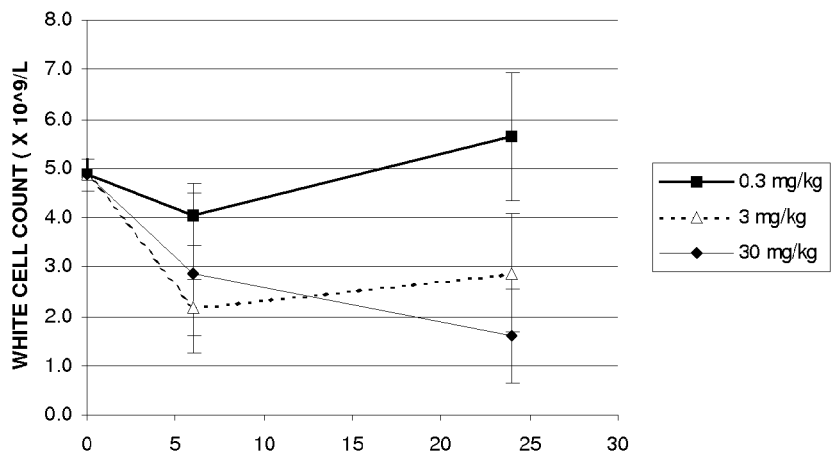

S1P RECEPTORS MODULATORS

RELATED APPLICATIONS

This application is a national stage application, filed under 35 U.S.C. §371, of International Application No. PCT/AU2009/001368, filed on Oct. 16, 2009 which claims the benefit of and priority to Australian Application No. 2008905356, filed Oct. 17, 2008 and Australian Application No. 2009902561, filed on Jun. 4, 2009, the disclosure of each is incorporated herein by reference in its entirety.

FIELD OF THE INVENTION

This invention relates to novel compounds having S1P receptor modulating activity. The novel compounds may also have apoptotic activity against cancer cells and other target cells. The invention also relates to the use of such compounds to treat diseases and/or conditions associated with inappropriate S1P receptor modulating activity or expression such as cancer.

BACKGROUND OF THE INVENTION

Sphingosine 1-phosphate (S1P) is a natural sphingolipid that functions as an intramolecular messenger in many types of cells and as an extracellular signalling molecule (for a recent review see Cooke et al, Annual Reports in Medicinal Chemistry, 2007, 42, pp 245-263 and references therein). The cellular effects induced by S1P are associated with platelet aggregation, cell morphology and proliferation, tumour cell invasion, endothelial cell chemotaxis and in vitro angiogenesis. The extracellular signalling occurs through interaction of S1P with G-protein-coupled receptors S1P1, S1P2, S1P3, S1P4 and S1P5. The intracellular activity of S1P and modulators has not been fully explored. S1P and its target have an essential role in lymphocyte migration through secondary lymphoid organs such the spleen, lymph nodes and mucosa-associated tissues such as the tonsils and Peyer's patches. The lymphocytes move from the peripheral circulation into the lymph nodes and mucosa associated tissues in order to generate immune responses. T and B lymphocytes are effectively sequestered within the thymus and secondary lymphoid tissue. Essentially, S1P and its receptor subtype −1 are required for lymphocytes to move out of the thymus and secondary lymphoid organs.

S1P type molecular modulators have been shown to be effective in multiple animal disease models. The S1P signalling, mainly through its receptor subtype −1, is important in halting the $T_{reg}$ response and has been recommended for immunotherapy of cancer and infectious disease (Liu, G., et al, Nature Immunology, 2009, 10, 769-777; Wolf, A. M., et al, J. Immunology, 2009, 183, 3751-60). The S1P mediated trans-activation of insulin receptor has been reported to help treat insulin resistance and type 2 diabetes (Rapizzi E. et al, Cell Mol. Life. Sci., 2009, 66, 3207-18). S1P1 receptor axis has a role in the migration of neural stem cells toward the site of spinal cord injury (Kimura, A., et al, Stem Cells, 2007, 25, 115-24). The S1P and its modulators supports the trafficking of hematopoietic progenitor cells and are helpful in tissue repair in myocardial infarction (Seitz, G., et al, Ann. N.Y. Acad. Sci., 2005, 1044, 84-89; Kimura, et al, Blood, 2004, 103, 4478-86) and a have great potential applications in regenerative medicines. S1P receptors play a critical role in endothelial barrier enhancement and vasculature maturation (McVerry, B. J., et al, Journal of Cellular Biochemistry, 2004, 1075-85; Allende, M. L., et al, Blood, 2003, 102, pp 3665-7; Paik, J., et al, Genes and Development, 2004, 18, 2392-2403; Garcia, J. G. N., et al, J. Clinical Investigation, 2001, 689-701). The vasculature normalization helps the cytotoxic T cells to access the remote and inner part of the tumour (Hamzah J. et al, Nature, 2008, 453, pp 410-414). The lymphocyte egress and endothelial barrier function is mediated through S1P1 receptor (Brinkmann, et al, American J. of Transplantation, 2004, 4, 1019-25; McVerry B. J. et al, Cellular Signalling, 2005, 17, pp 131-39). S1P type modulation reduces ischemia reperfusion injuries (Lein, Y. H., et al, Kidney International, 2006, 69, 1601-8; Tsukada, Y. T. et al, J Cardiovascular Pharmocol, 2007, 50, 660-9). S1P1 signalling is critical in preventing inflammation induced vascular leakage (Niessen, F. et al, Blood, 2009, 113, 2859-66; Wang L et al, Microvascular Research, 2009, 77, 39-45; Lee, J. F., et al, Am. J. Physiol. Heart Circ. Physiol., 2009, 296, H33-H42). It also reduces a vascular leakage in models of acute lung injury (McVerry, B. J., et al, Am. J. of Respiratory and Critical Care Medicine, 2004, 170, 987-93). The S1P vasculo-protection effect, mediated by nitric oxide and prostacyclin (Rodriguez C et al, Thromb. Haemost., 2009, 101, 66-73), prevents the development of atherosclerotic lesions (Nofer, J. R. et al, Circulation, 2007, 115, 501-8; Tolle, M., et al, European J. Clin. Inv., 2007, 37, 17-9; Keul, P., et al, Arterioscler. Thromb. Vasc. Biol., 2007, 27, 607-13). S1P prevents tumour necrosis factor alpha mediated monocyte adhesion to endothelial cells, implicated in the pathology of arthrosclerosis and inflammatory diseases (Bolick, D. T. et al, Arterioscler. Thromb. Vasc. Biol, 2005, 25, 976-81). Recently reported targets of S1P includes the family of Histone Deacylases (HDACs) (Hait, N. C., et al, Science, 2009, 325, 125-7), which are known for their epigenetic role. The S1P has been reported to help treatment of the latent *mycobacterium tuberculosis* infection by promoting the processing and presentation of antigens (Santucci, M. B. et al, Biochem. Biophys. Res. Comm., 2007, 361, 687-93). Additionally, the S1P and its modulators have cardio protective effects (Means, C. K., et al, Cardiovascular Research; 2009, 82, 193-200; Hofmann, U., et al, Cardiovascular Research, 2009, 83, 285-93; Tao, R., et al, J Cardiovasc. Pharmacol., 2009, 53, 486-94) and the signalling axis of S1P are important in the treatment of myocardial infarction (Yeh, C. C., et al, Am. J. Physiol. Heart Circ. Physiol., 2009, 296, H1193-9). Thus, S1P like molecular modulators have a great developmental potential in wide range of cardiovascular medicines.

Fingolimod (2-amino-2-(2-[4-octylphenyl]ethyl)-1,3-propanediol) (FTY-720) is metabolised to a structural analogue of S1P and has been found to effect S1P receptors. The discovery of FTY-720 and its efficiency in animal models and clinical studies, related to many autoimmune diseases and cancer treatment, has resulted in research efforts into S1P receptors.

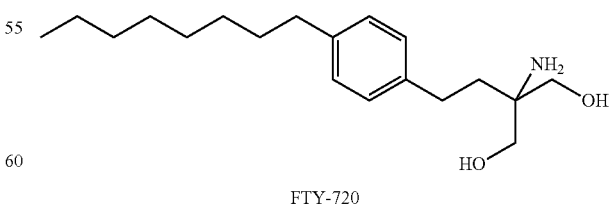

FTY-720

FTY-720 decreases peripheral blood lymphocyte counts (lymphopenia) reversibly, without impairing the effector function of the immune cells (Pinschewer, D. et al, J. Immunology, 2000, 164, 5761-70). FTY-720 is an emerging novel drug for Multiple Sclerosis (MS) (Kieseier, B. C., et al, Pharmacological Research, 2009, 60, 207-11; Brown, B. A., The Annals of Pharmacotherapy, 2007, 41, 1660-8) and has a direct cyto-protective and process extension effect in oligodendrocyte progenitors (Coelho, R. P. et al, J. Pharmacology and Experimental Therapeutics, 2007, 323, 626-35; Miron, V. E. et al, Ann. Neurol, 2008, 63, 61-71). It is effective against autoimmune related pathologies such as type-1 diabetes (Yang, Z., et al, Clin. Immunology, 2003, 107, 30-5), arthritis (Matsuura, et al, Inflamm. Res., 2000, 49, 404-10) and oxazolone stimulated colitis (Daniel, et al, Molecular Immunology, 2007, 44, 3305-16). FTY-720 interaction with cytosolic Phospholipase A2 and modulation of the eicosanoids synthesis (Payne S. G. et al; Blood, 2007, 109, pp 1077-1085) indicates its potential as anti-inflammatory and antinociceptive agents and a safe pain killer (Coste, O., et al, J. Cell Mol. Med., 2008, Vol 12, 995-1004). The anticancer activity of FTY-720 is well documented by in vitro apoptotic activity studies as well as numerous animal model studies. Apoptosis is the process of programmed cell death (PCD) that may occur in multicellular organisms. Programmed cell death involves a series of biochemical events leading to a characteristic cell morphology and death; in more specific terms, a series of biochemical events that lead to a variety of morphological changes, including blebbing, changes to the cell membrane such as loss of membrane asymmetry and attachment, cell shrinkage, nuclear fragmentation, chromatin condensation, and chromosomal DNA fragmentation. The apoptotic mechanism observed in hepatocellular carcinoma cell lines is linked to the activation of protein kinase C delta (PKC-δ) (Hung, J. H., et al, 2008, 68, 1204-12). The apoptotic activity of FTY-720 against chronic myelogenous leukaemia and Philadelphia chromosome positive acute lymphocytic leukaemia was reported to be due to its control of Protein Phosphates 2A (PP2A) (Neviani et al, J of Clinical Investigation, 2007, 117, 24-21). Phosphorylated form of FTY-720 is speculated to be an anti-metastasis drug (Meeteren, et al, Cancer Lett., 2008, 266, 203-8). FTY-720 inhibits vascular endothelial cell growth factor induced vascular permeability (Sanchez, T., et al, J. Biological Chem., 2003, 278, 47281-90), linked to an anticancer and anti-metastatic effect in animal models (Azuma, H., et al, Cancer Res, 2002, 1410-19; Chua, C-W., at al, Int. J Cancer, 2005, 117, 1039-48; LaMontange, K. et al, 2006, 66, 221-31). The anti-angiogenic effect of FTY-720 through its interaction with S1P receptor subtype –1, was described recently (Schmid, G., et al, J. Cellular Biochem., 2007, 101, 259-70). FTY-720 helps favourable central nervous system (CNS) gene expression and improves the blood brain barrier function (Foster, C. A., et al, Brain Pathology, 2009, 19, 254-66). A few days of treatment with FTY-720 leads to complete eradication of chronic viral infection of lymphocytic choriomeningitis (Lanier, et al, Nature, 2008, 894-899). Its anti-fibrotic activity was reported recently (Brunati, A. M., et al, Biochem. Biophys. Acta, 2008, 1783, 347-59; Delbridge, M. S., et al, Transplantation Proceedings, 2007, 39, 2992-6). FTY 720 inhibits development of atherosclerosis in low density lipoprotein receptor deficient mice (Nofer, J. R., et al, Circulation, 2007, 115, 501-8; Tolle, M. et al, European J. Clinical Investigation, 2007, 37, 171-79). FTY720 was effective in the treatment of cerebral ischemia in the mouse model (Czech, B., et al, Biochem. Biophys. Res. Comm., 2009, online), indicating the great potential of S1P receptors modulators in the wide range of cardiovascular medicine. The derivatives of FTY-720 were reported as pulmonary barrier enhancers and thus potential agents for the development of critical care medicines (Camp, S. M., et al, J. Pharmacol. Experimental Therapeutics, 2009, online).

Of the classical mimics of S1P, the amino alcohols and their respective monophosphates, amino phosphonates, amino acids, alkoxyamino alcohols and alkyl carboxylates appear to be the most effective S1P receptors modulators. While an in vivo phosphorylation of the hydroxyl group of FTY 720 appears to be necessary for the most effective extracellular signalling and agonistic effect upon binding to S1P1-5, the apoptotic effect is limited to its non-phosphorylated form.

S1P type modulators have been shown to have a favourable response in multiple disease models and this response has been successfully translated to humans. The best explored is FTY 720, which apart from acting through S1P receptors, interacts with several intracellular receptors. It is advantageous to provide alternatives to FTY 720 in order to produce compounds with a greater range of activity, and/or altered or enhanced specificity, and/or improved pharmacological properties or reduction in side effects such as bradycardia, headache, fatigue and/or flu-like symptoms.

It is desirable to provide alternatives to FTY 720 and in particular alternative compounds with improved properties and/or activity. For example, this could include compounds with a greater range of activity, altered or enhanced specificity, improved pharmacological properties or reduction in side effects.

In particular, it is desirable to provide novel compounds having S1P receptor modulating activity as well as apoptotic activity and/or anti proliferative action against cancer cells and other cell types (dual activity).

Throughout this specification, use of the terms "comprises" or "comprising" or grammatical variations thereon shall be taken to specify the presence of stated features, integers, steps or components but does not preclude the presence or addition of one or more other features, integers, steps, components or groups thereof not specifically mentioned.

SUMMARY OF INVENTION

In one aspect of the present invention there is provided a compound of formula (1)

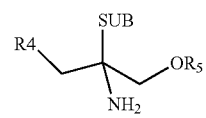

(1)

wherein SUB represents an organic substituent comprising at least one aromatic moiety, $R_4$ is selected from the group consisting of hydrogen, alkoxy, cyano, amino, hydroxyl, halogen, nitro, carbonyl, carboxy, amido, trifluoromethyl, trihaloalkyl, trifluoroalkoxy or a $C_{1-8}$ substituted or unsubstituted alkyl, alkenyl or alkynyl, $R_5$ is hydrogen or —P(O)(OR$_x$)(OR$_y$) wherein R$_x$ and R$_y$ are as defined for $R_4$;

including stereoisomers and/or isotopic forms of the compound formula (1) and their pharmaceutically acceptable salts or prodrugs thereof.

As used herein, a prodrug is a pharmacological substance that is administered to a subject in an inactive (or significantly less active) form. Once administered, the prodrug is metabolised in vivo into an active metabolite.

In a further aspect of the present invention there is provided a compound of formula (2)

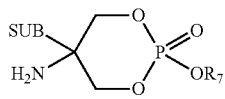
(2)

wherein SUB represents an organic substituent comprising at least one aromatic moiety, R7 is selected from the group consisting of hydrogen, trifluoromethyl, trihaloalkyl or a $C_{1-8}$ substituted or unsubstituted alkyl, alkenyl or alkynyl;

including stereroisomers and/or isotopic forms of the compound of formula (2) and their pharmaceutically acceptable salts.

In a preferred embodiment of any of the aforementioned aspects of the present invention the organic substituent SUB contains at least one oxygen, sulphur, nitrogen or phosphorous atom.

Preferably, the organic substituent SUB has the structure of formula (3)

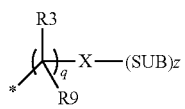
(3)

wherein (SUB), represents hydrogen or an organic substituent, wherein z=1-3, with the proviso that at least one of (SUB), is an organic substituent comprising at least one aromatic moiety, $R_3$ being optionally linked by a bridging moiety to one of (SUB), and when z>2 one of (SUB), being optionally linked by a bridging moiety to another of $(SUB)_z$, and wherein, X is O, N(R)$_n$, CR$_n$ or S(O)$_n$, wherein R, $R_3$ and $R_9$ are independently selected from the group consisting of hydrogen, alkoxy, cyano, amino, hydroxyl, halogen, nitro, carbonyl, carboxy, amido, trifluoromethyl, trihaloalkyl, trifluoroalkoxy or a $C_{1-8}$ substituted or unsubstituted alkyl, alkenyl or alkynyl, q is 0-10 and n is 0-2.

More preferably, the organic substituent SUB has the structure of formula (4)

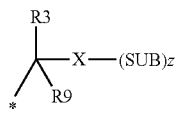
(4)

wherein $(SUB)_Z$ represents hydrogen or an organic substituent, wherein z=1-3, with the proviso that at least one of $(SUB)_Z$ is an organic substituent comprising at least one aromatic moiety, $R_3$ being optionally linked by a bridging moiety to one of $(SUB)_Z$ and when z>2 one of $(SUB)_Z$ being optionally linked by a bridging moiety to another of $(SUB)_Z$, and wherein, X is O, N(R)$_n$, CR$_n$ or S(O)$_n$, wherein R, $R_3$ and $R_9$ are independently selected from the group consisting of hydrogen, alkoxy, cyano, amino, hydroxyl, halogen, nitro, carbonyl, carboxy, amido, trifluoromethyl, trihaloalkyl, trifluoroalkoxy or a $C_{1-8}$ substituted or unsubstituted alkyl, alkenyl or alkynyl, q is 0-10 and n is 0-2.

In one embodiment the compound of formula (1) has a structure of formula (5)

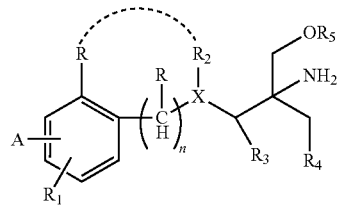
(5)

wherein

X is C(R); N, O and S(O)$_n$ (n=0-2), with the proviso that when X is O or S(O)$_n$, the substituent $R_2$ is not present;

R, $R_2$ and $R_3$ are independently selected from the group consisting of hydrogen, alkoxy, cyano, amino, hydroxyl, halogen, nitro, carbonyl, carboxy, amido, trifluoromethyl, trihaloalkyl, trifluoroalkoxy or a $C_{1-8}$ substituted or unsubstituted alkyl, alkenyl or alkynyl;

and optionally R and $R_2$ together with an aromatic ring form homo or hetero six-five or six-six member bis-cyclic ring systems;

n=0-5;

$R_4$ is selected from the group consisting of hydrogen, alkoxy, cyano, amino, hydroxyl, halogen, nitro, carbonyl, carboxy, amido, trifluoromethyl, trihaloalkyl, trifluoroalkoxy or a $C_{1-8}$ substituted or unsubstituted alkyl, alkenyl or alkynyl, $R_5$ is hydrogen or —P(O)(OR$_x$)(OR$_y$) wherein R$_x$ and R$_y$ are as defined for $R_4$;

A is selected from the group consisting of hydrogen or independently optionally substituted $(C_1-C_{20})$alkyl, $(C_3-C_{20})$cycloalkyl, $(C_3-C_{18})$cycloalkyl$(C_1-C_{18})$alkyl, $(C_6-C_{24})$aryl, $(C_7-C_{25})$aralkyl, $(C_2-C_{18})$alkenyl, $(C_8-C_{26})$aralkenyl, $(C_2-C_{18})$-alkynyl, $(C_8-C_{26})$aralkynyl, or heterocyclic;

$R_1$ is hydrogen or an optionally substituted $(C_1-C_{18})$alkyl, $(C_3-C_{18})$cycloalkyl, $(C_3-C_{18})$cycloalkyl$(C_1-C_{18})$alkyl, $(C_6-C_{24})$aryl, $(C_7-C_{25})$aralkyl, $(C_2-C_{18})$alkenyl, $(C_8-C_{26})$aralkenyl, $(C_2-C_{18})$alkynyl, $(C_8-C_{26})$aralkynyl, or heterocyclic, heteroaryl substituted $C_{1-20}$ alkyl, $C_{3-20}$ cycloalkyl substituted aryl, $C_{3-20}$ cycloalkyl substituted heteroaryl, heteroaryl substituted $C_{2-20}$ alkenyl, heteroaryl substituted $C_{2-20}$ alkynyl, aryl substituted alkoxyl, $C_{3-20}$ cycloalkyl substituted aryl alkoxyl, alkylaryl substituted alkoxyl, heteroaryl, heteroaryloxy, fused 4-5, 4-6, 5-5, 5-6 or 6-6 heterobicylic ring system, or a group (a-d)

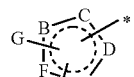
(a)

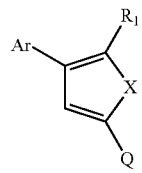
(b)

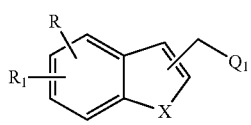
(c)

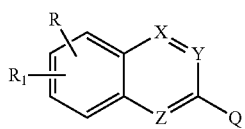
(d)

wherein

Ar is an optionally substituted 5-12 atom aromatic or heteroaromatic ring system; B, C, D, E and F are independently selected from $C(R)_n$, O, $S(O)_n$, $N(R)_m$ groups; G and H are independently selected from A or R; Q and $Q_1$ are independently represented by —$C(R)_n$—X—* the asterisk indicating the bond that is linked to the phenyl ring of formula 5, n is 0-2; m is 0-1; X is $C(R)_n$, $N(R)_n$, O or $S(O)_n$ (n is 0-2) in groups (b) and (c); X, Y and Z are independently $C(R)_n$, or N (n is 0-1) in group (d) ⁓ is alkylidene, R and $R_1$ are independently selected from the group consisting of hydrogen, alkoxy, cyano, amino, hydroxyl, halogen, nitro, carbonyl, carboxy, amido, trifluoromethyl, trihaloalkyl, trifluoroalkoxy or a $C_{1-8}$ substituted or unsubstituted alkyl, alkenyl or alkynyl.

In a preferred embodiment the compound of formula (5) has the structure of any one of formulae (6) to (10)

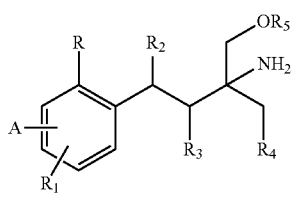
(6)

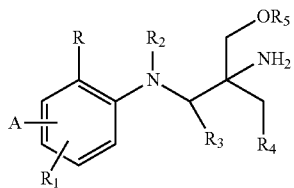
(7)

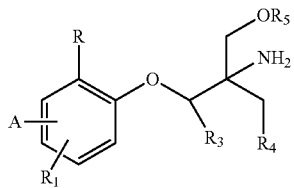
(8)

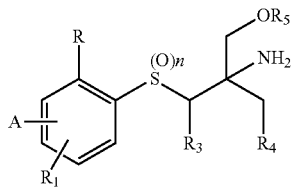
(9)

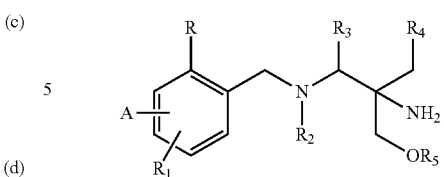
(10)

wherein

A, R, and R1-R5 are as defined for formula (5) and n=0-2.

In a further preferred embodiment the compound of formula (1) has the structure of any one of formulae (11) to (16)

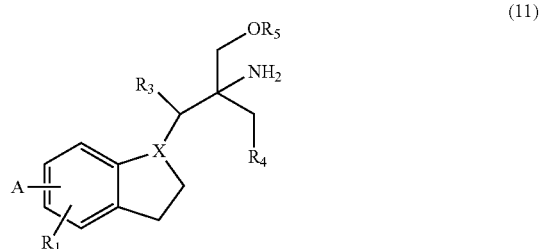
(11)

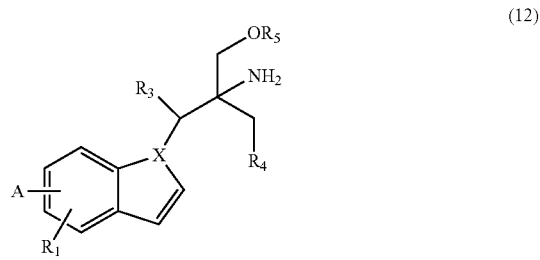
(12)

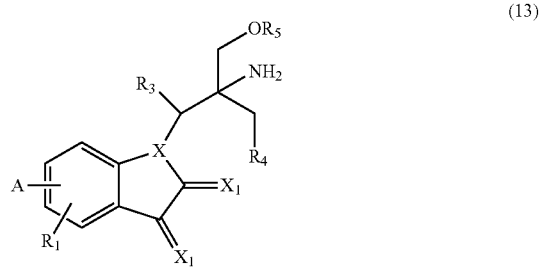
(13)

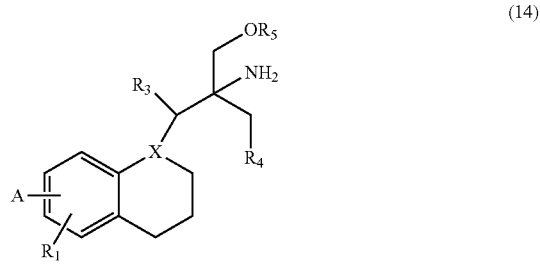
(14)

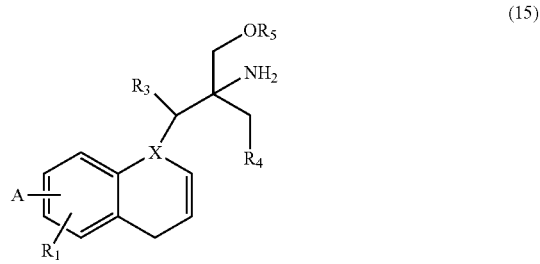
(15)

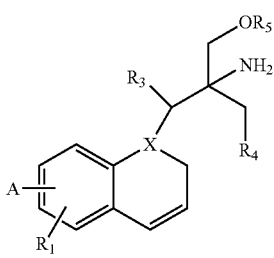

(16)

wherein

X is C(R) or N;

$X_1$ is O or S, and $R_1$-$R_5$ and A are as defined for formula (5).

In a particularly preferred embodiment structures (11) to (13) have A equal to a substituted phenyl(or aryl/heteroaryl)-1,2,4-oxadiazol-3-yl group and R1, R3 and R5=hydrogen, R4=hydroxyl and X=N and the preferred substitution position on the indoline (indole) is 4.

In a further particularly preferred embodiment structures (11) to (13) have A equal to a (substituted benzofuran-2-yl) alkoxy and/or (substituted benzofuran-2-yl)alkyl group and R1, R3 and R5=hydrogen, R4=hydroxyl and X=N and the preferred substitution position on the indoline (indole) is 5.

In another particularly preferred embodiment structures (14) to (16) have A equal to a substituted phenyl(or aryl/heteroaryl)-1,2,4-oxadiazol-3-yl group and R1, R3 and R5=hydrogen, R4=hydroxyl and X=N and the preferred substitution position on the tetrahydroquinoline and/or dihydroquinoline ring is 5.

In an even further preferred embodiment the compound of formula (1) has the structure of formula (17)

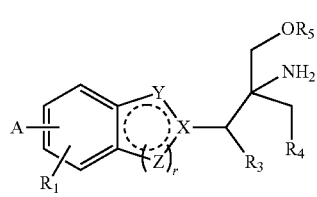

(17)

wherein

A, Y, Z and $R_1$-$R_5$ are as previously defined for formula (5) and r is 1-3; X is C(R) or N.

In a still further preferred embodiment the compound of formula (1) has the structure of any one of formulae (18) to (29)

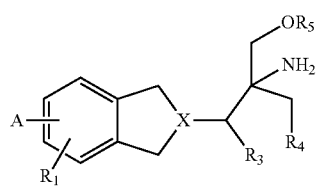

(18)

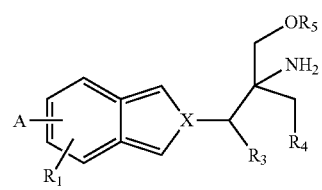

(19)

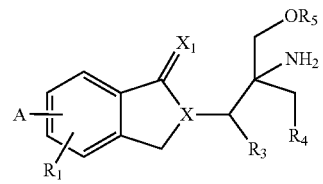

(20)

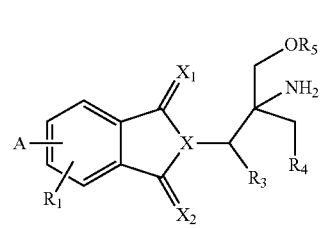

(21)

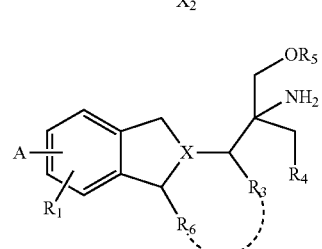

(22)

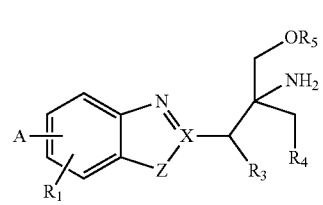

(23)

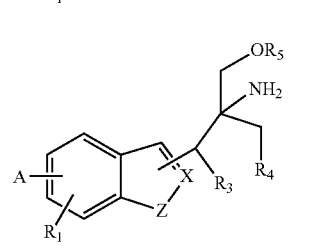

(24)

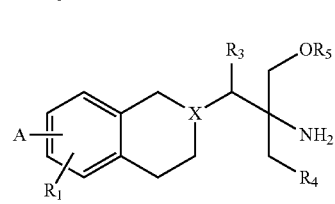

(25)

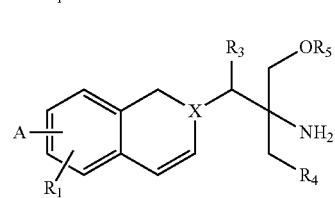

(26)

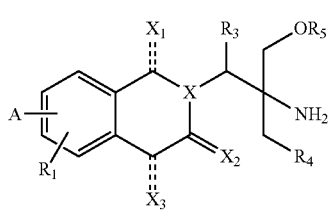

(27)

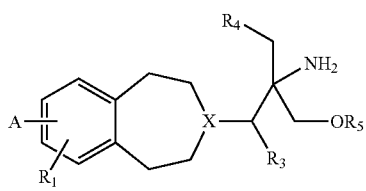

(28)

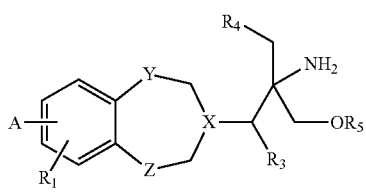

(29)

wherein
X is C(R) or N;
A, $R_1$, $R_3$-$R_5$ and ⋯, are as defined for formula (5), $X_1$ is as defined for formula (13), $R_6$ is as defined for $R_1$, $X_2$ and $X_3$ are independently selected from $C(R)_n$, $N(R)_n$, O or $S(O)_n$ wherein n=0-2, $R_6$ and $R_3$ may optionally together form a fused 4-8 member heterocyclic saturated or unsaturated ring system.

In a particularly preferred embodiment structures (18) to (21) have A equal to a substituted phenyl(or aryl/heteroaryl)-1,2,4-oxadiazol-3-yl group or any is defined as in compound of formula (5) and R1, R3 and R5=hydrogen, R4=hydroxyl and X=N and the preferred substitution position on the isoindoline (isoindole) ring is 5.

The compounds of the invention have S1P receptor modulating activity and, preferably, apoptotic activity and/or anti proliferative activity against cancer cells and other cell types (dual activity).

In a further aspect of the invention there is provided compounds having S1P receptor modulating activity that concurrently induces apoptosis and/or anti proliferative action against a target cell.

Accordingly, a further aspect of the invention provides a pharmaceutical preparation comprising at least one compound described herein in any of its stereoisomeric and/or isotopic forms or physiologically tolerable and/or therapeutically effective salts or mixtures thereof in any ratio together with a pharmaceutically acceptable carrier(s) and/or excipient(s).

In a further aspect the invention provides the use of a compound of the invention in any of its stereoisomeric and/or isotopic forms or physiologically tolerable and/or therapeutically effective salts or mixtures thereof in any ratio, for the production of a pharmaceutical for modulation of S1P receptor activity and/or expression against target cells.

In a further aspect the invention provides the use of a compound of the invention in any of its stereoisomeric and/or isotopic forms or physiologically tolerable and/or therapeutically effective salts or mixtures thereof in any ratio, for the production of a pharmaceutical for modulation of S1P receptor activity and/or expression and induction of apoptosis against target cells.

In a further aspect the invention provides the use of a compound of the invention in any one of its stereoisomeric and/or isotopic forms and mixtures thereof in any ratio and/or physiologically tolerable and/or therapeutically effective salts for the production of a pharmaceutical for modulation of S1P receptor (extracellular and or intracellular binders) activity and/or expression.

S1P receptors are cell surface receptors which include known receptor subtypes 1, 2, 3, 4, 5 and are regarded herein as S1P receptors. These extracellular S1P receptors may be present inside the cell on Golgi bodies, etc. There are other intracellular receptor/s, target/s, protein/s, enzyme/s where S1P interacts and are regarded as S1P receptor/s. The compounds of the invention could function as substrates of Sphingosine Kinases like SK1 and SK2 which are responsible for phosphorylation of S1P and are regarded as S1P receptor/s. Histone Deacylase/s (HDACs) are known intra-nuclear receptors of S1P and thus are regarded as S1P receptors. In broad terms, the invention includes any receptor binder, agonists or antagonists, or inverse agonists of the S1P receptor family including S1P1, S1P2, S1P3, S1P4 and S1P5, which is responsible for direct and or indirect effect of S1P and regards them as S1P receptor/s.

Further, the invention relates to the use of a pharmaceutical comprising at least one compound of the invention in any of its stereoisomeric and/or isotopic forms or physiologically tolerable and/or therapeutically effective salts or mixtures thereof in any ratio.

Further, the invention relates to the use of a pharmaceutical comprising at least one compound of the invention in any of its stereoisomeric and/or isotopic forms or physiologically tolerable and/or therapeutically effective salts or mixtures thereof in any ratio for the treatment of diseases and/or conditions caused by or associated with inappropriate S1P receptor modulating activity or expression, for example, cancer.

A further aspect of the invention relates to the use of a pharmaceutical comprising at least one compound of the invention in any of its stereoisomeric or isotopic forms or physiologically tolerable and/or therapeutically effective salts or mixtures thereof in any ratio for the manufacture of a medicament for the treatment of diseases and/or conditions caused by or associated with inappropriate S1P receptor modulating activity or expression such as cancer.

In yet a further aspect of the invention, the compounds of the invention can be used for the prevention and/or prophylaxis and/or treatment and/or immunotherapy of infectious diseases including any infection caused by viruses, bacteria, fungi, parasites, prions and/or any other pathogens.

Viral infections including but not limited to human immunodeficiency virus, Hepatitis (HAV, HBV, HCV), $H_1N_1$ influenza, chickenpox, cytomegalovirus infection, dengue fever, Ebola hemorrhagic fever, hand foot and mouth disease, herpes simplex, herpes zoster, HPV, influenza (Flu), Lassa fever, measles, Marburg Hemorrhagic fever, infectious mononucleosis, mumps, norovirus, poliomyelitis, progressive multifocal Leu-encephalopathy, rabies, rubella, SARS, smallpox (Variola), viral encephalitis, viral gastroenteritis, viral meningitis, viral pneumonia, west Nile disease and yellow fever.

Bacterial Infections including but not limited to actinomycosis, anaplasmosis, anthrax, bacterial meningitis, botulism, brucellosis, *burkholderia* infections, campylobacteriosis, cellulitis, chlamydiaceae infections, cholera, *clostridium* infections, coccidiomycosis, diphtheria, ehrlichiosis, empyema, gonorrhea, impetigomelioidosis legionellosis, leprosy (Hansen's Diseases), leptospirosis, listeriosis, lyme disease, bacterial endocarditis, endophthalmitis, pseudomembranous enterocolitis, erysipelas, *Escherichia coli* infections, necrotizing fasciitis, Fournier gangrene, furunculosis, *fusobacterium* infections, gram negative bacterial infections, gram positive bacterial infections, granuloma inguinale, hidradenitis suppurativa, histoplasmosis, hordeolum, impetigo, *Klebsiella* infections, ludwig's angina, lymphogranuloma venereum, maduromycosis, *mycobacterium* infections, MRSA infection, *Mycoplasma* infections, *nocardia* infections, onychomycosis, osteomyelitis, paronychia, pelvic inflammatory disease, plague pneumococcal infections, pseudomonas infections, psittacosis, puerperal infection, respiratory tract infections, retropharyngeal abscess, rheumatic fever, rhinoscleroma, *rickettsia* infections, rocky mountain disease, *salmonella* infections, scarlet fever, scrub typhus, sinusitis, shigellosis, spotted fever, bacterial skin disease, staphylococcal infections, streptococcal infections, syphilis, tetanus, trachoma, tick borne disease, epidemic typhus, tuberculosis, tularaemia, typhoid fever, urinary tract infections, whipple disease, whooping cough, *vibrio infections, Yersinia* infections, zoonoses, and zygomycosis, Fungal infections including but not limited to aspergillosis, blastomycosis, candidiasis, coccidioidomycosis, cryptococcosis, tinea pedis and histoplasmosis.

Prion infections including but not limited to transmissible spongiform encephalopathy, bovine spongiform encephalopathy, Creutzfeldt-Jakob disease, Kuru fatal Familial insomnia and Alpers Syndrome.

In a further aspect of the invention, the compounds of the invention can be used for the prevention and/or prophylaxis and/or treatment and/or immunotherapy of cancer and immune mediated diseases which include immune related and inflammatory diseases; autoimmune diseases; allergic conditions; pain; central nervous system diseases; neurodegenerative diseases, cardiovascular diseases; haematological pathologies. For example, Multiple Sclerosis, Alzheimer's, dementia, Parkinson's, Huntington's, Amyotrophic Lateral Sclerosis, Coeliac, inflammatory bowel, Crohn's, ulcerative colitis, Lupus Erythematosus, Lupus Nehritis, osteoarthritis, psoriasis, pruritus, arthritis, rheumatoid arthritis, osteoporosis, Sjogren Syndrome, uveitis, asthma, hay fever, sleep disorders, macular degeneration, glaucoma, type1 and 2 diabetes, myasthenia gravis, non-glomerular nephrosis, autoimmune hepatitis, Behcet's, glomerulonephritis, chronic thrombocytopenia purpure, haemolytic anaemia, Wegner's granuloma and fibrosis, nervous system (spasticity), spinal cord injury, spinocerebellar ataxia, tardive dyskinesia, cognitive disorders.

The compounds of the invention can be used for the prevention and/or prophylaxis and/or treatment and/or immunotherapy of or in, Down's syndrome, schizophrenia, bipolar disorder, drug dependence, Wernicke-Korsakoff syndrome, eating disorders, depression resulting from infection, hepatic encephalopathy, lung diseases such as grain handler's, Hermansky-Pudlak Syndrome, and adult respiratory distress syndrome (ARDS, obesity, digestive tract disease, anxiety, hyperalgesia, migraine, epilepsy and neuromuscular disorder.

In another embodiment the compounds of the invention can be used for prevention and/or treatment of vascular and/or cardiovascular diseases including, but not limited to, hypoxia, atherosclerosis, diabetic blood vessel inflammation, hyper vascularisation related disorders such as cancer and neoplasm, heart failure, myocardial infarction, myocarditis, ischemia, hypotension, hypertension, reperfusion injury, angina pectoris, coronary artery disease, stroke, thrombosis, artery/vein blockage or obstruction, diabetic retinopathy, sepsis and kidney failure, reperfusion or injury.

In another embodiment the compounds of the invention can be used for prevention and/or prophylaxis and/or treatment and/or immunotherapy of liver diseases including but not limited to liver cirrhosis, viral liver infections, autoimmune hepatitis, liver failure, portal hypertension, hemochromatosis, Wilson's diseases, Gaucher disease, hepatoma, primary biliary cirrhosis, primary sclerosing cholangitis, sarcoidosis and Zwellweger syndrome.

In another embodiment the compounds of the invention can be used for the prevention and/or treatment and/or immunotherapy of solid and haematological cancers and tumor metastasis, including but not limited to acute B-cell leukaemia, lymphoma, chronic lymphocytic leukaemia, chronic myeloid leukaemia, hairy cell leukaemia, multiple myeloma, acute lymphocytic leukaemia, acute granulocytic leukaemia, acute myelogenous leukaemia, lung cancer, adrenal gland cancer, astrocytoma, glioma, brain cancer, bile duct cancer, bladder cancer, bone cancer, bowel cancer, colorectal cancer, breast cancer, cervical cancer, endometrial cancer, oesophageal cancer, melanoma, gallbladder cancer, Kaposi sarcoma, renal cancer, laryngeal cancer, liver cancer, mesothelioma, prostate cancer, sarcoma, skin cancer, stomach cancer, testicular cancer, uterine cancer, thyroid cancer, and pancreatic cancer.

In another embodiment the compounds of the invention can be used for prevention and/or treatment and/or immunotherapy of pain including chronic pain, which could either be somatogenic (organic) or psychogenic. The somatogenic pain may be of nociceptive, inflammatory and or neuropathic origin. The pain related to nociceptive pain, peripheral neuropathy, central neuropathy, neuralgia, migraine, psychotic, inflammatory and or neurological disorders.

In another embodiment the compounds of the invention can be used for organ transplant and/or allograft and/or autograft, for example, kidney, liver, lung, heart, skin, stem cell or bone marrow transplant and in the treatment of graft versus host disease.

In another embodiment the disclosed molecules can be used for prevention and/or treatment and/or immunotherapy for the pathologies caused by bioterrorism agents.

In another embodiment the compounds of the invention can be used as a vaccine adjuvant to boost and/or enhance the action of a vaccine and/or immune agent and/or for immunization; for example antigen, tumour cell lysate, B cell vaccine, T cell vaccine, dendritic cell vaccine boosting the immune response of cytotoxic cells, helper T cells and dendritic cells for eradication and immunotherapy of immune related diseases and other preventable diseases such as chickenpox, cholera, diphtheria, whooping cough, meningococcal disease, hepatitis, *Hemophilus influenzae* type B (HIB), measles, mumps, rubella, poliomyelitis and tetanus.

In another embodiment the compounds of the invention can be used to mobilize the progenitor/stem cells preferably towards the site of injury, ischemia, stroke etc. The compounds can be used as cyto-protective agents, cardio-protective agent, neuro-protective agents and regenerative agents that may help host/patient to repair any organ damage, grow organs like muscle, nerve, blood vessel etc and to increase immune cells number.

In another embodiment the present invention provides the use of at least one compound of the invention in any of its stereoisomeric and/or isotopic forms or physiologically tolerable and/or therapeutically effective salts or mixtures thereof in any ratio for the treatment of diseases and/or conditions caused by or associated with inappropriate S1P receptor modulating activity and/or expression.

In another embodiment any of the aforementioned uses may additionally induce apoptosis and/or anti-proliferative action in a target cell.

In another embodiment the present invention provides the use of at least one compound of the invention in any of its stereoisomeric and/or isotopic forms and/or physiologically tolerable and/or therapeutically effective salts or mixtures thereof in any ratio for the treatment and/or immunotherapy of cancer wherein the compound also induces apoptosis and/or anti-proliferative action against the cancer cells.

In another embodiment the invention provides a modulator of an S1P receptor activity and/or expression using at least one compound according to the invention. In one form of this embodiment of the invention the modulator also induces apoptosis and/or anti proliferative action against a target cell. In an alternate or additional form of this embodiment the apoptosis and/or anti proliferative action against a target cell is induced concurrently.

In a further aspect of the invention there is provided a process for the preparation of any of the aforementioned compounds of the invention.

In a further embodiment of the invention there is provided a method of modulation of S1P receptor activity and/or expression by the administration of an effective amount of a compound according to the invention or a stereoisomer and/or isotopic form or a pharmaceutically acceptable salt or derivative thereof, to a subject in need.

In another embodiment the invention provides a method for the treatment of diseases and/or conditions caused by or associated with inappropriate S1P receptor modulating activity or expression by the administration of an effective amount of a compound according to the invention or a stereoisomer and/or isotopic form or a pharmaceutically acceptable salt or derivative thereof, to a subject in need.

In another embodiment the invention provides a method of treating immunological disorders and/or immune mediated disorders or allograft/autograft rejection by the administration of an effective amount of a compound according to the invention or a stereoisomer and/or isotopic form or a pharmaceutically acceptable salt or derivative thereof, to a subject in need.

In another embodiment the invention provides a method of prevention and/or treatment and/or immunotherapy of cancer by the administration of an effective amount of a compound according to the invention or a stereoisomer and/or isotopic form or a pharmaceutically acceptable salt or derivative thereof, to a subject in need.

In another embodiment the invention provides a method of prevention and/or prophylaxis and/or treatment and/or immunotherapy of viral, bacterial or fungal infections by the administration of an effective amount of a compound according to the invention or a stereoisomer and/or isotopic form or a pharmaceutically acceptable salt or derivative thereof, to a subject in need.

In another embodiment the invention provides a method of prevention and/or prophylaxis and/or treatment and/or immunotherapy of pathogens other than viral, bacterial or fungal infections such as prions and parasites by the administration of an effective amount of a compound according to the invention or a stereoisomer and/or isotopic form or a pharmaceutically acceptable salt or derivative thereof, to a subject in need.

In another embodiment the invention provides a method of prevention and/or prophylaxis and/or treatment and/or immunotherapy of proliferative and vascular pathologies/injury, cardiovascular pathologies/injuries, liver pathologies/injuries, lung pathologies/injuries, hypoxia and pain, by the administration of an effective amount of a compound according to the invention or a stereoisomer and/or isotopic form or a pharmaceutically acceptable salt or derivative thereof, to a subject in need.

In another embodiment the invention provides a method of boosting the action of immunization/vaccination by the administration of an effective amount of a compound according to the invention or a stereoisomer and/or isotopic form or a pharmaceutically acceptable salt or derivative thereof, to a subject in need.

In an alternate embodiment the compound according to the invention additionally induces apoptosis and/or anti proliferative action in or against a target cell.

As used herein, "treatment" includes any effect such as lessening, reducing, modulating and/or eliminating resulting in the improvement of the condition, disease or disorder to be treated.

An appropriate concentration level in treatment is from 0.01 nM to 100 µM.

The compounds and compositions of the invention may be administered in combination with a variety of pharmaceutical excipients, including stabilizing agents carriers and/or encapsulation formulations known in the art.

BRIEF DESCRIPTION OF FIGURES

FIG. 1.1 illustrates post-treatment lymophocyte counts.
FIG. 1.2 illustrates post-treatment white blood cell counts.

DETAILED DESCRIPTION OF THE INVENTION

The terms "compound", "agent", "active agent", "chemical agent", "pharmacologically active agent", "medicament", "active", "molecule" and "drug" are used interchangeably herein to refer to a chemical compound that induces a desired pharmacological and/or physiological effect. The terms also encompasses pharmaceutically acceptable and pharmacologically active ingredients of those active agents/compounds specifically mentioned herein and compounds of the invention including but not limited to salts, esters, amides, prodrugs, active metabolites, analogs and the like. When the terms "compound", "agent", "active agent", "chemical agent" "pharmacologically active agent", "medicament", "active" and "drug" are used, then it is to be understood that this includes the active agent per se as well as pharmaceutically acceptable and/or, pharmacologically active salt/s, esters, amides, prodrug/s, metabolites, analogs and the like.

The terms "effective amount" and "therapeutically effective amount" of an agent/s/compounds and compounds of the invention as used herein mean a sufficient amount of the compound to provide the desired therapeutic or physiological effect or outcome. A practitioner balances the potential benefits against the potential risks in determining what an appropriate "effective amount" is. The exact amount required will vary from subject to subject, depending on the species, age and general condition of the subject, mode of administration and the like.

A "pharmaceutically acceptable" carrier, excipient or diluent may include a pharmaceutical vehicle comprised of a material that may not be biologically active or otherwise undesirable, i.e. the material may be administered to a subject along with the selected active agent without causing any and/or a substantial adverse reaction. Carriers may include excipients and other additives such as diluents, detergents, colouring agents, wetting or emulsifying agents, pH buffering agents, preservatives, and the like.

The compositions and combination therapies of the invention may be administered in combination with a variety of pharmaceutical excipients, including stabilizing agents, carriers or encapsulation formulations. Effective combinations are those which provide favourable synergistic effect which assist in treatment and/or prevention and/or immunotherapy better than the agents alone. As used herein, the term "optionally substituted" means that one or more hydrogen atoms may be replaced by a group or groups selected from: —F, —Cl, —Br, —I, —CF3, —OH, —OR7, —NH2, —NHR7, —NR7R8, —CN, —NO2, —SH, —SR7, —SOR7, —SO2R7, =O, =S, =NOH, =NOR7, —NHOH, —NHOR7, —CHO, where R7 and R8 are independently $(C_1-C_{18})$alkyl, typically $(C_1-C_{12})$alkyl; $(C_3-C_{18})$cycloalkyl, typically $(C_3-C_{12})$cycloalkyl; $(C_3-C_{18})$cycloalkyl$(C_1-C_{18})$alkyl, typically $(C_3-C_{12})$cycloalkyl$(C_1-C_6)$alkyl; $(C_6-C_{24})$aryl, typically $(C_6-C_{16})$aryl; $(C_7-C_{25})$aralkyl, typically $(C_7-C_{16})$aralkyl; $(C_2-C_{18})$alkenyl, typically $(C_2-C_{12})$alkenyl; $(C_8-C_{26})$aralkenyl, typically $(C_8-C_{16})$aralkenyl; $(C_2-C_{18})$alkynyl, typically $(C_2-C_{12})$alkynyl; $(C_8-C_{26})$-aralkynyl, typically $(C_8-C_{16})$aralkynyl; or heterocyclic.

As used herein, the term "alkyl" includes within its meaning straight and branched chain alkyl groups. Examples of such groups are methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- or 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1- or 2-pentylheptyl, and the like.

A used herein, the term "cycloalkyl" refers to mono- or polycyclic alkyl groups, or alkyl substituted cyclic alkyl groups. Examples of such groups include cyclopropyl, methylcyclopropyl, cyclobutyl, methylcyclobutyl, cyclopentyl, methylcyclopentyl, ethylcyclopentyl, cyclohexyl, methylcyclohexyl, ethylcyclohexyl, cycloheptyl, cyclooctyl, cyclononyl, cyclodecyl, cycloundecyl, cyclododecyl, decahydronaphthyl, bicyclo[2.2.1]heptanyl, bicyclo[2.2.2]octanyl, bicyclo[3.3.2]decyl, bicyclo4.4.3]dodecyl, bicyclo[4.4.0]octyl and the like.

As used herein, the term "cycloalkylalkyl" refers to an alkyl group substituted with a cycloalkyl group as defined above.

As used herein, the term "alkenyl" includes within its meaning ethylenically mono-, di- or poly-unsaturated alkyl or cycloalkyl groups as previously defined. Examples of such alkenyl groups are vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-headienyl, 1,4-hexadienyl, 1,3-cyclohexadienyl, 1,4-cyclohexadienyl, 1,3 cycloheptadienyl, 1,3,5-cycloheptatrienyl and 1,3,5,7-cyclooctatetraenyl.

As used herein, the term "alkynyl" includes within its meaning acetylenically unsaturated alkyl groups as previously defined. Examples of such alkynyl groups are ethynyl, propynyl, n-butynyl, n-pentynyl, 3-methyl-1-butynyl, n-hexynyl, methyl-pentynyl, (C7-C12)alkynyl and (C7-C12) cycloalkynyl.

As used herein, the term "alkylidene" refers to optionally unsaturated divalent alkyl radicals. Examples of such radicals are —CH2-, —CH2CH2-, —CH=CH—, —CH2CH2CH2-, —C(=CH2)CH2-, —CH2CH=CH—, —(CH2)4-, —CH2CH2CH=CH—, —CH2CH=CHCH2-, and —(CH2)r- where r is 5-8. The term also refers to such radicals in which one or more of the bonds of the radical from part of a cyclic system. Examples of such radicals are groups of the structures

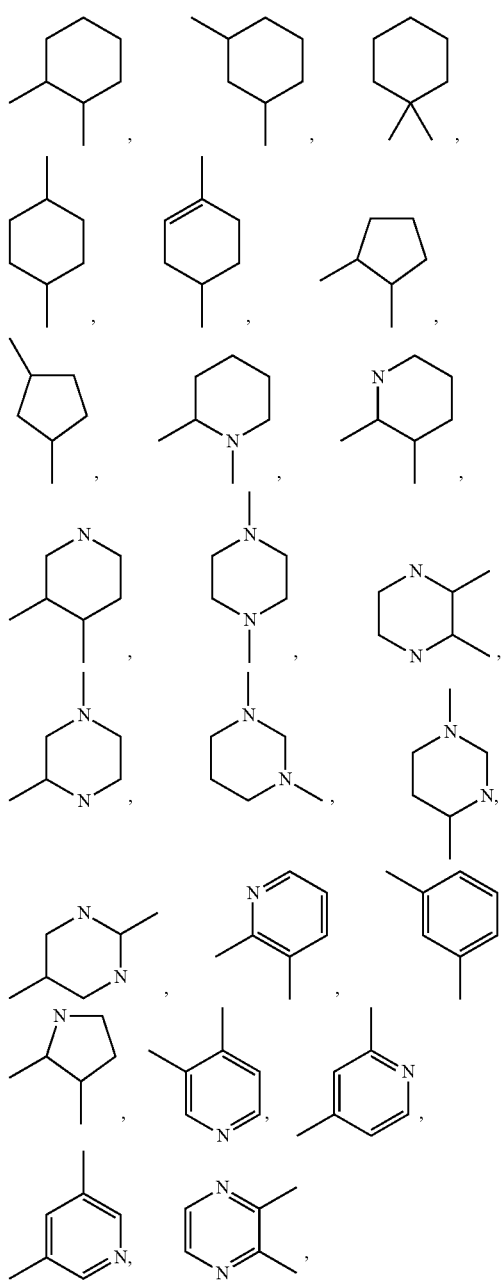

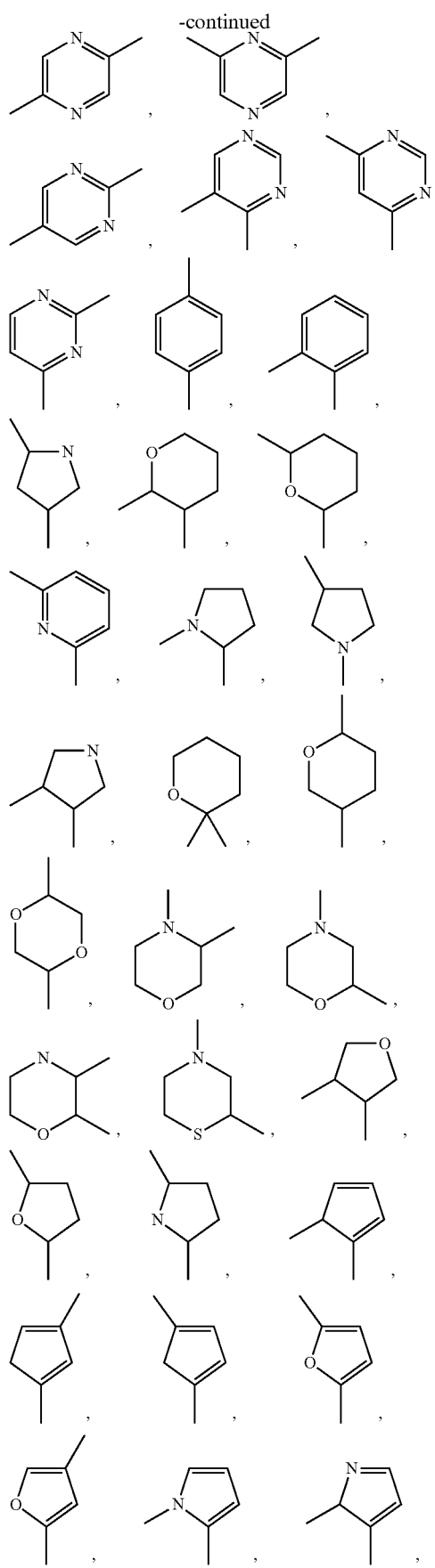

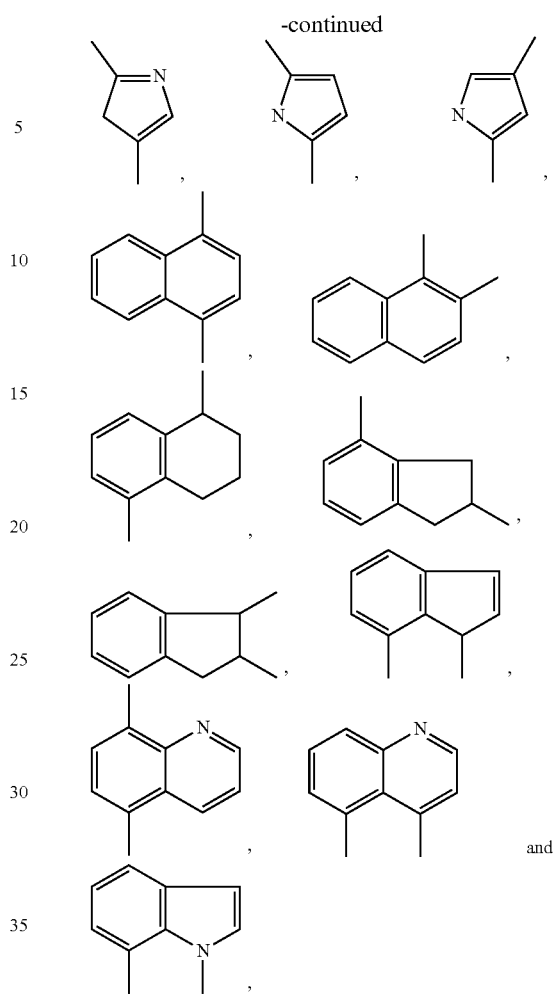

and similar groups wherein any N or O atom is replaced by S or Se.

As used herein, the term "aryl" refers to single, polynuclear, conjugated and fused residues of aromatic hydrocarbons or aromatic heterocyclic ring systems. Examples of such groups are phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, indenyl, azulenyl, chrysenyl, pyridyl, 4-phenylpyridyl, 3-phenylpyridyl, thienyl, furyl, pyrryl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl and the like. In all cases, any available position of the fused or conjugated bicyclic system can be used for attachment to the remainder of the molecule of formula (1).

As used herein, the term "aralkyl" refers to alkyl groups substituted with one or more aryl groups as previously defined. Examples of such groups are benzyl, 2-phenylethyl and 1-phenylethyl.

As used herein, the terms "aralkenyl" and "aralkynyl" refer to alkenyl and alkynyl groups respectively, substituted with one or more aryl groups as previously defined. Examples of such groups are styryl, phenylacetylenyl and 2-phenyl-2-butenyl.

As used herein the term "saturated or unsaturated cyclic, bicyclic or fused ring system" refers to a cyclic system of up to 16 carbon atoms, up to 3 of which may be replaced by O, S or N, which ring system may be substituted with one or more of R, —NH$_2$, —NHR, —NR2, —CHO, —C(O)R, —CN, halo, —CF$_3$, —SR, —S(O)R, —S(O)$_2$R, —CONH$_2$, —CONHR, —CONR2, —NHOH, —NHOL, —NO2, =O, =S or —NHNH2; wherein each R are independently as previously defined. Examples of such ring systems are those cyclic alkylidene groups exemplified above and

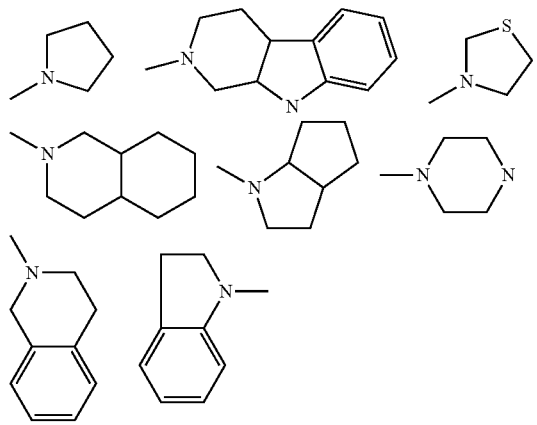

As used herein, the term "heterocyclic" refers to any 3- to 16-membered monocyclic, bicyclic or polycyclic ring containing, for 3- and 4-membered rings, one heteroatom; for 5-membered rings, one or two heteroatoms; for 6- and 7-membered rings, one to three heteroatoms; for 8- and 9-membered rings, from one to four heteroatoms; for 10- and 11-membered rings, from one to five heteroatoms; for 12- and 13-membered rings, from one to six heteroatoms; for 14- and 15-membered rings, from one to seven heteroatoms; and for 16-membered rings, from one to eight heteroatoms; the heteroatom(s) being independently selected from oxygen, nitrogen and sulphur. The term "heterocyclic" includes any group in which a heterocyclic ring is fused to a benzene ring. Examples of heterocyclics are pyrryl, pyrimidinyl, quinolinyl, isoquinolinyl, indolyl, piperidinyl, pyridinyl, furyl, thiophenyl, tetrahydrofuryl, imidazolyl, oxazolyl, thiazolyl, pyrenyl, oxazolidinyl, isoxazolyl, isothiazolyl, isoxazolidinyl, imidazolidinyl, morpholinyl, pyrrolidinyl, pyrazolyl, pyrazolinyl, furfuryl, thienyl, benzothienyl, benzoxazolyl, benzisoxazolyl, benzothiazolyl, benzoisothiazolyl, benzothiadiazolyl, tetrazolyl, triazolyl, thiadiazolyl, benzimidazolyl, pyrrolinyl, quinuclidinyl, azanorbornyl, isoquinuclidinyl and the like. Nitrogen-containing heterocyclics may be substituted at nitrogen with an oxygen atom. Sulfur-containing heterocyclics may be substituted at sulfur with one or two oxygen atoms.

Configurations which result in unstable heterocyclics are not included within the scope of the definition of "heterocyclic" or "saturated or unsaturated cyclic, bicyclic or fused ring system".

As used herein, the term "alkylheterocyclic" refers to a heterocyclic group as defined above, which is substituted with an alkyl group as defined above.

As used herein, the term "heterocyclic-oxy-alkyl" refers to a group of the formula heterocyclic-O-alkyl, wherein the heterocyclic and alkyl are as defined above.

As used herein, the term "alkoxy" refers to a group of the formula alkyl-O—, wherein the alkyl group is as defined above.

As used herein, the term "aryloxy" refers to a group of the formula aryl-O—, wherein the aryl group is as defined above.

As used herein, the term "alkanoyloxy" refers to a group of the formula alkyl-C(O)O—, wherein the alkyl group is as defined above.

As used herein, the term group (a) refers to five member saturated or unsaturated cyclic or heterocyclic ring systems. Examples of such ring systems are:

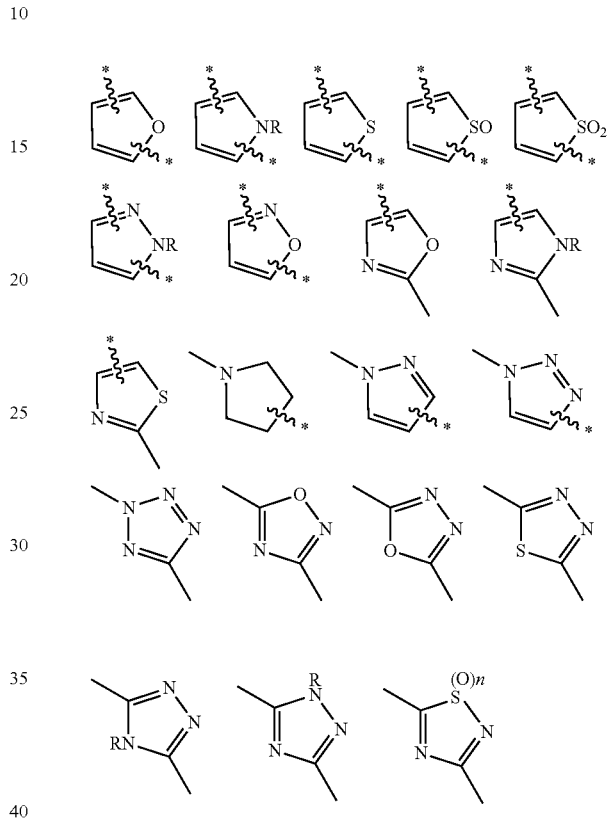

As used herein, the term group (b) refers to five member unsaturated cyclic or heterocyclic ring systems. Examples of such ring systems are:

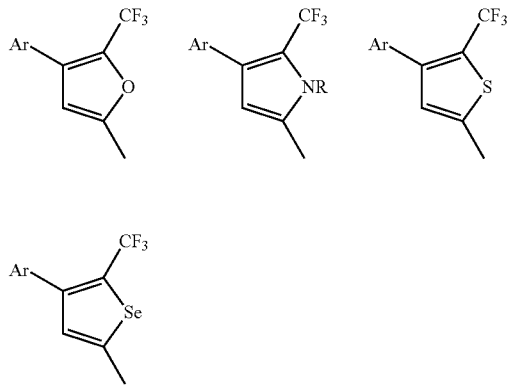

wherein each Ar and R are independently as previously defined and S and Se can be in the oxidized form S(O), S(O)$_2$ and Se(O) and Se(O)$_2$ respectively.

As used herein, the term group (c) refers to five-six bicyclic member ring systems. Examples of such ring systems are:

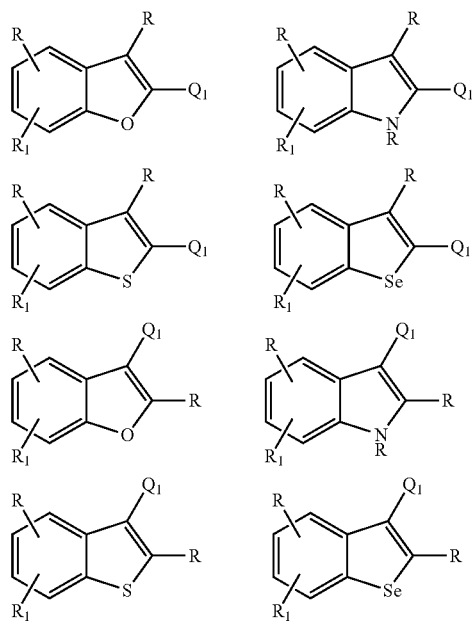

wherein each R, R₁ and Q₁ are independently as previously defined and S and Se can be in the oxidized form such as S(O), S(O)₂ and Se(O) and Se(O)₂ respectively.

As used herein, the term group (d) refers to six-six heterobicyclic member ring system. Examples of such ring systems are:

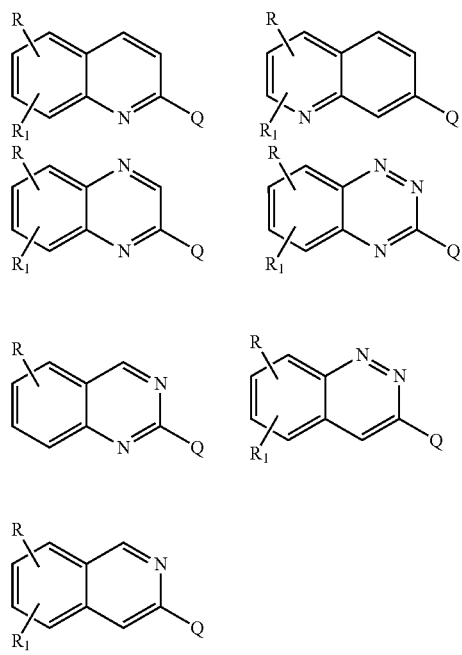

wherein each R, R₁ and Q are independently as previously defined. The structures of representative compounds of the invention are as follows:

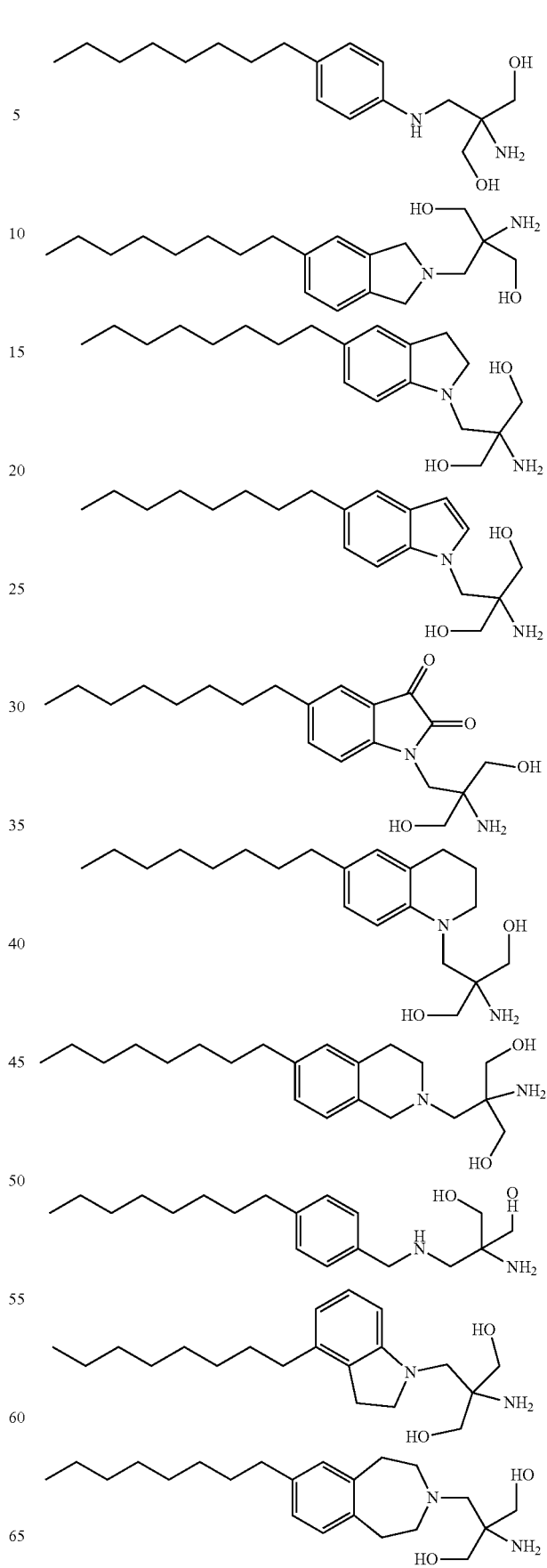

25
-continued
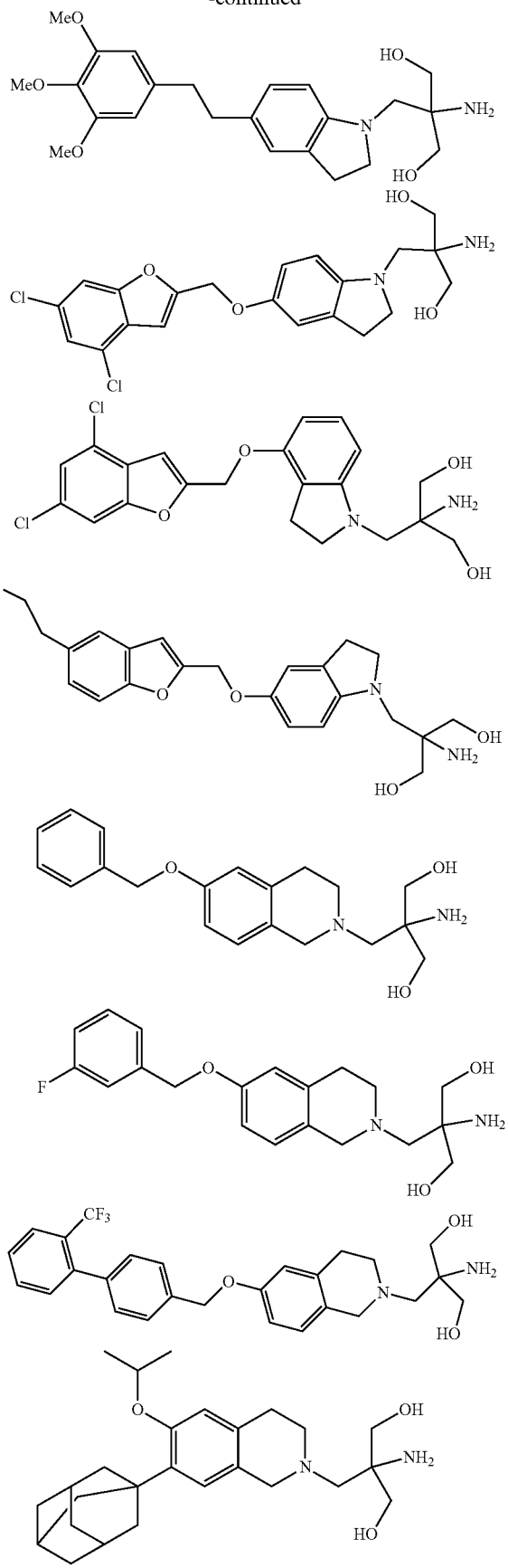
26
-continued
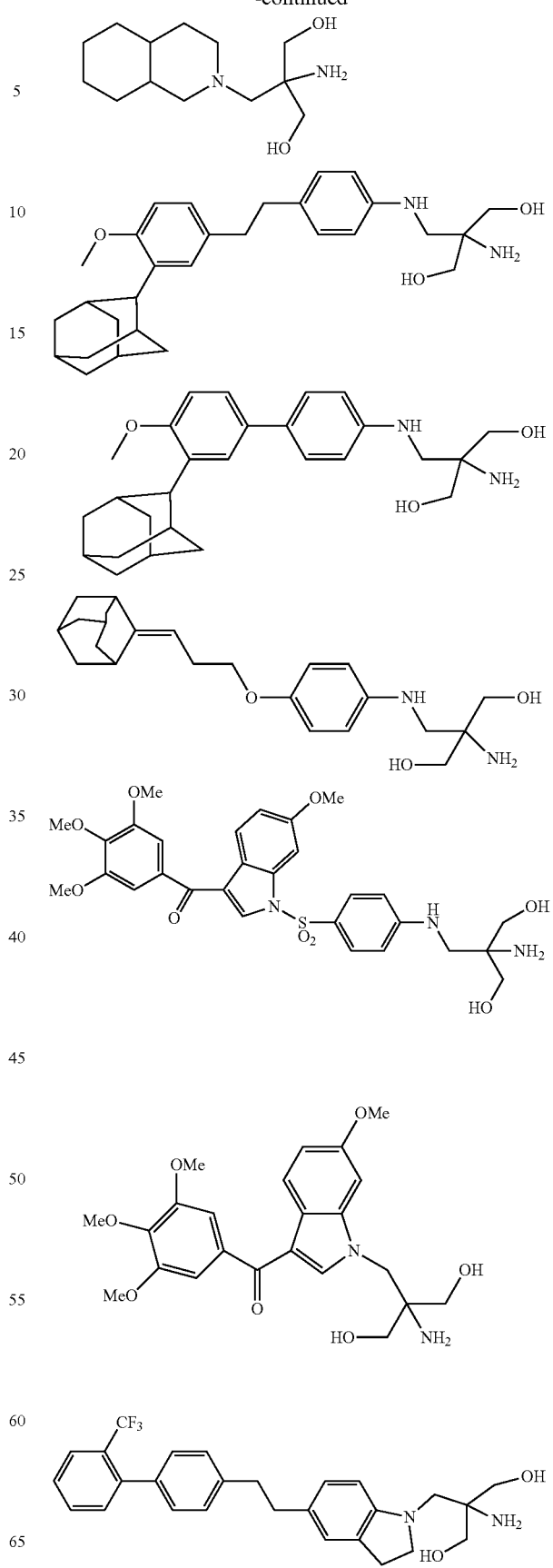

27
-continued
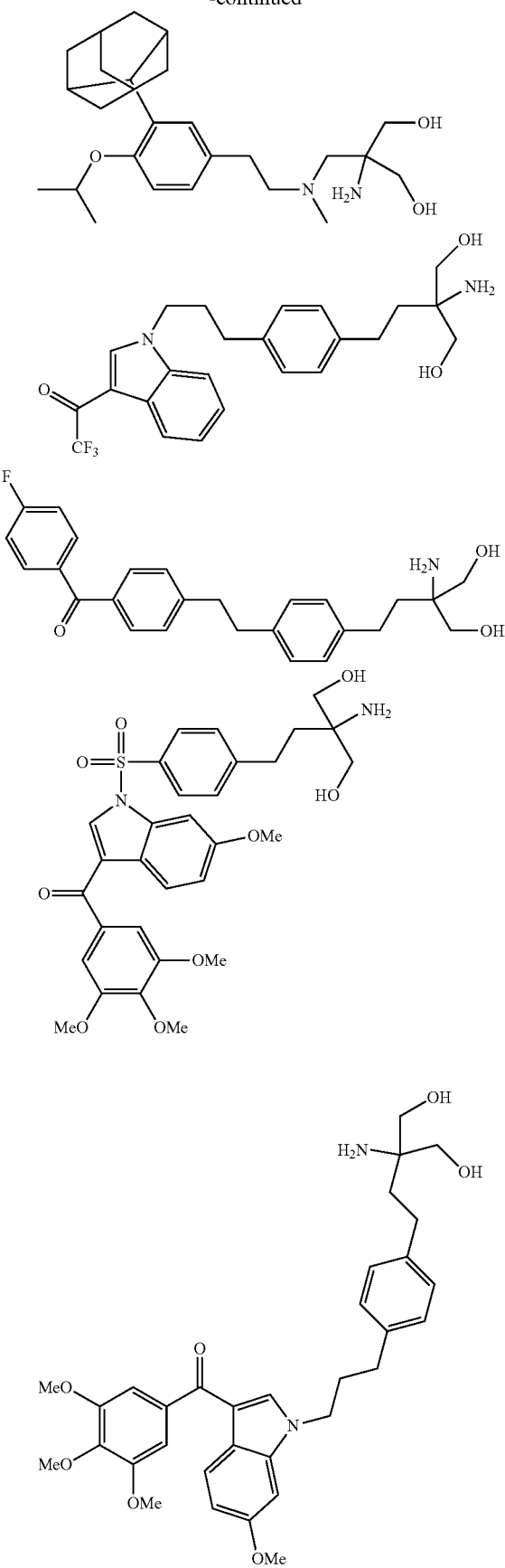
28
-continued
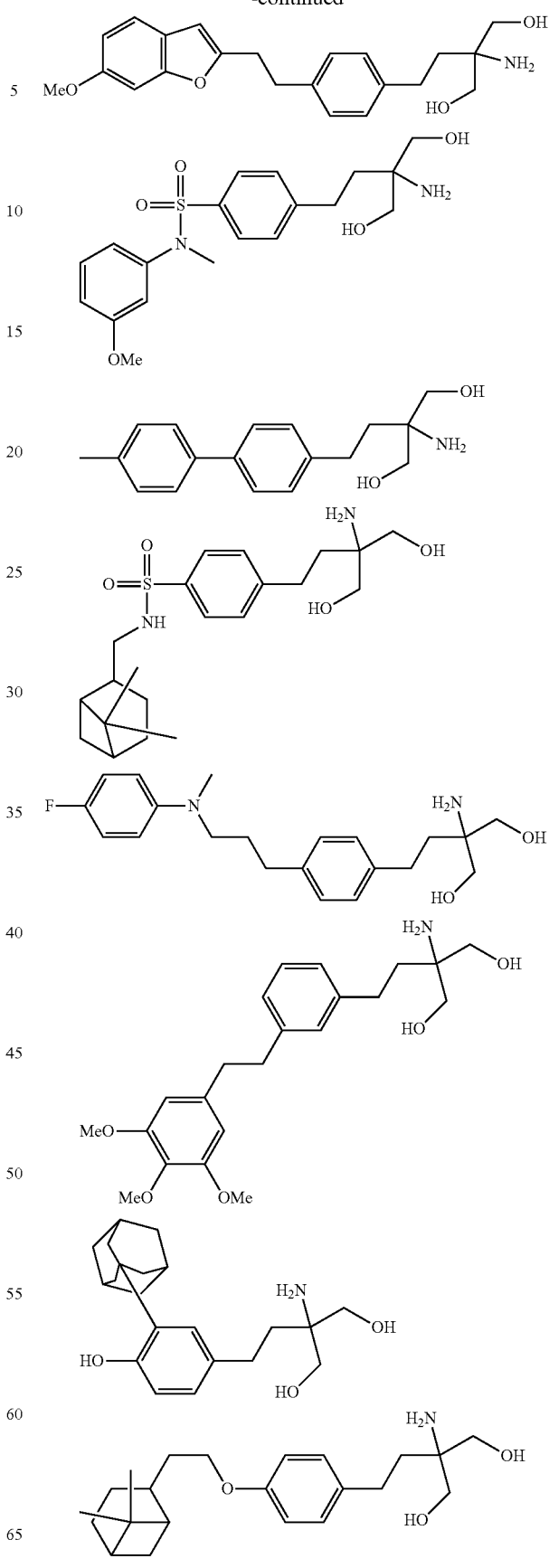

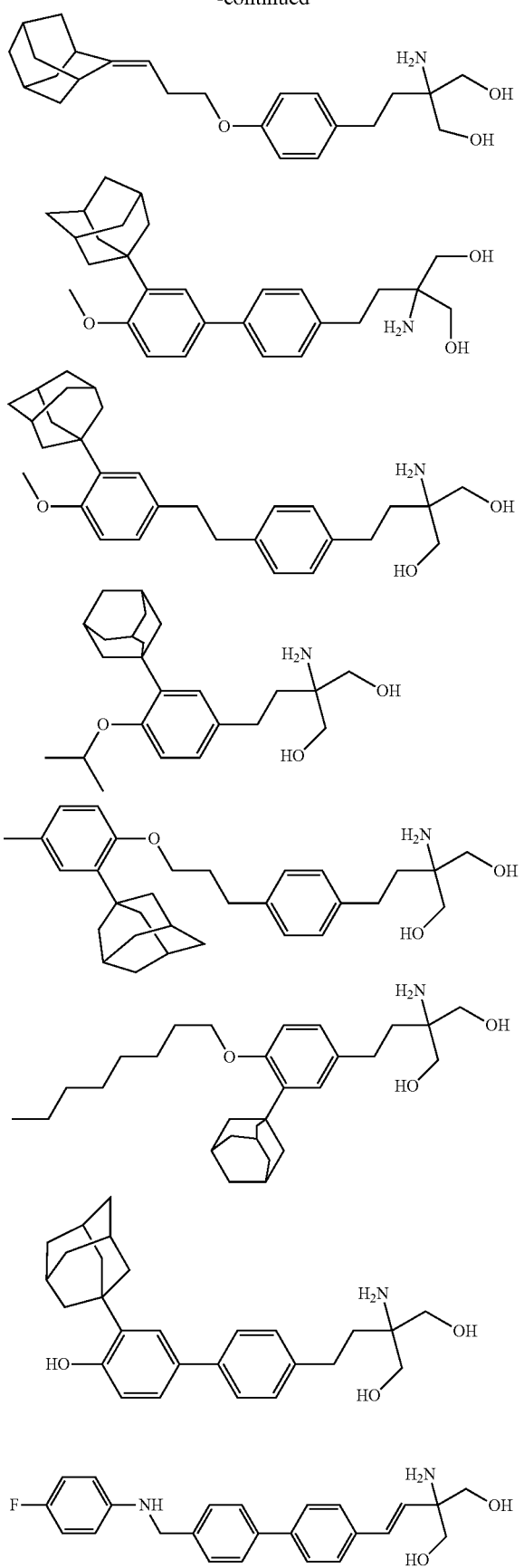
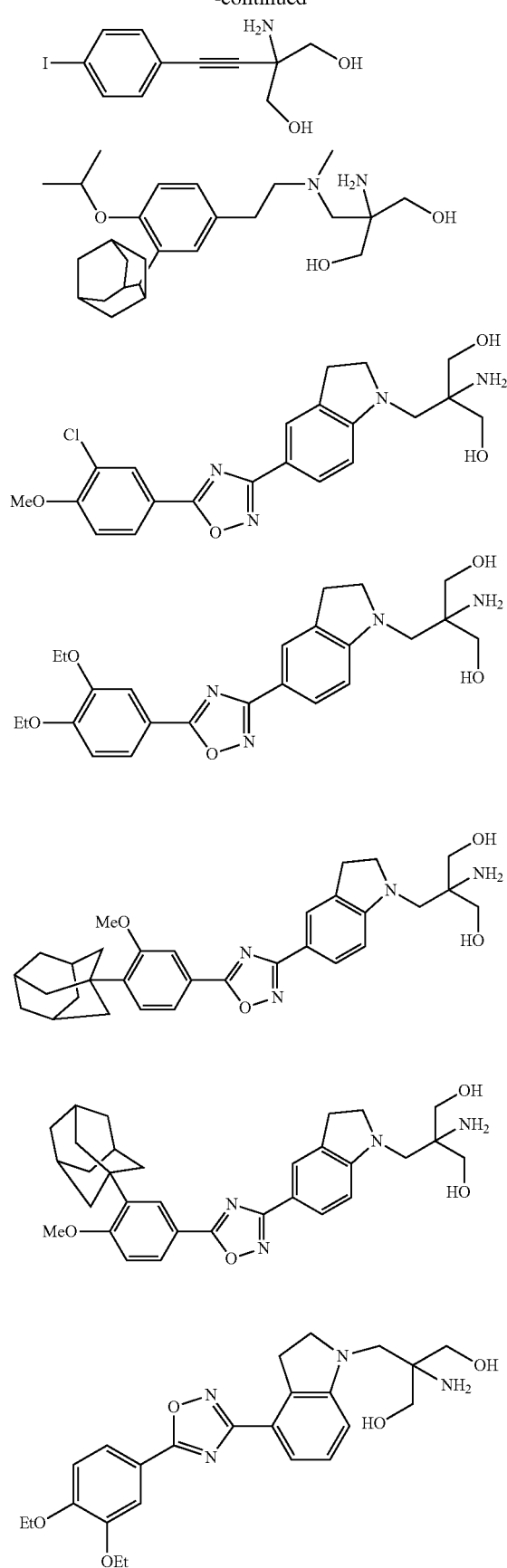

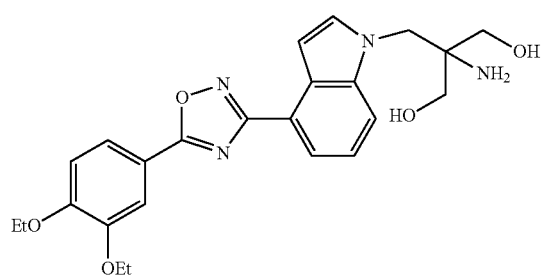
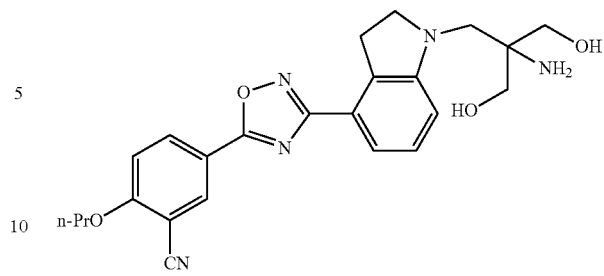
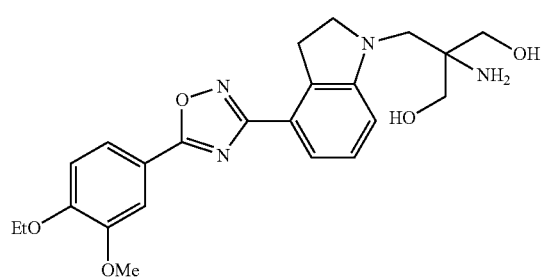
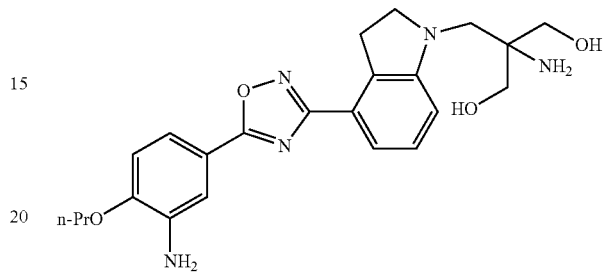
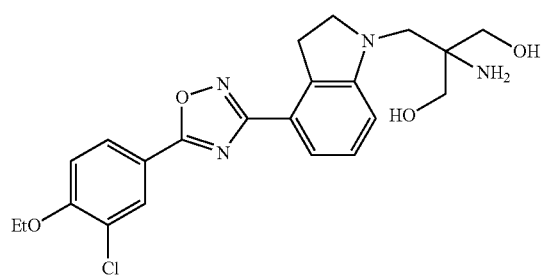
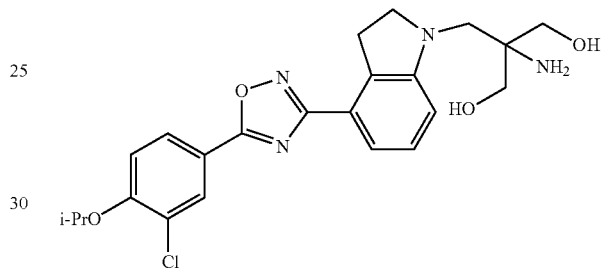
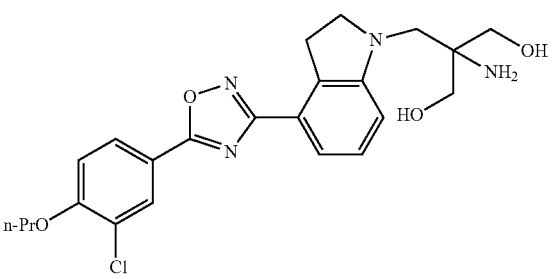
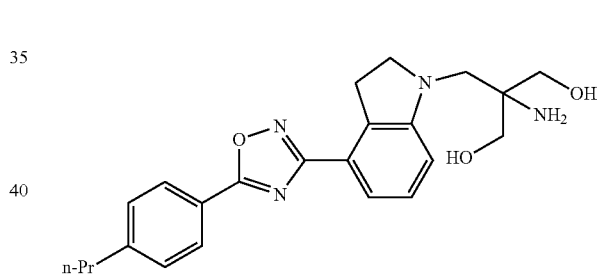
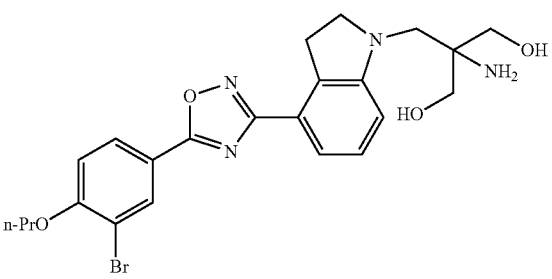
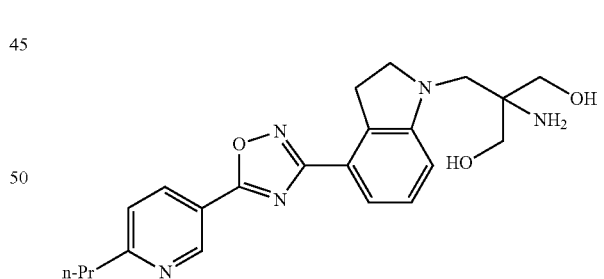
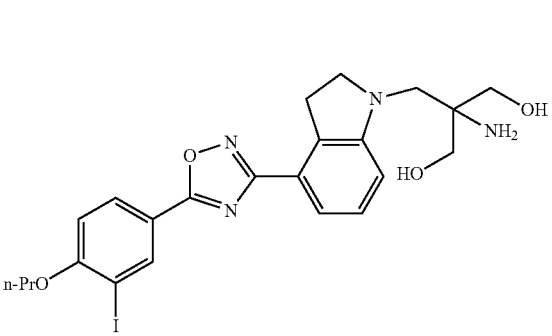
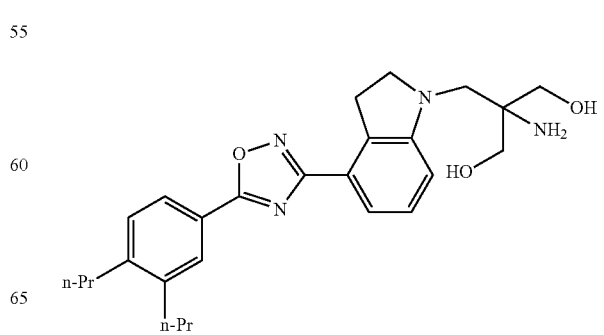

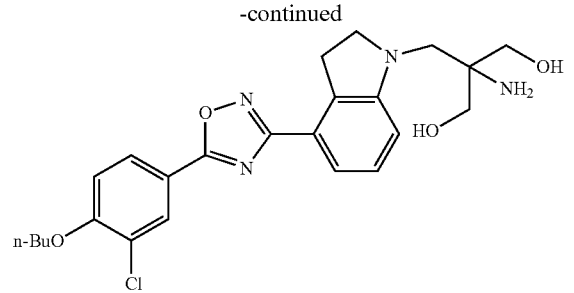
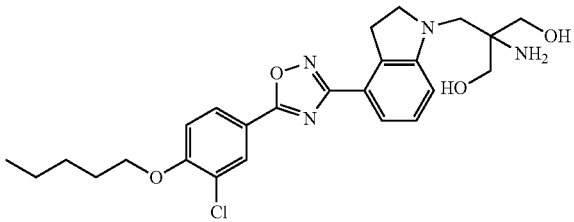
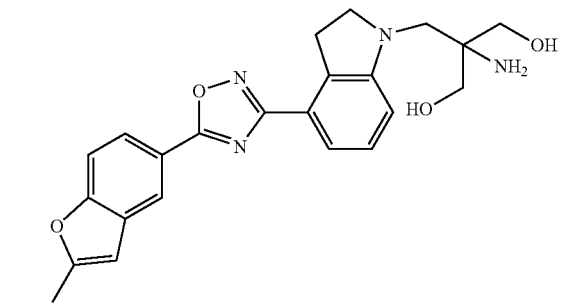
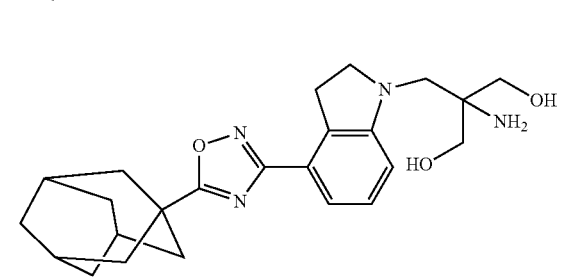
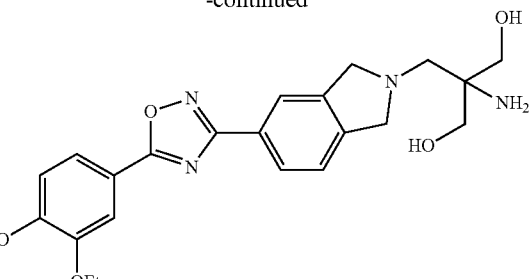
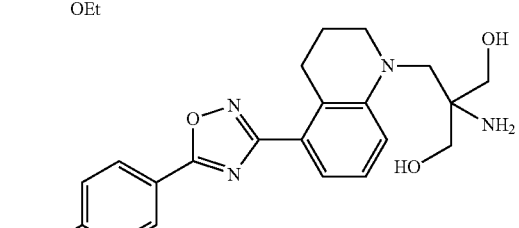
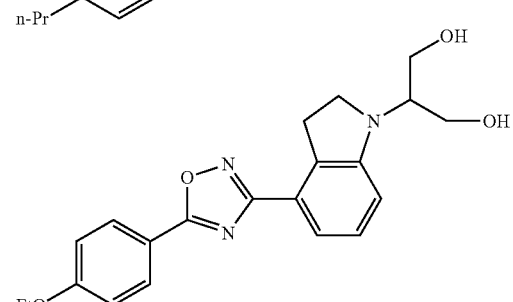
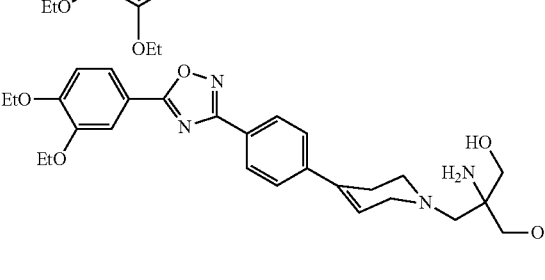
Other representative compounds in accordance with the invention are described in the following Tables:
TABLE 1
Compounds of formula:
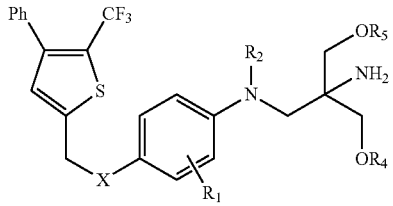
| Compound No. | R1 | R2 | R4 | R5 | X |
|---|---|---|---|---|---|
| 1 | H | H | H | H | —O— |
| 2 | 2-CF3 | H | H | H | —CH2— |
| 3 | 3-CF3 | Me | —OP(O)(OH)2— | H | —O— |
| 4 | 3-Cl | H | H | —OP(O)(OH)2— | —CH2—CH2— |
| 5 | 3-F | i-Pr- | H | —OP(O)(OH)2— | —S— |

TABLE 1-continued
Compounds of formula:
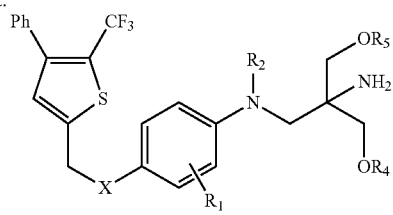
| Compound No. | R1 | R2 | R4 | R5 | X |
|---|---|---|---|---|---|
| 6 | 3-adamantyl | H | H | H | —CH$_2$— |
| 7 | —OMe | H | H | H | —O— |
TABLE 2
Compounds of formula:
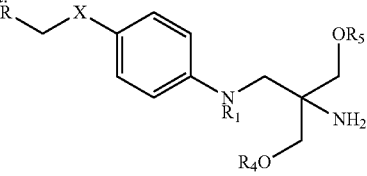
| Compound No. | R | X | R1 | R4 | R5 |
|---|---|---|---|---|---|
| 8 | 6-MeO-benzofuran-2-yl | —CH$_2$— | H | H | H |
| 9 | 6-MeO-benzofuran-2-yl | —CH$_2$— | H | H | —OP(O)(OH)$_2$ |
| 10 | 6-MeO-benzofuran-3-yl | —CH$_2$— | Me | H | H |
| 11 | 6-MeO-indol-2-yl (N-R) | —CH$_2$— | H | H | H |
| 12 | 6-MeO-indol-2-yl (N-R) | —O— | H | H | H |
| 13 | 6-MeO-indol-2-yl (N-R) | —S— | H | H | H |

TABLE 2-continued

Compounds of formula:

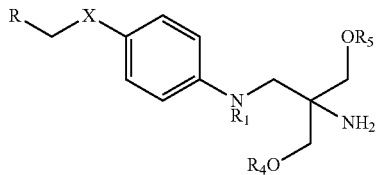

| Compound No. | R | X | R1 | R4 | R5 |
|---|---|---|---|---|---|
| 14 | 4,6-dichloro-2-methylbenzofuran | —O— | H | H | H |
| 15 | 4,6-dichloro-3-methylbenzofuran | —CH$_2$— | Me | H | H |
| 16 | 4,6-dichloro-2-methylbenzothiophene | —O— | H | H | H |
| 17 | 6-methoxy-2-methyl-3-(3,4,5-trimethoxybenzoyl)benzofuran | —CH$_2$— | H | H | H |
| 18 | 6-isopropyl-X-2-methylbenzofuran | —O—<br>—CH$_2$—<br>—S—<br>—Se—<br>NH | H | H | H |
| 19 | 6-isopropyl-X-2-methyl-3-trifluoromethylbenzofuran | —O—<br>—CH$_2$—<br>—S—<br>—Se—<br>N(R) | H | H | H |
| 20 | 6-trifluoromethyl-2-methyl-3-trifluoromethylfuro[2,3-b]pyridine | —O— | H | H | H |

TABLE 2-continued
Compounds of formula:
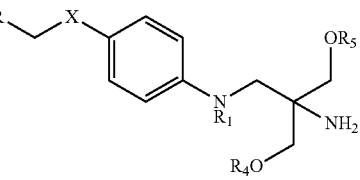
| Compound No. | R | X | R1 | R4 | R5 |
|---|---|---|---|---|---|
| 21 | 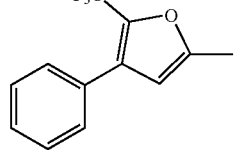 | —O— | H | H | H |
| 22 | 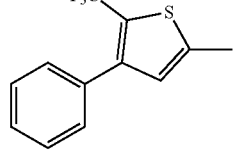 | —O— | H | H | H |
| 23 | 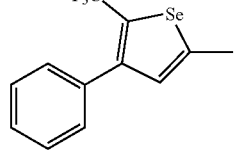 | —O— | H | H | H |
and variations thereof.
TABLE 3
Compounds of formula:
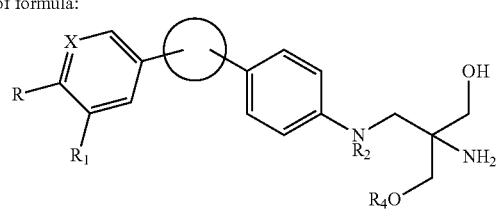
| Compound No. | X | ⌬ | R | R1 | R2 | R4 |
|---|---|---|---|---|---|---|
| 24 | CH | 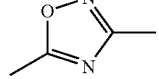 | iPrO— | 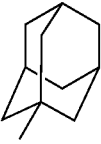 | H | H |
| 25 | CH | 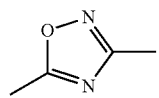 | iPrO— | 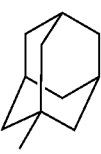 | Me | H |

TABLE 3-continued
Compounds of formula:
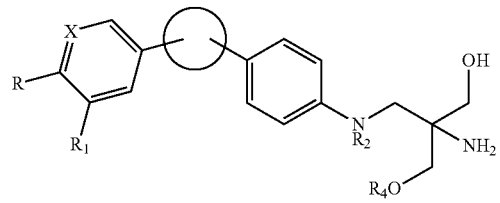
| Compound No. | X | ⬡ | R | R1 | R2 | R4 |
|---|---|---|---|---|---|---|
| 26 | CH | 1,2,4-oxadiazole (Me) | iPrO— | 80 | H | OP(O)(OH)₂— |
| 27 | CH | 1,2,4-oxadiazole (Me) | MeO— | Cl | H | H |
| 28 | CH | 1,2,4-oxadiazole (Me) | Cl | Cl | H | H |
| 29 | CH | 1,2,4-oxadiazole (Me) | Me | CF3 | H | H |
| 30 | CH | 1,2,4-oxadiazole (Me) | i-Pr | CF3 | H | H |
| 31 | CH | 1,2,4-oxadiazole (Me) | n-Bu | F | H | H |
| 32 | N | 1,2,4-oxadiazole (Me) | methylcyclohexyl | Br | H | H |
| 33 | N | 1,3,4-oxadiazole (Me) | iPrO— | adamantyl | H | H |
| 34 | CH | 1,2,4-triazole (Me) | Cl | Cl | H | H |
| 35 | CH | N-methyl tetrazole | i-Pr | CF3 | H | H |

TABLE 3-continued

Compounds of formula:

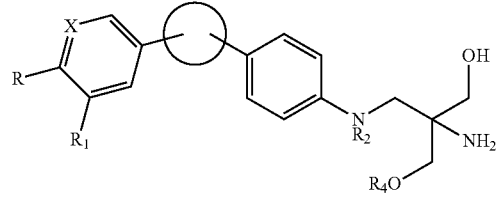

| Compound No. | X | ⬡ | R | R1 | R2 | R4 |
|---|---|---|---|---|---|---|
| 36 | CH | (3,5-dimethyl-1,2,4-oxadiazole) | (adamantyl) | CF3 | H | H | and variations thereof.

Compounds of the formulae of Table 1-3 with aniline replaced by the ring system of formulae (11)-(29).

TABLE 4

Compounds of formula:

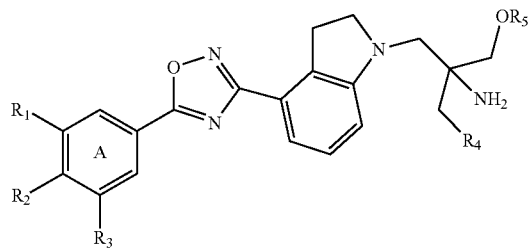

| Compound No. | A | R1 | R2 | R3 | R4 | R5 |
|---|---|---|---|---|---|---|
| 37 | C | EtO | H | EtO | OH | OP(O)OH |
| 38 | C | H | BuO | MeO | H | H |
| 39 | C | H | BuO | Cl | OH | H |
| 40 | C | H | BuO | PrO | H | H |
| 41 | C | Cl | PrO | CN | H | H |
| 42 | C | Me | BuO | I | H | H |
| 43 | C | H | HexO | NH2 | H | H |
| 44 | C | H | PentO | Cl | H | H |
| 45 | C | H | BuO | MeO | H | H |
| 46 | C | H | Pr | H | OH | H |
| 47 | C | Cl | Pr | PrO | H | H |
| 48 | C | H | Pr | CF3 | H | H |
| 49 | C | PrO | CF3 | H | H | H |
| 50 | 3-N | H | EtO | H | OH | H |

A = Carbon or heteroatom at any positon in aromatic ring.

TABLE 5

Compounds of formula:

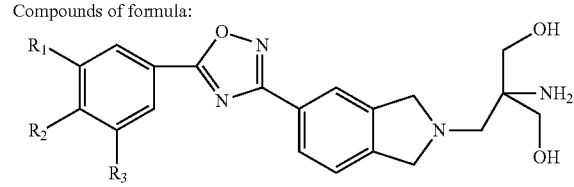

| Compound No. | R1 | R2 | R3 |
|---|---|---|---|
| 51 | EtO | H | EtO |
| 52 | H | BuO | MeO |
| 53 | H | BuO | Cl |
| 54 | H | BuO | PrO |
| 55 | Cl | PrO | CN |
| 56 | Me | BuO | I |
| 57 | H | HexO | NH2 |
| 58 | H | PentO | Cl |
| 59 | H | BuO | MeO |
| 60 | H | Pr | H |
| 61 | Cl | Pr | PrO |
| 62 | H | Pr | CF3 |
| 63 | PrO | CF3 | H | and variations thereof.

TABLE 6

Compounds of the formula:

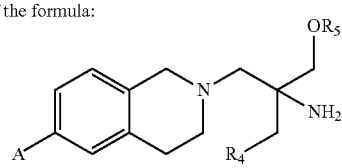

| Compound No. | A | R4 | R5 |
|---|---|---|---|
| 64 | 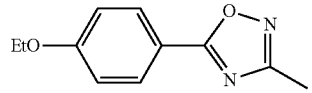 | OH | H |

TABLE 6-continued

Compounds of the formula:

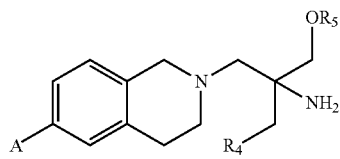

| Compound No. | A | R4 | R5 |
|---|---|---|---|
| 65 | Pr—⟨phenyl⟩—⟨3-methyl-1,2,4-oxadiazol-5-yl⟩ | OH | OP(O)OH |
| 66 | Pr—⟨pyridyl⟩—⟨3-methyl-1,2,4-oxadiazol-5-yl⟩ | OH | H |
| 67 | Pr—⟨pyridyl⟩—⟨3-methyl-1,2,4-oxadiazol-5-yl⟩ | OH | H |
| 68 | Pr—⟨phenyl⟩—⟨3-methyl-1H-1,2,4-triazol-5-yl⟩ | OH | H |
| 69 | Pr—⟨phenyl(NC)⟩—⟨3-methyl-1,2,4-oxadiazol-5-yl⟩ | OH | H |
| 70 | EtO—⟨benzofuran-2-yl⟩-propyl | OH | H | and variations thereof.

TABLE 7

Compounds of the formula:

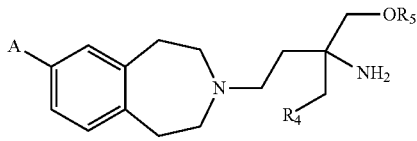

| Compound No. | A | R4 | R5 |
|---|---|---|---|
| 71 | ⟨alkyl-O-⟩ | OH | H |
| 72 | EtO—⟨phenyl⟩—⟨3-methyl-1,2,4-oxadiazol-5-yl⟩ | OH | H |
| 73 | Pr—⟨phenyl(NC)⟩—⟨3-methyl-1,2,4-oxadiazol-5-yl⟩ | OH | H |
| 74 | EtO,EtO—⟨phenyl⟩—⟨3-methyl-1,2,4-oxadiazol-5-yl⟩ | OH | OP(O)OH |
| 75 | Pr—⟨pyridyl⟩—⟨3-methyl-1,2,4-oxadiazol-5-yl⟩ | OH | H |
| 76 | Pr—⟨phenyl(methyl)⟩—⟨3-methyl-1,2,4-oxadiazol-5-yl⟩ | H | H |
| 77 | $R_1$—⟨benzofuran/indole with $X_1$⟩—X— | OH | H | and variations thereof.

The compounds of formula (5)-(29) can exist in optically isomeric forms and the present invention includes within its scope all these forms in all proportions including all diastereoisomers and racemic mixtures.

The compounds of formula (5)-(29) can exist in different isotopic forms and the present invention includes within its scope all these forms in all proportions.

The compounds of formula (5) and (20) may be prepared by known methods for the synthesis of substituted amines. For example, a compound of the formula

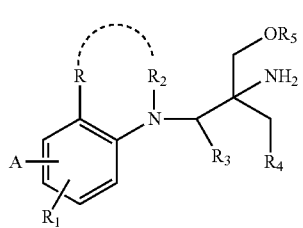

may be prepared by reductive alkylation of an amine of the formula

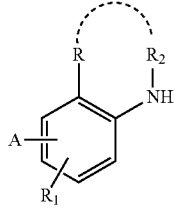

with the substituted aldehyde or ketone of formula

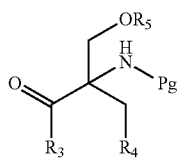

followed by removal of protecting group Pg.

This compound may also be prepared by alkylation of amine of formula

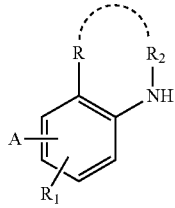

with the substituted alkyl halide, mesylate, tosylate or trifluorosulfonylate of formula

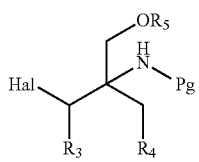

followed by removal of protecting group Pg.

A compound of formula (12) and (13) may be obtained from a compound of formula (11) by oxidation in accordance with known methods of oxidative transformations of indolines to indoles and indolin-(di)ones.

A compound of formula (15) and (16), may be obtained from compound of formula (14) by oxidative transformation of 1,2,3,4-tetrahydroquinoline to relevant dihydroquinolines.

A compound of formula (19), may be obtained from compound of formula (18) by oxidative transformation of isoindoline to 2H-isoindole.

The compounds of formula (20) and (21) may be prepared by known methods for the synthesis of substituted amides. For example, a compound of the formula

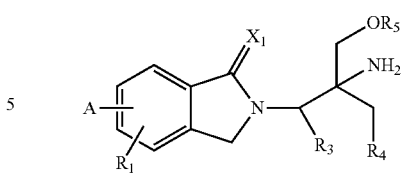

may be prepared by alkylation of an alkali metal salt of the amide of the formula

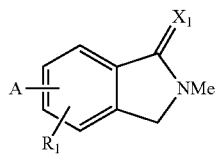

with the substituted alkyl halide, mesylate, tosylate or trifluoromethanesulfonate of formula

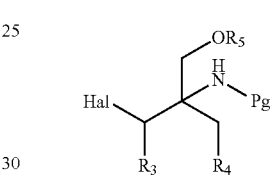

followed by removal of protecting group Pg.

The compound preparations illustrated can be carried out by generally known methods as exemplified hereinafter. The starting materials and intermediates used in the synthesis of compounds of this invention are generally commercially available or may be prepared by conventional methods of organic chemistry. Suitable methods for the synthesis of compounds of this invention and intermediates thereof are described, for example, in Houben-Weyl, Methoden der Organischen Chemie; J. March, Advanced Organic Chemistry, 3rd Edition (John Wiley & Sons, New York, 1985); D. C. Liotta and M. Volmer, eds, Organic Syntheses Reaction Guide (John Wiley & Sons, Inc., New York, 1991); R. C. Larock, Comprehensive Organic Transformations (VCH, New York, 1989), H. O. House, Modern Synthetic Reactions 2nd Edition (W. A. Benjamin, Inc., Menlo Park, 1972); N. S. Simpkins, ed. 100 Modern Reagents (The Royal Society of Chemistry, London, 1989); A. H. Haines Methods for the Oxidation of Organic Compounds (Academic Press, London, 1988) and B. J. Wakefield Organolithium Methods (Academic Press, London, 1988).

EXAMPLES

The following Examples describe the preparation of compounds according to the invention and are intended to illustrate the invention. The Examples are not to be construed as limiting in any way the scope of the present invention. Proton NMR spectra were recorded at 300 MHz on a Bruker EM 300 spectrometer in $CDCl_3$ unless otherwise stated. Chemical shifts for proton NMR are reported as ppm downfield from tetramethylsilane and or by taking chloroform as standard at δ 7.24.

Example 1

2-Amino-2-((4-octylphenylamino)methyl)propane-1,3-diol

Step A: tert-Butyl 2,2-dimethyl-5-((4-octylphenylamino)methyl)-1,3-dioxan-5-ylcarbamate To a mixture of 4-n-octylaniline (0.21 g; 1 mmol), tert-butyl 5-formyl-2,2-dimethyl-1,3-dioxan-5-ylcarbamate (Ooii et al, J. Org. Chem., 2004, 69, 7765; 0.26 g; 1 mmol) and NaBH(OAc)$_3$ (0.3 g; 1.4 mmol) in 1,2-dichloroethane (3.5 ml) acetic acid (AcOH)(0.06 ml; 1 mmol) was added at room temperature with stirring under N$_2$. After stirring for 2 h, the mixture was diluted to 20 ml with diethyl ether (Et$_2$O), washed with 1.M NaOH (2×5 ml), brine and dried over anhydrous MgSC$_4$ and filtered. The filtrate was evaporated to dryness under reduced pressure. The residue was dissolved in hexane (5 ml) and kept in the freezer (−18° C.) overnight. The crystals formed were filtered off, washed with small volume of hexane and dried to give pure title compound (0.32 g; 71%), as colourless crystals. $^1$H-NMR (CDCl$_3$) 0.86 (tr, 2H, J=6.95 Hz); 1.26 (m, 10H, 1.42, (s, 3H); 1.43 (s, 9H); 1.45 (s, 3H); 1.5 (m, 2H); 2.46 (tr, 2H, J=7.9 Hz); 3.44 (5, 2H); 3.8 (d, 2H, J=11.9 Hz); 3.85 (broad s, 1H); 4.01 (d, 2H, J=11.9); 4.84 (broad s, 1H); 6.58 (d, 2H, J=8.4 Hz); 6.96 (d, 2H, J=8.4 Hz).

Step B: 2-Amino-2-((4-octylphenylamino)methyl)propane-1,3-diol

A solution of a product of Step A (0.32 g; 0.71 mmol) in 60% trifluoroacetic acid in CH$_2$Cl$_2$ (4 ml) was stirred for 15 min at room temperature then diluted to 6 ml with methanol (MeOH). The resulting mixture was evaporated to dryness under reduced pressure and the residue dried in vacuo for 1 h. This was purified by flash column chromatography (FCC) (SiO$_2$; CH$_2$Cl$_2$ saturated with NH$_4$OH:MeOH 95:5), to give pure title compound (0.18 g; 82%), as colourless solid. $^1$H-NMR (CDCl$_3$) 0.86 (tr, 2H, J=6.96 Hz); 1.25 (m, 10H); 1.52 (m, 2H); 2.1-2.51 (broad m, 4H); 2.47 (tr, 2H, J=7.9 Hz); 3.1 (s, 2H); 3.55 (m, 4H); 4.05 (broad s, 1H); 6.6 (d, 2H, J=8.34 Hz); 6.96 (d, 2H, J=8.34 Hz).

Example 2

2-Amino-2-((5-octylisoindolin-2-yl)methyl)propane-1,3-diol

Step A: 4-Iodo-1,2-dimethylbenzene

A mixture of 1,2-dimethylbenzene (1.06 g; 10 mmol), silver trifluoromethanesulfonate (2.56 g; 10 mmol) and I$_2$ (2.53 g; 10 mmol) in CH$_2$Cl$_2$ (50 ml) was stirred for 7 h at room temperature, then filtered through a Celite pad, washed with fresh CH$_2$Cl$_2$ (2×20 ml) and combined filtrates were washed with 5% Na$_2$SO$_3$, H$_2$O, brine and dried over anhydrous MgSO$_4$ and filtered. The filtrate was evaporated to dryness under reduced pressure to give crude title compound (1.8 g; 78%) as brownish oil, which was used in next step without further purification. $^1$H-NMR (CDCl$_3$) 2.23 (s, 6H), 6.84 (d, 1H, J=8.0 Hz); 7.39 (dd, 1H, J=1.7; 8.0 Hz); 7.46 (broad s, 1H).

Step B: 1,2-Bis(bromomethyl)-4-iodobenzene

A mixture of the of the product of Step A (1.8 g; 7.76 mmol), N-bromosuccinimide (NBS) (2.9 g; 6.3 mmol) and benzoyl peroxide (0.1 g; 0.41 mmol) in CCl$_4$ (7 ml) was refluxed for 1 h, cooled to room temperature and filtered off. The filtrate was evaporated to dryness and the residue was purified by crystallization from hexane to give pure title compound (0.34 g; 11%) as colourless solid. $^1$H-NMR (CDCl$_3$) 4.54 (s, 2H); 4.57 (s, 2H); 7.07 (d, 2H, J=8.1 Hz); 7.61 (dd, 1H, J=1.8; 8.1 Hz); 7.7 (d, 1H, J=1.8 Hz).

Step C: 5-Iodo-2-tritylisoindoline

A mixture of the product of Step B (0.34 g; 0.87 mmol) hydrochloride salt of tritylamine (0.22 g; 0.87 mmol) and N,N-diisopropylethylamine (DIPEA) (0.49 ml; 2.8 mmol) in anhydrous DMF (3 ml) was stirred for 2 h at 60° C. under N$_2$. After removing the solvent in vacuo, the residue was diluted to 15 ml with ethyl acetate (EtOAc) and washed with, H$_2$O, brine and dried over anhydrous MgSO$_4$ and filtered. The filtrate was evaporated to dryness under reduced pressure and the residue was purified by FCC (SiO$_2$; hexane/EtOAc, 8:2) to give pure title compound (0.2 g; 48%) as colourless heavy syrup. $^1$H-NMR (CDCl$_3$) 3.86 (s, 2H); 3.87 (s, 2H); 6.81-7.57 (m, 18H).

Step D: 5-(Oct-1-ynyl)-2-tritylisoindoline

A mixture of the product of Step C (0.2 g; 0.41 mmol), 1-octyne (0.091 ml; 0.62 mmol), Cl$_2$Pd(PPh$_3$)$_2$ (0.02 g; 0.028 mmol) and CuI (0.005 g; 0.026 mmol) in anhydrous DMF (2 ml) was degassed under reduced pressure and saturated with dry N$_2$. After addition of DIPEA (0.5 ml), the resulting mixture was stirred overnight at room temperature under N$_2$. The solvents were removed in vacuo and the residue was diluted to 15 ml with EtOAc and washed with 5% citric acid, 5% NaHCO$_3$, H$_2$O, brine and dried over anhydrous MgSO$_4$ and filtered. The filtrate was evaporated to dryness under reduced pressure and the residue was purified by FCC (SiO$_2$; hexane/EtOAc; 9:1) to give the title compound (0.17 g; 89%) as a colourless syrup. $^1$H-NMR (CDCl$_3$) 0.93 (m, 3H); 1.34-1.64 (m, 8H); 2.4 (tr, 2H, J=7.1 Hz); 3.94 (s, 4H); 7.0-7.64 (m, 18H).

Step E: 5-n-Octylisoindoline hydrochloride salt

A mixture of the product of Step D (0.17 g; 0.36 mmol) and 10% Pd/carbon (0.1 g) in ethanol (EtOH) (15 ml) was stirred at room temperature for 5 h under H$_2$ (balloon). The catalyst was removed by filtration through a pad of Celite, washed with CH$_2$Cl$_2$ and combined filtrates were evaporated to dryness under reduced pressure. The residue was diluted to 10 ml with anhydrous CH$_2$Cl$_2$ and a HCl gas was bubbled through it for 5 min. This was evaporated to dryness and the residue was treated with CH$_2$Cl$_2$/hexane mixture. The precipitate formed was filtered off, washed with hexane to give the title compound (0.03 g; 31%) as colourless solid. $^1$H-NMR (CDCl$_3$) 0.86 (tr, 3H, J=6.94 Hz); 1.25 (m, 10H); 1.56 (m, 2H); 2.58 (tr, 2H, J=7.84 Hz); 4.63 (s, 4H); 7.07-7.2 (m, 3H).

Step F: tert-Butyl 2,2-dimethyl-5-((5-octylisoindolin-2-yl)methyl)-1,3-dioxan-5-ylcarbamate To a mixture of the product of Step E (0.03 g; 0.112 mmol), tert-butyl 5-formyl-2,2-dimethyl-1,3-dioxan-5-ylcarbamate (0.037 g; 0.115 mmol) and NaBH(OAc)$_3$ (0.035 g; 0.17 mmol) in 1,2 dichloroethane (3 ml), Et$_3$N (0.016 ml; 0.112 mmol) was added at room temperature, followed by AcOH (0.064 ml; 0.112 mmol). The resulting mixture was stirred overnight under N$_2$. After dilution to 10 ml with Et$_2$O, the mixture was washed with 1.M NaOH (2×2 ml), brine and dried over anhydrous MgSO₄ and filtered. The filtrate was evaporated to dryness under reduced pressure. The residue was purified by FCC (SiO₂; hexane/EtOAc 8:2) to give pure title compound (0.05 g; 92%) as colourless solid. ¹H-NMR (CDCl₃) 0.86 (tr, 3H, J=7 Hz); 1.25 (m, 10H); 1.41 (s, 3H); 1.44 (s, 9H); 1.47 (s, 3H); 1.57 (m, 2H); 2.56 (tr, 2H, J=7.92 Hz); 3.18 (s, 2H): 3.79 (d, 2H, J=11.7 Hz); 4.05 (s, 4H); 4.14 (d, 2H, J=11.7 Hz); 5.03 (s, 1H); 6.98 (s, 1H); 6.99 (d, 1H, J=8.14 Hz); 7.06 (d, 1H, J=8.14 Hz).

Step G: 2-Amino-2-((5-octylisoindolin-2-yl)methyl) propane-1,3-diol

When the product of Step F was substituted for tert-butyl 2,2-dimethyl-5-((4-octylphenylamino)methyl)-1,3-dioxan-5-ylcarbamate in Example 1, Step B, the identical process afforded the title compound in 70% yield. ¹H-NMR (CDCl₃) 0.86 (tr, 3H, J=6.94 Hz); 1.25 (m, 10H); 1.56 (m, 2H); 2.56 (tr, 2H, J=7.86 Hz); 2.66 (broad m, 4H); 2.89 (s, 2H); 3.57 (s, 4H); 4.07 (s, 4H); 6.98 (s, 1H); 7.0 (d, 1H, J=7.6 Hz); 7.06 (d, 1H, J=7.6 Hz).

Example 3

2-Amino-2-((5-octylindolin-1-yl)methyl)propane-1,3-diol

Step A: 5-(Oct-1-ynyl)-1H-indole

When 5-iodo-1H-indole was substituted for 5-iodo-2-tritylisoindoline in Example 2, Step D, the identical process afforded the title compound in 36% yield. ¹H-NMR (CDCl₃) 0.9 (tr, 3H, J=6.9 Hz); 1.31 (m, 6H); 1.46 (m, 2H); 1.6 (m, 2H); 2.41 (tr, 2H, J=7.1 Hz); 6.49 (m, 1H); 7.14-7.31 (m, 3H); 7.71 (s, 1H); 8.13 (broad s, 1H).

Step B: 5-n-Octyl-1H-indole

A mixture of the product of Step A (0.17 g; 0.75 mmol) and 10% Pd/carbon (0.2 g) in EtOH (15 ml) was stirred at room temperature for 40 min under H₂ (balloon). The catalyst was removed by filtration through the Celite pad, washed with CH₂Cl₂ (2×10 ml) and combined filtrates were evaporated to dryness under reduced pressure. The residue was purified by FCC (SiO₂; hexane/EtOAc: 9:1) to give the title compound (0.08 g; 46%) as a colourless syrup. ¹H-NMR (CDCl₃) 0.86 (tr, 3H, J=6.7 Hz); 1.28 (m, 10H); 1.65 (m, 2H); 2.68 (tr, 2H, J=7.9 Hz); 6.47 (m, 1H); 7.02 (dd, 1H, J=1.5, 8.3 Hz); 7.16 (m, 1H); 7.29 (d, 1H, J=8.3 Hz); 7.42 (s, 1H); 8.04 (broad s, 1H).

Step C: 5-n-Octylindoline

To a solution of the product of Step B (0.08 g; 0.35 mmol) in AcOH (1.5 ml) NaBH₃CN was added at 0° C., with stirring. The resulting mixture was stirred for 2 h at room temperature, then diluted to 20 ml with diethyl ether and washed with 10% NaOH (2×5 ml), H2), brine, dried over anhydrous MgSO₄ and filtered. The filtrate was evaporated to dryness under reduced pressure and the residue was purified by FCC (SiO₂; hexane/EtOAc: 9:1) to give the title compound (0.05 g; 62%) as a colourless syrup. ¹H-NMR (CDCl₃) 0.86 (tr, 3H, J=7 Hz); 1.26 (m, 10H); 1.54 (m, 2H); 2.48 (tr, 2H, J=7.9 Hz); 2.98 (tr, 2H, 9.2 Hz) 3.52 (tr, 2H, J=9.2 Hz); 6.56 (d, 1H, 7.8 Hz); 6.83 (d, 1H, J=7.8 Hz); 6.93 (s, 1H).

Step D: tert-Butyl 2,2-dimethyl-5-((5-octylindolin-1-yl)methyl)-1,3-dioxan-5-ylcarbamate When the product of Step C was substituted for 4-n-octylaniline in Example 1, Step A, the identical process afforded the title compound in 77% yield., as colourless syrup. ¹H-NMR (CDCl₃) 0.87 (tr, 3H, J=6.74 Hz); 1.26 (m, 10H); 1.45 (m, 15H); 1.53 (m, 2H); 2.47 (tr 2H, J=8 Hz); 2.96 (tr, 2H, J=8.3 Hz); 3.41 (tr, 2H, J=8.3 Hz); 3.47 (5, 2H); 3.9 (d, 2H, J=11.54 Hz); 4.0 (d, 2H, J=11.54 Hz); 4.71 (broad s, 1H); 6.49 (d, 1H, J=7.96 Hz); 6.86 (d, 1H, J=7.96 Hz); 6.9 (s, 1H).

Step E: 2-Amino-2-((5-octylindolin-1-yl)methyl) propane-1,3-diol

When the product of Step D was substituted for tert-butyl 2,2-dimethyl-5-((4-octylphenylamino)methyl)-1,3-dioxan-5-ylcarbamate in Example 1, Step B, the identical process afforded the title compound in 71% yield., as colourless solid. ¹H-NMR (CDCl₃) 0.86 (tr, 3H, J=6.84 Hz); 1.26 (m, 10H); 1.52 (m, 2H); 2.17 (broad s, 4H); 2.47 (tr, 2H, J=7.92 Hz); 2.94 (tr, 2H, J=8.1 Hz); 3.04 (s, 2H); 3.42 (tr, 2H, J=8.1 Hz); 3.58 (s, 4H); 6.53 (d, 1H, J=7.92 Hz); 6.87 (d, 1H, J=7.92 Hz); 6.91 (s, 1H).

Example 4

2-Amino-2-((5-octyl-1H-indol-1-yl)methyl)propane-1,3-diol

Step A: tert-Butyl 2,2-dimethyl-5-((5-octyl-1H-indol-1-yl)methyl)-1,3-dioxan-5-ylcarbamate (i) and tert-butyl 2,2-dimethyl-5-((5-octyl-2,3-dioxoindolin-1-yl)methyl)-1,3-dioxan-5-ylcarbamate (ii)

A mixture of the product of Example 3, Step D (0.06 g; 0.126 mmol), MnO₂ (0.5 g; 5.75 mmol) and anhydrous MgSO₄ (0.5 g; 4.15 mmol) in 1,2 dichloromethane (5 ml) was stirred for 2 h at 55° C. and overnight at room temperature. This was filtered through the pad of Celite, washed with CH₂Cl₂ (3×10 ml) and combined filtrates were evaporated to dryness under reduced pressure to give a mixture of the titled products (i) and (ii), which were separated by FCC (SiO₂; hexane/EtOAc: 9:1) to give the title compound (i) (0.03 g; 50%) as a colourless syrup and (ii) (0.02 g; 15%) as a brown solid. (i)—¹H-NMR (CDCl₃) 0.87 (tr, 3H, J=6.9 Hz); 1.23 (m, 10H); 1.46 (s, 3H); 1.48 (s, (H); 1.5 (s, 3H); 1.62 (m, 2H); 2.68 (tr, 2H, J=7.84 Hz); 3.78 (d, 2H, J=11.7 Hz); 3.88 (d, 2H, J=11.7 Hz); 4.32 (s, 2H); 4.64 (s, 2H); 6.44 (d, 1H, J=3 Hz); 7.01 (d, 1H, J=9.9 Hz); 7.05 (d, 1H, J=3 Hz); 7.38 (d, 1H, J=9.9 Hz); 7.38 (5, 1H): (ii)—¹H-NMR (CDCl₃) 0.86 (tr, 3H, J=6.91 Hz); 1.25 (m, 10H); 1.4 (s, 9H); 1.53-1.57 (m, 8H); 2.56 (tr, 2H, J=7.84 Hz); 3.62 (d, 2H, J=12.02 Hz); 4.06 (s, 2H); 4.48 (d, 2H, J=12.02 Hz); 5.57 (broad s, 1H); 7.27 (d, 1H, J=8.8 Hz); 7.39 (d, 1H, 8.8 Hz); 7.41 (s 1H).

Step B: 2-Amino-2-((5-octyl-1H-indol-1-yl)methyl) propane-1,3-diol

To a solution of the product of (i) of Step A (0.03 g; 0.0634 mmol), NaI (0.02 g; 0.123 mmol) in anhydrous CH₃CN (2 ml) Me₃SiCl (0.12 ml; 0.095 mmol) was added at room temperature with stirring under N₂. After stirring for 2 h, the mixture was diluted to 15 ml with Et₂O, washed with saturated NaHCO₃, brine, dried over anhydrous MgSO₄ and filtered. The filtrate was evaporated to dryness under reduced pressure and the residue was purified by FCC (SiO₂; CH₂Cl₂ saturated with NH$_4$OH/MeOH; 95:5) to give the title compound (0.01 g; 48%), as a creamy solid. $^1$H-NMR (CDCl$_3$) 0.86 (tr, 3H, J=6.9 Hz); 1.28 (m, 10H); 1.58-2 (broad m, 6H+H$_2$O); 2.67 (tr, 2H, J=7.9 Hz); 3.75 (s, 4H); 4.27 (s, 2H); 6.44 (d, 1H, J=3 Hz); 7.03 (dd, 1H, J=1.3, 8.5 Hz); 7.13 (d, 1H, J=3 Hz); 7.38 (s, 1H); 7.39 (d, 1H, J=8.5 Hz).

Example 5

1-(2-Amino-3-hydroxy-2-(hydroxymethyl)propyl)-5-octylindoline-2,3-dione

When the product (ii) of Example 4, Step A was substituted for tert-butyl 2,2-dimethyl-5-((5-octyl-1H-indol-1-yl)methyl)-1,3-dioxan-5-ylcarbamate in Example 4, Step B, the identical process afforded the title compound in 55% yield., as a deep orange solid. $^1$H-NMR (CDCl$_3$+CD$_3$OD) 0.82 (tr, 3H, J=6.84 Hz); 1.21 (m, 10H); 1.5 (m, 2H); 2.2-2.5 (m, 2H+H$_2$O); 3.3 (s, 2H); 3.66 (d, 2H, J=11.8 Hz); 3.77 (d, 2H, J=11.8 Hz); 6.5-6.69 (m, 3H).

Example 6

2-Amino-2-((5-(3,4,5-trimethoxyphenethyl)indolin-1-yl)methyl)propane-1,3-diol

Step A:
5-((3,4,5-Trimethoxyphenyl)ethynyl)-1H-indole

When 5-ethynyl-1,2,3-trimethoxybenzene is substituted for 1-octyne in Example 3, Step A, the identical process afforded the title compound in 70% yield., as a creamy foam. $^1$H-NMR (CDCl$_3$) 3.86 (s, 3H); 3.88 (s, 6H); 6.55 (m, 1H): 6.78 (s, 2H); 7.22 (m, 1H); 7.35 (d, 2H, 0.8 Hz); 7.84 (d, 1H, J=0.8 Hz); 8.22 (broad s, 1H).

Step B: 5-(3,4,5-Trimethoxyphenethyl)-1H-indole

When the product of Step A was substituted for 5-(oct-1-ynyl)-1H-indole in Example 3, Step B, the identical process afforded the title compound in 86% yield., as a colourless syrup. $^1$H-NMR (CDCl$_3$) 2.79-3.03 (m, 4H); 3.8 (s, 3H); 3.82 (s, 6H); 6.4 (s, 2H); 6.47 (m, 1H); 7.03 (dd, 1H, J=1.3; 8.3 Hz); 7.18 (m, 1H); 7.31 (d, 1H, J=8.3 Hz); 7.45 (s, 1H); 8.09 (broad s, 1H);

Step C: 5-(3,4,5-Trimethoxyphenethyl)indoline

To a solution of the product of Step B (0.12 g; 0.38 mmol) in tetrahydrofuran (THF)/acetic acid 1:1 mixture (6 ml) NaBH$_3$CN (0.1 g; 1.16 mmol) was added at room temperature. After stirring for 1 h the solvents were removed in vacuo and the residue was diluted to 15 ml with Et$_2$O and washed with 1 N NaOH (5 ml), H$_2$O (2×5 ml), brine, dried over anhydrous MgSO$_4$ and filtered. The filtrate was evaporated to dryness under reduced pressure to give the title compound (0.12 g; 100%), which was used in next step without further purification. $^1$H-NMR (CDCl$_3$) 2.85 (s, 4H); 2.99 (tr, 2H, J=8.3 Hz); 3.52 (tr, 2H, J=8.3 Hz); 3.66 (broad s, 1H); 3.8 (s, 9H); 6.39 (s, 2H); 6.57 (d, 1H, J=7.9 Hz); 6.84 (d, 1H, J=7.9 Hz); 6.96 (s, 1H).

Step D: tert-Butyl 2,2-dimethyl-5-((5-(3,4,5-trimethoxyphenethyl)indolin-1-yl)methyl)-1,3-dioxan-5-ylcarbamate When the product of Step C was substituted for 5-n-octyl-indoline in Example 3, Step D, the identical process afforded the title compound in 85% yield, as a colourless foam. $^1$H-NMR (CDCl$_3$) 1.41-1.53 (m, 15H+H2O); 2.78 (s, 4H); 2.96 (tr, 2H, J=8.22 Hz); 3.42 (tr, 2H, J=8.22 Hz); 3.48 (s, 2H); 3.81 (s, 3H); 3.82 (s, 6H); 3.86-4.04 (m, 4H); 4.68 (broad s, 1H); 6.38 (s, 2H); 6.51 (d, 1H, J=8.2 Hz); 6.8-6.92 (m, 2H).

Step E: 2-Amino-2-((5-(3,4,5-trimethoxyphenethyl) indolin-1-yl)methyl) propane-1,3-diol When the product of Step D was substituted for tert-butyl 2,2-dimethyl-5-((4-octylphenylamino)methyl)-1,3-dioxan-5-ylcarbamate in Example 1, Step B, the identical process afforded the title compound in 68% yield, as a creamy solid. $^1$H-NMR (CDCl$_3$) 1.77 (broad s, 4H+H2O); 2.79 (s, 4H); 2.96 (tr, 2H, J=8.3 Hz); 3.07 (s, 2H); 3.44 (tr, 2H, J=8.3 Hz); 3.57-3.61 (m, 4H); 3.82 (m, 9H); 6.38 (s, 2H); 6.55 (d, 1H, J=7.95 Hz); 6.9 (d, 1H, J=7.95 Hz); 7.03 (s, 1H).

Example 7

2-Amino-2-((5-(5-(3-chloro-4-methoxyphenyl)-1,2,4-oxadiazol-3-yl)indolin-1-yl)methyl)propane-1,3-diol Step A: 5-Cyanoindole A mixture of 5-iodoindole (0.36 g; 1.48 mmol), NaCN (0.15 g; 3 mmol), Pd(Ph$_3$)$_4$ (0.23 g; 0.22 mmol) and CuI (0.06 g; 0.3 mmol) in anhydrous CH$_3$CN (3 ml) was refluxed for 2.5 h under N$_2$. After cooling to room temperature, the mixture was diluted to 20 ml with EtOAc and filtered through a pad of Celite. The filtrate was washed with H$_2$O, brine, dried over anhydrous MgSO4 and filtered. The filtrate was evaporated to dryness under reduced pressure, dissolved in a small volume of CH$_2$Cl$_2$ and filtered through a small pad of SiO2, which was washed with fresh CH$_2$Cl$_2$. The combined filtrates were evaporated to dryness under reduced pressure to give the title compound (0.2 g; 95%) as colourless solid. $^1$H-NMR (CDCl$_3$) 6.62 (tr, 1H, J=2.5 Hz); 7.33 (tr, 1H, J=2.5 Hz); 7.39-7.47 (m, 2H); 7.98 (s, 1H); 8.51 (broad s, 1H).

Step B: 3-Chloro-4-methoxybenzoic acid

A mixture of 4-methoxybenzoic acid (0.46 g; 3 mmol) and N-chlorosuccinimide (NCS) (0.36 g; 2.7 mmol) in trifluoroacetic acid (5 ml) was stirred for 3 h at ~70° C. After removing solvent under reduced pressure the residue was treated with H$_2$O (10 ml). The solid was filtered off and purified by FCC (SiO$_2$; EtOAc) to give the title compound (0.38 g; 68%) as a colourless solid. $^1$H-NMR (CDCl$_3$) 3.97 (s, 3H); 6.96 (d, 1H, J=8.7 Hz); 8.0 (dd, 1H, J=2; 8.7 Hz); 8.11 (d, 1H, J=2 Hz).

Step C: N-Hydroxy-1H-indole-5-carboximidamide

A mixture of the product of Step A (0.2 g; 1.41 mmol), HCl×H$_2$NOH (0.36 g; 5.2 mmol), and Na$_2$CO$_3$ (0.26 g; 2.44 mmol) in H$_2$O (8 ml) and EtOH (2 ml) was gently stirred for 10 min, then refluxed overnight under N$_2$. After cooling most of the ethanol was removed under reduced pressure and the product was extracted with EtOAc (20 ml). The organic phase was separated, dried over anhydrous MgSO$_4$ and filtered. The filtrate was evaporated to dryness under reduced pressure to give the title compound (0.23 g; 92%), as a creamy foam. $^1$H-NMR (CDCl$_3$+CD$_3$OD) 1.71 (broad s, H2O); 4.93* (broad s, 0.5H); 6.55 (d, 1H, J=3 Hz); 7.21 (d, 1H, J=3 Hz); 7.28-7.42 (m, 2H); 7.87 (d, 1H, J=1 Hz); 8.63* (broad s, 0.3H).

* NH partially exchanged with CD$_3$OD

Step D: N-(3-Chloro-4-methoxybenzoyloxy)-1H-indole-5-carboximidamide

To a solution of the product of Step B (0.25 g; 1.43 mmol), and the product of Step C (0.23 g; 1.31 mmol) in anhydrous THF (5 ml), PyBroP (0.67 g; 1.44 mmol) was added followed by DIPEA (0.57 ml; 3.3 mmol), with stirring, at room temperature under $N_2$. After 1 h of stirring, the mixture was diluted to 20 ml with EtOAc, washed with saturated $NH_4Cl$ (5 ml), brine, dried over anhydrous $MgSO_4$ and filtered. The filtrate was evaporated to dryness under reduced pressure and the residue was purified by crystallization from EtOAc/hexane to give the title compound (0.42 g; 93%), as a creamy solid. $^1$H-NMR ($CD_3OD$) 3.96 (s, 3H); 5.41 (s, 1H); 6.52 (d, 1H, J=3.2 Hz); 7.14 (d, 1H, J=8.7 Hz); 7.27 (d, 1H, J=3.2 Hz); 7.41-7.77 (m, 2H); 8.0 (s, 1H); 8.11 (dd, 1H, J=2; 8.7 Hz); 8.15 (d, 1H, J=2 Hz).

Step E: 5-(3-Chloro-4-methoxyphenyl)-3-(1H-indol-5-yl)-1,2,4-oxadiazole

A suspension of the product of Step D (0.4 g; 1.16 mmol) and 1M TBAF in THF (0.5 ml) in anhydrous toluene (10 ml) was refluxed for 3 h under $N_2$, cooled to room temperature and solvents were removed under reduced pressure. The residue was washed with $H_2O$ (5 ml) and the solid was purified by FCC ($SiO_2$; $CH_2Cl_2$) to give the title compound (0.35 g; 92%) as colourless solid. $^1$H-NMR ($CDCl_3$) 4.0 (s, 3H); 6.66 (m, 1H); 7.05 (d, 1H, J=8.7 Hz); 7.27 (m, 1H); 7.49 (d, 1H, J=8.7 Hz); 7.97-8.01 (m, 1H); 8.1-8.13 (m, 1H); 8.27 (d, 1H, J=2.1 Hz); 8.3 (broad s, 1H); 8.48 (m, 1H).

Step F: 5-(3-Chloro-4-methoxyphenyl)-3-(indolin-5-yl)-1,2,4-oxadiazole

To a solution of the product of Step E (0.11 g; 0.34 mmol) in 1M $BH_3$ in THF (0.68 ml; 0.68 mmol) $CF_3CO_2H$ (1 ml) was added drop wise at 0° C. with stirring. After the addition was completed (~5 min) the reaction was quenched with $H_2O$ (0.5 ml) and the solvents were removed under reduced pressure. The residue was diluted to 15 ml with EtOAc and was washed with 1 M NaOH (2×2 ml), brine and dried over anhydrous $MgSO_4$ and filtered. The filtrate was evaporated to dryness under reduced pressure to give the title compound (0.11 g; 100%) as a creamy foam, which was used in the next step without further purification. $^1$H-NMR ($CDCl_3$) 2.6 (broad s, 1H+$H_2O$); 3.12 (tr, 2H, J=8.4 Hz); 3.66 (tr, 2H, J=8.4 Hz); 3.98 (s, 3H); 6.71 (d, 1H, J=8.1 Hz); 7.07 (d, 1H, J=8.7 Hz); 7.83-7.88 (m, 2H); 8.05 (dd, 1H, J=2, 8.7 Hz); 8.21 (d, 1H, J=2 Hz).

Step G: tert-Butyl 5-((5-(5-(3-chloro-4-methoxyphenyl)-1,2,4-oxadiazol-3-yl)indolin-1-yl)methyl)-2,2-dimethyl-1,3-dioxan-5-ylcarbamate When the product of Step F was substituted for 5-n-octyl-indoline in Example 3, Step D, the identical process afforded the title compound in 68% yield., as a creamy solid. $^1$H-NMR ($CDCl_3$) 1.46 (s, 15H); 3.07 (tr, 2H, J=8.5 Hz); 3.57 (tr, 2H, J=8.5 Hz); 3.63 (s, 2H); 3.94 (s, 4H); 3.98 (s, 3H); 4.63 (broad s, 1H); 6.63 (d, 1H, J=8.3 Hz); 7.03 (d, 1H, J=8.7 Hz); 7.8 (s, 1H); 7.85 (d, 1H, J=8.3 Hz); 8.06 (dd, 1H, J=2; 8.7 Hz); 8.21 (d, 1H, J=2 Hz).

Step H: 2-Amino-2-((5-(5-(3-chloro-4-methoxyphenyl)-1,2,4-oxadiazol-3-yl)indolin-1-yl)methyl)propane-1,3-diol When the product of Step G was substituted for tert-butyl 2,2-dimethyl-5-((4-octylphenylamino)methyl)-1,3-dioxan-5-ylcarbamate in Example 1, Step B, the identical process afforded the title compound in 67% yield, as a creamy solid. $^1$H-NMR ($CDCl_3$) 1.54 (broad s, 4H+$H_2O$); 3.07 (m, 2H); 3.19 (s, 2H); 3.47 (s, 2H); 3.55-3.62 (m, 6H); 3.98 (s, 3H); 6.67 (m, 1H); 7.03 (m, 1H); 7.82-7.9 (m, 2H); 8.01-8.06 (m, 1H); 8.22 (s, 1H); $^1$H-NMR (DMSO-$d_6$) 1.52 (m, 2H); 2.9-3.03 (m, 4H); 3.57 (tr, 2H, J=8.6 Hz); 3.95 (s, 3H); 4.6 (s, 2H); 6.66 (d, 1H, J=8.4 Hz); 7.36 (d, 1H, J=8.4 Hz); 7.62-7.7 (m, 2H); 8.05-8.11 (m, 2H).

Example 8

2-Amino-2-((5-((4,6-dichlorobenzofuran-2-yl)methoxy)indolin-1-yl)methyl) propane-1,3-diol

Step A: 5-Methoxy-indoline

When 5-methoxy-1H-indole was substituted for 5-(3-chloro-4-methoxyphenyl)-3-(1H-indol-5-yl)-1,2,4-oxadiazole in Example 7, Step F, the identical process afforded the title compound in 84% yield., as a creamy syrup. $^1$H-NMR ($CDCl_3$) 2.99 (tr, 2H, J=8.35 Hz); 3.28 (broad s, 1H); 3.52 (tr, 2H, J=8.35 Hz); 3.73 (s, 3H); 6.57 (m, 2H); 6.75 (s, 1H).

Step B: 5-Hydroxy-indoline

A solution of the product Step A (0.32 g; 2.14 mmol) in 48% HBr/AcOH 1:1 (10 ml) was refluxed overnight, then evaporated to dryness under reduced pressure. The residue was dissolved in EtOH (10 ml) and the solvent was removed under reduced pressure. This process was repeated three times and the residue was suspended in acetonitrile. The greyish solid formed was filtered off, washed with fresh $CH_3CN$ and dried to give a hydrobromide salt of the title compound (0.28 g; 60%). $^1$H-NMR ($D_2O$) 3.18 (tr, 2H, J=7.8 Hz); 3.78 (tr, 2H, J=7.8 Hz); 4.66 (HDO); 6.78 (d, 1H, J=8.6 Hz); 6.87 (s, 1H); 7.23 (d, 1H, J=8.6 Hz).

Step C: tert-Butyl 5-((5-hydroxyindolin-1-yl)methyl)-2,2-dimethyl-1,3-dioxan-5-ylcarbamate When the product of Step B is substituted for 5-n-octyl-isoindoline hydrochloride salt in Example 2, Step F, the identical process afforded the title compound in 33% yield, as a creamy solid. $^1$H-NMR ($CDCl_3$) 1.27 (m, 15H); 2.95 (tr, 2H, J=8.2 Hz); 3.31 (tr, 2H, J=8.2 Hz); 3.43 (s, 2H); 3.72 (5, 1H+$H_2O$); 3.82-4.02 (m, 4H); 4.7 (broad s, 1H); 6.5 (d, 1H, J=8.5 Hz); 6.6 (d, 1H, J=8.5 Hz); 6.71 (s, 1H).

Step D: 3,5-Dichloro-2-iodophenol

To a suspension of 3,5-dichlorophenol (0.6 g; 3.68 mmol) in $H_2O$ (15 ml), 30% $H_2O_2$ was added followed by $I_2$ (0.47 g; 1.85 mmol). The resulting mixture was vigorously stirred for 8 h at room temperature, then extracted with $CH_2Cl_2$ (15 ml) and the organic phase was dried over anhydrous $MgSO_4$ and filtered. The filtrate was evaporated under reduced pressure and the residue was purified by FCC ($SiO_2$; $CH_2Cl_2$) to give the title compound (0.55 g; 52%) as colourless solid. $^1$H-NMR ($CDCl_3$) 5.58 (s, 1H); 6.89 (s, 1H); 7.06 (s, 1H).

Step E: (4,6-Dichlorobenzofuran-2-yl)methanol

Propargyl alcohol (0.12 ml; 1.96 mmol) was added drop wise to a refluxing mixture of the product of Step D (0.55 g; 1.96 mmol) and $Cu_2O$ (0.2 g; 1.4 mmol) in anhydrous pyridine (4 ml) under $N_2$. After refluxing for 1 h, the solvent was removed under reduced pressure and the residue was treated with EtOAc (15 ml). The insoluble material was filtered off and the filtrate was washed with 10% citric acid, $H_2O$, brine, dried over anhydrous $MgSO_4$ and filtered. The filtrate was evaporated under reduced pressure and the residue was purified by FCC ($SiO_2$; $CH_2Cl_2$) to give the title compound (0.24 g; 56%) as colourless solid. $^1$H-NMR ($CDCl_3$) 1.91 (tr, 1H, J=6.3 Hz); 4.75 (d, 1H, J=6.3 Hz); 6.72 (s, 1H); 7.23 (s, 1H); 7.37 (s, 1H).

Step F: 4,6-Dichloro-2-(chloromethyl)benzofuran

To a solution of the product of Step E (0.24 g; 1.1 mmol) and DIPEA (0.2 ml; 1.11 mmol) in anhydrous THF (1 ml), $SOCl_2$ (0.1 ml; 1.13 mmol) was added drop wise at 0° C. under $N_2$ with stirring. The mixture was allowed to warm up to room temperature and stirred overnight, then diluted to 15 ml with $Et_2O$ and washed with 0.1N HCl, 5% $NaHCO_3$, brine, dried over anhydrous $MgSO_4$ and filtered. The filtrate was evaporated under reduced pressure to give the title compound (0.25 g; 96%), as a creamy syrup, which was used in the next step without further purification. $^1$H-NMR ($CDCl_3$) 4.68 (s, 2H); 6.8 (s, 1H), 7.2 (s, 1H); 7.39 (s, 1H).

Step G: tert-Butyl 5-((5-((4,6-dichlorobenzofuran-2-yl)methoxy)indolin-1-yl)methyl)-2,2-dimethyl-1,3-dioxan-5-ylcarbamate A mixture of the product of Step F (0.05 g; 0.21 mmol) and the product of Step C (0.08 g; 0.21 mmol) and $Cs_2CO_3$ (0.07 g; 0.21 mmol) in anhydrous DMF (1 ml) was stirred overnight at room temperature under $N_2$. This was diluted to 10 ml with diethyl ether, washed with $H_2O$, brine, dried over anhydrous $MgSO_4$ and filtered. The filtrate was evaporated under reduced pressure and the residue was purified by FCC ($SiO_2$; hexane/EtOAc 7:3), to give the title compound (0.05 g; 41%) as a brownish syrup. $^1$H-NMR ($CDCl_3$) 1.44 (m, 15H); 2.95 (tr, 2H, J=8.5 Hz); 3.41 (tr, 2H, J=8.5 Hz); 3.45 (5, 2H); 3.87-4.01 (m, 4H); 4.69 (broad s, 1H); 5.03 (s, 2H); 6.49 (d, 1H, J=8.5 Hz); 6.69 (dd, 1H, J=2.5, 8.5 Hz); 6.79 (s, 2H); 7.23 (s, 1H, J=2.5 Hz); 7.39 (s, 1H).

Step H: 2-Amino-2-((5-((4,6-dichlorobenzofuran-2-yl)methoxy)indolin-1-yl)methyl)propane-1,3-diol When the product of Step G was substituted for tert-butyl 2,2-dimethyl-5-((4-octylphenylamino)methyl)-1,3-dioxan-5-ylcarbamate in Example 1, Step B, the identical process afforded the title compound in 37% yield, as a off white solid. $^1$H-NMR ($CD_3OD$) 2.9 (tr, 2H, J=8.2 Hz); 3.37 (tr, 2H, J=8.2 Hz); 3.43-3.53 (m, 4H); 5.0 (s, 2H); 6.5 (d, 1H, J=8.4 Hz); 6.65-6.7 (m, 1H); 6.76 (s, 2H); 7.19 (d, 1H, J=1.5 Hz); 7.37 (m, 1H).

Example 9

2-Amino-2-((6-octyl-3,4-dihydroquinolin-1(2H)-yl)methyl)propane-1,3-diol

Step A: 6-Iodo-1,2,3,4-tetrahydroquinoline

To a mixture of 1,2,3,4,-tetrahydroquinoline (0.34 g; 2.55 mmol) and $I_2$ (0.32 g; 1.27 mmol) in $H_2O$ (10 ml), 30% $H_2O_2$ (0.26 ml; 2.55 mmol) was added at room temperature. The resulting mixture was vigorously stirred overnight at room temperature, and then extracted with $Et_2O$ (2×15 ml). The combined organic phase was washed with $H_2O$, brine, dried over anhydrous $MgSO_4$ and filtered. The filtrate was evaporated under reduced pressure and the residue was purified by FCC ($SiO_2$; $CH_2Cl_2$), to give the title compound (0.33 g; 50%) as a creamy syrup. $^1$H-NMR ($CDCl_3$) 1.84-1.92 (m, 2H); 2.69 (tr, 2H, J=6.4 Hz); 3.27 (tr, 2H, J=6.4 Hz); 3.82 (broad s, 1H); 6.22 (d, 1H, J=8.2 Hz); 7.15-7.21 (m, 2H).

Step B: tert-Butyl 5-((6-iodo-3,4-dihydroquinolin-1(2H)-yl)methyl)-2,2-dimethyl-1,3-dioxan-5-ylcarbamate When the product of Step A is substituted for 4-n-octylaniline in Example 1, Step A, the identical process afforded the title compound in 30% yield, as a colourless foam. $^1$H-NMR ($CDCl_3$) 1.42 (m, 15H); 1.86-1.93 (m, 2H); 2.72 (tr, 2H, J=6.3 Hz); 3.28 (tr, 2H, J=5.6 Hz); 3.67 (s, 2H); 3.89 (s, 4H); 4.61 (broad s, 1H); 6.6 (d, 1H, J=8.8 Hz); 7.19-7.24 (m, 2H).

Step C: tert-Butyl 2,2-dimethyl-5-((6-(oct-1-ynyl)-3,4-dihydroquinolin-1(2H)-yl)methyl)-1,3-dioxan-5-ylcarbamate When the product of Step B is substituted for 5-iodo-2-tritylisoindoline in Example 2, Step D, the identical process afforded the title compound in 35% yield, as a brownish foam. $^1$H-NMR ($CDCl_3$) 0.88 (m, 3H); 1.41 (m, 8H); 1.50 (m, 2H); 1.87 (m, 2H); 2.34 (tr, 2H, J=7.0 Hz); 2.72 (tr, 2H, J=6.3 Hz); 3.26-3.32 (m, 2H); 3.69 (5, 2H); 3.9 (s, 3H); 4.65 (s, 1H); 6.68 (d, 1H, J=8.7 Hz); 6.98 (s, 1H); 7.04 (d, 1H, J=8.7 Hz).

Step D: tert-Butyl 2,2-dimethyl-5-((6-octyl-3,4-dihydroquinolin-1(2H)-yl)methyl)-1,3-dioxan-5-ylcarbamate When the product of Step C is substituted for 5-(oct-1-ynyl)-2-tritylisoindoline in Example 2, Step E, the identical process afforded the title compound in 90% yield, as a colourless foam. $^1$H-NMR ($CDCl_3$) 0.86 (tr, 3H, J=6.9 Hz); 1.24 (m, 10H); 1.42 (m, 15H); 1.91 (m, 2H); 2.43 (tr, 2H, J=8 Hz); 2.75 (tr, 2H, J=6.5 Hz); 3.25 (tr, 1H, J=5.5 Hz); 3.64 (s, 2H); 3.8-3.99 (m, 4H); 4.7 (s, 1H); 6.7 (d, 1H, J=8.4 Hz); 6.76 (s, 1H); 6.82 (d, 1H, J=8.4 Hz).

Step E: 2-Amino-2-((6-octyl-3,4-dihydroquinolin-1(2H)-yl)methyl)propane-1,3-diol When the product of Step D is substituted for tert-butyl 2,2-dimethyl-5-((5-octylisoindolin-2-yl)methyl)-1,3-dioxan-5-ylcarbamate in Example 2, Step G, the identical process afforded the title compound in 36% yield., as a colourless solid. $^1$H-NMR ($CDCl_3$) 0.86 (tr, 3H, J=7 Hz); 1.26 (m, 10H); 1.53 (m, 2H); 1.92 (m, 2H); 2.22 (broad s, 4H+$H_2O$); 2.43 (tr, 2H, J=8 Hz); 2.76 (tr, 2H, J=6.4 Hz); 3.23 (s, 2H); 3.26 (tr, 2H, J=3.7 Hz); 3.51-3.61 (m, 4H); 6.7-6.87 (m, 3H).

Example 10

2-Amino-2-((6-octyl-3,4-dihydroisoquinolin-2(1H)-yl)methyl)propane-1,3-diol

Step A: 1-(3,4-Dihydroisoquinolin-2(1H)-yl)-2,2,2-trifluoroethanone

To a solution of 1,2,3,4-tetrahydroquinoline (0.62 g; 4.66 mmol) in anhydrous pyridine (3 ml) ($CF_3CO_2$)O (0.7 ml; 5.12 mmol) was added drop wise at 0° C., with stirring. The mixture was allowed to warm up to room temperature and after 1 h of stirring, the solvents were removed in vacuo and the residue was diluted to 20 ml with $Et_2O$. This was washed with 10% citric acid, $H_2O$, brine, dried over anhydrous $MgSO_4$ and filtered. The filtrate was evaporated to dryness under reduced pressure and the residue was dissolved in small volume of $CH_2Cl_2$, passed through a short column with $SiO_2$, washed with $CH_2Cl_2$ (2×20 ml). The combined filtrates were evaporated to dryness under reduced pressure to give the title compound (0.9 g; 84%) as a colourless syrup. $^1$H-NMR ($CDCl_3$) 2.9 (m, 2H); 3.85 (m, 2H); 4.75 (m, 2H); 7.08-7.24 (m, 4H).

Step B: 2,2,2-Trifluoro-1-(6 and 7-iodo-3,4-dihydroisoquinolin-2(1H)-yl)ethanone To a solution of the product of Step A (0.9 g; 3.93 mmol); and $CF_3CO_2Ag$ (0.87 g; 3.93 mmol) in dry $CH_2Cl_2$ (15 ml), $I_2$ (1 g; 3.93 mmol) was added at 0° C. and the resulting mixture was allowed to warm up to room temperature with stirring. After 4 h of stirring the mixture was filtered through a pad of Celite, washed with fresh $CH_2Cl_2$ (2×15 ml) and combined filtrates were evaporated to dryness to give a brownish oil (1.3 g; 98%), which was a mixture of 6 and 7 isomers (~70 & 30%). $^1$H-NMR ($CDCl_3$) 2.91 (m, 2H); 3.85 (m, 2H); 4.7 (m, 2H); 6.87-6.95 (m, 0.7H); 7.11-7.23 (m, 1.1H); 7.46-7.55 (m, 0.9H); 7.63 (m, 0.3H).

Step C: 2,2,2-Trifluoro-1-(6-(oct-1-ynyl)-3,4-dihydroisoquinolin-2(1H)-yl)ethanone When the product of Step B is substituted for 5-iodo-2-tritylisoindoline in Example 2, Step D, the identical process afforded the title compound in 36% yield, as a brownish foam. $^1$H-NMR ($CDCl_3$) 0.89 (tr, 3H, J=6.9 Hz); 1.3 (m, 4H); 1.32-1.48 (m, 2H); 1.54-1.63 (m, 2H); 2.35 (tr, 2H, J=6.9 Hz); 2.8-3.05 (m, 2H); 3.79-3.89 (m, 2H); 4.67-4.84 (m, 2H); 6.99-7.2 (m, 3H).

Step D: 2,2,2-Trifluoro-1-(6-octyl-3,4-dihydroisoquinolin-2(1H)-yl)ethanone

When the product of Step C is substituted for 5-(oct-1-ynyl)-2-tritylisoindoline in Example 2, Step E, the identical process afforded the title compound in 75% yield after purification of the crude product by FCC ($SiO_2$; EtOAc/hexane, 3:7)., as a colourless foam. $^1$H-NMR ($CDCl_3$) 0.86 (tr, 3H, J=6.9 Hz); 1.28 (m, 10H); 1.56 (m, 2H); 2.55 (tr, 2H, J=6.9 Hz); 2.87-2.93 (m, 2H); 3.79-3.88 (m, 2H); 4.6-4.8 (m, 2H); 6.8-7.16 (m, 3H).

Step E: 6-Octyl-1,2,3,4-tetrahydroisoquinoline

A mixture of the product of Step D (0.1 g; 0.29 mmol) and $K_2CO_3$ (0.04 g; 0.29 mmol) in 50% aqueous MeOH (5 ml) was refluxed for 3 h, under $N_2$, then cooled to room temperature. The organic solvent was removed under reduced pressure and the residue was diluted to 15 ml with $Et_2O$, washed with, $H_2O$, brine, dried over anhydrous $MgSO_4$ and filtered. The filtrate was evaporated to dryness under reduced pressure to give a title compound (0.07 g; 98%), as a colourless syrup. $^1$H-NMR ($CDCl_3$) 0.86 (tr, 3H, J=6.9 Hz); 1.26 (m, 10H); 1.56 (m, 2H); 2.52 (tr, 3H, J=6.9 Hz); 2.71-2.8 (m, 2H); 3.08-3.16 (m, 2H); 3.96-4.01 (m, 2H); 6.8-7.07 (m, 3H).

Step F: tert-Butyl 2,2-dimethyl-5-((6-octyl-3,4-dihydroisoquinolin-2(1H)-yl)methyl)-1,3-dioxan-5-ylcarbamate When the product of Step E was substituted for 4-n-octylaniline in Example 1, Step A, the identical process afforded the title compound in 49% yield, as colourless syrup. $^1$H-NMR ($CDCl_3$) 0.86 (tr, 3H, J=6.9 Hz); 1.25 (m, 10H); 1.39-1.46 (m, 15H); 1.56 (m, 2H); 2.51 (tr, 2H, J=6.9 Hz); 2.83 (s, 4H); 2.93 (s, 2H); 3.71 (s, 2H); 3.81 (d, 2H, J=11.6 Hz); 4.07 (d, 2H, J=11.6 Hz); 4.88 (broad s, 1H); 6.7-7.07 (m, 3H).

Step G: 2-Amino-2-((6-octyl-3,4-dihydroisoquinolin-2(1H)-yl)methyl) propane-1,3-diol When the product of Step F is substituted for tert-butyl 2,2-dimethyl-5-((5-octylisoindolin-2-yl)methyl)-1,3-dioxan-5-ylcarbamate in Example 2, Step G, the identical process afforded the title compound in 68% yield., as a colourless solid. $^1$H-NMR ($CDCl_3$) 0.86 (tr, 3H, J=6.9 Hz); 1.26 (m, 10H); 1.54 (m, 2H); 2.48-3 (m, 3H); 3.54 (s, 4H); 3.76 (s, 2H); 6.7 p-7.06 (m, 3H).

Example 11

1-(1-(3-(4-(3-amino-4-hydroxy-3-(hydroxymethyl)butyl)phenyl)propyl)-1H-indol-3-yl)-2,2,2-trifluoroethanone Step A: 2,2,2-Trifluoro-1-(1H-indol-3-yl)ethenone To a stirred solution of indole (0.5 g, 4.3 mmol) in anhydrous $Et_2O$ (10 ml) at 0° C. anhydrous pyridine (0.5 ml) was added, followed by drop wise addition of $(CF_3CO)_2O$ (0.871 ml; 5.16 mmol). The mixture was stirred for 15 minutes and the solid was removed by filtration. The filtrate was evaporated to dryness and the residue was diluted to 20 ml with EtOAc, washed with $H_2O$, dried over $MgSO_4$ and filtered. The filtrate was evaporated to dryness. The residue was purified by crystallization from MeOH to give the product (0.56 g; 61%), as colourless solid. $^1$H-NMR ($CDCl_3$) 7.35-7.40 (m, 2H); 7.45-7.48 (m, 1H); 8.06 (s, 1H); 8.40 (tr, 1H, J=4.11 Hz); 9.04 (broad s, 1H).

Step B: 2,2,2-Trifluoro-1-(1-(prop-2-ynyl)-1H-indol-3-yl)ethanone

A mixture of 2,2,2-trifluoro-1H-indol-3-yl)ethanone (0.55 g, 2.58 mmol), $K_2CO_3$ (0.43 g, 3.11 mmol) and propyrgyl bromide (2 ml) was stirred in anhydrous DMF (8 ml) for 4 h. The mixture was quenched with aqueous $NH_4Cl$ and diluted to 50 ml with EtOAc. The organic layer was separated, washed with w $H_2O$, dried over $MgSO_4$, and filtered. The filtrate was evaporated to dryness to give the product (0.57 g; 87%), as yellow solid. $^1$H-NMR ($CDCl_3$) 2.58 (tr, 1H, J=2.55 Hz); 4.96 (d, 2H, J=2.55 Hz); 7.48-7.31 (m, 3H); 7.99 (s, 1H); 8.41-8.38 (m, 1H).

Step C: 2,2,2-Trifluoro-1-(1-(3-(4-iodophenyl)prop-2-ynyl)-1H-indol-3-yl)ethanone When the product of Step B was substituted for 1-octyne and 1,4 diiodobenzene was substituted for 5-iodo-2-tritylisoindoline in Example 2, Step D, the similar process afforded the title compound in 51% yield, as light yellow solid. $^1$H-NMR ($CDCl_3$) 5.16 (s, 2H); 7.14 (d, 2H, J=8.30 Hz); 7.38-7.44 (m, 2H); 7.51-7.55 (m, 1H); 7.66 (tr, 2H, J=8.36 Hz); 8.12 (b, 1H); 8.40-8.43 (m, 1H).

Step D: tert-Butyl-2,2-dimethyl-5-((4-(3-(3-(2,2,2-trifluoroacetyl)-1H-indol-1-yl)prop-1-ynyl)phenyl)ethynyl)-1,3-dioxan-5-ylcarbamate When tert-butyl-5-ethynyl-2,2-dimethyl-1,3-dioxan-5-yl-carbamate was substituted for 1-octyne and the product of Step C was substituted for 5-iodo-2-tritylisoindoline in Example 2, Step D, the similar process afforded the title compound in 90% yield, as light yellow paste. $^1$H-NMR (CDCl$_3$) 1.43 (s, 3H); 1.45 (s, 9H); 1.48 (s, 3H); 3.94-4.13 (m, 4H), 5.18 (s, 2H); 7.34-7.41 (m, 6H); 7.52-7.55 (m, 1H); 8.12 (b, 1H); 8.37-8.43 (m, 1H).

Step E: tert-Butyl-2,2-dimethyl-5-(4-(3-(3-(2,2,2-trifluoroacetyl)-1H-indol-1-yl)propyl)phenethyl)-1,3-dioxan-5-ylcarbamate A mixture of the product of Step D (0.6 g, 0.1 mmol) and 10% Pd/C (0.03 g) was stirred for 16 h under H$_2$ (balloon). The catalyst was removed by filtration through Celite pad and filtrate evaporated to give the product (0.019 g; 32%), as pale paste. $^1$H-NMR (CDCl$_3$) 1.4 (s, 3H); 1.42 (s, 3H); 1.46 (s, 9H); 1.94-2.0 (m, 2H); 2.22-2.29 (m, 2H); 2.51-2.57 (m, 2H); 2.63 (tr, 2H, J=7.30 Hz); 3.67 (d, 2H, J=11.79 Hz); 3.88 (d, 2H, J=11.69 Hz); 4.17 (tr, 2H, J=7.14 Hz); 4.98 (s, 1H); 7.05 (d, 2H, J=8.06 Hz); 7.11 (d, 2H, J=8.06 Hz); 7.30-7.38 (m, 3H); 7.85 (b, 1H); 8.37-8.42 (m, 1H).

Step F: 1-(1-(3-(4-(3-Amino-4-hydroxy-3-(hydroxymethyl)butyl)phenyl)propyl)-1H-indol-3-yl)-2,2,2-trifluoroethanone A solution of the product of Step E (0.15 g, 0.03 mmol) in a mixture of MeOH, CH$_2$Cl$_2$ and 30% HCl (1 ml, 3 ml, 15 drops respectively) was stirred at room temperature for 3 h. The solvent was distilled and co-distilled with iso-propanol (iPrOH), to give the product (0.01 g; 69%), as colourless solid. $^1$H-NMR (CDCl$_3$) 1.89-1.92 (m, 2H); 2.12-2.22 (m, 2H); 2.53-2.61 (b, 4H); 3.65-3.75 (m, 4H); 4.13 (tr, 2H, J=7.02 Hz); 6.97 (d, 2H, J=7.71 Hz); 7.07 (d, 2H, J=7.8 Hz); 7.28-7.32 (m, 3H); 7.82 (s, 1H); 8.28-8.31 (m, 1H).

Example 12

(4-(4-(3-Amino-4-hydroxy-3-(hydroxymethyl)butyl)phenethyl)phenyl)(4-fluoro phenyl)methanone hydrochloride salt

Step A: tert-Butyl 5-((4-iodophenyl)ethynyl)-2,2-dimethyl-1,3-dioxan-5-ylcarbamate When tert-butyl-5-ethynyl-2,2-dimethyl-1,3-dioxan-5-ylcarbamate was substituted for 1-octyne and 1,4 diiodobenzene was substituted for 5-iodo-2-tritylisoindoline in Example 2, Step D, the similar process afforded the title compound in 34% yield, as the pale solid. $^1$H-NMR (CDCl$_3$) 1.43 (s, 3H); 1.46 (s, 9H); 1.48 (s, 3H); 2.40 (s, 1H); 3.99 (d, 2H, J=11.34 Hz); 4.00 (d, 2H, J=11.37 Hz); 5.18 (broad s, 1H); 7.12 (d, 2H, J=8.28 Hz); 7.61 (d, 2H, J=8.28 Hz).

Step B: 4-((4-Fluorophenyl)(hydroxy)methyl)benzaldehyde

To a stirred solution of terepathaldehyde (0.5 g, 3.7 mmol) in anhydrous THF (8 ml) at 0° C. was added 2M THF solution of 4-fluorophenyl magnesium bromide (1.86 ml; 3.72 mmol) drop wise and the mixture was allowed to warm up to room temperature and stirred for 4 h. The mixture was then quenched with NH$_4$Cl solution and diluted with to 100 ml with EtOAc. The organic layer was washed with H$_2$O, dried over MgSO$_4$, filtered and the filtrate evaporated to dryness. The residue was purified by FCC (SiO$_2$) to give the desired product (0.23 g; 27%) as creamy paste. $^1$H-NMR (CDCl$_3$) 2.57 (s, 1H); 5.86 (s, 1H); 7.0 (tr, 2H, J=8.58 Hz); 7.28-7.33 (m, 2H); 7.51 (d, 2H, J=7.98 Hz); 7.81 (d, 2H, J=8.1 Hz); 9.95 (s, 1H).

Step C: (4-Ethynylphenyl)(4-fluorophenyl)methanol

A mixture of the product of Step B (0.21 g, 0.91 mmol), dimethyl(1-diazo-2-oxopropyl)phosphonate (0.21 g, 1.1 mmol) and K$_2$CO$_3$ (0.152 g, 1.1 mmol) in anhydrous MeOH (5 ml) was stirred for overnight at room temperature. The solvent was distilled off and the residue was taken in EtOAc (50 ml), washed with H$_2$O and dried over MgSO$_4$ and filtered. The filtrate was evaporated under reduced pressure to give the crude product (0.195 g; 95%), which was used in the next step without purification. $^1$H-NMR (CDCl$_3$) 3.05 (s, 1H); 5.76 (s, 1H); 7.0 (tr, 2H, J=8.58 Hz); 7.25-7.33 (m, 4H); 7.44 (d, 2H, J=8.29 Hz).

Step D: (4-Ethynylphenyl)(4-fluorophenyl)methanone

The product of Step C was dissolved in anhydrous dioxane (20 ml) and to it MnO$_2$ (0.5 g) was added. The suspension was stirred at reflux for 6 h and then filtered through Celite. The filtrate was distilled off and the residue was purified by FCC (SiO$_2$) to give the product (0.18 g; 89%), as creamy paste. $^1$H-NMR (CDCl$_3$) 3.24 (s, 1H); 7.15 (tr, 2H, J=8.73 Hz); 7.60 (d, 2H, J=6.69 Hz); 7.71 (d, 2H, J=6.58 Hz); 7.78-7.84 (m, 2H).

Step E: tert-Butyl-5-((4-((4-(4-fluorobenzoyl)phenyl)ethynyl)phenyl)ethynyl)-2,2-dimethyl-1,3-dioxan-5-ylcarbamate When the product of Step D was substituted for 1-octyne and tert-butyl-5-((4-iodophenyl)ethynyl)-2,2-dimethyl-1,3-dioxan-5-ylcarbamate was substituted for 5-iodo-2-tritylisoindoline in Example 2, Step D, the similar process afforded the title compound in 42% yield, as creamy paste. $^1$H-NMR (CDCl$_3$) 1.44 (s, 3H); 1.47 (s, 9H); 1.5 (s, 3H); 4.02 (d, 2H, J=11.37 Hz); 4.1 (d, 2H, J=11.31 Hz); 5.2 (s, 1H); 7.16 (tr, 2H, J=8.64 Hz); 7.40 (d, 2H, J=8.49 Hz); 7.46 (tr, 2H, J=8.46 Hz); 7.60 (d, 2H, J=8.43 Hz); 7.74 (d, 2H, J=8.39 Hz); 7.80-7.83 (m, 2H).

Step F: tert-Butyl-5-(4-(4-(4-fluorobenzoyl)phenethyl)phenethyl)-2,2-dimethyl-1,3-dioxan-5-ylcarbamate A mixture of the product of Step E (0.06 g, 0.13 mmol) and 10% Pd/C (0.03 g) was stirred for 16 h under H$_2$ the (balloon). The catalyst was removed by filtration through Celite pad and the filtrate evaporated to dryness to give the product (0.032 g; 53%) as pale paste. $^1$H-NMR (CDCl$_3$) 1.4 (s, 3H); 1.41 (s, 3H); 1.45 (s, 9H); 1.92-1.98 (m, 2H); 2.5-2.56 (m, 2H); 2.89-2.97 (m, 4H); 3.65 (d, 2H, J=11.8 Hz); 3.86 (d, 2H, J=11.76 Hz); 4.95 (s, 1H); 7.08 (s, 4H); 7.14 (tr, 2H, J=8.64 Hz), 7.25 (d, 2H); 7.67 (d, 2H, J=8.17 Hz); 7.78-7.84 (m, 2H).

Step G: (4-(4-(3-Amino-4-hydroxy-3-(hydroxymethyl)butyl)phenethyl)phenyl)(4-fluoro phenyl)methanone hydrochloride When the product of Step F was substituted for tert-butyl-2,2-dimethyl-5-(4-(3-(3-(2,2,2-trifluoroacetyl)-1H-indol-1-yl)propyl)phenethyl)-1,3-dioxan-5-ylcarbamate in Example 11, Step F, the identical process afforded the title compound in 84% yield, as colourless solid. $^1$H-NMR (D$_2$O) 1.22-1.73 (m, 2H); 2.24 (m, 2H); 2.61 (m, 4H); 3.51 (s, 4H); 6.84-6.87 (m, 4H); 6.94-6.98 (m, 4H); 7.15 (m, 2H), 7.40-7.53 (m, 2H).

Example 13

(1-(4-(3-Amino-4-hydroxy-3-(hydroxymethyl)butyl) phenylsulfonyl)-6-methoxy-1H-indol-3-yl)(3,4,5-trimethoxyphenyl)methanone Step A: 1-(2-(tert-Butyldimethylsilyl)-6-methoxy-3-(3,4,5-trimethoxybenzoyl)-1H-indol-1-yl)ethanone A mixture of N-(2-iodo-5-methoxyphenyl)acetamide (0.45 g; 1.55 mmol), 3-(tert-butyldimethylsilyl)-1-(3,4,5-trimethoxyphenyl)prop-2-yn-1-one (0.5 g; 1.51 mmol), LiCl (0.069 g; 1.6 mmol) and Na$_2$CO$_3$ (0.477 g; 4.5 mmol) in anhydrous DMF (8 ml) was degassed with N$_2$ and temperature was raised to 100° C. with stirring. Pd(OAc)$_2$ (0.15 g) was added and heating was continued for 1.5 h. The solvent was removed in vacuo and the residue was diluted to 100 ml with EtOAc. This was washed with H$_2$O, dried over MgSO$_4$, filtered and the filtrate was evaporated to dryness. The residue was purified by FCC (SiO$_2$) to give the desired product (0.53 g; 69%) as creamy gum. $^1$H-NMR (CDCl$_3$) 0.12 (s, 6H); 0.98 (s, 9H); 2.84 (s, 3H); 3.77 (s, 3H); 3.86 (s, 6H); 3.93 (s, 3H); 6.8 (dd, 1H, J=2.07, 8.73 Hz), 7.00 (d, 1H, J=8.73 Hz), 7.16 (broad s, 3H).

Step B: (6-Methoxy-1H-indol-3-yl)(3,4,5-trimethoxyphenyl)methanone

A mixture of the product of Step A (0.52 g, 1.05 mmol) and 1M TBAF in THF (1 ml) in THF (10 ml) was refluxed for 2 h. The solvent was evaporated and the residue was taken in EtOAc, washed with 1M HCl and organic layer was passed through silica gel bead. The solvent was evaporated and the residue was crystallized from MeOH to give the desired product (0.39 g; 100%), as creamy solid. $^1$H-NMR (CDCl$_3$) 3.83 (s, 3H); 3.87 (s, 3H); 3.91 (s, 3H); 6.93-6.96 (m, 2H); 7.06 (s, 2H); 7.62 (s, 1H); 8.22 (d, 1H, J=9.36 Hz); 9.24 (broad s, 1H).

Step C: (1-(4-Bromophenylsulfonyl)-6-methoxy-1H-indol-3-yl)(3,4,5-trimethoxyphenyl)methanone A mixture of the product of Step B (0.15 g, 0.44 mmol) and 4-bromo-sulphonyl chloride (0.125 g; 0.49 mmol) was stirred in a mixture of CH$_2$Cl$_2$/Et$_3$N (5 ml:1 ml) for 3 h. The solvent was distilled and the residue was taken up in EtOAc, filtered and the filtrate was evaporated to dryness. The residue was purified by FCC (SiO$_2$) to give the desired product (0.165 g; 67%), as pale solid. $^1$H-NMR (CDCl$_3$) 3.89 (s, 3H); 3.92 (s, 6H); 3.95 (s, 3H, OMe), 7.00 (dd, 1H, J=2.07, 8.82 Hz); 7.10 (s, 2H); 7.47 (d, 1H, J=2.16 Hz); 7.59 (d, 2H, J=8.4 Hz); 7.73 (d, 2H, J=8.37 Hz); 7.88 (s, 1H); 8.09 (d, 1H, J=8.82 Hz).

Step D: tert-Butyl-5-((4-(6-methoxy-3-(3,4,5-trimethoxybenzoyl)-1H-indol-1-ylsulfonyl)phenyl) ethynyl)-2,2-dimethyl-1,3-dioxan-5-ylcarbamate When tert-butyl-5-ethynyl-2,2-dimethyl-1,3-dioxan-5-ylcarbamate was substituted for 1-octyne and the product of Step C was substituted for 5-iodo-2-tritylisoindoline in Example 2, Step D, the similar process afforded the title compound in 56% yield, as yellow paste. $^1$H-NMR (CDCl$_3$) 1.41 (s, 3H); 1.43 (s, 9H); 1.45 (s, 3H), 3.88 (s, 3H), 3.90 (s, 6H), 3.95 (s, 3H), 3.96 (d, 2H, J=11.58 Hz); 4.05 (d, 2H, J=11.45 Hz); 7.0 (dd, 1H, J=2.25, 8.82 Hz); 7.00 (s, 2H); 7.44 (broad s, 1H); 7.46 (d, 2H, J=8.7 Hz); 7.80 (d, 2H, J=8.61 Hz); 7.89 (s, 1H); 8.08 (d, 1H, J=8.82 Hz), Step E: tert-Butyl-5-(4-(6-methoxy-3-(3,4,5-trimethoxybenzoyl)-1H-indol-1-ylsulfonyl)phenethyl)-2,2-dimethyl-1,3-dioxan-5-ylcarbamate A mixture of the product of Step D (0.09 g, 0.12 mmol) and 10% Pd/C (0.04 g) was stirred for 16 h under H$_2$ (balloon). The catalyst was removed by filtration through Celite pad, the filtrate evaporated to dryness, to give the product (0.065 g; 73%), as pale paste. $^1$H-NMR (CDCl$_3$) 1.37 (s, 3H); 1.40 (s, 3H); 1.42 (s, 9H); 1.87-1.93 (m, 2H); 2.52-2.57 (m, 2H); 3.62 (d, 2H, J=11.77 Hz); 3.80 (d, 2H, J=11.55 Hz); 3.89 (s, 3H); 3.90 (s, 6H); 3.95 (s, 3H); 6.98 (dd, 1H, J=2.26, 8.80 Hz); 7.11 (s, 2H); 7.26 (d, 2H, J=8.37 Hz); 7.49 (d, 1H, J=2.16 Hz); 7.78 (d, 2H, J=8.37 Hz); 7.91 (s, 1H); 8.09 (d, 1H, J=8.8 Hz).

Step F: (1-(4-(3-Amino-4-hydroxy-3-(hydroxymethyl)butyl)phenylsulfonyl)-6-methoxy-1H-indol-3-yl)(3,4,5-trimethoxyphenyl)methanone When the product of Step E was substituted for tert-butyl-2,2-dimethyl-5-(4-(3-(3-(2,2,2-trifluoroacetyl)-1H-indol-1-yl)propyl)phenethyl)-1,3-dioxan-5-ylcarbamate in Example 11, Step F, the identical process afforded the title compound in 65% yield, as colourless solid. $^1$H-NMR (D$_2$O) 1.65-1.68 (m, 2H); 2.44-2.46 (m, 2H); 3.50 (s, 3H); 3.56 (s, 3H); 3.59 (s, 6H), 6.10 (d, 1H, J=8.77 Hz); 6.55 (broad s, 2H); 6.98 (s, 2H); 7.18-7.20 (m, 2H); 7.60-7.62 (m, 3H).

Example 14

(1-(3-(4-(3-Amino-4-hydroxy-3-(hydroxymethyl) butyl)phenyl)propyl)-6-methoxy-1H-indol-3-yl)(3,4, 5-trimethoxyphenyl)methanone hydrochloride Step A: 1-(3-Bromoprop-1-ynyl)-4-iodobenzene When propyrgyl alcohol was substituted for 1-octyne and 1,4-diiodobenzene was substituted for 5-iodo-2-tritylisoindoline in Example 2, Step D, the similar process afforded 3-(4-iodophenyl)prop-2-yn-1-ol in 78% yield, as yellow paste. This (0.33 g, 1.29 mmol) was dissolved in anhydrous CH$_2$Cl$_2$ (10 ml) and CBr$_4$ (0.513 g, 1.55 mmol) was added, followed by the addition of PPh$_3$ (0.406 g, 1.55 mmol). The mixture was stirred for 1 h at room temperature and solvent was evaporated. The residue was diluted to 10 ml with EtOAc and hexane (10 ml) was added. This was passed through silica gel bead. The filtrate was evaporated to give the desired product (0.315 g; 77%), which was used as such in next step. $^1$H-NMR (CDCl$_3$) 4.11 (s, 2H); 7.14 (d, 2H, J=8.41 Hz); 7.64 (d, 2H, J=8.4 Hz).

Step B: (1-(3-(4-Iodophenyl)prop-2-ynyl)-6-methoxy-1H-indol-3-yl)(3,4,5-trimethoxyphenyl)methanone To a stirred suspension of (6-methoxy-1H-indol-3-yl)(3,4,5-trimethoxyphenyl)methanone (0.69 g, 0.5 mmol) and K$_2$CO$_3$ in anhydrous DMF (2 ml) was added the solution of 1-(3-bromoprop-1-ynyl)-4-iodobenzene (0.150 g, 0.47 mmol) in anhydrous DMF (0.5 ml) and the resulting mixture was stirred at 50° C. for 2 h, diluted with saturated solution of NH$_4$Cl (5 ml) and diluted to 30 ml with EtOAc. The organic layer was washed with H$_2$O and dried over MgSO$_4$ and filtered. The filtrate was evaporated to dryness and the residue was purified by FCC (SiO$_2$), to give the desired product (0.079 g; 32%), as light yellow paste. $^1$H-NMR (CDCl$_3$) 3.84 (s, 6H); 3.89 (s, 3H); 3.91 (s, 3H); 5.06 (s, 2H); 6.94 (d, 1H, J=2.06 Hz); 7.00 (dd, 1H, J=2.22, 7.1 (s, 2H); 8.75 Hz); 7.1 (d, 2H, J=8.27 Hz); 7.65 (d, 2H, J=8.42 Hz); 7.72 (s, 1H); 8.25 (d, 1H, J=8.78 Hz).

Step C: tert-Butyl-5-((4-(3-(6-methoxy-3-(3,4,5-trimethoxybenzoyl)-1H-indol-1-yl)prop-1-ynyl)phenyl)ethynyl)-2,2-dimethyl-1,3-dioxan-5-ylcarbamate When tert-butyl 5-ethynyl-2,2-dimethyl-1,3-dioxan-5-ylcarbamate was substituted for 1-octyne and the product of Step B was substituted for 5-iodo-2-tritylisoindoline in Example 2, Step D, the similar process afforded the title compound in 48% yield, as a light yellow paste. $^1$H-NMR (CDCl$_3$) 1.43 (s, 3H); 1.46 (s, 9H); 1.49 (s, 3H); 3.84 (s, 6H); 3.9 (s, 3H); 3.91 (s, 3H); 4.00 (d, 2H, J=11.34 Hz); 4.1 (d, 2H, J=11.35 Hz); 5.08 (s, 2H); 5.19 (s, 1H); 6.95 (d, 1H, J=2.04 Hz); 7.00 (dd, 1H, J=2.18, 8.75 Hz); 7.11 (s, 2H); 7.3 (d, 2H, J=8.5 Hz); 7.35 (d, 2H, J=8.49 Hz); 7.74 (s, 1H); 8.25 (d, 1H, J=8.7 Hz).

Step D: tert-Butyl-5-(4-(3-(6-methoxy-3-(3,4,5-trimethoxybenzoyl)-1H-indol-1-yl)propyl)phenethyl)-2,2-dimethyl-1,3-dioxan-5-ylcarbamate A mixture of the product of Step C (0.03 g, 0.04 mmol) and 10% P/C (0.03 g) was stirred for 16 h, at room temperature, under H$_2$ (balloon). The catalyst was removed by filtration through Celite pad and the filtrate evaporated, to give the product (0.025 g), as colourless paste. $^1$H-NMR (CDCl$_3$) 1.4 (s, 3H); 1.41 (s, 3H); 1.45 (s, 9H); 1.91-1.97 (m, 2H); 2.14-2.22 (m, 2H); 2.48-2.55 (m, 2H); 2.62 (tr, 2H, J=7.32 Hz); 3.66 (d, 2H, J=11.78 Hz); 3.87 (d, 2H, J=11.79 Hz); 3.91 (s, 3H); 4.09 (rt, 2H, J=7.18 Hz); 6.71 (d, 1H, J=2.12 Hz); 6.95 (dd, 1H, J=2.2, 8.78 Hz); 7.0 (d, 2H, J=8.06 Hz); 7.07 (s, 2H); 7.09 (d, 2H, J=8.12 Hz); 7.49 (s, 1H); 8.22 (d, 1H, J=8.76 Hz).

Step E: (1-(3-(4-(3-Amino-4-hydroxy-3-(hydroxymethyl)butyl)phenyl)propyl)-6-methoxy-1H-indol-3-yl)(3,4,5-trimethoxyphenyl)methanone hydrochloride When the product of Step C was substituted for tert-butyl-5-(4-(6-methoxy-3-(3,4,5-trimethoxybenzoyl)-1H-indol-1-ylsulfonyl)phenethyl)-2,2-dimethyl-1,3-dioxan-5-ylcarbamate in Example 13, Step F, the similar process afforded the title compound in 65% yield. $^1$H-NMR (CD$_3$OD) 1.86-1.92 (m, 2H); 2.13-2.18 (m, 2H); 2.55-2.62 (m, 4H); 3.66 (s, 4H); 3.82 (s, 3H); 3.83 (s, 3H); 3.86 (s, 6H); 4.21 (tr, 1H, J=6.7 Hz); 6.87-6.92 (m, 2H); 7.03-7.1 (m, 5H); 7.72 (5, 1H); 8.10 (d, 1H, J=8.59 Hz).

Example 15

2-Amino-2-(4-(2-(6-methoxybenzofuran-2-yl)ethyl)phenethyl)propane-1,3-diol hydrochloride

Step A: Ethyl 2-(2-formyl-5-methoxyphenoxy)acetate

A mixture of 2-hydroxy-4-methoxybenzaldehyde (1 g; 6.58 mmol), BrCH$_2$CO$_2$Et (0.806 ml; 7.24 mmol) and K$_2$CO$_3$ (1 g, 7.24 mmol) in anhydrous DMF (5 ml) was stirred overnight at room temperature. The mixture was diluted with EtOAc (100 ml) and H$_2$O (100 ml). The organic layer was separated and dried over MgSO$_4$, and filtrate evaporated, to give the product (1.29 g, 97%), as colourless solid. $^1$H-NMR (CDCl$_3$) 1.28 (tr, 3H, J=7.11 Hz); 3.84 (s, 3H); 4.25 (q, 2H, J=7.14, 14.28 Hz); 4.69 (s, 2H); 6.30 (d, 1H, J=2.16 Hz); 6.58 (dd, 1H, J=1.77, 8.73 Hz); 7.83 (d, 1H, J=8.7 Hz); 10.36 (s, 1H).

Step B: Ethyl 6-methoxybenzofuran-2-carboxylate

A mixture of the product of Step A (1.28 g, 5.37 mmol) and DBU (0.3 ml) was heated for 3 h at 160° C. with stirring, cooled to room temperature and dissolved in EtOAc:MeOH mixture (99:1). The mixture was filtered through the silica bead and the filtrate was evaporated to give the title compound (1.11 g; 77%), as colourless solid. $^1$H-NMR (CDCl$_3$) 1.40 (tr, 3H, J=7.13 Hz); 3.85 (s, 3H); 4.40 (q, 2H, J=7.13, 14.25 Hz); 4.45 (s, 1H); 6.91 (dd, 1H, J=2.25, 8.68 Hz); 7.04 (d, 1H, J=1.87 Hz); 7.51 (d, 1H, J=5.17 Hz),

Step C: 6-Methoxybenzofuran-2-carbaldehyde

To a stirred slurry LiAlH$_4$ (0.114 g, 3 mmol) in anhydrous Et$_2$O (5 ml) was added drop wise the solution of ethyl-6-methoxybenzofuran-2-carboxylate (0.380 g, 1.73 mmol) and stirring was continued for 0.5 h at room temperature. The reaction mixture was quenched with EtOAc:H$_2$O:MeOH mixture (7:3:1), diluted to 20 ml with EtOAc and filtered through Celite. The filtrate was evaporated and the residue was dried in vacuo to give the creamy paste (0.324 g) which was used as such for next step. This (0.310 g) was dissolved in anhydrous dioxane (10 ml) and MnO$_2$ (1 g, excess) was added to it. The suspension was stirred at reflux for 3 h, cooled to room temperature and filtered through Celite pad. The filtrate was evaporated to dryness and the residue was purified by FCC (SiO$_2$, hexane: EtOAc; 70:30), to give the title compound (0.182 g; 76%), as light pink crystalline solid. $^1$H-NMR (CDCl$_3$) 3.87 (s, 3H); 6.96 (dd, 1H, J=2.22, 8.73 Hz); 7.03 (d, 1H, J=1.83 Hz); 7.48 (5, 1H); 7.59 (d, 1H, J=8.7 Hz); 9.74 (s, 1H).

Step D: 2-Ethynyl-6-methoxybenzofuran

A mixture of 6-methoxybenzofuran-2-carbaldehyde (0.21 g, 1.19 mmol), dimethyl(1-diazo-2-oxopropyl)phosphonate (0.27 g, 1.43 mmol) and K$_2$CO$_3$ (0.33 g, 2.4 mmol) in anhydrous MeOH (5 ml) was stirred overnight at room temperature. The solvent was evaporated and the residue was taken in EtOAc (50 ml), washed with H$_2$O and dried over MgSO$_4$ and filtered. The filtrate was evaporated to dryness to give the crude product (0.18 g; 88%), which was used in the next step without purification. $^1$H-NMR (CDCl$_3$) 1.53 (s, 1H); 3.82 (s, 3H); 6.87 (dd, 1H, J=2.25, 8.58 Hz), 6.92 (s, 1H); 6.95 (d, 1H, J=2.01 Hz); 7.39 (d, 1H, J=8.61 Hz).

Step E: tert-Butyl 5-((4-((6-methoxybenzofuran-2-yl)ethynyl)phenyl)-ethynyl)-2,2-dimethyl-1,3-dioxan-5-ylcarbamate When the product of Step D was substituted for 1-octyne and tert-butyl-5-((4-iodophenyl)ethynyl)-2,2-dimethyl-1,3-dioxan-5-ylcarbamate was substituted for 5-iodo-2-tritylisoindoline in Example 2, Step D, the similar process afforded the title compound in 90% yield, as a light yellow paste. $^1$H-NMR (CDCl$_3$) 1.44 (s, 3H); 1.47 (s, 9H); 1.49 (s, 3H); 3.85 (s, 3H); 4.02 (d, 2H, J=11.34 Hz); 4.09 (d, 2H, J=11.38

Hz); 5.20 (s, 1H); 6.88 (dd, 1H, J=2.24, 8.6 Hz); 6.93 (s, 1H); 6.96 (d, 1H, J=1.97 Hz); 7.38-7.41 (m, 3H); 7.46 (d, 2H, J=8.44 Hz).

Step F: tert-Butyl-5-(4-(2-(6-methoxybenzofuran-2-yl)ethyl)phenethyl)-2,2-dimethyl-1,3-dioxan-5-ylcarbamate When the product of Step E was substituted for tert-butyl-5-((4-(3-(6-methoxy-3-(3,4,5-trimethoxybenzoyl)-1H-indol-1-yl)prop-1-ynyl)phenyl)ethynyl)-2,2-dimethyl-1,3-dioxan-5-ylcarbamate in Example 14, Step D, the similar process afforded the title compound in 69%, as light creamy crystalline compound. $^1$H-NMR CDCl$_3$) 1.40 (s, 3H); 1.42 (s, 3H); 1.46 (s, 9H); 1.92-2.03 (m, 2H); 2.49-2.55 (m, 2H); 2.99 (s, 4H); 3.65 (d, 2H, J=11.79 Hz); 3.83 (s, 3H); 3.87 (d, 2H, J=11.76 Hz); 4.94 (s, 1H); 6.25 (s, 1H); 6.80 (dd, 1H, J=2.24, 8.48 Hz); 6.97 (d, 1H), J=1.95 Hz); 7.09 (s, 4H); 7.30 (d, 2H, J=8.48 Hz).

Step G: 2-Amino-2-(4-(2-(6-methoxybenzofuran-2-yl)ethyl phenethyl-)propane-1,3-diol hydrochloride When the product of Step F was substituted for tert-butyl-5-(4-(6-methoxy-3-(3,4,5-trimethoxybenzoyl)-1H-indol-1-ylsulfonyl)-phenethyl)-2,2-dimethyl-1,3-dioxan-5-ylcarbamate in Example 13, Step F, the similar process afforded the title compound in 69% yield, as a light creamy solid. $^1$H-NMR (CDCl$_3$) 3.20-3.26 (m, 2H); 3.89-3.95 (m, 2H); 4.29 (s, 4H); 4.97 (d, 2H, J=11.97 Hz); 5.03 (d, 2H, J=12.03 Hz); 4.6 (s, 3H), 6.25 (s, 1H), 7.56 (s, 1H), 8.09 (dd, 1H, J=2.25, 8.52 Hz); 8.27 (b, 1H); 8.41 (s, 4H); 8.6 (d, 2H, J=8.9 Hz).

Example 16

4-(3-Amino-4-hydroxy-3-(hydroxymethyl)butyl)-N-(3-methoxyphenyl)-N-methyl benzenesulfonamide

Step A: 4-Bromo-N-(3-methoxyphenyl)benzenesulfonamide

To a stirred solution of aniline (0.482 g, 3.92 mmol) in anhydrous pyridine (5 ml) was added 4-bromobenzene-sulphonyl chloride (0.5 g, 1.96 mmol) and the mixture was stirred for 0.5 h. The solvent was evaporated and the residue was purified by FCC (SiO$_2$), to give the title compound (0.51 g; 37%), as a creamy paste. $^1$H-NMR (CDCl$_3$) 3.71 (s, 3H); 4.37 (s, 2H); 6.61-6.69 (m, 2H); 7.10 (tr, 1H, J=8.09 Hz), 7.52 (d, 2H, J=8.57 Hz); 7.65 (d, 2H, J=8.57 Hz).

Step B: 4-Bromo-N-(3-methoxyphenyl)-N-methyl-benzenesulfonamide

To a stirred solution of 4-bromo-N-(3-methoxyphenyl) benzenesulphonamide (0.5 g 1.46 mmol) and K$_2$CO$_3$ (0.5 g) in anhydrous DMF (7 ml) MeI (1 ml) was added and this was stirred at 50° C. for 0.5 h. The mixture was diluted to 50 ml with H$_2$O and extracted in EtOAc (50 ml). The organic layer was washed with H$_2$O, dried over MgSO$_4$, filtered and the filtrate was passed through silica gel bead. The filtrate was evaporated to dryness to give the product (0.5 g; 96%), as a pale solid. $^1$H-NMR (CDCl$_3$) 3.14 (5, 3H); 3.75 (s, 3H); 6.58 (broad d, 1H), 6.69 (t, 1H, J=2.20 Hz), 6.80 (dd, 1H, J=2.5, 8.34, Hz); 7.18 (tr, 1H, J=8.15 Hz); 7.40 (d, 2H, J=8.67 Hz); 7.58 (d, 2H, J=8.64 Hz).

Step C: tert-Butyl-5-((4-(N-(3-methoxyphenyl)-N-methylsulfamoyl)phenyl)ethynyl)-2,2-dimethyl-1,3-dioxan-5-ylcarbamate When tert-butyl 5-ethynyl-2,2-dimethyl-1,3-dioxan-5-yl-carbamate was substituted for 1-octyne and the product of Step B was substituted for 5-iodo-2-tritylisoindoline in Example 2, Step D, the similar process afforded the title compound in 59% yield, as a creamy paste. $^1$H-NMR (CDCl$_3$) 1.45 (s, 3H); 1.46 (s, 9H); 1.49 (5, 3H); 1.58 (s, 2H); 2.63 (s, 2H); 3.13 (s, 3H); 3.75 (s, 3H); 3.96 (d, 2H, J=17.23 Hz), 4.07 (d, 2H, J=17.23 Hz); 6.54 (dd, 1H, J=1.66, 7.92 Hz), 6.69 (tr, 1H, J=2.18 Hz); 6.79 (dd, 1H, J=2.39, 10.68 Hz); 7.16 (tr, 1H, J=8.15 Hz); 7.47 (s, 4H).

Step D: tert-Butyl-5-(4-(N-(3-methoxyphenyl)-N-methylsulfamoyl)phenethyl)-2,2-dimethyl-1,3-dioxan-5-ylcarbamate When the product of Step C was substituted for tert-butyl-5-((4-(3-(6-methoxy-3-(3,4,5-trimethoxybenzoyl)-1H-indol-1-yl)prop-1-ynyl)phenyl)ethynyl)-2,2-dimethyl-1,3-dioxan-5-ylcarbamate in Example 14, Step D, the similar process afforded the title compound in 59%, as creamy paste. $^1$H-NMR (CDCl$_3$) 1.45 (s, 3H); 1.46 (s, 9H); 1.49 (s, 3H); 1.58 (s, 2H); 2.63 (5, 2H); 3.13 (s, 3H); 3.75 (s, 3H), 3.96 (d, 2H, J=17.23 Hz); 4.07 (d, 2H, J=17.23 Hz); 6.54 (dd, 1H, J=1.66, 7.92 Hz); 6.69 (tr, 1H, J=2.18 Hz); 6.79 (dd, 1H, J=2.39, 10.68 Hz); 7.16 (tr, 1H, J=8.15 Hz); 7.47 (s, 4H).

Step E: 4-(3-Amino-4-hydroxy-3-(hydroxymethyl) butyl)-N-(3-methoxy-phenyl)-N-methyl benzenesulfonamide When the product of Step D was substituted for tert-butyl-5-(4-(6-methoxy-3-(3,4,5-trimethoxybenzoyl)-1H-indol-1-ylsulfonyl)phenethyl)-2,2-dimethyl-1,3-dioxan-5-ylcarbamate in Example 13, Step F, the similar process afforded the title compound in 80% yield, as colourless solid. $^1$H-NMR (CDCl$_3$) 1.87-1.93 (m, 2H); 2.65-2.71 (m, 2H); 3.05 (s, 3H); 3.62 (s, 3H); 3.70 (5, 4H); 6.55 (tr, 1H, J=2.20 Hz); 6.62 (d, 1H, J=7.62 Hz); 6.85 (dd, 1H, J=2.41, 8.34 Hz); 7.19 (tr, 1H, J=8.22 Hz); 7.34 (d, 2H, J=8.36 Hz); 7.43 (d, 2H, J=8.31 Hz).

Example 17

((E)-2-Amino-2-(2-(4'-(((4-fluorophenyl)(isopropyl) amino)methyl)biphenyl-4-yl)vinyl)propane-1,3-diol hydrochloride salt

Step A: tert-Butyl-5-((4-bromophenyl)ethynyl)-2,2-dimethyl-1,3-dioxan-5-ylcarbamate When tert-butyl 5-ethynyl-2,2-dimethyl-1,3-dioxan-5-yl-carbamate was substituted for 1-octyne and 4-bromo-iodo-benzene was substituted for 5-iodo-2-tritylisoindoline in Example 2, Step D, the similar process afforded the title compound in 63% yield, as a pale paste, which solidified on standing. $^1$H-NMR (CDCl$_3$) 1.43 (s, 2H); 1.46 (s, 9H); 1.48 (s, 3H); 4.00 (d, 2H, J=11.35 Hz); 4.08 (d, 2H, J=11.41 Hz); 5.19 (s, 1H); 7.26 (d, 2H, J=6.74 Hz); 7.41 (d, 2H, J=6.67 Hz).

Step B: tert-Butyl-5-((4'-formylbiphenyl-4-yl)ethynyl)-2,2-dimethyl-1,3-dioxan-5-yl carbamate To a stirred solution of the product of Step A (0.18 g; 0.44 mmol) and 4-carbaldehyde-boronic acid (0.1 g, 0.67 mmol)

in 1,4-dioxane (12 ml) Pd(PPh$_3$)$_4$ (0.05 g) was added at 80° C., followed by the addition of solution of NaHCO$_3$ (0.185 g) in H$_2$O (2 ml). This was stirred at reflux for 1 h and the solvents were evaporated. The residue was taken in EtOAc (100 ml) and washed with H$_2$O. The organic layer separated, dried over MgSO$_4$, filtered and the filtrate evaporated to dryness. The residue was purified by FCC (SiO$_2$) to give the titled product (0.173 g; 90%), as pale solid. $^1$H-NMR (CDCl$_3$) 1.48 (s, 2H); 1.5 (s, 9H); 1.61 (s, 3H); 4.0 (d, 2H, J=11.28 Hz); 4.10 (d, 2H, J=13.95 Hz); 5.22 (s, 1H); 7.5-7.7 (m, 4H), 7.72 (d, 2H, J=8.23 Hz); 7.94 (d, 2H, J=8.31 Hz); 10.04 (s, 1H).

Step C: (E)-tert-Butyl 4-(4'-(((4-fluorophenyl)(isopropyl)amino)-methyl)biphenyl-4-yl)-1-hydroxy-2-(hydroxymethyl)but-3-en-2-ylcarbamate To a stirred solution of the product of Step B (0.08 g, 0.18 mmol) and N-isopropyl-4-fluoroaniline (0.031 g; 0.2 mmol) in 1,2-dichloroethane (5 ml) DIPEA (4 drops) was added followed by AcOH (5 drops) and the addition NaBH(OAc)$_3$ (0.078 g, 0.36 mmol). The mixture was stirred for overnight at room temperature, than diluted to 20 ml with EtOAc, washed with H$_2$O, brine, dried over MgSO$_4$, filtered and filtrate evaporated to dryness. The residue was purified by crystallization from MeOH to give the title compound (0.09 g; 94%), as colourless solid. $^1$H-NMR (CDCl$_3$) 1.31-1.36 (m, 15H); 3.77 (d, 1H, J=11.66 Hz); 3.92 (d, 2H, J=11.66 Hz); 4.33 (s, 2H); 5.19 (s, 1H, NH); 5.59 (d, 1H, J=12.61 Hz); 6.55-6.59 (m, 2H); 6.68 (d, 1H, J=12.65 Hz); 6.88 (tr, 1H, 6.79 Hz); 7.31 (d, 2H, J=8.04 Hz); 7.41 (d, 2H, J=8.23 Hz); 7.49 (d, 2H, J=8.23 Hz), 7.54 (d, 2H, J=8.22 Hz).

Step D: ((E)-2-Amino-2-(2-(4'-(((4-fluorophenyl)(isopropyl)amino)methyl)-biphenyl-4-yl)vinyl)propane-1,3-diol hydrochloride salt When the product of Step E was substituted for tert-butyl-5-(4-(6-methoxy-3-(3,4,5-trimethoxybenzoyl)-1H-indol-1-ylsulfonyl)-phenethyl)-2,2-dimethyl-1,3-dioxan-5-ylcarbamate in Example 13, Step F, the similar process afforded the title compound in 56% yield, as colourless solid. $^1$H-NMR (CDCl$_3$) 1.00 (d, 6H, J=6.13 Hz); 3.50 (tr, 4H, J=12.47 Hz); 3.74-3.87 (m, 1H); 4.34 (s, 2H); 5.53 (d, 1H, J=12.77 Hz); 6.73 (d, 1H, J=12.74 Hz); 7.13 (d, 2H, J=7.84 Hz); 7.24-7.28 (m, 4H); 7.36-7.41 (m, 4H), 7.94 (tr, 2H, J=8.17 Hz).

Example 18

2-Amino-2-(2-(4'-methylbiphenyl-4-yl)ethyl)propane-1,3-diol

Step A: tert-Butyl-2,2-dimethyl-5-(2-(4'-methylbiphenyl-4-yl)ethyl)-1,3-dioxan-5-yl carbamate A mixture of (E)-tert-butyl-5-(2-(4'((4-fluorophenylamino)methyl)biphenyl-4-yl)vinyl)2,2-dimethyl-1,3-dioxan-5-ylcarbamate (0.071 g, 0.13 mmol) and 10% Pd/C (0.025 g) was stirred for 4 h in EtOAc (10 ml), under H$_2$ (balloon). The catalyst was removed by filtration through Celite pad, the filtrate evaporated to dryness to give the title product (0.026 g; 47%), as colourless solid. $^1$H-NMR (CDCl$_3$) 1.41 (s, 3H); 1.43 (s, 3H); 1.47 (s, 9H); 1.97-2.03 (m, 2H); 2.37 (s, 3H); 2.56-2.62 (m, 2H); 3.68 (d, 2H, J=11.74 Hz); 3.90 (d, 2H, J=11.72 Hz); 4.98 (s, 1H); 7.2-7.24 (m, 4H); 7.43-7.48 (m, 4H).

Step B: 2-Amino-2-(2-(4'-methylbiphenyl-4-yl)ethyl)propane-1,3-diol

When the product of Step A was substituted for tert-butyl-5-(4-(6-methoxy-3-(3,4,5-trimethoxybenzoyl)-1H-indol-1-ylsulfonyl)-phenethyl)-2,2-di methyl-1,3-dioxan-5-ylcarbamate in Example 13, Step F, the similar process afforded the title compound in 67% yield, as colourless solid. $^1$H-NMR (CDCl$_3$) 3.17-3.23 (m, 2H); 3.63 (s, 3H); 3.94-3.88 (m, 2H); 4.91 (d, 2H, J=12.36 Hz); 4.97 (d, 2H, J=11.94 Hz); 8.12 (tr, 4H, J=10.92 Hz); 8.66-8.88 (m, 4H).

Example 19

4-(3-Amino-4-hydroxy-3-(hydroxymethyl)butyl)-N-(6,6-dimethylbicyclo[3.1.1]heptan-2-yl)benzenesulfonamide Step A: 4-Bromo-N-(6,6-dimethylbicyclo[3.1.1]heptan-2-yl)benzenesulfonamide To a stirred solution of 4-bromo-benzenesulphonyl chloride (0.6 g, 2.34 mmol) in anhydrous CH$_2$Cl$_2$ (5 ml) and Et$_3$N (0.65 ml) (−)cis-myrtanylamine (0.36 g; 2.34 mmol) was added at 0° C. and the stirring was continued overnight at room temperature. The reaction mixture was diluted to 15 ml with CH$_2$Cl$_2$, washed with H$_2$O (2×100 ml). The organic layer was separated, dried over MgSO$_4$ and filtered. The filtrate was evaporated to dryness to give the title compound (0.87 g; 100%), as pale paste, which solidified on standing. $^1$H-NMR (CDCl$_3$) 0.86 (s, 3H); 1.11 (s, 3H); 1.31-1.39 (m, 1H); 1.81-1.91 (m, 6H); 2.06-2.11 (m, 1H); 2.29-2.32 (m, 1H); 2.91 (tr, 2H, J=7.59 Hz); 6.64 (d, 2H, J=6.90 Hz); 7.70 (d, 2H, J=6.78 Hz).

Step B: tert-Butyl-5-((4-(N-(6,6-dimethylbicyclo[3.1.1]heptan-2-yl)sulfamoyl)phenyl)ethynyl)-2,2-dimethyl-1,3-dioxan-5-ylcarbamate When tert-butyl 5-ethynyl-2,2-dimethyl-1,3-dioxan-5-ylcarbamate was substituted for 1-octyne and the product of Step A was substituted for 5-iodo-2-tritylisoindoline in Example 2, Step D, the similar process afforded the title compound in 46% yield, as a creamy paste. $^1$H-NMR (CDCl$_3$) 0.85 (s, 3H); 1.1 (s, 3H); 1.44 (s, 3H); 1.46 (s, 9H); 1.48 (s, 3H); 1.63-1.65 (m, 2H); 1.79-1.86 (m, 5H); 2.05-2.08 (m, 1H); 2.27-2.32 (m, 1H); 2.89 (tr, 2H, J=6.59 Hz); 4.0-4.13 (m, 4H); 4.6 (broad s, 1H); 5.23 (s, 1H); 7.52 (d, 2H, J=8.25 Hz); 7.75 (d, 2H, J=8.46 Hz).

Step C: tert-Butyl 5-(4-(N-(6,6-dimethylbicyclo[3.1.1]heptan-2-yl)sulfamoyl)phenethyl)-2,2-dimethyl-1,3-dioxan-5-ylcarbamate A mixture of the product of Step B (0.075 g, 0.14 mmol) and 10% Pd/C (0.04 g) in EtOH (10 ml) was stirred for 16 h under H$_2$. The catalyst was removed by filtration through Celite pad and the filtrate was evaporated to dryness, to give the desired product (0.067 g; 87%), as creamy gum. $^1$H-NMR (CDCl$_3$) 0.84 (s, 3H); 1.09 (s, 3H); 1.44 (m, 10H); 1.85 (m, 6H); 2.10 (m, 1H); 2.29 (m, 1H); 2.67 (m, 2H); 2.90 (m, 2H); 3.66 (m, 2H); 3.82 (m, 2H); 4.33 (s, 1H); 5.10 (s, 1H); 7.32 (m, 2H); 7.74 (m, 2H).

Step D: 4-(3-Amino-4-hydroxy-3-(hydroxymethyl)butyl)-N-(6,6-dimethylbicyclo[3.1.1]heptan-2-yl)benzenesulfonamide When the product of Step C was substituted for tert-butyl-5-(4-(6-methoxy-3-(3,4,5-trimethoxybenzoyl)-1H-indol-1- ylsulfonyl)-phenethyl)-2,2-dimethyl-1,3-dioxan-5-ylcarbamate in Example 13, Step F, the similar process afforded the title compound in 80% yield, as colourless solid. $^1$H-NMR (D$_2$O) 0.67 (s, 3H); 0.94 (s, 3H); 1.14-1.17 (m, 2H); 1.71 (m, 6H); 1.88-2.01 (b, 4H); 2.17 (m, 1H); 2.67-2.78 (m, 4H); 3.68 (s, 4H); 7.42 (d, 2H, J=8.17 Hz); 7.70 (d, 2H, J=8.18 Hz).

Example 20

2-Amino-2-(4-(3-((4-fluorophenyl)(methyl)amino) propyl)phenethyl)propane-1,3-diol hydrochloride salt Step A: 4-Fluoro-N-propyrgylaniline A mixture of 4-fluoroaniline (0.950 ml, 9.9 mmol), propyrgyl bromide (1.6 ml) and K$_2$CO$_3$ (1.62 g, 11.7 mmol) in anhydrous DMF (10 ml) was stirred for 5 h at room temperature. The mixture was quenched with the solution of NH$_4$Cl and extracted with EtOAc. The organic layer was separated, dried over MgSO$_4$ and filtered. The filtrate was evaporated to dryness and the residue was purified by FCC (SiO$_2$) to give the desired product (1.3 g; 87%), as yellow oil. $^1$H-NMR (CDCl$_3$) 2.20 (tr, 1H, J=2.37 Hz); 3.76 (broad s, 1H); 3.89 (broad s, 2H); 6.6-6.64 (m, 2H); 6.89-6.94 (m, 2H).

Step B: tert-Butyl 5-((4-(3-(4-fluorophenylamino) prop-1-ynyl)phenyl)-ethynyl)-2,2-dimethyl-1,3-dioxan-5-ylcarbamate When 4-fluoro-N-propyrgylaniline was substituted for 1-octyne and tert-butyl-5-((4-bromophenyl)ethynyl)-2,2-dimethyl-1,3-dioxan-5-ylcarbamate was substituted for 5-iodo-2-tritylisoindoline in Example 2, Step D, the similar process afforded the title compound in 96% yield, as a pale paste, which solidified on standing. $^1$H-NMR (CDCl$_3$) 1.43 (s, 3H); 1.46 (s, 9H); 1.48 (s, 3H); 3.92-4.14 (m, 6H); 5.18 (s, 1H); 6.63-6.67 (m, 2H); 6.88-6.95 (m, 2H); 7.24-7.33 (m, 4H).

Step C: tert-Butyl-5-(4-(3-(4-fluorophenylamino) propyl)phenethyl)-2,2-dimethyl-1,3-dioxan-5-ylcarbamate When the product of Step B was substituted for tert-butyl-5-((4-(N-(6,6-dimethylbicyclo[3.1.1]heptan-2-yl)sulfamoyl)phenyl-)ethynyl)-2,2-dimethyl-1,3-dioxan-5-ylcarbamate in Example 19, Step C, the similar process afforded the title compound in 94% yield, as creamy gum. $^1$H-NMR (CDCl$_3$) 1.42 (s, 3H); 1.44 (s, 3H); 1.46 (s, 9H); 1.87-1.96 (m, 4H); 2.5-2.56 (m, 2H); 2.67 (tr, 2H, J=7.32 Hz); 3.04 (tr, 2H, J=7.05 Hz); 3.86 (d, 2H, J=11.8 Hz); 3.88 (d, 2H, J=11.7 Hz); 4.9 (s, 1H); 6.45-6.50 (m, 2H); 6.82-6.88 (m, 2H); 7.09 (s, 4H).

Step D: tert-Butyl 5-(4-(3-((4-fluorophenyl)(methyl) amino)propyl)phenethyl)-2,2-dimethyl-1,3-dioxan-5-ylcarbamate To a stirred solution of the product of Step C (0.04 g, 0.08 mmol), formaldehyde solution in H$_2$O (0.25 ml) in 1,2-dichloroethane (5 ml) 4 drops of DIPEA was added at room temperature, followed by 5 drops of AcOH and NaBH(OAc)$_3$ (0.04 g, 0.19 mmol). The mixture was stirred overnight at room temperature and diluted to 20 ml with CH$_2$Cl$_2$. The organic layer was washed with aqueous NaHCO$_3$, H$_2$O, dried over MgSO$_4$ and filtered. The filtrate was evaporated to dryness and the residue was purified by FCC (SiO$_2$) to give the product (0.035 g), as creamy paste. $^1$H-NMR (CDCl$_3$) 1.40 (s, 3H); 1.42 (s, 3H); 1.46 (s, 9H); 1.84-1.99 (m, 4H); 2.5-2.61 (m, 4H); 2.85 (s, 3H); 3.25 (tr, 2H, J=7.41 Hz); 3.66 (d, 2H, J=11.8 Hz); 3.88 (d, 2H, J=11.7 Hz); 4.85 (s, 1H); 6.54-6.59 (m, 2H); 6.86-6.92 (m, 2H); 7.07 (s, 4H).

Step E: 2-Amino-2-(4-(3-((4-fluorophenyl)(methyl) amino) propyl)phenethyl) propane-1,3-diol hydrochloride When the product of Step D was substituted for tert-butyl-5-(4-(6-methoxy-3-(3,4,5-trimethoxybenzoyl)-1H-indol-1-ylsulfonyl)-phenethyl)-2,2-dimethyl-1,3-dioxan-5-ylcarbamate in Example 13, Step F, the similar process afforded the title compound in 75% yield, as colourless solid. $^1$H-NMR (CDCl$_3$) 1.68-1.76 (m, 2H); 1.81-1.87 (m, 4H); 2.48-2.57 (m, 4H); 3.15 (s, 3H); 3.45 (tr, 2H, J=7.55 Hz); 3.65 (s, 4H); 7.01 (d, 2H, J=7.9 Hz); 7.11 (d, 2H, J=7.92 Hz); 7.21 (tr, 2H, J=8.47 Hz); 7.41-7.48 (m, 2H).

Example 21

2-Amino-2-(3-(3,4,5-trimethoxyphenethyl)phenethyl)propane-1,3-diol

Step A: tert-Butyl 5-((3-iodophenyl)ethynyl)-2,2-dimethyl-1,3-dioxan-5-ylcarbamate When tert-butyl 5-((3-iodophenyl)ethynyl)-2,2-dimethyl-1,3-dioxan-5-ylcarbamate was substituted for 1-octyne and 1,3-diiodobenzene was substituted for 5-iodo-2-tritylisoindoline in Example 2, Step D, the similar process afforded the title compound in 59% yield, as pale paste. $^1$H-NMR (CDCl$_3$) 1.43 (s, 3H); 1.46 (s, 9H); 3.50 (s, 3H); 3.99 (d, 2H, J=11.37 Hz); 4.07 (d, 2H, J=11.42 Hz); 5.19 (s, 1H); 7.0 (tr, 1H, J=7.85 Hz); 7.36 (broad d, 1H, J=7.76 Hz); 7.61 (d, 1H, J=6.74 Hz); 7.77 (tr, 1H, J=1.57 Hz).

Step B: tert-Butyl-2,2-dimethyl-5-((3-((3,4,5-trimethoxyphenyl)ethynyl)-phenyl)ethynyl)-1,3-dioxan-5-ylcarbamate When 3,4,5-trimethoxyphenyl-acetylene was substituted for 1-octyne and the product of Step A was substituted for 5-iodo-2-tritylisoindoline in Example 2, Step D, the similar process afforded the title compound in 64% yield, as pale paste. $^1$H-NMR (CDCl$_3$) 1.43 (s, 3H); 1.47 (s, 9H); 1.49 (s, 3H); 3.84 (s, 3H); 3.87 (s, 6H); 4.00 (d, 2H, J=11.4 Hz); 4.10 (d, 2H, J=11.33 Hz); 5.19 (broad s, 1H), 6.74 (s, 2H); 6.74-6.76 (m, 1H); 7.26-7.38 (m, 1H); 7.43 (d, 1H, J=7.67 Hz); 7.60 (broad s, 1H).

Step C: tert-Butyl-2,2-dimethyl-5-(3-(3,4,5-trimethoxyphenethyl)phenethyl)-1,3-dioxan-5-ylcarbamate A mixture of the product of Step B (0.09 g, 0.17 mmol) and 10% Pd/C (0.04 g) in EtOH (10 ml) was stirred for 36 h at room temperature under H$_2$. The catalyst was removed by filtration through Celite pad and the filtrate was evaporated to dryness to give the title product (0.063 g; 70%), as colourless paste. $^1$H-NMR (CDCl$_3$) 1.41 (s, 3H); 1.42 (s, 3H); 1.46 (s, 9H); 1.92-1.98 (m, 2H); 2.49-2.55 (m, 2H); 2.81-2.86 (m, 4H); 7.18 (tr, 1H, J=7.59 Hz). 3.67 (d, 2H, J=11.72 Hz); 3.80

(s, 6H); 3.83 (s, 3H); 3.88 (d, 2H, J=11.65 Hz); 5.01 (broad s, 1H); 6.37 (s, 2H); 6.98-7.01 (m, 3H).

Step D: 2-Amino-2-(3-(3,4,5-trimethoxyphenethyl) phenethyl)propane-1,3-diol

When the product of Step C was substituted for tert-butyl-5-(4-(6-methoxy-3-(3,4,5-trimethoxybenzoyl)-1H-indol-1-ylsulfonyl)-phenethyl)-2,2-dimethyl-1,3-dioxan-5-ylcarbamate in Example 13, Step F, the similar process afforded the title compound in 74% yield, as colourless solid. $^1$H-NMR (CDCl$_3$) 1.7-1.8 (m, 2H); 2.51-2.52 (m, 2H); 2.77 (s, 4H); 3.31-3.42 (m, 13H); 6.26 (s, 2H); 6.81 (s, 1H); 6.95-6.97 (m, 2H); 7.13 (tr, 1H, J=7.44 Hz).

Example 22

2-Amino-2-(3-(admantyl)-4-hydroxyphenethyl)propane-1,3-diol hydrochloride salt

Step A: 2-(1-Admantanyl)-4-iodophenol

To a solution of 4-iodophenol (0.5 g, 2.27 mmol) and admantol-1-ol (0.345 g, 2.27 mmol) in AcOH (3 ml) concentrated H$_2$SO$_4$ (0.5 ml) was added drop wise and the stirring was continued for 50 h, while a creamy solid was separated. The solvent was evaporated to half of the volume and the residue was poured onto ice cold water (100 ml) and EtOAc (150 ml) was added. The organic layer was separated, washed with the solution of NaHCO$_3$, dried over MgSO$_4$, and filtered. The filtrate was evaporated to dryness and the residue was purified by FCC (SiO$_2$) to give the title product (0.65 g; 77%), as pale solid. $^1$H-NMR (CDCl$_3$) 1.64 (m, 6H); 2.04-2.1 (m, 9H); 4.96 (s, 1H); 6.41 (d, 1H, J=8.28 Hz); 7.31 (dd, 1H, J=2.19, 8.28 Hz); 7.43 (d, 1H, J=2.13 Hz).

Step B: tert-Butyl-5-((3-admantyl)-4-hydroxyphenyl)ethynyl)2,2-dimethyl-1,3-dioxan-5-yl carbamate When tert-butyl-5-ethynyl-2,2-dimethyl-1,3-dioxan-5-ylcarbamate was substituted for 1-octyne and the product of Step A was substituted for 5-iodo-2-tritylisoindoline in Example 2, Step D, the similar process afforded the title compound in 36% yield, as pale paste. $^1$H-NMR (CDCl$_3$) 1.43 (s, 3H); 1.44 (s, 3H); 1.47 (s, 9H); 1.74 (m, 5H); 2.05 (m, 9H); 3.99 (d, 2H, J=11.43 Hz); 4.08 (d, 2H, J=11.46 Hz); 5.2 (broad s, 1H); 5.29 (broad s, 1H); 6.55 (d, 1H, J=8.16 Hz); 7.02 (broad d, 1H, J=8.1 Hz); 7.23 (d, 1H, J=1.98 Hz).

Step C: tert-Butyl-5-((3-admantyl)-4-hydroxyphenylethyl)2,2-dimethyl-1,3-dioxan-5-yl carbamate A mixture of the product of Step B (0.1 g, 0.21 mmol) and 10% Pd/C (0.1 g) in EtOH (5 ml) was stirred for 36 h under H$_2$. The catalyst was removed by filtration through Celite pad and filtrate was evaporated to dryness to give the title product (0.065 g; 64%). $^1$H-NMR (CDCl$_3$) 1.40 (s, 3H); 1.42 (s, 3H); 1.46 (s, 9H); 1.76 (m, 5H); 1.9-1.96 (m, 2H); 2.02-2.08 (m, 9H); 2.44-2.49 (m, 2H); 3.66 (d, 2H, J=11.72 Hz); 3.88 (d, 2H, J=11.56 Hz); 4.68 (broad s, 1H); 4.94 (broad s, 1H); 6.54 (d, 1H, J=8.04 Hz); 6.84 (broad d, 1H, J=8.1 Hz); 6.98 (d, 1H, J=1.73 Hz).

Step D: 2-Amino-2-(3-(admantyl)-4-hydroxyphenethyl)propane-1,3-diol hydrochloride When the product of Step C was substituted for tert-butyl-5-(4-(6-methoxy-3-(3,4,5-trimethoxybenzoyl)- 1H-indol-1-ylsulfonyl)-phenethyl)-2,2-dimethyl-1,3-dioxan-5-ylcarbamate in Example 13, Step F, the similar process afforded the title compound in 51% yield, as colourless solid. $^1$H-NMR (CDCl$_3$) 1.75 (broad s, 6H); 1.85-1.91 (m, 2H); 2.00 (broad s, 3H); 2.10 (broad s, 6H); 2.49-2.56 (m, 2H); 3.29 (s, 4H); 6.61 (d, 1H, J=8 Hz); 6.81 (broad d, 1H, J=8.16 Hz); 6.95 (broad s, 1H).

Example 23

2-Amino-2-(4-(2-(6,6-dimethylbicyclo[3.1.1]heptan-2-yl)ethoxy)phen ethyl) propane-1,3-diol hydrochloride salt Step A: 2-(2-Bromoethyl)-6,6-dimethylbicyclo[3.1.1]hept-2-ene A mixture of 2-(6,6-dimethylbicyclo[3.1.1]hept-2-en-2-yl)ethanol (0.835 g, 4.87 mmol), CBr$_4$ (1.83 g, 5.5 mmol) and PPh$_3$ (1.44 g, 5.5 mmol) in anhydrous CH$_2$Cl$_2$ (10 ml) was stirred for 2 h at room temperature. The solvent was evaporated to dryness and the residue was treated with EtOAc (10 ml) and filtered through a SiO$_2$ bead to give the title compound (1.03 g; 90%), as colourless oil. $^1$H-NMR (CDCl$_3$) 0.82 (s, 3H); 1.26 (s, 3H); 1.99-2.37 (m, 6H); 2.5 (tr, 2H, J=7.88 Hz); 3.34 (tr, 2H, J=7.27 Hz); 5.31 (broad s, 1H).

Step B: 2-(2-(4-Iodophenoxy)ethyl)-6,6-dimethylbicyclo[3.1.1]hept-2-ene

A mixture of 4-iodophenol (0.4 g; 1.82 mmol), 2-(2-bromoethyl)-6,6-dimethylbicyclo[3.1.1]hept-2-ene (0.45 g, 1.97 mmol) and K$_2$CO$_3$ (0.3 g, 2.17 mmol) in anhydrous DMF (5 ml) was stirred overnight at room temperature. Another portion of 2-(2-bromoethyl)-6,6-dimethylbicyclo[3.1.1]hept-2-ene (0.3 g) was added and stirring was continued for 6 h. The mixture was diluted to 50 ml with EtOAc and washed with H$_2$O (50 ml). The organic layer was separated, dried over MgSO$_4$ and filtered. The filtrate was evaporated to dryness and the residue was purified by FCC (SiO$_2$) to give the title product (0.189 g; 28%), as pale paste. $^1$H-NMR (CDCl$_3$) 0.81 (s, 3H); 1.26 (s, 3H); 2.06-2.44 (m, 8H); 3.91 (tr, 2H, J=6.97 Hz); 5.32 (s, 1H); 6.64 (d, 2H, J=8.96 Hz); 7.51 (d, 2H, J=8.96 Hz).

Step C: tert-Butyl-5-((4-(2-(6,6-dimethylbicyclo[3.1.1]hept-2-en-2-yl)ethoxy)phenyl)ethynyl)-2,2-dimethyl-1,3-dioxan-5-ylcarbamate When tert-butyl-5-ethynyl-2,2-dimethyl-1,3-dioxan-5-ylcarbamate was substituted for 1-octyne and the product of Step B was substituted for 5-iodo-2-tritylisoindoline in Example 2, Step D, the similar process afforded the title compound in 66% yield, as pale paste. $^1$H-NMR (CDCl$_3$) 0.80 (s, 3H); 1.25 (s, 3H); 1.41 (s, 3H); 1.46 (s, 9H); 2.06 (d, 2H, J=5.47 Hz); 2.21 (d, 2H, J=8.44 Hz); 2.33-2.44 (m, 4H); 3.93 (tr, 2H, J=7.0 Hz); 3.98 (d, 2H, J=11.4 Hz); 4.08 (d, 2H, J=11.5 Hz); 5.18 (s, 1H); 5.32 (s, 1H); 6.76 (d, 2H, J=8.8 Hz); 7.29 (d, 2H, J=8.7 Hz).

Step D: tert-Butyl-5-(4-(2-(6,6-dimethylbicyclo[3.1.1]hept-2-en-2-yl)ethoxy)-phenethyl)-2,2-dimethyl-1,3-dioxan-5-ylcarbamate A mixture of the product of Step C (0.07 g, 0.14 mmol), and 10% Pd/C (0.05 g) in EtOH (5 ml) was stirred for 36 h under H$_2$. The catalyst was removed by filtration through Celite pad and filtrate evaporated to dryness, to give the title product (0.055 g; 78%), as colourless paste. $^1$H-NMR (CDCl$_3$) 1.02 (s, 3H); 1.18 (s, 3H); 1.39 (s, 3H); 1.41 (s, 3H); 1.46 (s, 9H); 1.84-2.35 (m, 13H); 2.45-2.6 (m, 2H); 3.65 (d, 2H, J=11.8 Hz); 3.84-3.92 (m, 4H); 4.94 (broad s, 1H); 6.77 (d, 2H, J=8.6 Hz); 7.05 (d, 2H, J=8.5 Hz).

Step E: 2-Amino-2-(4-(2-(6,6-dimethylbicyclo[3.1.1] heptan-2-yl)ethoxy)-phenethyl)propane-1,3-diol hydrochloride salt When the product of Step D was substituted for tert-butyl-5-(4-(6-methoxy-3-(3,4,5-trimethoxybenzoyl)-1H-indol-1-ylsulfonyl)-phenethyl)-2,2-dimethyl-1,3-dioxan-5-ylcarbamate in Example 13, Step F, the similar process afforded the title compound in 75% yield, as colourless solid. $^1$H-NMR (CDCl$_3$) 1.34 (s, 3H); 1.5 (s, 3H); 2.15-2.65 (m, 11H); 2.87-2.93 (m, 2H); 4.0 (d, 2H, J=11.8 Hz); 3.96 (d, 2H, J=11.7 Hz); 4.21-4.63 (m, 4H); 7.12 (d, 2H, J=8.48 Hz); 7.42 (d, 2H, J=8.52 Hz).

Example 24

$H_2$. The catalyst was removed by filtration through Celite pad and the filtrate as evaporated to dryness to give the title product (0.043 g; 60%), as colourless paste. $^1$H-NMR (CDCl$_3$) 1.35 (s, 9H); 1.39 (s, 3H); 1.41 (s, 3H); 1.48-1.49 (m, 20H); 2.15 (d, 2H, J=11.22 Hz); 2.49-2.45 (m, 2H); 3.64 (d, 2H, J=11.73 Hz); 3.86 (d, 2H, J=11.7 Hz); 3.94 (m, 2H); 4.95 (s, 1H); 6.78 (d, 2H, J=8.58 Hz); 7.04 (d, 2H, J=8.55 Hz).

Step D: Mixture

When the product of Step D was substituted for tert-butyl-5-(4-(6-methoxy-3-(3,4,5-trimethoxybenzoyl)-1H-indol-1-ylsulfonyl)-phenethyl)-2,2-dimethyl-1,3-dioxan-5-ylcarbamate in Example 13, Step F, the similar process afforded the product in 71% yield, as colourless solid, which was a mixture of above 2 compounds. $^1$H-NMR (CDCl$_3$) 1.11-1.81 (m, 14H); 1.97-2.10 (m, 2H); 2.44-2.47 (m, 2H); 3.45 (d, 2H, J=12.3 Hz); 3.5 (d, 2H, J=12.3 Hz, minor); 3.59 (s, 4H, major); 3.85 (tr, 3H, major); 4.95 (broad tr, 1H, minor); 6.58 (d, 2H, J=8.21 Hz); 6.79 (d, 2H, J=8.43 Hz, major); 7.00 (d, 2H, J=7.94 Hz, minor); 7.10 (d, 2H, J=8.45 Hz, major).

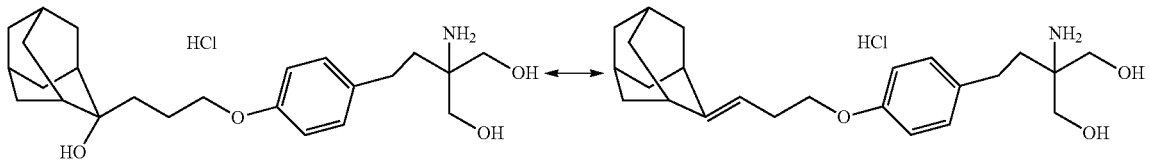 [SMILES: NC(CO)(CO)CCc1ccc(OCCCC2(O)C3CC4CC(C3)CC2C4)cc1 ; Cl ; NC(CO)(CO)CCc1ccc(OCCC=C2C3CC4CC(C3)CC2C4)cc1 ; Cl]

Example 25

2-Amino-2-(2-(3'-cyclohexyl-4'-methoxybiphenyl-4-yl)ethyl)propane-1,3-diol hydrochloride salt Step A: 4'-Bromo-3-(1-admantanyl)-4-methoxybiphenyl To a stirred solution of 2-(1-admantanyl)-4-iodo-1-methoxybenzene (0.19 g; 0.5 mmol) and 4-bromophenylboronic acid (0.1 g, 0.47 mmol) in 1,4-dioxane (10 ml) Pd(PPh$_3$)$_4$ (0.04 g) was added at 80° C., followed by the addition of the solution of NaHCO$_3$ (0.2 g) in H$_2$O (2 ml). The mixture was stirred at reflux for 2 h and the solvents were evaporated. The residue was diluted to 100 ml with EtOAc and washed with H$_2$O. The organic layer was separated, dried over MgSO$_4$, filtered and the filtrate was evaporated to dryness to give The residue was purified by FCC (SiO$_2$) to give the title product (0.08 g; 39%), as creamy gum. $^1$H-NMR (CDCl$_3$) 1.77 (s, 6H); 2.07 (s, 3H); 2.12 (s, 6H); 3.86 (s, 3H); 6.92 (d, 1H, J=8.39 Hz); 7.34 (dd, 1H, J=2.42, 8.42 Hz), 7.38-7.42 (m, 3H); 7.50 (d, 2H, J=8.57 Hz).

Step B: tert-Butyl 5-((3'-1-admantanyl-4'-methoxybiphenyl-4-yl)ethynyl)-2,2-dimethyl-1,3-dioxan-5-ylcarbamate When tert-butyl-5-ethynyl-2,2-dimethyl-1,3-dioxan-5-ylcarbamate was substituted for 1-octyne and the product of Step A was substituted for 5-iodo-2-tritylisoindoline in Example 2, Step D, the similar process afforded the title compound in 35% yield, as pale paste. $^1$H-NMR (CDCl$_3$) 1.47 (s, 3H); 1.48 (s, 9H); 1.5 (s, 3H); 1.77 (broad s, 6H); 2.07

Step A: 1-(4-(4-Iodophenyl)but-1-ynyl)-2-admantanol

To a stirred solution of 1-(but-3-ynyl)-4-iodobenzene (0.36 g, 1.48 mmol) in anhydrous THF (0.5 ml) 2.8 M MeMgBr in THF (0.6 ml) was added at 0° C. under N$_2$. After stirring for 0.5 h, the solution of 2-admantanone (0.24 g, 1.6 mmol) was added drop wise. This was stirred for 2 h at room temperature, than quenched with the solution of NH$_4$Cl. The mixture was extracted with Et$_2$O. The organic layer was dried over MgSO$_4$ and filtered. The filtrate was evaporated to dryness and the residue was purified by FCC (SiO$_2$) to give the title product (0.34 g; 56%), as the creamy paste. $^1$H-NMR (CDCl$_3$) 2.14-2.23 (m, 16H); 4.69 (s, 2H); 6.74 (d, 2H, J=6.87 Hz); 7.54 (d, 2H, J=6.81 Hz).

Step B: tert-Butyl-5-((4-(4-(1-hydroxycyclohexyl) but-3-ynyl)phenyl)ethynyl)-2,2-dimethyl-1,3-dioxan-5-ylcarbamate When tert-butyl-5-ethynyl-2,2-dimethyl-1,3-dioxan-5-ylcarbamate was substituted for 1-octyne and the product of Step A was substituted for 5-iodo-2-tritylisoindoline in Example 2, Step D, the similar process afforded the title compound in 62% yield, as pale paste. $^1$H-NMR (CDCl$_3$) 1.46 (s, 3H); 1.48 (s, 9H); 1.50 (s, 3H); 1.47-2.14 (m, 16H); 3.94-4.11 (m, 4H); 4.72 (5, 2H); 5.19 (s, 1H); 6.87 (d, 2H, J=8.85 Hz); 7.33 (d, 2H, J=8.79 Hz).

Step C: tert-Butyl-5-(4-(4-(1-hydroxycyclohexyl) butyl)phenethyl)-2,2-dimethyl-1,3-dioxan-5-ylcarbamate A mixture of the product of Step B (0.07 g, 0.13 mmol), and 10% Pd/C (0.04 g) was stirred for 36 h in EtOH (5 ml) under (broad s, 3H); 2.12 (s, 6H); 3.86 (s, 3H); 4.00 (d, 2H, J=11.38 Hz); 4.10 (d, 2H, J=11.45 Hz); 5.20 (s, 1H); 6.9 (d, 1H, J=8.46 Hz); 7.28-7.5 (s, 6H).

Step C: tert-Butyl 5-(2-(3'-(1-admantanyl-4'-methoxybiphenyl-4-yl)ethyl)-2,2-dimethyl-1,3-dioxan-5-ylcarbamate A mixture of the product of Step B (0.025 g, 0.04 mmol), and 10% Pd/C (0.025 g) in EtOH (5 ml) was stirred for 16 h under $H_2$. The catalyst was removed by filtration through Celite pad and the filtrate was evaporated to dryness to give the title compound (0.013 g; 57%), as colourless paste. $^1$H-NMR (CDCl$_3$) 1.42 (s, 3H); 1.46 (s, 3H); 1.47 (s, 9H); 1.77 (s, 6H); 1.97-2.06 (m, 5H); 2.13 (s, 6H); 2.56-2.61 (m, 2H); 3.68 (d, 2H, J=11.8 Hz); 3.85 (s, 3H); 3.9 (d, 2H, J=11.86 Hz); 6.91 (d, 1H, J=8.43 Hz); 7.2 (d, 2H, J=8.1 Hz); 7.35 (d, 1H, J=8.36 Hz); 7.4 (d, 1H, J=2.26 Hz); 7.44 (d, 2H, J=8.1 Hz).

Step D: 2-Amino-2-(2-(3'-cyclohexyl-4'-methoxybiphenyl-4-yl)ethyl) propane-1,3-diol hydrochloride salt When the product of Step C was substituted for tert-butyl-5-(4-(6-methoxy-3-(3,4,5-trimethoxybenzoyl)-1H-indol-1-ylsulfonyl)-phenethyl)-2,2-dimethyl-1,3-dioxan-5-ylcarbamate in Example 13, Step F, the similar process afforded the title compound in 74% yield, as colourless solid. $^1$H-NMR (CDCl$_3$) 1.71 (s, 6H); 1.88-1.94 (m, 2H); 2.01 (s, 3H); 2.07 (s, 6H); 2.59-2.66 (m, 2H); 3.63 (d, 2H, J=11.96 Hz); 3.68 (d, 2H, J=11.94 Hz); 6.87 (d, 1H, J=8.47 Hz); 7.18 (d, 2H, J=8.14 Hz); 7.30 (dd, 1H, J=2.33, 8.2, Hz); 7.35 (d, 1H, J=2.25 Hz); 7.41 (d, 2H, J=8.15 Hz).

Example 26

2-Amino-2-(4-(3-(1-admantanyl-4-methoxyphenethyl)phenethyl)propane-1,3-diol hydrochloride salt

Step A: 2-(1-Admantanyl)-4-ethynyl-1-methoxybenzene

A mixture of 3-(1-admantanyl)-4-methoxybenzaldehyde (0.12 g, 0.42 mmol), dimethyl(1-diazo-2-oxopropyl)phosphonate (0.097 g, 0.51 mmol) and $K_2CO_3$ (0.069 g, 0.5 mmol) in anhydrous MeOH (5 ml) was stirred overnight at 80° C. The solvent was evaporated and the residue was diluted to 50 ml with EtOAc, washed with $H_2O$, dried over MgSO$_4$ and filtered. The filtrate was passed through SiO$_2$ bead and the filtrate was evaporated to dryness to give the title product (0.05 g; 42%), which was used for the next step without purification. $^1$H-NMR (CDCl$_3$) 1.75 (s, 3H); 2.05 (broad s, 9H); 2.96 (s, 1H); 3.82 (s, 3H); 6.77 (d, 1H, J=8.31 Hz); 7.29-7.34 (m, 2H).

Step B: tert-Butyl 5-((4-((3-(1-admantanyl-4-methoxyphenyl)ethynyl)phenyl)ethynyl)-2,2-dimethyl-1,3-dioxan-5-ylcarbamate When the product of Step A was substituted for 1-octyne and tert-butyl 5-((4-iodophenyl)ethynyl)-2,2-dimethyl-1,3-dioxan-5-ylcarbamate was substituted for 5-iodo-2-tritylisoindoline in Example 2, Step D, the similar process afforded the title compound in 21% yield, as pale paste. $^1$H-NMR (CDCl$_3$) 1.43 (s, 3H); 1.47 (s, 9H); 1.49 (s, 3H); 1.91 (m, 6H); 2.07-2.13 (m, 9H); 3.83 (s, 3H); 4.00 (d, 2H, J=11.4 Hz); 4.09 (d, 2H, J=11.42 Hz); 5.20 (s, 1H); 6.81 (d, 1H, J=8.42 Hz); 7.26-7.43 (m, 6H).

Step C: 2-Amino-2-(4-(3-(1-admantanyl-4-methoxyphenethyl)phenethyl)-propane-1,3-diol hydrochloride salt A mixture of the product of Step B (0.015 g, 0.025 mmol), and 10% Pd/C (0.02 g) in EtOH (5 ml) was stirred for 16 h under $H_2$. The catalyst was removed by filtration through Celite pad and the filtrate was evaporated to dryness. The residue was dissolved in a mixture of MeOH (1 ml), CH$_2$Cl$_2$ (0.5 ml) and concentrated HCl (10 drops). After stirring for 15 min at room temperature the solvents were evaporated to dryness. The residue was treated with iPrOH and the solid formed was filtered off and dried in oven at 60° C. to give the title product (0.08 g; 64%), as off white solid. $^1$H-NMR (CDCl$_3$) 1.7 (broad s, 6H); 1.86-1.92 (m, 2H); 2.00 (s, 9H); 2.55-2.61 (m, 2H); 2.77 (m, 4H); 3.62 (d, 2H, J=11.92 Hz); 3.67 (d, 2H, J=11.84 Hz); 3.76 (s, 3H); 6.74 (d, 1H, J=8.85 Hz); 6.91-6.94 (m, 2H); 7.07 (s, 4H).

Example 27

2-Amino-2-((4-iodophenyl)ethynyl)propane-1,3-diol hydrochloride salt

When the product of Example 21, Step A was substituted for tert-butyl-5-(4-(6-methoxy-3-(3,4,5-trimethoxybenzoyl)-1H-indol-1-ylsulfonyl)-phenethyl)-2,2-dimethyl-1,3-dioxan-5-ylcarbamate in Example 13, Step F, the similar process afforded the title compound in 75% yield, as a creamy paste. $^1$H-NMR (D$_2$O) 3.81 (broad s, 4H); 7.19 (d, 2H, J=8.3 Hz); 8.26 (d, 2H, J=8.26 Hz).

Example 28

2-Amino-2-(3-1-admantanyl-4-isopropoxyphenethyl)propane-1,3-diol hydrochloride salt

Step A: 2-(1-Admantanyl)-4-iodo-1-isopropoxybenzene

To a stirred mixture of 2-(1-admantanyl)-4-iodophenol (0.25 g, 0.71 mmol) and $K_2CO_3$ (0.15 g, 1.1 mmol) in anhydrous DMF (10 ml) 2-bromopropane (2 ml) was added. The mixture was stirred for 4 h at 80° C. (external oil bath temperature), than cooled to room temperature. This was diluted to 200 ml with $H_2O$ and extracted with EtOAc (100 ml). The organic layer was separated and dried over MgSO$_4$ and filtered. The filtrate was passed through SiO$_2$ bead and the filtrate evaporated to dryness to give the title product (0.31 g; 79%), as light cream solid. $^1$H-NMR (CDCl$_3$) 1.36 (d, 6H, J=6.02 Hz); 1.73 (s, 6H); 2.06 (s, 9H); 4.55-4.6 (m, 1H); 6.57 (d, 1H, J=8.52 Hz); 7.37-7.43 (m, 2H).

Step B: tert-Butyl-5-((3-1-admantanyl-4-isopropoxyphenyl)ethynyl)-2,2-dimethyl-1,3-dioxan-5-ylcarbamate When tert-butyl-5-ethynyl-2,2-dimethyl-1,3-dioxan-5-ylcarbamate was substituted for 1-octyne and the product of Step A was substituted for 5-iodo-2-tritylisoindoline in Example 2, Step D, the similar process afforded the title compound in 58% yield, as pale paste. $^1$H-NMR (CDCl$_3$) 1.35 (d, 6H, J=6.01 Hz); 1.43 (s, 3H); 1.47 (s, 9H); 1.48 (s, 3H); 1.74 (s, 6H); 2.06 (s, 9H); 3.99 (d, 2H, J=11.45 Hz); 4.08 (d, 2H, J=11.51 Hz); 4.59-4.64 (m, 1H); 5.17 (broad s, 1H); 6.72 (d, 1H, J=8.61 Hz); 7.21 (dd, 1H, J=2.08, 8., Hz); 7.25 (d, 1H, J=2.09 Hz).

Step C: tert-Butyl-5-(3-1-admantanyl-4-isopropoxyphenethyl)-2,2-dimethyl-1,3-dioxan-5-ylcarbamate A mixture of the product of Step B (0.035 g, 0.07 mmol), and 10% Pd/C (0.025 g) in EtOH (5 ml) was stirred for 16 h under $H_2$. The catalyst was removed by filtration through Celite pad and the filtrate was evaporated to dryness to give the title product (0.035 g; 100%); as colourless paste. $^1$H-NMR (CDCl$_3$) 1.35 (d, 6H, J=5.99 Hz); 1.4 (s, 3H); 1.42 (s, 3H); 1.46 (s, 9H); 1.91-1.97 (m, 2H); 2.03 (s, 3H); 2.09 (s, 6H); 2.45-2.5 (m, 2H); 3.67 (d, 2H, J=11.73 Hz); 3.89 (d, 2H, J=11.67 Hz); 4.54-4.62 (m, 1H); 4.93 (s, 1H); 6.72 (d, 1H, J=8.27 Hz); 6.92 (broad d, 1H, J=9.98 Hz); 6.99 (broad s, 1H).

Step D: 2-Amino-2-(3-1-admantanyl-4-isopropoxyphenethyl)propane-1,3-diol hydrochloric salt When the product of Step C was substituted for tert-butyl-5-(4-(6-methoxy-3-(3,4,5-trimethoxybenzoyl)-1H-indol-1-ylsulfonyl)-phenethyl)-2,2-dimethyl-1,3-dioxan-5-ylcarbamate in Example 13, Step F, the similar process afforded the title compound in 67% yield, as a creamy paste. $^1$H-NMR (CDCl$_3$) 1.28 (d, 6H, J=6 Hz); 1.68 (s, 6H); 1.82-1.88 (m, 2H); 1.97 (s, 3H); 2.02 (s, 6H); 2.47-2.54 (m, 2H); 3.61 (d, 2H, J=12.1 Hz); 3.68 (d, 2H, J=12.1 Hz); 4.48-4.57 (m, 1H); 6.68 (d, 1H, J=8.4 Hz); 6.88 (dd, 1H, J=8.29, 2.1 Hz); 6.94 (d, 1H, J=2.14 Hz).

Example 29

2-Amino-2-(4-(3-(2-(1-admanynyl)-4-methylphenoxy)propyl)phenethyl) propane-1,3-diol hydrochloride salt

Step A: 2-(1-Admantanyl)-4-methyl-1-(prop-2-ynyloxy)benzene

To a stirred mixture of 2-(1-admantanyl)-4-methylphenol (0.25 g, 0.71 mmol) and K$_2$CO$_3$ (0.25 g, 1.03 mmol) in anhydrous DMF (10 ml) propyrgyl bromide (80% solution in toluene, 2 ml) was added. The mixture was stirred for 6 h at 60° C., than cooled to room temperature. This was diluted to 200 ml with H$_2$O and extracted with EtOAc (100 ml). The organic layer was separated and dried over MgSO$_4$ and filtered. The filtrate was passed through SiO$_2$ bead and the filtrate evaporated to dryness to give the title product (0.22 g), as colourless solid. $^1$H-NMR (CDCl$_3$) 1.76 (s, 6H); 2.07 (s, 3H); 2.11 (s, 6H); 2.13 (s, 3H); 4.86 (s, 2H); 6.81-6.98 (m, 2H); 7.02 (d, 1H); 7.12 (d, 2H, J=8.16 Hz); 7.64 (d, 2H, J=8.38 Hz).

Step B: 2-(1-Admantanyl)-1-(3-(4-iodophenyl)prop-2-ynyloxy)-4-methyl-benzene When 2-cyclohexyl-4-methyl-1-(prop-2-ynyloxy)benzene was substituted for 1-octyne and 1,4-diiodobenzene was substituted for 5-iodo-2-tritylisoindoline in Example 2, Step D, the similar process afforded the title compound in 77% yield, as pale paste. $^1$H-NMR (CDCl$_3$) 1.76 (s, 6H); 2.0 (s, 3H); 2.04 (s, 6H); 2.28 (s, 3H); 2.47 (tr, 1H, J=2.41 Hz); 4.68 (d, 2H, J=2.38 Hz); 6.84 (d, 1H, J=8.17 Hz); 6.96 (dd, 1H, J=1.61, 8.21 Hz); 7.03 (d, 1H, J=2.0 Hz).

Step C: tert-Butyl-5-((4-(3-(2-(1-admanynyl-4-methylphenoxy)prop-1-ynyl)phenyl)ethynyl)-2,2-dimethyl-1,3-dioxan-5-ylcarbamate When tert-butyl-5-ethynyl-2,2-dimethyl-1,3-dioxan-5-ylcarbamate was substituted for 1-octyne and the product of Step B was substituted for 5-iodo-2-tritylisoindoline in Example 2, Step D, the similar process afforded the title compound in 75% yield, as pale paste. $^1$H-NMR (CDCl$_3$) 1.43 (s, 3H); 1.46 (s, 9H); 1.48 (s, 3H); 1.76 (s, 6H); 2.06 (s, 3H); 2.11 (s, 6H); 2.28 (s, 3H); 4.00 (d, 2H, J=11.28 Hz); 4.08 (d, 2H, J=11.46 Hz); 4.88 (s, 2H); 5.18 (s, 1H); 6.9 (d, 1H, J=7.93 Hz); 6.97 (d, 1H, J=8.05 Hz); 7.03 (s, 1H); 7.33 (s, 4H).

Step D: tert-Butyl-5-(4-(3-(2-(1-admanynyl)-4-methylphenoxy)propyl)phenethyl)-2,2-dimethyl-1,3-dioxan-5-ylcarbamate A mixture of the product of Step C (0.03 g, 0.05 mmol), and 10% Pd/C (0.025 g) in EtOH (5 ml) was stirred for 16 h under H$_2$. The catalyst was removed by filtration through Celite pad and the filtrate was evaporated to dryness to give the title product (0.03 g; 100%), as colourless paste. $^1$H-NMR (CDCl$_3$) 1.4 (s, 3H); 1.42 (s, 3H); 1.46 (s, 9H); 1.99 (s, 6H); 2.07 (s, 3H); 2.11 (s, 6H); 2.27 (s, 3H); 2.51-2.56 (m, 2H); 2.83 (tr, 2H); 3.66 (d, 2H, J=11.87 Hz); 3.86-3.95 (m, 4H); 4.95 (s, 1H); 6.7 (d, 1H, J=8.22 Hz); 6.92 (broad d, 1H, J=8.15 Hz); 7.01 (broad s, 1H); 7.10 (s, 4H).

Step E: 2-Amino-2-(4-(3-(2-(1-admanynyl)-4-methylphenoxy)propyl)phenethyl) propane-1,3-diol hydrochloride salt When the product of Step D was substituted for tert-butyl-5-(4-(6-methoxy-3-(3,4,5-trimethoxybenzoyl)-1H-indol-1-ylsulfonyl)-phenethyl)-2,2-dimethyl-1,3-dioxan-5-ylcarbamate in Example 13, Step F, the similar process afforded the title compound in 52% yield, as a colourless solid. $^1$H-NMR (CDCl$_3$) 1.68 (s, 6H); 1.81-1.87 (m, 2H); 1.97 (s, 3H); 2.05 (s, 6H); 2.17 (s, 3H); 2.49-2.57 (m, 2H); 2.75 (tr, 2H, J=7.42 Hz); 3.57 (d, 2H, J=12.08 Hz); 3.64 (d, 2H, J=12.02 Hz); 3.84 (tr, 2H, J=5.97 Hz); 6.61 (d, 1H, J=8.18 Hz); 6.82 (d, 1H, J=7.77 Hz); 6.92 (broad s, 1H); 7.04 (s, 4H).

Example 30

2-Amino-2-((5-(5-3-(1-admantyl)-4-methoxyphenyl)-1,2,4-oxadiazol-3-yl)indolin-1-yl)methyl)propane-1,3-diol

Step A: Methyl-3-(1-admantyl)-4-methoxybenzoate

To a mixture of 4-methoxymethyl-benzoate (0.332 g, 2 mmol) and 1-adamantanol (0.304 g, 2 mmol) in AcOH (3 ml) was added concentrated H$_2$SO$_4$ (0.5 ml) and the reaction mixture was stirred for 50 h at room temperature. The crude mixture was taken in EtOAc (100 ml) and washed with NaHCO$_3$ solution, dried over MgSO$_4$ and filtered. The filtrate was evaporated to dryness and the residue was crystallized from MeOH to give the product as colourless solid (0.51 g, 83%). $^1$H-NMR (CDCl$_3$) 1.76 (s, 6H); 2.06 (s, 3H); 2.08 (s, 6H); 3.86 (s, 3H); 3.87 (s, 3H); 6.86 (d, 1H, J=8.45 Hz); 7.85-7.91 (m, 2H).

Step B: 3-(1-Admantyl)-4-methoxybenzoic acid

To a stirred solution of methyl-3-(1-adamantyl)-4-methoxybenzoate (0.27 g, 0.85 mmol) in THF (30 ml) was added a solution of NaOH (0.04 g) in $H_2O$ (1 ml), followed by the addition of EtOH (2 ml). The mixture was refluxed for 4 h, then cooled to room temperature and acidified with 1M HCl solution. The crude product was taken in EtOAc (100 ml) and the organic layer was washed with $H_2O$, and dried over $MgSO_4$ and filtered. The filtrate was evaporated to dryness to give the title product (0.22 g, 85%) as colourless solid. $^1$H-NMR (CDCl$_3$) 1.77 (s, 6H), 2.03 (s, 3H), 2.09 (s, 6H), 3.89 (s, 3H), 6.88 (d, 1H, J=8.44 Hz), 7.93-7.98 (m, 2H).

Step C: N-(3-(1-Adamantyl)-4-methoxybenzoyloxy)-1H-indole-5-carboximidamide

When 3-(1-adamantyl)-4-methoxybenzoic acid was substituted for 3-chloro-4-methoxybenzoic acid in Example 7, Step D, the identical process afforded the title compound in 70% yield., as a colourless foam. $^1$H-NMR (CDCl$_3$) 1.77 (s, 6H); 1.98-2.12 (m, 9H); 3.28-3.37 (m, 1H); 3.93 (s, 3H); 5.12 (broad s, 2H); 6.57 (s, 1H); 6.9 (d, 1H, J=8.3 Hz); 7.37 (d, J=8.5 Hz); 7.56 (dd, 1H, J=1.5; 8.5 Hz); 8.46 (broad s, 1H).

Step D: 3-(1H-Indol-5-yl)-5-(3-(1-adamantyl)-4-methoxyphenyl)-1,2,4-oxadiazole The suspension of the product of Step C (0.16 g; 0.36 mmol) and 1 M TBAF in THF (0.3 ml; 0.3 mmol) in anhydrous toluene was refluxed for 1 h under reduced pressure, cool to room temperature and evaporated to dryness under reduced pressure. The residue was diluted to 15 ml with EtOAc, washed with water, brine, dried over anhydrous $MgSO_4$ and filtered. The filtrate was evaporated to dryness under reduced pressure and the residue was purified by crystallization from hexane/EtOAc to give the title compound (0.16 g; 100%) as colourless solid. $^1$H-NMR (CDCl$_3$) 1.79 (s, 6H); 2.0-2.16 (m, 9H); 3.92 (s, 3H); 6.66 (s, 1H); 6.98 (d, 1H, J=8.6 Hz); 7.26 (m, 1H); 7.48 (d, 1H, J=8.5 Hz); 7.9-8.11 (m, 2H); 8.29 (broad s, 1H); 8.51 (s, 1H).

Step E: 3-(1H-Indolin-5-yl)-5-(3-(1-adamantyl)-4-methoxyphenyl)-1,2,4-oxadiazole When the product of Step D was substituted for 5-(3-chloro-4-methoxyphenyl)-3-(1H-indol-5-yl)-1,2,4-oxadiazole in Example 7, Step F, the identical process afforded the title compound in 44% yield., as a colourless foam. $^1$H-NMR (CDCl$_3$) 1.78 (s, 6H); 2.14-2.12 (m, 9H); 3.08 (tr, 2H, J=8.45 Hz); 3.62 (tr, 2H, J=8.45 Hz); 3.89 (s, 3H); 4.04 (broad s, 1H); 6.64 (d, 1H, J=8.1 Hz); 6.94 (d, 1H, J=8.6 Hz); 7.83-8.06 (m, 4H).

Step F: tert-Butyl 5-((5-(5-(3-(1-adamantyl-4-methoxyphenyl)-1,2,4-oxadiazol-3-yl)indolin-1-yl)methyl)-2,2-dimethyl-1,3-dioxan-5-ylcarbamate When the product of Step E was substituted for 4-n-octylaniline in Example 1, Step A, the identical process afforded the title compound in 79% yield., as colourless foam. $^1$H-NMR (CDCl$_3$) 1.44-1.48 (m, 15H); 1.78 (s, 6H); 2.02-2.14 (m, 9H); 3.07 (tr, 2H, J=8.7 Hz); 3.56 (tr, 2H, J=8.7 Hz); 3.62 (s, 2H); 3.9 (s, 3H); 3.94 (s, 4H); 4.64 (broad s, 1H); 6.64 (d, 1H, J=8.33 Hz); 6.95 (d, 1H, J=8.55 Hz); 7.83-8.05 (m, 4H).

Step G: 2-Amino-2-((5-(5-3-(1-adamantyl)-4-methoxyphenyl)-1,2,4-oxadiazol-3-yl)indolin-1-yl)methyl)propane-1,3-diol When the product of Step F was substituted for tert-butyl 2,2-dimethyl-5-((4-octylphenylamino)methyl)-1,3-dioxan-5-ylcarbamate in Example 1, Step B, the identical process afforded the title compound in 80% yield, as a colourless solid. $^1$H-NMR (DMSO-d$_6$+D$_2$O) 1.68 (s, 6H); 2.01 (broad s, 9H); 2.97 (tr, 2H, J=8.6 Hz); 3.12 (s, 2H); 3.37 (m, 4H); 3.51 (tr, 2H, J=8.6 Hz); 3.75 (s, HDO); 3.84 (s, 3H); 6.66 (d, 1H, J=8.25 Hz); 7.15 (d, 1H, J=8.8 Hz); 7.62 (s, 1H); 7.67 (d, 1H, J=8.5 Hz); 7.8-7.95 (m, 2H).

Example 31

2-Amino-2-((4-octylbenzylamino)methyl)propane-1,3-diol

Step A: 4-n-Octylbenzaldehyde

A mixture of n-octylbenzene (1.2 g; 6.3 mmol) hexamethylenetetramine (0.97 g; 6.93 mmol) in trifluoroacetic acid was refluxed for 4 h, cooled to room temperature and evaporated to dryness under reduced pressure. The residue was neutralized with 5% NaHCO$_3$ and extracted with diethyl ether (3×5 ml). The combined organic phase was washed with H$_2$O, brine, dried over anhydrous MgSO$_4$ and filtered. The filtrate was evaporated under reduced pressure and the residue was purified by FCC (SiO$_2$, hexane) to give the title compound (0.4 g; 29%) as a colourless oil and starting n-octylbenzene (0.8 g; 67%). $^1$H-NMR (CDCl$_3$) 0.86 (tr, 3H, J=6.9 Hz); 1.26 (m, 10H); 1.6 (m, 2H); 2.67 (tr, 2H, J=7.9 Hz); 7.31 (d, 2H, J=8.1 Hz); 7.77 (d, 2H, J=8.1 Hz); 9.96 (s, 1H).

Step B: 4-n-Octylbenzyl alcohol

NaBH$_4$ (0.04 g; 1.06 mmol) was added portion wise to a solution of the product of Step A in MeOH (5 ml) at room temperature, with vigorous stirring. After 30 min of stirring, the mixture was evaporated to dryness, diluted to 10 ml with Et$_2$O and washed with 1N NaOH, H$_2$O, brine, dried over anhydrous MgSO$_4$ and filtered. The filtrate was evaporated under reduced pressure to give the title compound (0.082 g; 100%), as colourless syrup, which was used in next Step without further purification. $^1$H-NMR (CDCl$_3$) 0.86 (tr, 3H, J=6.9 Hz); 1.26 (m, 10H); 1.56 (m, 3H); 2.58 (tr, 2H, J=7.9 Hz); 4.64 (s, 2H); 7.15 (d, 2H, J=8 Hz); 7.26 (d, 2H, J=8 Hz).

Step C: 4-n-Octylbenzyl bromide

PBr$_3$ (0.23 ml) was added drop wise to a stirred solution of the product of Step B (0.082 g; 0.37 mmol) in Et$_2$O (2 ml) at −15° C. The mixture was allowed to warm up to room temperature and the stirring was continued for 4 h. This was poured onto ice (5 g) and the product was extracted with fresh Et$_2$O (2×10 ml). The combined extracts were washed with 5% NaHCO$_3$, H$_2$O, brine, dried over anhydrous MgSO$_4$ and filtered. The filtrate was evaporated under reduced pressure and the residue was purified by FCC (SiO$_2$, hexane) to give the title compound (0.04 g; 40%) as a colourless solid. $^1$H-NMR (CDCl$_3$) 0.86 (tr, 3H, J=7 Hz); 1.26 (m, 10H); 1.57 (m, 2H); 2.57 (tr, 2H, J=7.9 Hz); 4.48 (s, 2H); 7.13 (d, 2H, J=8 Hz); 7.28 (d, 2H, J=8 Hz).

Step D: 4-n-Octylbenzylamine

To a solution of the product of Step C (0.13 g; 0.459 mmol) in anhydrous hexamethylenedisilazane (HMDSA) 1M NaH- MDSA in THF was added at room temperature under N₂ with stirring. After stirring overnight at room temperature the solvents were removed under reduced pressure and the residue was diluted to 5 ml with MeOH and 1 drop of concentrated HCl was added. This was evaporated under reduced pressure, diluted to 15 ml with Et₂O and washed with 1N NaOH, brine, dried over anhydrous MgSO₄ and filtered. The filtrate was evaporated under reduced pressure to give the title compound (0.1 g; 100%), as colourless oil, which was used in the next Step without further purification. $^1$H-NMR (CDCl₃) 0.86 (tr, 3H, J=7 Hz); 1.26 (m, 10H); 1.41 (s, 2H); 1.58 (m, 2H); 2.57 (tr, 2H, J=7.9 Hz); 3.82 (s, 2H); 7.13 (d, 2H, J=8 Hz); 7.2 (d, 2H, J=8 Hz).

Step E: tert-Butyl 2,2-dimethyl-5-((4-octylbenzylamino)methyl)-1,3-dioxan-5-ylcarbamate When the product of Step D is substituted for 4-n-octylaniline in Example 1, Step A, the identical process afforded the title compound in 82% yield., as colourless solid. $^1$H-NMR (CDCl₃) 0.86 (tr, 3H, J=6.96 Hz); 1.26 (m, 10H); 1.37 (s, 3H); 1.41 (s, 9H); 1.45 (s, 3H); 1.56 (m, 2H); 2.56 (tr, 2H, J=7.92 Hz); 2.89 (s, 2H); 3.63 (d, 2H, J=11.82 Hz); 3.74 (s, 2H); 4.13 (d, 2H, J=11.82 Hz); 5.03 (broad s, 1H); 7.11 (d, 2H, J=7.95 Hz); 7.20 (d, 2H, J=7.95 Hz).

Step F: 2-Amino-2-((4-octylbenzylamino)methyl)propane-1,3-diol

A solution of the product of Step D (0.06 g; 0.13 mmol) in 60% CF₃CO₂H in CH₂Cl₂ (2 ml) was stirred for 15 min at room temperature and the mixture was diluted to 5 ml with MeOH and evaporated to dryness under reduced pressure. The residue was dissolved in iPrOH (2 ml) and one drop of concentrated HCl was added. This was evaporated under reduced pressure and treated with anhydrous Et₂O. The precipitate formed was filtered off, dried in vacuo for 1 h to give a hydrochloride salt of the title compound (0.04 g; 85%), as colourless solid. $^1$H-NMR (D₂O) 0.74 (m, 3H); 1.16 (m, 10H); 1.49 (m, 2H); 2.52 (tr, 2H, J=7.47 Hz); 3.36 (s, 2H); 3.69 (s, 4H); 4.2 (s, 2H); 4.66 (DHO); 7.21 (d, 1H, J=7.56 Hz); 7.32 (d, 1H, J=7.56 Hz).

Example 32

1-(2-Amino-3-hydroxy-2-(hydroxymethyl)propyl)-6-methoxy-1H-indol-3-yl)(3,4,5-trimethoxyphenyl)methanone Step A: (5-(tert-Butoxycarbonylamino)-2,2-dimethyl-1,3-dioxan-5-yl)methyl methanesulfonate To a solution of tert-butyl 5-(hydroxymethyl)-2,2-dimethyl-1,3-dioxan-5-ylcarbamate (Ooii et al, J. Org. Chem., 2004, 69, 7765; 0.4 g; 1.53 mmol) and Et₃N (0.55 ml; 3.98 mmol) in CH₂Cl₂ (3 ml) methanesulfonyl chloride (0.16 ml; 1.99 mmol) was added at 0° C., with stirring under N₂. The mixture was allowed to warm up to room temperature and stirring was continued for 1 h. This was diluted to 20 ml with Et₂O, washed with H₂O, 5% NaHCO₃, brine, dried over anhydrous MgSO₄ and filtered. The filtrate was evaporated to dryness under reduced pressure to give the title compound (0.51 g; 98%), as a creamy solid, which was used in the next step without further purification. $^1$H-NMR (CDCl₃) 1.39 (s, 3H); 1.42 (s, 9H); 1.46 (s, 3H); 3.02 (s, 3H); 3.85 (d, 2H, J=11.9 Hz); 3.99 (d, 2H, J=11.9 Hz); 4.56 (s, 2H); 4.71 (broad s, 1H).

Step B: tert-Butyl 5-((6-methoxy-3-(3,4,5-trimethoxybenzoyl)-1H-indol-1-yl)methyl)-2,2-dimethyl-1,3-dioxan-5-ylcarbamate To a solution of the product of Example 13, Step B (0.11 g; 0.32 mmol) in anhydrous DMF (0.6 ml) 60% NaH in mineral oil (0.02 g; 0.5 mmol) was added and the mixture was stirred for 1 h at room temperature under N₂. To it, a product of Step A (0.13 g; 0.383 mmol) was added and the resulting mixture was stirred for 3 days at ~55° C. under N₂, cooled to room temperature and diluted to 15 ml with Et₂O, washed with H₂O, brine, dried over anhydrous MgSO₄ and filtered. The filtrate was evaporated to dryness under reduced pressure and the residue was purified by FCC (SiO₂, CH₂Cl₂/EtOAc 8:2) to give the title compound (0.07 g; 37%) as a colourless solid. $^1$H-NMR (CDCl₃) 1.23 (s, 9H); 1.46 (s, 3H); 1.53 (s, 3H); 3.71 (d, 2H, J=11.8 Hz); 3.84-3.94 (m, 15H); 4.12 (s, 1H); 4.76 (s, 2H); 6.96 (dd, 1H, J=2.2, 8.8 Hz); 7.06 (s, 2H); 7.16 (d, 1H, J=2.2 Hz); 7.44 (s, 1H); 8.24 (d, 1H, J=8.8 Hz).

Step C: 1-(2-Amino-3-hydroxy-2-(hydroxymethyl)propyl)-6-methoxy-1H-indol-3-yl)(3,4,5-trimethoxyphenyl)methanone When the product of Step B was substituted for tert-butyl 2,2-dimethyl-5-((4-octylphenylamino)methyl)-1,3-dioxan-5-ylcarbamate in Example 1, Step B, the identical process afforded the title compound in 65% yield, as a colourless solid. $^1$H-NMR (CDCl₃) 1.51 (broad s, 4H+2H₂O); 3.46 (d, 2H, J=10.7 Hz); 3.52 ((d, 2H, J=10.7 Hz); 3.87-3.92 (m, 12H); 4.21 (s, 2H); 6.96 (dd, 1H, J=2.2, 8.8 Hz); 7.1 (s, 2H); 7.13 (d, 1H, J=2.2 Hz); 7.7 (s, 1H); 8.24 (d, 1H, J=8.8 Hz).

Example 33

2-Amino-2-((5-(5-3-(1-admantyl)-3-methoxyphenyl)-1,2,4-oxadiazol-3-yl)indolin-1-yl)methyl)propane-1,3-diol Step A: Methyl 4-(1-admantyl)-3-methoxybenzoate To a mixture of 3-methoxymethyl-benzoate (0.45 g, 2.7 mmol) and 1-adamantanol (0.41 g, 2.7 mmol) in AcOH (3 ml) was added concentrated H₂SO₄ (0.5 mL) and the reaction mixture was stirred for 50 h at room temperature. The crude mixture was taken in EtOAc (100 ml) and washed with NaHCO₃ solution, dried over MgSO₄ and filtered. The filtrate was evaporated to dryness and the residue was crystallized from MeOH to give the title compound (0.81 g, 95%), as a colourless solid. $^1$H-NMR, (CDCl₃) 1.76 (s, 6H); 2.07 (bs, 9H); 3.87 (s, 3H); 3.88 (s, 3H); 7.25 (d, 1H); 7.49 (d, 1H, J=1.63 Hz); 7.57 (dd, 1H, J=8.1, 1.7 Hz).

Step B: 4-(1-Admantyl)-3-methoxybenzoic acid

When the product of Step A was substituted for methyl-3-(1-admantyl)-4-methoxybenzoate in Example 30, Step B the similar process afforded the title compound in 88% yield. $^1$H-NMR (CDCl₃) 1.7 (s, 6H); 2.01 (s, 3H); 2.06 (s, 6H); 3.81 (s, 3H); 7.19 (d, 1H, J=8.1 Hz); 7.45 (d, 1H, J=1.49 Hz); 7.53 (d, 1H, J=1.61, 8.11 Hz).

Step C: N-(4-(1-Admantyl)-3-methoxybenzoyloxy)-1H-indole-5-carboximidamide

When 4-(1-admantyl)-3-methoxybenzoic acid was substituted for 3-(1-admantyl)-4-methoxybenzoic acid in Example 30, Step C, the identical process afforded the title compound in 57% yield, as a colourless foam. ¹H-NMR (CDCl₃) 1.77 (s, 6H); 2.1 (m, 9H); 3.15 (s, 1H); 3.9 (s, 3H); 5.14 (s, 1H); 6.58 (s, 1H); 7.2-7.4 (m, 6H); 7.5-7.65 (m, 3H); 8.02 (s, 1H); 8.45 (s, 1H).

Step D: 3-(1H-Indol-5-yl)-5-(4-(1-adamantyl)-3-methoxyphenyl)-1,2,4-oxadiazole

The suspension of the product of Step C (0.13 g; 0.293 mmol) and 1 M TBAF in THF (0.3 ml; 0.3 mmol) in anhydrous toluene (5 ml) was refluxed for 1 h under N₂, cooled to room temperature and evaporated to dryness under reduced pressure. The residue was purified by FCC (SiO₂; CH₂Cl₂) to give the title compound (0.12 g; 99%) as a colourless solid. ¹H-NMR (CDCl₃) 1.78 (s, 6H); 2.01-2.16 (m, 9H); 3.96 (s, 3H); 6.66 (m, 1H); 6.98 (d, 1H, J=8.6 Hz); 7.26 (m, 1H); 7.36 (d, 1H, J=8.14 Hz); 7.48 (d, 1H, J=8.14 Hz); 7.68 (d, 1H, J=1.6 Hz); 7.77 (dd, 1H, J=1.6, 8.1 Hz); 8.01 (dd, 1H, J=1.6, 8.1 Hz); 8.32 (broad s, 1H); 8.51 (s, 1H).

Step E: 3-(1H-Indolin-5-yl)-5-(4-(1-adamantyl)-3-methoxyphenyl)-1,2,4-oxadiazole When the product of Step D was substituted for 5-(3-chloro-4-methoxyphenyl)-3-(1H-indol-5-yl)-1,2,4-oxadiazole in Example 7, Step F, the identical process afforded the title compound in 50% yield., as a colourless foam. ¹H-NMR (CDCl₃) 1.77 (s, 6H); 2.02-2.11 (m, 9H); 3.1 (tr, 2H, J=8.6 Hz); 3.64 (tr, 2H, J=8.6 Hz); 3.94 (s, 3H); 4.01 (broad s, 1H); 6.66 (d, 1H, J=8.1 Hz); 7.35 (d, 1H, J=8.1 Hz); 7.63 (d, 1H, J=1.6 Hz); 7.73 (dd, 1H, J=1.6, 8.1 Hz); 7.83-87.89 (m, 2H).

Step D: tert-Butyl 5-((5-(5-(4-(1-adamantyl-3-methoxyphenyl)-1,2,4-oxadiazol-3-yl)indolin-1-yl)methyl)-2,2-dimethyl-1,3-dioxan-5-ylcarbamate When the product of Step E was substituted for 4-n-octylaniline in Example 1, Step A, the identical process afforded the title compound in 64% yield., as a colourless foam. ¹H-NMR (CDCl₃) 1.4-1.5 (m, 15H); 1.77 (s, 6H); 2.02-2.11 (m, 9H); 3.08 (tr, 2H, J=8.6 Hz); 3.57 (tr, 2H, J=8.6 Hz); 3.63 (s, 2H); 3.9 (s, 3H); 3.94 (s, 3H); 4.63 (broad s, 1H); 7.34 (d, 1H, J=8.1 Hz); 7.62 (d, 1H, J=1.6 Hz); 7.72 (dd, 1H, J=1.6, 8.1 Hz); 7.83 (s, 1H); 7.88 (d, 1H, J=8.1 Hz).

Step E: 2-Amino-2-((5-(4-3-(1-adamantyl)-3-methoxyphenyl)-1,2,4-oxadiazol-3-yl)indolin-1-yl)methyl)propane-1,3-diol When the product of Step D was substituted for tert-butyl 2,2-dimethyl-5-((4-octylphenylamino)methyl)-1,3-dioxan-5-ylcarbamate in Example 1, Step B, the identical process afforded the title compound in 80% yield, as a colourless solid. ¹H-NMR (CDCl₃) 1.66 (broad s, 6H+H₂O); 1.77 (s, 6H); 2.02-2.39 (m, 9H); 3.07 (tr, 2H, J=8.3 Hz); 3.18 (s, 2H); 3.49-3.7 (m, 4H); 3.94 (s, 3H); 6.66 (d, 1H, J=7.8 Hz); 7.34 (d, 1H, J=7.8 Hz); 7.62 (s, 1H); 7.63 (s, 1H); 7.73 (d, 1H, J=8.1 Hz); 7.84 (s, 1H); 7.9 (d, 1H, J=8.1 Hz).

Example 34

2-Amino-2-((4-(5-(3,4-diethoxyphenyl)-1,2,4-oxadiazol-3-yl)indolin-1-yl)methyl)propane-1,3-diol Step A: N-Hydroxy-1H-indole-4-carboximidamide A mixture of 4-cyanoindole (0.64 g; 4.5 mmol), HCl×H₂NOH (1.1 g; 15.8 mmol), and Na₂CO₃ (0.79 g; 7.43 mmol) in H₂O (8 ml) and EtOH (2 ml) was gently stirred for 15 min, then refluxed for 6 h under N₂. After cooling most of the EtOH was removed under reduced pressure and the product was extracted with EtOAc (3×10 ml). The organic phase was separated, dried over anhydrous MgSO₄ and filtered. The filtrate was evaporated to dryness under reduced pressure to give the title compound (0.74 g; 94%), as a creamy foam. ¹H-NMR (DMSO-d₆+CDCl₃+CD₃OD) 1.71 (broad s, H₂O); 3.68 (HDO); 6.74 (d, 1H, J=3.1 Hz); 7.01 (tr, 1H, J=7.8 Hz); 7.12-7.2 (m, 2H); 7.3-7.4 (m, 1H).

Step B: 5-(3,4-Diethoxyphenyl)-3-(1H-indol-4-yl)-1,2,4-oxadiazole

To a solution of 3,4-diethoxybenzoic acid (0.11 g; 0.52 mmol), and the product of Step A (0.09 g; 0.51 mmol) in anhydrous THF (2 ml), PyBroP (0.25 g; 0.54 mmol) was added followed by DIPEA (0.21 ml; 1.22 mmol), with stirring, at room temperature under N₂. After 2 h of stirring, the mixture was diluted to 15 ml with EtOAc, washed with saturated NH₄Cl (2×5 ml), brine, dried over anhydrous MgSO₄ and filtered. The filtrate was evaporated to dryness under reduced pressure and the residue was suspended in anhydrous toluene (10 ml). To it 1M TBAF in THF (0.5 ml) was added and the reaction mixture was refluxed for 3 h under N₂, cooled to room temperature and solvents were removed under reduced pressure. The residue was washed with H₂O (5 ml) and the solid was purified by FCC (SiO₂; CH₂Cl₂) to give the title compound (0.06 g; 34%) as colourless solid. ¹H-NMR (CDCl₃) 1.5 (m, 6H); 4.16-4.26 (m, 4H); 6.98 (d, 1H, J=8.5 Hz), 7.31-7.37 (m, 3H); 7.54 (d, 1H, J=8.1 Hz); 7.74 (d, 1H, J=2 Hz); 7.83 (d, 1H, J=8.4 Hz); 8.06 (dd, 1H, J=2, 8.4 Hz); 8.42 (s, 1H).

Step C: 5-(3,4-Diethoxyphenyl)-3-(indolin-4-yl)-1,2,4-oxadiazole

To a solution of the product of Step B (0.06 g; 0.172 mmol) in 1M BH₃ in THF (0.35 ml; 0.35 mmol) CF₃CO₂H (0.4 ml) was added drop wise at 0° C. with stirring. After the addition was completed (~5 min) the reaction was quenched with H₂O (0.5 ml) and solvents were removed under reduced pressure. The residue was diluted to 10 ml with EtOAc and was washed with 10% NaOH (2×2 ml), brine and dried over anhydrous MgSO₄ and filtered. The filtrate was evaporated to dryness under reduced pressure to give the title compound (0.026 g; 43%) as a creamy foam, which was used in the next step without further purification. ¹H-NMR (CDCl₃) 1.49 (m, 6H); 1.7 (broad s, 1H+H₂O); 3.45 (tr, 2H, J=8.9 Hz); 3.65 (tr, 2H, J=8.9 Hz); 4.19 (m, 4H); 6.75 (d, 1H, J=7.7 Hz); 6.97 (d, 1H, J=8.5 Hz); 7.17 (tr, 1H, J=7.7); 7.52 (d, 1H, J=7.2 Hz); 7.68 (d, 1H, J=1.9 Hz); 7.78 (dd, 1H, J=1.9, 7.2 Hz).

Step D: tert-Butyl 5-((4-(5-(3,4-diethoxyphenyl)-1,2,4-oxadiazol-3-yl)indolin-1-yl)methyl)-2,2-dimethyl-1,3-dioxan-5-ylcarbamate When the product of Step C was substituted for 5-n-octyl-indoline in Example 3, Step D, the identical process afforded the title compound in 46% yield., as a creamy solid. ¹H-NMR (CDCl₃) 1.39-1.5 (m, 21H); 3.4 (tr, 2H, J=9.2 Hz); 3.69 (tr, 2H, J=9.2 Hz); 3.71 (5, 2H); 4.09-4.19 (m, 8H); 4.71 (broad s, 1H); 6.71 (d, 1H, J=7.8 Hz); 6.94 (d, 1H, J=8.5 Hz); 7.17 (tr, 1H, J=7.8 Hz); 7.46 (d, 1H, J=7.7 Hz); 7.65 (d, 1H, J=1.9 Hz); 7.75 (dd, 1H, J=1.9; 7.7 Hz).

Step E: 2-Amino-2-((4-(5-(3,4-diethoxyphenyl)-1,2,4-oxadiazol-3-yl)indolin-1-yl)methyl)propane-1,3-diol When the product of Step D was substituted for tea-butyl 2,2-dimethyl-5-((4-octylphenylamino)methyl)-1,3-dioxan-5-ylcarbamate in Example 1, Step B, the identical process afforded the title compound in 71% yield, as a creamy solid. $^1$H-NMR (CDCl$_3$) 1.5 (m, 6H); 1.82 (broad s, 4H+H$_2$O); 3.16 (m, 2H); 3.41-3.59 (m, 8H); 4.13-4.3 (m, 4H); 6.96 (d, 1H, J=7.9 Hz); 7.2 (tr, 1H, J=7.9 Hz); 7.5 (d, 1H, 7.8 Hz); 7.67 (d, 1H, J=1.9 Hz); 7.7 (dd, 1H, J=1.9, 8.4 Hz).

Example 35

2-Amino-2-((4-(5-(3,4-diethoxyphenyl)-1,2,4-oxadiazol-3-yl)-1H-indol-1-yl)methyl)propane-1,3-diol

Step A: tert-Butyl 5-((4-(5-(3,4-diethoxyphenyl)-1,2,4-oxadiazol-3-yl)indol-1-yl)methyl)-2,2-dimethyl-1,3-dioxan-5-ylcarbamate A suspension of the product of Example 34, Step D (0.07 g; 0.118 mmol), MnO$_2$ (0.58 g; 6.67 mmol) and anhydrous MgSO$_4$ (0.5 g; 4.2 mmol) in 1,2-dichloroethane (2.5 ml) was vigorously stirred for 2 h at ~50° C., then overnight at room temperature. This was diluted to 20 ml with CH$_2$Cl$_2$ and filtered through Celite pad, washed with fresh CH$_2$Cl$_2$ (10 ml). The combined organic phase was evaporated under reduced pressure and the residue was purified by FCC (SiO$_2$, CH$_2$Cl$_2$/EtOAc 9:1) to give the title compound (0.02 g; 28%), as creamy solid. $^1$H-NMR (CDCl$_3$) 1.43-1.53 (m, 21H+H$_2$O); 3.78 (d, 2H, J=11.9 Hz); 3.90 (d, 2H, J=11.9 Hz); 4.13-4.38 (m, 5H); 4.76 (s, 1H); 6.98 (d, 1H, J=8.5 Hz); 7.15 (s, 1H); 7.28-7.34 (m, 2H); 7.68 (d, 1H, J=8.4 Hz); 7.73 (d, 1H, J=1.9 Hz); 7.83 (dd, 1H, J=1.9, 8.4 Hz); 8.03 (d, 1H, J=7.2 Hz).

Step B: 2-Amino-2-((4-(5-(3,4-diethoxyphenyl)-1,2,4-oxadiazol-3-yl)indol-1-yl)methyl)propane-1,3-diol To a solution of the product of Step A (0.02 g; 0.0337 mmol), NaI (0.015 g; 0.1 mmol) in anhydrous acetonitrile (1.5 ml) Me$_3$SiCl (0.1 ml; 0.79 mmol) was added at room temperature with stirring under N$_2$. After stirring for 1 h, MeOH (1 ml) was added and the mixture was evaporated to dryness under reduced pressure and the residue was diluted to 10 ml with EtOAc, washed with 1 M NaOH, H$_2$O, brine and dried over anhydrous MgSO$_4$, filtered and the filtrate evaporated to dryness. The residue was purified by FCC (SiO$_2$; CH$_2$Cl$_2$ saturated with concentrated NH$_4$OH (95)/MeOH (5) to give the title compound (0.01 g; 48%), as a creamy solid. $^1$H-NMR (DMSO-d$_6$) 1.36 (m, 6H); 3.17-3.34 (m, 4H+H$_2$O); 4.1-4.19 (m, 6H); 4.77 (m, 2H); 7.05 (d, 1H, J=3.1 Hz); 7.19 (d, 1H, J=8.6 Hz); 7.27 (tr, 1H, J=7.6 Hz); 7.54 (d, 1H, J=3.1 Hz); 7.65 (d, 1H, J=2 Hz); 7.77 (dd, 1H, J=2, 8.5 Hz); 7.8 (d, 1H, J=8.3 Hz); 7.88 (d, 1H, J=7.3 Hz).

Example 36

2-Amino-2-((4-(5-(2'-(trifluoromethyl)biphenyl-4-yl)-1,2,4-oxadiazol-3-yl)indolin-1-yl)methyl)propane-1,3-diol

Step A: 2'-(Trifluoromethyl)biphenyl-4-carbaldehyde

To a stirred solution of 2-trifluoromethyl-bromobenzene (0.7 g, 2.75 mmol) and 4-carbaldehyde boronic acid (0.5 g, 3.3 mmol) in dioxane (20 mL) under nitrogen at 80° C. was added Pd(PPh$_3$)$_4$ (0.05 g) followed by the addition of a solution of Na$_2$CO$_3$ (0.7 g) in H$_2$O (5 m). The mixture was stirred at 100° C. for 6 h. The solvent was evaporated and the residue was diluted to 50 ml with EtOAc and washed with H$_2$O. The solvent was evaporated to dryness and the residue was purified by FCC (SiO$_2$) to give the title compound (0.61 g; 88%), as creamy solid. $^1$H-NMR (CDCl$_3$) 7.49 (d, 1H, J=7.41 Hz); 7.48 (d, 2H, J=8.13 Hz); 7.61-7.53 (m, 2H); 7.76 (d, 1H, J=7.8 Hz); 7.91 (d, 2H, J=8.34 Hz); 10.07 (s, 1H).

Step B: 2'-(Trifluoromethyl)biphenyl-4-carboxylic acid

A suspension of the product of step A (0.4 g, 1.6 mmol) and KMnO$_4$ (0.502 g, 3.2 mmol) in dioxane (15 ml) was refluxed for 2 h with stirring. The solution was filtered through silica gel bead and washed with EtOAc (30 ml). The solvent was evaporated to dryness to give the title compound (0.35 g, 81.6%), as white solid. $^1$H-NMR (CDCl$_3$) 7.30-7.58 (m, 5H); 7.76 (d, 1H, J=8.15 Hz); 8.11 (d, 2H, J=8.03 Hz).

Step C: 3-(1H-Indol-4-yl)-5-(2'-(trifluoromethyl)biphenyl-4-yl)-1,2,4-oxadiazole When the product of Step B was substituted for 3,4-diethoxybenzoic acid in Example 34, Step B the identical process afforded the title compound (0.24 g, 83.6%), as a colourless solid. $^1$H-NMR (CDCl$_3$) 7.31-7.39 (m, 4H); 7.51-7.63 (m, 5H); 7.78 (d, 1H, J=7.59 Hz); 8.1 (bd, 1H, J=7.41 Hz); 8.3 (d, 2H, J=8.49 Hz); 8.48 (b, 1H).

Step D: 3-(Indolin-4-yl)-5-(2'-(trifluoromethyl)biphenyl-4-yl)-1,2,4-oxadiazole When the product of Step C is substituted for 5-(3,4-diethoxyphenyl)-3-(1H-indol-4-yl)-1,2,4-oxadiazole in Example 34, Step C, the identical process afforded the title compound in 99% yield., as a colourless foam. $^1$H-NMR (CDCl$_3$) 3.49 (tr, 2H, J=8.7 Hz); 3.66 (tr, 2H, J=8.7 Hz); 4.09 (broad s, 1H); 6.76 (d, 1H, J=7.6 Hz); 7.16 (tr, 1H, J=7.2 Hz); 7.34 (d, 1H, J=7.6 Hz); 7.4-7.63 (m, 5H); 7.77 (d, 1H, J=7.6 Hz); 8.24 (d, 1H, J=8.5 Hz).

Step E: tert-Butyl 2,2-dimethyl-5-((4-(5-(2'-(trifluoromethyl)biphenyl-4-yl)-1,2,4-oxadiazol-3-yl)indolin-1-yl)methyl)-1,3-dioxan-5-ylcarbamate When the product of Step D was substituted for 5-n-octylindoline in Example 3, Step D, the identical process afforded the title compound in 73% yield., as a colourless solid. $^1$H-NMR (CDCl$_3$) 1.46-1.49 (m, 15H); 3.42-3.61 (m, 6H); 3.92-4.03 (m, 4H); 4.68 (broad s, 1H); 6.74 (d, 1H, J=7.7 Hz); 7.2 (tr, 1H, J=7.7 Hz); 7.34 (d, 1H, J=7.3 Hz); 7.49-7.63 (m, 5H); 7.77 (d, 1H, J=7.6 Hz); 8.24 (d, 1H, J=8.4 Hz).

Step F: 2-Amino-2-((4-(5-(2'-(trifluoromethyl)biphenyl-4-yl)-1,2,4-oxadiazol-3-yl)indolin-1-yl)methyl)propane-1,3-diol When the product of Step E was substituted for tert-butyl 2,2-dimethyl-5-((4-octylphenylamino)methyl)-1,3-dioxan-5-ylcarbamate in Example 1, Step B, the identical process afforded the title compound in 71% yield, as a creamy solid. $^1$H-NMR (CD$_3$OD+CDCl$_3$) 3.1 (s, 2H); 3.35-3.6 (m, 8H); 4.1

(HDO); 6.76 (d, 1H, J=7.8 Hz); 7.17 (tr, 1H, J=7.8 Hz); 7.33 (tr, 1H, J=7.5 Hz); 7.41-7.51 (m, 4H); 7.57 (tr, 1H, J=7.3 Hz); 8.19 (d, 2H, J=8.3 Hz).

Example 37

2-Amino-2-((6-(3-fluorobenzyloxy)-3,4-dihydroisoquinolin-2(1H)-yl)methyl)propane-1,3-diol Step A: 3-(3-Fluorobenzyloxy)benzaldehyde A mixture of 3-fluorobenzyl chloride (0.71 g; 4.91 mmol), 3-hydroxybenzaldehyde (0.6 g; 4.91 mmol) and $Cs_2CO_3$ (1.6 g; 4.91 mmol) in anhydrous DMF (5 ml) was stirred for 4 h at ~60° C. under $N_2$, cooled to room temperature and poured onto $H_2O$ (15 ml). The precipitate formed was filtered off, washed with $H_2O$ and dried in vacuo to give the title compound (0.9 g; 80%), as creamy solid. $^1$H-NMR (CDCl$_3$) 5.11 (s, 2H); 7.13-7.25 (m, 3H+CDCl$_3$); 7.3-7.36 (m, 1H); 7.44-7.48 (m, 3H); 9.96 (5, 1H).

Step B: (E)-1-(3-Fluorobenzyloxy)-4-(2-nitrovinyl)benzene

A solution of the product of Step A (0.5 g; 4.1 mmol) and NH$_4$OAc (0.31 g; 4.1 mmol) in CH$_3$NO$_2$ (10 ml) was refluxed for 1 h under N$_2$. After evaporation of the solvent under reduced pressure, the residue was purified by crystallization from MeOH to give pure title compound (0.29 g; 50%), as yellow crystals. $^1$H-NMR (CDCl$_3$) 5.09 (s, 2H); 7.02-7.21 (m, 6H); 7.32-7.52 (m, 1H); 7.54 (d, 1H, J=13.7 Hz); 7.94 (d, 1H, J=13.7 Hz).

Step C: 2-(4-(3-Fluorobenzyloxy)phenyl)ethanamine

A solution of the product of Step B (0.29 g; 1.0 mmol), 36% HCl (0.16 ml) and 10% Pd/C (0.17 g) in EtOH (15 ml) was stirred for 3 h at 0° C. under H$_2$ (balloon). The catalyst was removed by filtration through Celite pad, washed with EtOH (2×10 ml) and combined filtrates were evaporated to dryness under reduced pressure and the dark residue was diluted to 10 ml with CH$_3$CN and the white precipitate was filtered off, washed with fresh CH$_3$CN (2 ml) and dried to give the title compound (0.2 g; 70%) as off white solid. $^1$H-NMR (D$_2$O) (2.86 (tr, 2H, J=7.2 Hz); 3.15 (tr, 2H, J=7.2 Hz); 4.66 (HDO); 5.07 (s, 2H); 6.85-6.89 (m, 3H); 7.02 (m, 1H); 7.11-7.34 (m, 4H).

Step D: 6-(3-Fluorobenzyloxy)-1,2,3,4-tetrahydroisoquinoline

A mixture of the product of Step C (0.2 g; 3.1 mmol) and (CH$_2$O)$_n$ (0.022 g; 0.74 mmol) in 97% HCOOH (1 ml) was stirred in a septum sealed flask for 24 h at ~40° C. under N$_2$. After removing the solvent in vacuo, the residue was purified by FCC (SiO$_2$; CH$_2$Cl$_2$ saturated with concentrated NH$_4$OH/MeOH; 95:5) to give the title compound (0.04 g; 22%), as creamy foam. $^1$H-NMR (CDCl$_3$) 2.68-2.77 m, 2H); 3.07-3.11 (m, 2H); 3.93 (s, 2H); 5.01-5.07 (m, 3H); 6.68-6.82 (m, 2H); 6.89-7.02 (m, 2H); 7.11-7.2 (m, 2H); 7.28-7.33 (m, 1H).

Step E: tert-Butyl 5-((6-(3-fluorobenzyloxy)-3,4-dihydroisoquinolin-2(1H)-yl)methyl)-2,2-dimethyl-1,3-dioxan-5-ylcarbamate When the product of Step D was substituted for n-octylaniline in Example 1, Step A, the identical process afforded the title compound in 57% yield, as a colourless solid. $^1$H-NMR (CDCl$_3$) 1.35-1.45 (m, 15H+H$_2$O); 2.73 (tr, 2H, J=7.2 Hz); 2.86 (tr, 2H, J=7.2 Hz); 3.61 (d, 2H, J=11.8 Hz); 4.12 (d, 2H, J=11.8 Hz); 5.0 (broad s, 1H); 5.03 (s, 2H); 6.76-6.82 (m, 3H); 6.96-7.03 (m, 1H); 7.12-7.21 (m, 2H); 7.29-7.34 (m, 1H).

Step F: 2-Amino-2-((6-(3-fluorobenzyloxy)-3,4-dihydroisoquinolin-2(1H)-yl)methyl)propane-1,3-diol When the product of Step E was substituted for tert-butyl 2,2-dimethyl-5-((4-octylphenylamino)methyl)-1,3-dioxan-5-ylcarbamate in Example 1, Step B, the identical process afforded the title compound in 21% yield, as a creamy solid. $^1$H-NMR (CDCl$_3$) 2.31 (broad s, 6H); 2.69 (s, 2H); 2.73 (tr, J=6.5 Hz); 2.86 (tr, J=6.5 Hz); 3.47 (s, 4H); 5.03 (5, 2H); 6.78-6.81 (m, 3H); 6.96-7.02 (m, 1H); 7.12-7.25 (m, 2H, +CDCl$_3$); 7.31-7.36 (m, 1H).

Example 38

2-Amino-2-((6-(benzyloxy)-3,4-dihydroisoquinolin-2(1H)-yl)methyl)propane-1,3-diol Step A: 3-Benzyloxybenzaldehyde A mixture of benzyl bromide (1.4 g; 8.2 mmol), 3-hydroxybenzaldehyde (1.0 g; 8.2 mmol) and Cs$_2$CO$_3$ (2.67 g; 8.2 mmol) in anhydrous DMF (5 ml) was stirred overnight at room temperature under N$_2$. After evaporation of solvent in vacuo, the residue was diluted to 20 ml with CH$_2$Cl$_2$, washed with H$_2$O, brine, dried over anhydrous MgSO$_4$, filtered and filtrate evaporated to dryness to give the title compound (1.33 g; 76%) as creamy foam. $^1$H-NMR (CDCl$_3$) 5.11 (s, 2H); 7.2-7.48 (m, 9H); 9.96 (s, 1H).

Step B: (E)-1-(Benzyloxy)-4-(2-nitrovinyl)benzene

A solution of the product of Step A (1.33 g; 6.3 mmol) and NH$_4$OAc (0.5 g; 6.5 mmol) in CH$_3$NO$_2$ (12 ml) was refluxed for 1 h under N$_2$. After evaporation of the solvent under reduced pressure, the residue was purified by crystallization from MeOH to give the title compound (1.06 g; 66%), as yellow crystals. $^1$H-NMR (CDCl$_3$) 3.47 (d, 1H, J=5.2 Hz); 5.09 (s, 2H); 7.1-7.15 (m, 3H); 7.32-7.42 (m, 5H); 7.52 (d, 1H, J=13.6 Hz); 7.94 (d, 1H, J=13.6 Hz).

Step C: 2-(4-(Benzyloxy)phenyl)ethanamine

A solution of the product of Step B (1.06 g; 4.15 mmol) in anhydrous THF (20 ml) was added drop wise to a suspension of LiAlH$_4$ (0.52 g; 13.7 mmol) in anhydrous THF (10 ml) over a period of 1 h at room temperature with vigorous stirring. After additional stirring for 2 h, the reaction mixture was quenched with H$_2$O (1 ml), followed by 10% NaOH (2 ml) and H$_2$O (1 ml). This was stirred for additional 30 min and precipitate formed was filtered off, washed with CH$_2$Cl$_2$ (3×20 ml) and combined filtrates were evaporated to dryness to give the crude title compound (0.71 g; 75%), as a creamy foam, which was used in the next step without further purification. $^1$H-NMR (CDCl$_3$) 1.5 (broad s, 2H+H$_2$O); 2.71 (tr, 2H, J=6.8 Hz); 2.94 (tr, 2H, J=6.8 Hz); 5.04 (s, 2H); 6.17-6.84 (m, 3H); 7.17-7.43 (m, 6H).

Step D: 2-(4-(Benzyloxy)phenyl)ethanamine

A mixture of the product of Step C (0.71 g; 3.1 mmol) and (CH$_2$O)$_n$ (0.13 g; 4.3 mmol) in 90% HCOOH (6 ml) was stirred in a septum sealed flask for 24 h at ~40° C. under $N_2$. After removing the solvent in vacuo, the residue was purified by FCC ($SiO_2$; $CH_2Cl_2$ saturated with concentrated $NH_4OH$ (95)/MeOH (5)) to give the title compound (0.36 g; 50%), as creamy foam. $^1$H-NMR ($CDCl_3$) 2.03 (broad s, 1H+0.5; $H_2O$); 2.75 (tr, 2H, J=65.9 Hz); 3.1 (tr, 2H, J=5.9 Hz); 3.93 (s, 2H); 5.02 (s, 2H); 6.69-6.89 (m, 2H); 6.9 (d, 1H, J=8.4 Hz); 7.3-7.43 (m, 5H).

Step E: tert-Butyl 5-((6-(benzyloxy)-3,4-dihydroisoquinolin-2(1H)-yl)methyl)-2,2-dimethyl-1,3-dioxan-5-ylcarbamate When the product of Step D was substituted for n-octylaniline in Example 1, Step A, the identical process afforded the title compound in 57% yield, as a colourless solid. $^1$H-NMR ($CDCl_3$) 1.39 (s, 3H); 1.43 (s, 9H); 1.46 (s, 3H); 2.83 (5, 4H); 2.93 (s, 2H); 3.68 (s, 2H); 3.81 (d, 2H, J=11.6 Hz); 4.06 (d, 2H, J=11.6 Hz); 4.87 (broad s, 1H); 5.02 (s, 2H); 6.7-6.87 (m, 2H); 6.88 (d, 1H, J=8.3 Hz); 7.29-7.42 (m, 5H).

Step F: 2-Amino-2-((6-(benzyloxy)-3,4-dihydroisoquinolin-2(1H)-yl)methyl)propane-1,3-diol When the product of Step E was substituted for tea-butyl 2,2-dimethyl-5-((4-octylphenylamino)methyl)-1,3-dioxan-5-ylcarbamate in Example 1, Step B, the identical process afforded the title compound in 71% yield, as a creamy solid. $^1$H-NMR ($CDCl_3$) 2.5-2.9 (m, 10H+$H_2O$); 3.4-3.6 (m, 4H); 3.72 (s, 2H); 5.01 (s, 2H); 6.6-6.8 (m, 2H); 6.81-6.95 (m, 1H); 7.25-7.45 (m, 5H).

Example 39

2-Amino-2-((6-((2'-(trifluoromethyl)biphenyl-4-yl)methoxy)-3,4-dihydroisoquinolin-2(1H)-yl)methyl)propane-1,3-diol Step A: tert-Butyl 5-((6-hydroxy-3,4-dihydroisoquinolin-2(1H)-yl)methyl)-2,2-dimethyl-1,3-dioxan-5-ylcarbamate A mixture of the product of Example 38, Step E, (0.13 g; 0.27 mmol) and 10% Pd/C (0.3 g) in EtOAc (15 ml) was vigorously stirred at room temperature for 3 h under $H_2$ (balloon). The catalyst was removed by filtration through the Celite pad, washed with $CH_2Cl_2$ (2×10 ml) and combined filtrates were evaporated to dryness under reduced pressure to give the title compound (0.105 g; 99%) as colourless solid. $^1$H-NMR ($CDCl_3$) 1.4 (s, 3H); 1.42 (s, 9H); 1.44 (s, 3H); 2.7-2.85 (m, 4H); 2.91 (s, 2H); 3.8 (s, 2H); 3.82 (d, 2H, J=11.6 Hz); 4.05 (d, 2H, J=11.6 Hz); 4.98 (broad s, 1H); 5.5 broad s, 1H); 6.52-6.6 (m, 2H); 6.76 (d, 1H, J=8.2 Hz).

Step B: 4'-(Chloromethyl)-2-(trifluoromethyl)biphenyl

To a solution of the product of Example 36, Step A (0.15 g, 0.6 mmol) in MeOH (3 m) $NaBH_4$ (0.028 g; 0.74 mmol) was added in portion wise at room temperature. After 1 h of stirring the solvent was evaporated and the residue was diluted to 20 ml with EtOAc and washed with $H_2O$. The organic layer was separated, dried over $MgSO_4$ and filtered. The filtrate was evaporated to dryness and the residue (0.25 g, 0.99 mmol) was dissolved in anhydrous THF (5 ml). To this DIPEA (0.19 ml, 1.1 mmol) was added at 0° C. under $N_2$, with stirring, followed by $SOCl_2$ (0.08 ml, 1.1 mmol). This was stirred overnight at room temperature. The solvent was distilled off and the crude product was diluted to 20 ml with EtOAc and washed with $NaHCO_3$ solution. The organic layer was separated, dried over $MgSO_4$ and filtered. The filtrate was passed through silica gel bead and washed with fresh EtOAc (20 ml). The combined filtrates were evaporated to dryness to give the title compound (0.24 g, 89%) as colourless oil. $^1$H-NMR ($CDCl_3$) 4.64 (s, 2H); 7.30 (d, 3H, J=8.12 Hz); 7.4-7.58 (m, 4H); 7.73 (d, 2H, J=7.84 Hz).

Step C: tert-Butyl 2,2-dimethyl-5-((6-((2'-(trifluoromethyl)biphenyl-4-yl)methoxy)-3,4-dihydroisoquinolin-2(1H)-yl)methyl)-1,3-dioxan-5-ylcarbamate A mixture of the product of Step A (0.105 g; 0.27 mmol), the product of Step B (0.08 g; 0.03 mmol) and $Cs_2CO_3$ (0.09 g; 0.27 mmol) in anhydrous DMF (1 ml) was stirred overnight at room temperature and solvent was removed in vacuo. The residue was diluted to 15 ml EtOAc and washed with $H_2O$, brine, dried over anhydrous $MgSO_4$, filtered and filtrate evaporated to dryness under reduced pressure. The residue was purified by FCC ($SiO_2$, hexane/EtOAc 9:1) to give the tilted compound (0.12 g; 71%), as colourless solid. $^1$H-NMR ($CDCl_3$) 1.4 (s, 3H); 1.43 (s, 9H); 1.46 (s, 3H); 2.84 (s, 4H); 2.94 (s, 2H); 3.7 (s, 2H); 3.82 (d, 2H, J=11.5 Hz); 4.07 (d, 2H, J=11.5 Hz); 4.88 (broad s, 1H); 5.07 (s, 2H); 6.74 (d, 1H, J=2.4 Hz); 6.78 (dd, 1H, J=2.4, 8.4 Hz); 6.91 (d, 1H, J=8.4 Hz); 7.29-7.35 (m, 3H); 7.43-7.48 (m, 3H); 7.55 (tr, 1H, J=7.7 Hz); 7.73 (d, 1H, J=7.7 Hz).

Step D: 2-Amino-2-((6-((2'-(trifluoromethyl)biphenyl-4-yl)methoxy)-3,4-dihydroisoquinolin-2(1H)-yl)methyl)propane-1,3-diol When the product of Step C was substituted for tert-butyl 2,2-dimethyl-5-((4-octylphenylamino)methyl)-1,3-dioxan-5-ylcarbamate in Example 1, Step B, the identical process afforded the title compound in 75% yield, as an off white solid. $^1$H-NMR ($CDCl_3$+$CD_3OD$) 2.5-3.9 (m, 16H+$H_2O$); 5.02 (s, 2H); 6.69-6.91 (m, 3H); 7.25-7.53 (m, 7H); 7.68 (d, 1H, J=7.8 Hz).

Example 40

2-Amino-2-((5-(5-(3,4-diethoxyphenyl)-1,2,4-oxadiazol-3-yl)indolin-1-yl)methyl)propane-1,3-diol Step A: 5-(3,4-Diethoxyphenyl)-3-(1H-indol-5-yl)-1,2,4-oxadiazole To a solution of 3,4-diethoxybenzoic acid (0.11 g; 0.52 mmol), and the product of Example 7, Step C (0.09 g; 10.52 mmol) in anhydrous THF (2 ml), PyBroP (0.25 g; 0.53 mmol) was added, followed by DIPEA (0.21 ml; 1.2 mmol), with stirring, at room temperature under $N_2$. After overnight stirring, the mixture was diluted to 15 ml with EtOAc, washed with saturated $NH_4Cl$ (3×5 ml), brine, dried over anhydrous $MgSO_4$ and filtered. The filtrate was evaporated to dryness under reduced pressure and the residue was purified by FCC ($SiO_2$, EtOAc) to give the coupling product. This was suspended in anhydrous toluene (3 ml) and 1M TBAF was added. The resulting mixture was refluxed for 1 h under $N_2$, cooled to room temperature and diluted to 15 ml with EtOAc, washed with $H_2O$, brine, dried over anhydrous $MgSO_4$, filtered and filtrate evaporated to dryness. The residue was purified by crystallization from MeOH, to give the title compound (0.096 g; 53%), as a colourless solid. $^1$H-NMR ($CDCl_3$) 1.5 (m, 6H); 4.19 (m, 4H); 6.66 (s, 1H); 6.98 (d, 1H, J=8.4 Hz); 7.26 (m, 1H); 7.47 (d, 1H, J=8.5 Hz); 7.71 (d, 1H, J=1.8 Hz); 7.8 (dd, 1H, J=1.8, 8.5 Hz); 8.0 (dd, 1H, J=1.3, 8.5 Hz); 8.37 (broad s, 1H); 8.5 (s, 1H).

Step B: 5-(3,4-Diethoxyphenyl)-3-(1H-indolin-5-yl)-1,2,4-oxadiazole

When the product of Step A was substituted for 5-(3-chloro-4-methoxyphenyl)-3-(1H-indol-5-yl)-1,2,4-oxadiazole in Example 7, Step F, the identical process afforded the title compound in 46% yield, as an colourless solid. $^1$H-NMR (CDCl$_3$) 1.49 (m, 6H); 3.2 (tr, 2H, J=8.2 Hz); 3.28 (m, 1H); 3.77 (tr, 2H, J=8.2 Hz); 4.19 (m, 4H); 6.96 (d, 1H, J=8.5 Hz); 7.03 (d, 1H, J=8 Hz); 7.66 (d, 1H, J=1.9 Hz); 7.76 (dd, 1H, J=1.9, 8.4 Hz); 7.94-7.99 (m, 2H).

Step C: tert-Butyl 5-((5-(5-(3,4-diethoxyphenyl)-1,2,4-oxadiazol-3-yl)indolin-1-yl)methyl)-2,2-dimethyl-1,3-dioxan-5-ylcarbamate When the product of Step B was substituted for 5-n-octylindoline in Example 3, Step D, the identical process afforded the title compound in 61% yield., as a creamy solid. $^1$H-NMR (CDCl$_3$) 1.41-1.67 (m, 21H+H$_2$O); 3.09 (tr, 2H, J=8.4 Hz); 3.6 (tr, 2H, J=8.4 Hz); 3.66 (s, 2H); 3.93 (s, 4H); 4.13-4.24 (m, 4H); 4.64 (broad s, 1H); 6.64 (d, 1H, J=8.3 Hz); 6.95 (d, 1H, J=8.5 Hz); 7.66 (dd, 1H, J=1.9, 8.4 Hz); 7.8-7.89 (m, 2H).

Step D: 2-Amino-2-((5-(5-(3,4-diethoxyphenyl)-1,2,4-oxadiazol-3-yl)indolin-1-yl)methyl)propane-1,3-diol When the product of Step C was substituted for tert-butyl 2,2-dimethyl-5-((4-octylphenylamino)methyl)-1,3-dioxan-5-ylcarbamate in Example 1, Step B, the identical process afforded the title compound in 80% yield, as a creamy solid. $^1$H-NMR (DMSO-d$_6$) 1.35 (m, 6H); 3.0 (tr, 2H, J=8.2 Hz); 3.17-3.29 (m, 2H+H$_2$O); 3.42 (s, 2H); 3.55 (tr, 2H, J=8.2 Hz); 3.97 (s, 4H); 4.14 (m, 4H); 5.06 (broad s, 2H); 6.71 (d, 1H, J=8.4 Hz); 7.56 (m, 1H); 7.6-8.3 (m, 3H).

Example 41

2-Amino-2-((4-((4,6-dichlorobenzofuran-2-yl)methoxy)indolin-1-yl)methyl)propane-1,3-diol (a) and t-butyl 1-(4-((4,6-dichlorobenzofuran-2-yl)methoxy)indolin-1-yl)-3-hydroxy-2-(hydroxymethyl)propan-2-ylcarbamate (b)

Step A: 4-Hydroxyindoline

A solution of 4-hydroxyindole (0.16 g; 1.2 mmol) in AcOH (6 ml) was treated with NaBH$_3$CN (0.23 g; 3.6 mmol), at rate keeping the temperature below 15° C. The mixture was then stirred for 1 h at room temperature and H$_2$O (0.4 ml) was added and solvents removed in vacuo. The residue was diluted to 15 ml with EtOAc, washed with 5% NaHCO$_3$, brine, dried over anhydrous MgSO$_4$, filtered and filtrate evaporated under reduced pressure to give the title compound (0.16 g; 99%) as creamy solid. $^1$H-NMR (CDCl$_3$) 2.93 (tr, 2H, J=8.4 Hz); 3.58 (tr, 2H, J=8.4 Hz); 3.74 (broad s, 2H); 6.17 (d, 1H, J=8 Hz); 6.26 (d, 1H, J=7.72 Hz); 6.88 (tr, 1H, J=7.85 Hz).

Step B: tert-Butyl 5-((4-hydroxyindolin-1-yl)methyl)-2,2-dimethyl-1,3-dioxan-5-ylcarbamate When the product of Step A was substituted for tert-butyl 5-((5-hydroxyindolin-1-yl)methyl)-2,2-dimethyl-1,3-dioxan-5-ylcarbamate in Example 8, Step G, the identical process afforded the title compound in 74% yield, as a creamy solid. $^1$H-NMR (CDCl$_3$) 1.4-1.65 (m, 15H+H$_2$O); 2.94 (tr, 2H, J=8.4 Hz); 3.5 (tr, 2H, J=8.4 Hz); 3.52 (s, 2H); 3.8-3.99 (m, 4H); 4.64 (broad s, 1H); 4.7 (broad s, 1H); 6.15-6.23 (m, 2H); 6.93 (tr, 1H, J=7.96 Hz).

Step C: tert-Butyl 5-((4-((4,6-dichlorobenzofuran-2-yl)methoxy)indolin-1-yl)methyl)-2,2-dimethyl-1,3-dioxan-5-ylcarbamate When the product of Step A was substituted for 5-n-octylindoline in Example 3, Step D, the identical process afforded the title compound in 75% yield, as a creamy solid. $^1$H-NMR (CDCl$_3$) 1.4-1.64 (m, 15H+H$_2$O); 2.98 (tr, 2H, J=8.5 Hz); 3.48 (tr, 2H, J=8.5 Hz); 3.52 (s, 2H); 3.8-3.99 (m, 4H); 4.69 (broad s, 1H); 5.13 (s, 2H); 6.13-6.38 (m, 2H); 6.8 (s, 1H); 7.03 (tr, 1H, J=8.12 Hz). 7.24 (s, 1H+CDCl$_3$); 7.4 (s, 1H).

Step D: 2-Amino-2-((4-((4,6-dichlorobenzofuran-2-yl)methoxy)indolin-1-yl)methyl)propane-1,3-diol (a) and tert-butyl 1-(4-((4,6-dichlorobenzofuran-2-yl)methoxy)indolin-1-yl)-3-hydroxy-2-(hydroxymethyl)propan-2-ylcarbamate(b)

A mixture of the product of Step C (0.09 g; 0.16 mmol) in 60% CF$_3$CO$_2$H/CH$_2$Cl$_2$ (2 ml) was stirred for 3 min at room temperature, then diluted to 5 ml with MeOH and solvents were removed under reduced pressure. The residue was purified by FCC (SiO$_2$; CH$_2$Cl$_2$ saturated with concentrated NH$_4$OH/MeOH; 95/5) to give the title compound (a) (0.03 g; 43%) and (b) (0.02 g; 8%), as colourless solids. $^1$H-NMR- (a) (CDCl$_3$) 1.22 (broad s, 4H); 2.95 (tr, 2H, J=8.4 Hz); 3.05 (s, 2H); 3.4-3.65 (m, 6H); 5.12 (s, 2H); 6.23-6.4 (m, 2H); 6.8 (s, 1H); 7.03 (tr, 1H, J=8.13 Hz); 7.22 (s, 1H); 7.38 (5, 1H). $^1$H-NMR-(b) (CDCl$_3$) 1.24 (s, 2H); 1.43 (s, 9H); 1.55 (broad s, 2H+H2O); 3.02 (t, 2H, J=8.3 Hz); 3.29 (s, 2H); 3.52-3.67 (m, 4H); 5.14 (s, 2H); 5.38 (broad s, 1H); 6.38-6.47 (m, 2H); 6.82 (s, 1H); 7.11 (t, 1H, J=8 Hz). 7.24 (s, 1H+CDCl$_3$); 7.4 (s, 1H).

Example 42

2-Amino-2-((4-(5-(2-methylbenzofuran-5-yl)-1,2,4-oxadiazol-3-yl)indolin-1-yl)methyl)propane-1,3-diol

Step A: 4-Hydroxy-3-iodobenzonitrile

To a solution of 4-hydroxybenzonitrile (0.5 g; 4.18 mmol) in 25% NH$_4$OH (22 ml) a solution of I$_2$ (1.06 g; 4.18 mmol) and KI (3.41 g; 20.54 mmol) in H$_2$O (5 ml) was added at once with stirring. The stirring was continued for 6 h, during which time the mixture turn from black into colourless. The precipitate formed was filtered off and filtrate was evaporated to dryness under reduced pressure. The residue was treated with H$_2$O (3 ml). The precipitate formed was filtered off, washed with cold H$_2$O (3×2 ml), and dried in vacuo to give the title compound (0.82 g; 80%), as colourless solid. $^1$H-NMR (CDCl$_3$) 6.03 (s, 1H); 7.03 (d, 1H, J=8.5 Hz); 7.53 (dd, 1H, J=1.9 Hz, 8.5 Hz); 7.96 (d, 1H, 1.9 Hz).

Step B: 4-Hydroxy-3-(prop-1-ynyl)benzonitrile

A suspension of the product of Step A (0.3 g; 1.22 mmol) in HMDSA (2 ml) and saccharine (0.1 g) was refluxed under N$_2$ until reaction became homogenous (~30 min). After cooling to room temperature, the HMDSA was removed in vacuo and the residue was diluted to 4 ml with anhydrous THF. At the same time ZnCl$_2$ (0.2 g; 1.47 mmol) was heated to ~110°

C., in separate flask, in vacuo, cooled to room temperature under $N_2$ and diluted to 4 ml with anhydrous THF. To it 0.5 M prop-1-ynyl-magnesium bromide in THF (4.9 ml; 2.45 mmol) was added at room temperature and this was stirred for 10 min under $N_2$. To it a solution of silinated product of Step A was added, followed by $Pd(PPh_3)_4$ (0.11 g; 0.095 mmol) and CuI (0.05 g; 0.26 mmol). After stirring for 1 h at room temperature under $N_2$, MeOH (5 ml) was added and solvents were removed under reduced pressure. The residue was diluted to 20 ml with EtOAc, washed with saturated $NH_4Cl$ (2×5 ml), $H_2O$ (10 ml), brine, dried anhydrous $MgSO_4$, filtered and filtrate evaporated to dryness under reduced pressure. The residue was purified by FCC ($SiO_2$, $CH_2Cl_2$) to give title compound (0.16 g; 78%), as colourless solid. $^1$H-NMR ($CDCl_3$) 2.14 (s, 3H); 6.26 (s, 1H); 6.97 (d, 1H, J=8.5 Hz); 7.46 (dd, 1H, J=2.1 Hz, 8.5 Hz); 7.57 (d, 1H, 2.1 Hz).

Step C: 2-Methylbenzofuran-5-carboxylic acid

A mixture of the product of Step B (0.16 g; 1.02 mmol) and 1M TBAF in THF (0.1 ml) in dioxane (3 ml) was refluxed for 1 h under $N_2$. After cooling to room temperature the solvents were removed under reduced pressure and the residue was filtered through a small pad of $SiO_2$, washed with fresh $CH_2Cl_2$ (3×15 ml). The combined organic phase was evaporated to dryness to give 2-methylbenzofuran-5-carbonitrile (0.16 g; 100%), as greyish solid. This was dissolved in dioxane (5 ml) and KOH (0.2 g; 3.6 mmol) was added, followed by $H_2O$ (1 ml). The resulting mixture was refluxed overnight, cooled to room temperature and solvents were removed under reduced pressure. The residue was diluted to 1 ml with $H_2O$. The insoluble material was filtered off, washed with fresh $H_2O$, and combined filtrates were acidified to pH~5 with concentrated citric acid. The solid formed was filtered off, dissolved in EtOAc (10 ml), dried over anhydrous $MgSO_4$, filtered and filtrate evaporated to dryness to give title compound (0.08 g; 44%) as creamy solid. $^1$H-NMR ($CDCl_3$) 2.47 (s, 3H); 6.42 (s, 1H); 7.43 (d, 1H, J=8.6 Hz); 7.99 (dd, 1H, J=1.6, 8.6 Hz); 8.26 (d, 1H, J=1.6 Hz).

Step D: 3-(1H-Indol-4-yl)-5-(2-methylbenzofuran-5-yl)-1,2,4-oxadiazole

When the product of Step C was substituted for 3,4-diethoxybenzoic acid in Example 34, Step B, the identical process afforded the title compound in 41% yield, as a colourless foam. $^1$H-NMR ($CDCl_3$) 2.5 (s, 3H); 6.5 (s, 1H); 7.3-7.38 (m, 3H); 7.55 (tr, 2H, J=8.66 Hz); 8.07-8.16 (m, 2H); 8.37 (broad s, 1H). 8.4 (s, 1H).

Step E: 3-(indolin-4-yl)-5-(2-methylbenzofuran-5-yl)-1,2,4-oxadiazole

When the product of Step D was substituted for 5-(3,4-diethoxyphenyl)-3-(1H-indol-4-yl)-1,2,4-oxadiazole in Example 34, Step C, the identical process afforded the title compound in 100% yield, as a colourless foam. $^1$H-NMR ($CDCl_3$) 2.49 (s, 3H); 2.52 (broad s, 1H+$H_2O$); 3.48 (tr, 2H, J=8.44 Hz); 3.68 (tr, 2H, J=8.44 Hz); 6.48 (s, 1H); 6.85 (d, 1H, J=7.75 Hz); 7.2 (tr, 2H, J=7.6 Hz); 7.38 (d, 1H, J=8.16 Hz); 7.51 (d, 1H, J=8.5 Hz); 8.06 (d, 1H, J=8.5 Hz); 8.32 (s, 1H).

Step F: tert-Butyl 2,2-dimethyl-5-((4-(5-(2-methylbenzofuran-5-yl)-1,2,4-oxadiazol-3-yl)indolin-1-yl)methyl)-1,3-dioxan-5-ylcarbamate When the product of Step E was substituted for 5-(3,4-diethoxyphenyl)-3-(1H-indolin-4-yl)-1,2,4-oxadiazole in Example 34, Step D, the identical process afforded the title compound in 75% yield., as a colourless foam. $^1$H-NMR ($CDCl_3$) 1.46-1.56 (m, 15H+$H_2O$); 2.49 (s, 3H); 3.42-3.61 (m, 6H); 4.01 (m, 4H); 4.7 (broad s, 1H) 6.48 (s, 1H); 6.74 (d, 1H, J=7.5 Hz); 7.2 (tr, 2H, J=7.9 Hz); 7.51 (d, 2H, J=8.36 Hz); 8.07 (dd, 1H, J=1.7, 8.6 Hz); 8.33 (d, 1H, J=1.7 Hz).

Step G: 2-Amino-2-((4-(5-(2-methylbenzofuran-5-yl)-1,2,4-oxadiazol-3-yl)indolin-1-yl)methyl)propane-1,3-diol When the product of Step F was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 67% yield., as a colourless foam. $^1$H-NMR (DMSO-$d_6$) 1.36 (broad s, 3H); 2.91 (s, 2H); 3.29 (m, 2H+$H_2O$); 3.55 (tr, 2H, J=8.02 Hz); 4.55 (m, 2H); 6.75-6.79 (m, 2H); 7.14 (tr, 1H, J=7.9 Hz); 7.26 (d, 1H, 7.8 Hz); 7.72 (d, 1H, J=8.5 Hz); 8.02 (d, 1H, J=9.17 Hz); 8.36 (s, 1H).

Example 43

2-Amino-2-((4-(5-(3,4-di-propoxyphenyl)-1,2,4-oxadiazol-3-yl)indolin-1-yl)methyl)propane-1,3-diol Step A: Propyl 3,4-di-n-propoxybenzoate A mixture of 3,4-dihydroxybenzoic acid (0.65 g; 4.22 mmol), anhydrous $K_2CO_3$ (1.75 g; 12.7 mmol) and n-PrBr (1.5 ml; 4 mmol) in anhydrous DMF (5 ml) was stirred at ~55° C. overnight. After cooling to room temperature, the mixture was diluted to 25 ml with EtOAc, washed with $H_2O$ (2×10 ml), brine, dried over anhydrous $MgSO_4$, filtered and the filtrate evaporated to dryness to give the title compound (0.94 g; 80%), as heavy syrup, which was used in next step without further purification. $^1$H-NMR ($CDCl_3$) 0.97-1.04 (m, 9H); 1.7-1.9 (m, 6H); 3.97-4.02 (m, 4H); 4.2-4.26 (m, 2H); 6.85 (d, 1H, J=8.4 Hz); 7.53 (s, 1H); 7.62 (d, 1H, J=8.4 Hz).

Step B: 3,4-Di-propoxybenzoic acid

A mixture of the product of Step A (0.94 g; 3.35 mmol), KOH (0.56 g; 10 mmol), $H_2O$ (2 ml) and dioxane was stirred at reflux overnight. After evaporation of solvents under reduced pressure, the residue was dissolved on $H_2O$ (5 ml) and insoluble material was removed by filtration. The filtrate was acidified to pH~3 with diluted HCl and the product was taken up by extraction with $CH_2Cl_2$ (3×15 ml). The combined organic phase was dried over anhydrous $MgSO_4$, filtered and filtrate evaporated to dryness to give the title compound (0.75 g; 94%) as creamy solid. $^1$H-NMR ($CDCl_3$) 1.02-1.08 (m, 6H); 1.79-1.93 (m, 4H); 3.98-4.05 (m, 4H); 6.87 (d, 1H, J=8.5 Hz); 7.57 (d, 1H, J=2 Hz)); 7.7 (dd, 1H, J=2, 8.5 Hz).

Step C: 5-(3,4-Di-propoxyphenyl)-3-(1H-indol-4-yl)-1,2,4-oxadiazole

When the product of Step B was substituted for 3,4-diethoxybenzoic acid and PyBroP was substituted by EDC (1.2 equivalent) and THF was substituted by anhydrous DMF in Example 34, Step B, the similar process afforded the title compound in 24% overall yield., as a colourless foam. $^1$H-NMR ($CDCl_3$) 1.04-1.11 (m, 6H); 1.85-2.03 (m, 4H); 4.02-4.11 (m, 4H); 6.99 (d, 1H, J=9 Hz); 7.28-7.85 (m, 1H); 8.06-8.08 (m, 1H); 8.51 (broad s, 1H).

Step D: 5-(3,4-Di-propoxyphenyl)-3-(1H-indolin-4-yl)-1,2,4-oxadiazole

When the product of Step C was substituted for 5-(3,4-diethoxyphenyl)-3-(1H-indol-4-yl)-1,2,4-oxadiazole in Example 34, Step C, the identical process afforded the title compound in 100% yield., as a colourless solid. $^1$H-NMR (CDCl$_3$) 1.01-1.11 (m, 6H); 1.85-1.92 (m, 4H); 3.46 (m, 2H); 2.2 (broad s, 1H); 3.64 (m, 2H); 4.02-4.11 (m, 4H); 6.75-7.84 (m, 6H+CDCl$_3$).

Step E: tert-Butyl 5-((4-(5-(3,4-di-propoxyphenyl)-1,2,4-oxadiazol-3-yl)indolin-1-yl)methyl)-2,2-dimethyl-1,3-dioxan-5-ylcarbamate When the product of Step D was substituted for 5-(3,4-diethoxyphenyl)-3-(1H-indolin-4-yl)-1,2,4-oxadiazole in Example 34, Step D, the identical process afforded the title compound in 75% yield., as a colourless foam. $^1$H-NMR (CDCl$_3$) 1.06-1.09 (m, 6H); 1.4-1.49 (m, 15H); 3.42 (tr, 2H, J=9 Hz); 3.57 (tr, 2H, J=9 Hz); 3.59 (s, 2H); 3.91-4.14 (m, 8H); 4.67 (broad s, 1H); 6.73 (d, 1H, J=9 Hz); 6.97 (d, 1H, J=9 Hz); 7.16-7.21 (m, 1H); 7.48 (d, 1H); J=9 Hz); 7.67 (d, 1H, J=3 Hz); 7.77 (dd, 1H, J=3, 9 Hz).

Step F: 2-Amino-2-((4-(5-(3,4-di-propoxyphenyl)-1,2,4-oxadiazol-3-yl)indolin-1-yl)methyl)propane-1,3-diol When the product of Step E was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 67% yield., as a colourless solid. $^1$H-NMR (DMSO-d$_6$) 0.95-1.01 (m, 6H); 1.37 (s, 2H); 1.68-1.8 (m, 4H); 2.98 (s, 2H); 3.2-3.3 (m, 6H+H2O); 3.5-3.57 (m, 2H); 3.9-4.05 (m, 4H); 4.55 (broad s, 2H); 6.77 (d, 1H, J=9 Hz); 7.1-7.26 (m, 3H); 7.58 (d, 1H, J=3 Hz); 7.71 (dd, 1H, J=3, 9 Hz).

Example 44

2-Amino-2-((4-(5-(3-iodo-4-propoxyphenyl)-1,2,4-oxadiazol-3-yl)indolin-1-yl)methyl)propane-1,3-diol

Step A: 3-Iodo-4-hydroxybenzoic acid

A solution of I$_2$ (1.06 g; 4.18 mmol) and KI (3.41 g; 20.54 mmol) in H$_2$O was added at once to a solution of 4-hydroxybenzoic acid (0.58 g; 4.18 mmol) in 25% NH$_4$OH (22 ml). The reaction mixture turn instantly from black to colourless upon stirring at room temperature. This was evaporated under reduced pressure, diluted to 5 ml with H$_2$O and acidified to pH~5 with 10% citric acid. The solid formed was filtered off, washed with H$_2$O (2×5 ml) and dried to give title compound (0.91 g; 89%), as colourless solid. $^1$H-NMR (DMSO-d$_6$) 6.9 (d, 1H, J=8.5 Hz); 7.75 (dd, 1H, J=2, 8.5 Hz); 8.17 (d, 1H, J=2 Hz); 11.4 (s, 1H).

Step B: Propyl 3-iodo-4-propoxybenzoate

When the product of Step A was substituted for 3,4-dihydroxy benzoic acid in Example 43, Step A, the similar process afforded the title compound in 94%, as creamy syrup, which was used in the next step without further purification. $^1$H-NMR (CDCl$_3$) 1.21-1.37 (m, 6H); 1.5-1.96 (m, 4H); 3.98-4.04 (m, 2H); 4.2-4.26 (m, 2H); 6.71 (d, 1H, J=8.6 Hz); 7.97 (dd, 1H, J=2.1, 8.6 Hz); 8.43 (d, 1H, J=2.1 Hz).

Step C: 3-Iodo-4-propoxybenzoic Acid

When the product of Step B was substituted for propyl 3,4-dipropoxybenzoate in Example 43, Step B, the identical process afforded the title compound in 94%, as creamy solid. $^1$H-NMR (CDCl$_3$) 1.04-1.15 (m, 3H); 1.83-1.94 (m, 2H); 3.99-4.08 (m, 2H); 6.8 (d, 1H, J=6 Hz); 8.04 (dd, 1H, J=3, 6 Hz); 8.5 (d, 1H, J=3 Hz).

Step D: 5-(3-Iodo-4-propoxyphenyl)-3-(1H-indol-4-yl)-1,2,4-oxadiazole

When the product of Step C was substituted for 3,4-dipropoxybenzoic acid in Example 43, Step C, the similar process afforded the title compound in 38% yield., as a colourless solid. $^1$H-NMR (CDCl$_3$) 1.03-1.11 (m, 3H); 1.83-1.98 (m, 2H); 4.1-4.19 (m, 2H); 7.21-7.43 (m, 4H+CDCl$_3$); 7.53-7.57 (m, 1H); 8.04-8.06 (m, 1H); 8.11-8.2 (m, 1H); 8.29-8.39 (m, 2H); 8.7-8.77 (m, 1H).

Step E: 5-(3-Iodo-4-propoxyphenyl)-3-(1H-indolin-4-yl)-1,2,4-oxadiazole

When the product of Step D was substituted for 5-(3,4-dipropoxyphenyl)-3-(1H-indol-4-yl)-1,2,4-oxadiazole in Example 43, Step D, the similar process afforded the title compound in 100% yield., as a creamy solid. $^1$H-NMR (CDCl$_3$) 1.12 (tr, 3H, J=9 Hz); 1.85-1.97 (m, 2H); 2.68 (broad s, 1H+H2O); 3.46 (tr, 2H, J=9 Hz); 3.7 (tr, 2H, J=9 Hz); 4.09 (tr, 2H, J=9 Hz); 6.87-6.91 (m, 2H); 7.19-7.24 (m, 1H); 7.65 (d, 1H, J=9 Hz); 8.11 (dd, 1H, J=3, 6 Hz); 8.6 (d, 1H, J=3 Hz).

Step F: tert-Butyl 5-((4-(5-(3-iodo-4-propoxyphenyl)-1,2,4-oxadiazol-3-yl)indolin-1-yl)methyl)-2,2-dimethyl-1,3-dioxan-5-ylcarbamate When the product of Step E was substituted for 5-(3,4-diethoxyphenyl)-3-(1H-indolin-4-yl)-1,2,4-oxadiazole in Example 34, Step D, the identical process afforded the title compound in 60% yield., as a colourless foam. $^1$H-NMR (CDCl$_3$) 1.11 (tr, 3H, J=9 Hz); 1.45-1.48 (m, 15H); 1.86-1.94 (m, 2H); 3.42 (tr, 2H, J=7.5 Hz); 3.57 (tr, 2H, J=7.5 Hz); 3.59 (s, 2H); 3.91-4.09 (m, 6H); 4.67 (s, 1H); 6.73 (d, 1H, J=7.7 Hz); 6.88 (d, 1H, J=8.7 Hz); 7.18 (tr, 1H, J=7.8 Hz); 7.46 (d, 1H, J=7.4 Hz); 8.12 (dd, 1H, J=2.1, 8.6 Hz); 8.61 (d, 1H, J=2.1 Hz).

Step G: 2-Amino-2-((4-(5-(3-iodo-4-propoxyphenyl)-1,2,4-oxadiazol-3-yl)indolin-1-yl)methyl)propane-1,3-diol When the product of Step F was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 75% yield., as a colourless solid. $^1$H-NMR (DMSO-d$_6$) 1.02 (tr, 3H, J=7.3 Hz); 1.4 (broad s, 2H); 1.72-1.8 (m, 2H); 2.98 (s, 2H); 3.2-3.4 (m, 6H+H$_2$O); 3.53 (tr, 2H, J=8.3 Hz); 4.09 3.53 (tr, 2H, J=6.1 Hz); 4.56 (broad s, 2H); 6.76 (d, 1H, J=7.7 Hz); 7.09-7.25 (m, 3H); 8.1 (d, 1H, J=8.8 Hz); 8.44 (s, 1H).

Example 45

2-Amino-2-((4-(5-(3-iodo-4-propoxyphenyl)-1,2,4-oxadiazol-3-yl)indolin-1-yl)methyl)propane-1,3-diol

Step A: 3-Cyano-4-hydroxybenzoic acid

A mixture of the product of Example 44 Step C (0.22 g; 0.72 mmol), NaCN (0.04 g; 0.8 mmol) and CuCN (0.07 g; 0.8 mmol) in anhydrous DMF (2 ml) was stirred at ~110° C. for 2 h under $N_2$. This was evaporated to dryness in vacuo and the residue was suspended in $H_2O$ (10 ml) and pH was adjusted to ~10 with 1 M NaOH. The insoluble material was removed by filtration and the filtrate was acidified to pH~3 with diluted HCl and the product was taken up by $CH_2Cl_2$ (2×20 ml). The organic phase was dried over anhydrous $MgSO_4$, filtered and the filtrate evaporated to dryness under reduced pressure to give the title compound (0.1 g; 67%) as brownish solid. $^1$H-NMR (CDCl$_3$) 1.06-1.14 (m, 3H); 1.85-1.97 (m, 2H); 4.1-4.18 (m, 2H); 7.02 (d, 1H, J=9 Hz); 8.24 (dd, 1H, J=3, 9 Hz); 8.31 (d, 1H, J=3 Hz).

Step B: 5-(3-Cyano-4-propoxyphenyl)-3-(1H-indol-4-yl)-1,2,4-oxadiazole

When the product of Step A was substituted for 3,4-dipropoxybenzoic acid in Example 43 Step C, the similar process afforded the title compound in 27% yield., as a colourless solid. $^1$H-NMR (CDCl$_3$) 1.1 (tr, 3H, J=7.4 Hz); 1.86-1.97 (m, 2H); 4.14 (tr, 2H, J=6 .Hz); 7.11 (d, 1H, J=8.9 Hz); 7.3-7.39 (m, 3H); 7.59 (d, 1H, J=8.1 Hz); 8.04 (d, 1H, J=7.3 Hz); 8.36-8.5 (m, 3H).

Step C: 5-(3-Cyano-4-propoxyphenyl)-3-(1H-indolin-4-yl)-1,2,4-oxadiazole

When the product of Step B was substituted for 5-(3-Iodo-4-propoxyphenyl)-3-(1H-indol-4-yl)-1,2,4-oxadiazole in Example 43 Step D, the similar process afforded the title compound in ~35% yield., as a creamy solid, which was used in next step without further purification. $^1$H-NMR (CDCl$_3$) 1.06-1.11 (m, 3H); 1.54 (broad s, 1H+H$_2$O); 1.87-1.96 (m, 2H); 3.47 (m, 2H); 3.7 (m, 2H); 4.14 (m, 2H); 6.76 (d, 1H, J=6 Hz); 7.08-7.15 (m, 2H); 7.3-7.51 (m, 2H); 7.57 (d, 1H, J=9 Hz).

Step D: tert-Butyl 5-((4-(5-(3-cyano-4-propoxyphenyl)-1,2,4-oxadiazol-3-yl)indolin-1-yl)methyl)-2,2-dimethyl-1,3-dioxan-5-ylcarbamate When the product of Step E was substituted for 5-(3,4-diethoxyphenyl)-3-(1H-indolin-4-yl)-1,2,4-oxadiazole in Example 34, Step D, the identical process afforded the title compound in 42% yield., as a colourless foam. $^1$H-NMR (CDCl$_3$) 1.24 (m, 3H); 1.44-1.49 (m, 15H); 1.86-1.99 (m, 2H); 3.41 (tr, 2H, J=9 Hz); 3.57 (tr, 2H, J=9 Hz); 3.6 (s, 2H); 3.91-4.16 (m, 6H); 4.67 (broad s, 1H); 6.73 (d, 1H, J=9 Hz); 7.08-7.46 (m, 3H); 8.3-8.47 (m, 2H).

Step E: 2-Amino-2-((4-(5-(3-iodo-4-propoxyphenyl)-1,2,4-oxadiazol-3-yl)indolin-1-yl)methyl)propane-1,3-diol When the product of Step D was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 7% yield, as a creamy solid. $^1$H-NMR (DMSO-d$_6$) 0.98 (tr, 3H, J=7.4 Hz); 1.76-1.8 (m, 2H); 2.99 (s, 2H); 3.28-3.56 (m, 10H, +H$_2$O); 4.2 (tr, 2H, J=6.4 Hz); 4.65 (m, 2H); 6.78 (m, 1H); 7.13 (m, 1H); 7.23 (m, 1H); 7.47 (d, 1H, J=9 Hz); 8.45 (m, 1H); 8.46 (d, 1H, 2 Hz).

Example 46

2-Amino-2-((4-(5-(3-amino-4-propoxyphenyl)-1,2,4-oxadiazol-3-yl)indolin-1-yl)methyl)propane-1,3-diol

Step A: Propyl-3-nitro-4-propoxybenzoate

When the product of 4-hydroxy-3-nitrobenzoic acid was substituted for 3,4-dihydroxy benzoic acid in Example 43 Step A and reaction time was 48 h, the similar process afforded the title compound in 100%, as creamy syrup, which was used in the next step without further purification. $^1$H-NMR (CDCl$_3$) 1.18-1.38 (m, 6H); 1.71-1.94 (m, 4H); 4.07-4.14 (m, 2H); 4.24-4.3 (m, 2H); 7.08 (d, 1H, J=8.8 Hz); 8.17 (dd, 1H, J=2.2, 8.8 Hz); 8.46 (d, 1H, J=2.2 Hz).

Step B: 3-Nitro-4-propoxybenzoic Acid

When the product of Step A was substituted for propyl 3,4-dipropoxybenzoate in Example 43 Step B, the identical process afforded the title compound in 97%, as creamy solid. $^1$H-NMR (CDCl$_3$) 1.05-1.09 (m, 3H); 1.83-1.96 (m, 2H); 4.12-4.17 (m, 2H); 7.13 (d, 1H, J=9 Hz); 8.23 (dd, 1H, J=3, 9 Hz); 8.53 (d, 1H, J=3 Hz).

Step C: 3-(tert-Butoxycarbonylamino)-4-propoxybenzoic acid

A mixture of the product of Step B (0.38 g; 1.69 mmol) and 10% Pd/C (0.2 g) in EtOH (15 ml) was vigorously stirred for 1 h at room temperature under H$_2$ (balloon). The catalyst was removed by filtration through Celite pad, washed with CH$_2$Cl$_2$ (2×15 ml) and combined filtrates were evaporated to dryness under reduced pressure to give relevant aniline (0.32 g; 97%), which was suspended in H$_2$O (3.3 ml) and t-BuOH (2.5 ml). To this (Boc)$_2$O (0.72 g; 3.3 mmol) was added, followed by solid NaOH (0.07 g; 1.75 mmol) and the resulting mixture was stirred at ~60° C. for 3 h. The solvent were removed under reduced pressure and the residue was diluted to 5 ml with H$_2$O, washed with Et$_2$O (3 ml) and aqueous solution was acidified to pH 3 with diluted HCl. The product was taken up with CH$_2$Cl$_2$ (2×10 ml). The organic phase was dried over anhydrous MgSO$_4$, filtered and filtrate evaporated to dryness under reduced pressure to give the title compound (0.17 g; 34%) as creamy solid. $^1$H-NMR (CDCl$_3$) 1.05 (tr, 3H, J=9 Hz); 1.54 (s, 1H); 1.84-1.91 (m, 2H); 4.02-4.07 (m, 2H); 6.86 (d, 1H, J=6 Hz); 7.02 (s, 1H); 7.73-7.76 (m, 1H); 8.76 (5, 1H).

Step D: tert-Butyl 5-(3-(1H-indol-4-yl)-1,2,4-oxadiazol-5-yl)-2-propoxyphenyl carbamate When the product of Step C was substituted for 3,4-dipropoxybenzoic acid in Example 43 Step C, the similar process afforded the title compound in 43% yield., as a colourless solid. $^1$H-NMR (CDCl$_3$) 1.03-1.08 (m, 3H); 1.58 (s, 9H); 1.84-1.91 (m, 2H); 4.04 (tr, 2H, J=6 .Hz); 6.95 (d, 1H, J=9 Hz); 7.1 (s, 1H); 7.25-7.35 (m, 2H); 7.87 (dd, 1H, J=3, 6 Hz); 8.06-8.09 (m, 1H); 8.53 (s, 3H); 8.97 (s, 1H).

Step E: tert-Butyl 5-(3-(1H-indolin-4-yl)-1,2,4-oxadiazol-5-yl)-2-propoxyphenyl carbamate When the product of Step D was substituted for 5-(3-Iodo-4-propoxyphenyl)-3-(1H-indol-4-yl)-1,2,4-oxadiazole in Example 43 Step D, the similar process afforded the title compound in 100% yield., as a creamy solid, which was used in next step without further purification. $^1$H-NMR (CDCl$_3$) 1.04-1.09 (m, 3H); 1.56 (s, 9H); 1.86-1.93 (m, 2H); 3.46 (tr, 2H, J=9 Hz); 3.64 (tr, 2H, 9 Hz); 4.04-4.1 (m, 2H); 6.74 (d, 1H, J=6 Hz); 6.94 (d, 1H, J=9 Hz); 7.08-7.16 (m, 2H); 7.55 (d, 1H, J=6 Hz); 7.82 (dd, 1H, J=3, 6 Hz); 8.9 (s, 1H).

Step F: tert-Butyl 5-((4-(5-(3-(tert-butoxycarbonylamino)-4-propoxyphenyl)-1,2,4-oxadiazol-3-yl)indolin-1-yl)methyl)-2,2-dimethyl-1,3-dioxan-5-ylcarbamate When the product of Step E was substituted for 5-(3,4-diethoxyphenyl)-3-(1H-indolin-4-yl)-1,2,4-oxadiazole in Example 34, Step D, the identical process afforded the title compound in 65% yield., as a colourless foam. $^1$H-NMR (CDCl$_3$) 1.04-1.08 (m, 3H); 1.37-1.59 (m, 24H); 1.85-1.92 (m, 2H); 3.42 (tr, 2H, J=9 Hz); 3.55 (tr, 2H, J=9 Hz); 3.58 (s, 2H); 3.91-4.07 (m, 6H); 4.7 (broad s, 1H); 6.71 (d, 1H, J=6 Hz); 6.93 (d, 1H, J=9 Hz); 7.06-7.21 (m, 2H); 7.5 (d, 1H, J=6 Hz); 7.78-87.84 (m, 1H); 8.89 (s, 1H).

Step G: 2-Amino-2-((4-(5-(3-amino-4-propoxyphenyl)-1,2,4-oxadiazol-3-yl)indolin-1-yl)methyl)propane-1,3-diol When the product of Step F was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 70% yield, as a creamy solid. $^1$H-NMR (DMSO-d$_6$) 0.92-1.05 (m, 3H); 1.42 (broad s, 2H); 1.7-1.81 (m, 2H); 2.99 (s, 2H); 2.42-2.51 (m, 2H); 2.95 (s, 2H); 3.11-3.4 (m, 2H, +H$_2$O); 3.53 (tr, 2H, J=9 Hz); 3.93-4.05 (m, 2H); 4.56 (m, 2H); 5.11 (s, 2H); 6.76 (d, 1H, J=6 Hz); 6.97 (d, 1H, J=9 Hz); 7.0 (d, 1H, J=6 Hz); 7.1-7.25 (m, 2H); 7.32-7.42 (m, 2H).

Example 47

2-Amino-2-((4-(5-(3,4-dipropylphenyl)-1,2,4-oxadiazol-3-yl)indolin-1-yl)methyl)propane-1,3-diol

Step A: 3-Iodo-4-propylbenzoic acid

A mixture of 4-propylbenzoic acid (0.3 g; 1.83 mmol), CF$_3$SO$_3$Ag (0.47 g; 1.83 mmol) and I$_2$ (0.46 g; 1.83 mmol) in CH$_2$Cl$_2$ was stirred for 48 h at room temperature, then filtered through Celite pad, washed with fresh CH$_2$Cl$_2$ (2×15 ml). The combined filtrates were washed with 5% NaHSO$_3$, H$_2$O, brine, dried over anhydrous MgSO$_4$, filtered and filtrate evaporated under reduced pressure to give the title compound (0.49 g; 92%) as creamy solid. $^1$H-NMR (CDCl$_3$) 1.0 (tr, 3H, J=9 Hz); 1.57-1.7 (m, 2H); 1.72-1.77 (m, 2H); 7.28 (d, 1H, 9 Hz); 7.98 (dd, 1H, J=3, 6 Hz); 8.53 (d, 1H, J=3 Hz).

Step B: 3-(Prop-1-ynyl)-4-propylbenzoic acid

A suspension of the product of Step A (0.36 g; 1.24 mmol) in HMDSA (2 ml) and saccharine (0.1 g) was refluxed under N$_2$ until reaction became homogenous (~30 min). After cooling to room temperature, the HMDSA was removed in vacuo and the residue was diluted to 4 ml with anhydrous THF. At the same time ZnCl$_2$ (0.2 g; 1.47 mmol) was heated to ~120° C., in separate flask, in vacuo, cooled to room temperature under N$_2$ and diluted to 4 ml with anhydrous THF. To it 0.5 M prop-1-ynyl-magnesium bromide in THF (4.9 ml; 2.45 mmol) was added at room temperature and this was stirred for 10 min under N$_2$. To it a solution of the protected product of Step A was added, followed by Pd(PPh$_3$)$_4$ (0.11 g; 0.095 mmol) and CuI (0.05 g; 0.26 mmol). After stirring for 1 h at room temperature under N$_2$, MeOH (5 ml) was added and solvents were removed under reduced pressure. The residue was suspended in H$_2$O (5 ml) and pH was adjusted to ~10 with diluted NaOH. The insoluble material was removed by filtration and filtrate acidified to ~3 with diluted HCl. The product was taken up by (2×10 ml). The organic phase was dried over anhydrous MgSO$_4$, filtered and filtrate evaporated to dryness under reduced pressure to give the title compound (0.19 g; 76%), as creamy solid. $^1$H-NMR (CDCl$_3$) 0.91-0.99 (m, 3H); 1.6-1.74 (m, 2H); 2.09 (s, 3H); 2.7-2.81 (m, 2H); 7.2-7.27 (m, 1H+CDCl$_3$); 7.8-7.92 (m, 1H); 8.52 (m, 1H).

Step C: 3,4-Dipropylbenzoic acid

A mixture of the product of Step B (0.19 g; 0.94 mmol) and 10% Pd/C (0.1 g) in EtOH (15 ml) was stirred over the weekend under H$_2$ (10 psi; Parr apparatus). The catalyst was removed by filtration through Celite pad, washed with CH$_2$Cl$_2$ (2×20 ml) and combined filtrates were evaporated to dryness to give the title compound (0.17 g; 88%) as creamy solid. $^1$H-NMR (CDCl$_3$) 0.93-1.0 (m, 6H); 1.55-1.69 (m, 4H); 2.6-2.66 (m, 4H); 6.6 (broad s, 1H); 7.2-7.27 (m, 1H+CDCl$_3$); 7.83-7.88 (m, 2H).

Step D: 5-(3,4-Dipropylphenyl)-3-(1H-indol-4-yl)-1,2,4-oxadiazole

When the product of Step C was substituted for 3,4-dipropoxybenzoic acid in Example 43 Step C, the similar process afforded the title compound in 33% yield., as a colourless solid. $^1$H-NMR (CDCl$_3$) 0.98-1.05 (m, 6H); 1.59-1.75 (m, 4H); 2.64-2.72 (m, 4H); 7.3-7.39 (m, 4H); 7.56 (d, 1H, J=6 Hz); 7.98-8.09 (m, 3H); 8.38 (broad s, 1H).

Step E: 5-(3,4-Dipropylphenyl)-3-(1H-indolin-4-yl)-1,2,4-oxadiazole

When the product of Step D was substituted for 5-(3-Iodo-4-propoxyphenyl)-3-(1H-indol-4-yl)-1,2,4-oxadiazole in Example 43 Step D, the similar process afforded the title compound in 100% yield., as a creamy solid, which was used in next step without further purification. $^1$H-NMR (CDCl$_3$) 0.95-1.04 (m, 6H); 1.57-1.73 (m, 4H); 2.63-2.7 (m, 4H); 2.94 (broad s, 1H); 3.47 (tr, 2H, J=8.4 Hz); 3.67 (tr, 2H, J=8.4 Hz); 6.82 (d, 1H, J=7.8 Hz); 7.15-7.35 (m, 2H+CDCl$_3$); 7.6 (d, 1H, J=7.8 Hz); 7.91-7.96 (m, 2H).

Step F: tert-Butyl 5-((4-(5-(3,4-dipropylphenyl)-1,2,4-oxadiazol-3-yl)indolin-1-yl)methyl)-2,2-dimethyl-1,3-dioxan-5-ylcarbamate When the product of Step E was substituted for 5-(3,4-diethoxyphenyl)-3-(1H-indolin-4-yl)-1,2,4-oxadiazole in Example 34, Step D, the identical process afforded the title compound in 57% yield., as a colourless foam. $^1$H-NMR (CDCl$_3$) 0.95-1.04 (m, 6H); 1.46-1.48 (m, 15H); 1.58-1.71 (m, 4H); 2.63-2.7 (m, 4H); 3.43 (tr, 2H, J=9 Hz); 3.57 (tr, 2H, J=9 Hz); 3.59 (s, 2H); 3.91-4.01 (m, 4H); 4.67 (broad s, 1H); 6.72 (d, 1H, J=9 Hz); 7.16-7.3 (m, 3H+CDCl₃); 7.49 (d, 1H, J=9 Hz); 7.91-7.98 (m, 2H).

Step G: 2-Amino-2-((4-(5-(3,4-dipropylphenyl)-1,2, 4-oxadiazol-3-yl)indolin-1-yl)methyl)propane-1,3-diol When the product of Step F was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 80% yield, as a creamy solid. ¹H-NMR (DMSO-d₆) 0.94-0.97 (m, 6H); 1.33 (s, 2H); 1.53-1.62 (m, 4H); 2.61-2.68 (m, 4H); 2.98 (s, 2H); 3.2-3.3 (m, 6H, +H₂O); 3.54 (tr, 2H, J=9 Hz); 4.55 (m, 2H); 6.77 (d, 1H, J=6 Hz); 7.1-7.16 (m, 1H); 7.25 (d, 1H, J=6 Hz); 7.87-7.91 (m, 2H).

Example 48

2-Amino-2-((4-(5-(4-propylphenyl)-1,2,4-oxadiazol-3-yl)indolin-1-yl)methyl)propane-1,3-diol Step A: 5-(4-Propylphenyl)-3-(1H-indol-4-yl)-1,2,4-oxadiazole When 4-propylbenzoic acid was substituted for 3,4-dipropoxybenzoic acid in Example 43, Step C, the similar process afforded the title compound in 38% yield, as a colourless solid. ¹H-NMR (CDCl₃) 0.94-1.04 (m, 3H); 1.61-1.76 (m, 2H); 2.61-2.71 (m, 2H); 7.25-7.41 (m, 5H); 7.49-7.6 (m, 1H); 8.03-8.23 (m, 3H); 8.45 (broad s, 1H).

Step B: 5-(4-Propylphenyl)-3-(1H-indolin-4-yl)-1,2,4-oxadiazole

When the product of Step A was substituted for 5-(3-Iodo-4-propoxyphenyl)-3-(1H-indol-4-yl)-1,2,4-oxadiazole in Example 43 Step D, the similar process afforded the title compound in 100% yield, as a creamy solid, which was used in next step without further purification. ¹H-NMR (CDCl₃) 0.95-1.04 (m, 6H); 1.57-1.73 (m, 4H); 2.63-2.7 (m, 4H); 2.94 (broad s, 1H); 3.47 (tr, 2H, J=8.4 Hz); 3.67 (tr, 2H, J=8.4 Hz); 6.82 (d, 1H, J=7.8 Hz); 7.15-7.35 (m, 2H+CDCl₃); 7.6 (d, 1H, J=7.8 Hz); 7.91-7.96 (m, 2H).

Step C: tert-Butyl 5-((4-(5-(4-propylphenyl)-1,2,4-oxadiazol-3-yl)indolin-1-yl)methyl)-2,2-dimethyl-1, 3-dioxan-5-ylcarbamate When the product of Step B was substituted for 5-(3,4-diethoxyphenyl)-3-(1H-indolin-4-yl)-1,2,4-oxadiazole in Example 34, Step D, the identical process afforded the title compound in 57% yield, as a colourless foam. ¹H-NMR (CDCl₃) 0.91-1.0 (m, 3H); 1.41-1.52 (m, 15H); 1.61-1.72 (m, 2H); 2.63-2.7 (m, 2H); 3.43 (tr, 2H, J=7.5 Hz); 3.57 (tr, 2H, J=7.5 Hz); 3.63 (s, 2H); 3.91-4.01 (m, 4H); 4.67 (broad s, 1H); 6.72 (d, 1H, J=7.77 Hz); 7.16-7.22 (m, 1H); 7.26-7.34 (m, 2H); 7.49 (d, 1H, J=7.7 Hz); 8.08-8.13 (m, 2H).

Step D: 2-Amino-2-((4-(5-(4-propylphenyl)-1,2,4-oxadiazol-3-yl)indolin-1-yl)methyl)propane-1,3-diol When the product of Step C was substituted for tea-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 80% yield, as a creamy solid. ¹H-NMR (DMSO-d₆) 0.85-0.95 (m, 3H); 1.33 (broad s, 2H); 2.6-2.66 (m, 2H); 2.98 (s, 2H); 3.2-3.34 (m, 8H+H₂O); 3.54 (tr, 2H, J=8.3 Hz); 4.56 (broad s, 2H); 6.77 (d, 1H, J=7.77 Hz); 7.1-7.26 (m, 2H); 7.38-7.49 (m, 2H); 7.9-8.1 (m, 2H).

Example 49

2-Amino-2-((4-(5-(3-chloro-4-ethoxyphenyl)-1,2,4-oxadiazol-3-yl)-1H-indol-1-yl)methyl)propane-1,3-diol Step A: 3-Chloro-4-ethoxybenzoic acid A mixture of 3-chloro-4-hydroxybenzaldehyde (0.4 g, 2.55 mmol), EtI (0.31 ml) and K₂CO₃ (0.421 g; 3.1 mmol) was stirred overnight at room temperature. The mixture was diluted 100 ml with H₂O and extracted with EtOAc (50 ml). The organic layer was separated and dried over MgSO₄ and filtered. The filtrate was evaporated to dryness to give the crude product (0.41 g, 87%) used as such in next step. ¹H-NMR (CDCl₃) 1.49 (tr, 3H, J=6.96 Hz); 4.18 (q, 2H, J=6.99, 13.97 Hz); 6.98 (d, 1H, J=8.49 Hz); 7.72 (dd, 1H, J=1.94, 8.46 Hz); 7.87 (d, 1H, J=1.95 Hz); 9.82 (s, 1H). The above benzaldehyde (0.4 g 2.16 mmol) was dissolved in a mixture of dioxane: H₂O (30:10) and to it KMnO₄ (0.341 g; 2.16 mmol) was added at room temperature and the mixture was stirred for 1 h. The solvent was evaporated and the residue was diluted to 100 ml with EtOAc and the mixture was filtered through a silica gel bead. The filtrate was evaporated to dryness to give the title compound (0.36 g, 83%), as creamy solid. ¹H-NMR (DMSO-d₆) 2.44 (tr, 3H, J=6.99 Hz); 5.11 (q, 2H, J=13.95 Hz); 6.96 (d, 1H, J=8.55 Hz); 8.9 (d, 1H, J=8.55 Hz); 9.5 (m, 1H).

Step B: 5-(3-Chloro-4-ethoxyphenyl)-3-(1H-indol-4-yl)-1,2,4-oxadiazole

When the product of Step A was substituted for 3,4-dipropoxybenzoic acid and diisopropylcarbodiimide was substituted for EDC in Example 43, Step C, the similar process afforded the title compound in 49%. ¹H-NMR (CDCl₃) 1.52 (tr, 3H, J=6.98 Hz); 4.21 (q, 2H, J=14, 7 Hz); 7.04 (d, 1H, J=8.66 Hz); 7.32-7.55 (m, 3H); 7.56 (d, 1H, J=8.14 Hz); 8.07 (d, 1H, J=7.4 Hz); 8.10 (dd, 1H, J=2.05, 8.06 Hz); 8.28 (d, 1H, J=2.07 Hz); 8.4 (broad s, 1H).

Step C: 5-(3-Chloro-4-ethoxyphenyl)-3-(indolin-4-yl)-1,2,4-oxadiazole

When the product of Step B was substituted for 5-(3,4-dipropoxyphenyl)-3-(1H-indol-4-yl)-1,2,4-oxadiazole in Example 43 Step D, the similar process afforded the title compound in 100% yield, as a creamy solid. ¹H-NMR (CDCl₃) 1.52 (tr, 3H, J=6.95 Hz); 3.69 (tr, 2H, J=7.53 Hz); 3.92 (tr, 2H, J=7.43 Hz); 4.18 (q, 2H, J=6.98 Hz); 7.03 (d, 1H, J=8.67 Hz); 7.39-7.45 (m, 2H), 7.94-8.10 (m, 2H), 8.21 (d, 1H, J=2.07 Hz).

Step D: tert-Butyl-5-((4-(5-(3-chloro-4-ethoxyphenyl)-1,2,4-oxadiazol-3-yl)-1H-indol-1-yl)methyl)-2, 2-dimethyl-1,3-dioxan-5-ylcarbamate When the product of Step C was substituted for 5-(3,4-diethoxyphenyl)-3-(1H-indolin-4-yl)-1,2,4-oxadiazole in Example 34, Step D, the identical process afforded the title compound in 50% yield. ¹H-NMR (CDCl₃) 1.43-1.53 (m, 18H), 3.42 (tr, 2H, J=7.75 Hz), 3.91-4.07 (m, 4H), 4.19 (q, 2H, J=6.95, 13.95 Hz), 4.68 (broad s, 1H); 6.73 (d, 1H, J=7.87 Hz); 7.00 (d, 1H, J=8.7 Hz); 7.19 (tr, 1H, J=7.85 Hz); 7.46 (d, 1H, J=7.79 Hz); 8.04 (dd, 1H, J=2.11, 8.63 Hz); 8.21 (d, 1H, J=2.09 Hz).

Step E: 2-Amino-2-((4-(5-(3-chloro-4-ethoxyphenyl)-1,2,4-oxadiazol-3-yl)-1H-indol-1-yl)methyl)propane-1,3-diol When the product of Step D was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 83.3% yield, as off white solid. $^1$H-NMR (DMSO-$d_6$) 1.46 (tr, 3H, J=6.85 Hz); 2.99-3.44 (m, 4H); 3.52 (tr, 2H, J=8.96 Hz); 3.71 (tr, 4H, J=10.46 Hz); 4.15 (q, 2H, J=6.97, 13.97 Hz); 6.77 (d, 1H, J=8.12 Hz); 6.99 (d, 1H, J=8.65 Hz); 7.17 (tr, 2H, J=7.74 Hz); 7.45 (d, 1H, J=8.68 Hz); 7.98 (d, 1H, J=8.75 Hz); 8.14, (broad s, 1H).

Example 50

2-Amino-2-((4-(5-(3-chloro-4-propoxyphenyl)-1,2,4-oxadiazol-3-yl)indolin-1-yl)methyl)propane-1,3-diol Step A: 4-Propoxybenzaldehyde A mixture of 4-hydroxybenzaldehyde (0.5 g, 4.1 mmol), 1-bromopropane (0.3 ml) and $K_2CO_3$ (0.69 g, 5 mmol) in anhydrous DMF (5 ml) was stirred for 1 h at reflux. This was diluted to 100 ml with EtOAc and washed with $H_2O$. The organic layer was separated, dried over $MgSO_4$ and filtered. The filtrate was evaporated to dryness to give the title compound (0.55 g, 82.3%), as yellow oil $^1$H-NMR (CDCl$_3$) 1.0 (tr, 3H, J=7.41 Hz); 1.7-2.0 (m, 2H); 3.95 (tr, 2H, J=6.57 Hz); 6.95 (d, 2H, J=8.73 Hz); 8.00 (d, 2H, J=8.76 Hz).

Step B: 3-Chloro-4-propoxybenzaldehyde

To a stirred solution of the product of Step A (0.5 g, 3.07 mmol) in anhydrous DMF (3 ml) NCS (0.5 g, 3.73 mmol) was added and the mixture was stirred overnight at room temperature. This was diluted to 100 ml with EtOAc and washed with NaHCO$_3$ solution (100 ml). The organic layer was separated, dried over MgSO$_4$ and filtered. The filtrate was evaporated to dryness to give the crude product (0.59 g; 97%), as light yellow oil. $^1$H-NMR (CDCl$_3$) 1.1 (tr, 3H, J=7.4 Hz); 1.82-1.91 (m, 2H); 4.1 (tr, 2H, J=6.3 Hz); 6.98 (d, 1H, J=8.47 Hz); 7.71 (dd, 1H, J=2.02-8.47 Hz); 7.87 (d, 1H, J=2.01 Hz); 9.81 (s, 1H).

Step C: 3-Chloro-4-propoxybenzoic acid

When the product of Step B was substituted for 3-chloro-4-ethoxybenzaldehyde in Example 49, Step A the identical process afforded the title compound in 95% yield, as a colourless solid. $^1$H-NMR (CDCl$_3$) 1.00 (tr, 3H, J=7.38 Hz); 1.73-1.87 (m, 2H); 3.98 (tr, 2H, J=6.47 Hz); 6.85 (d, 1H, J=8.65 Hz); 7.84 (dd, 1H, J=2.09, 8.68 Hz); 7.98 (d, 1H, J=2.07 Hz).

Step D: 5-(3-Chloro-4-propoxyphenyl)-3-(1H-indol-4-yl)-1,2,4-oxadiazole

When the product of Step C was substituted for 5-(3,4-dipropoxyphenyl)-3-(1H-indol-4-yl)-1,2,4-oxadiazole in Example 43 Step C, the similar process afforded the title compound in 35% yield, as off white solid. $^1$H-NMR (CDCl$_3$) 1.1 (tr, 3H, J=7.37 Hz); 1.78-1.95 (m, 2H); 4.09 (t, 2H, J=6.47 Hz); 7.03 (d, 1H, J=8.66 Hz); 7.34-7.39 (m, 3H); 7.56 (d, 1H, J=8.14 Hz); 8.04 (d, 1H, J=6.8 Hz); 8.1 (dd, 1H, J=8.6, 2.1 Hz); 8.28 (d, 1H, J=3.21 Hz); 8.38 (broad s, 1H).

Step E: 5-(3-Chloro-4-propoxyphenyl)-3-(indolin-4-yl)-1,2,4-oxadiazole

When the product of Step D was substituted for 5-(3,4-diethoxyphenyl)-3-(1H-indol-4-yl)-1,2,4-oxadiazole in Example 34, Step C, the identical process afforded the title compound in 99% yield. $^1$H-NMR (CDCl$_3$) 1.09 (tr, 3H, J=7.37 Hz); 1.81-1.94 (m, 2H); 3.51 (tr, 2H, J=8.08 Hz); 3.71 (tr, 2H, J=8.48 Hz); 4.08 (tr, 2H, J=6.47 Hz); 6.92 (d, 1H, J=7.44 Hz); 7.00 (d, 1H, J=8.72 Hz); 7.22 (tr, 1H, J=7.85 Hz); 7.65 (d, 1H, J=7.78 Hz); 8.04 (dd, 1H, J=8.63, 2.11 Hz); 8.21 (d, 1H, J=2.09 Hz).

Step F: tert-Butyl-5-((4-(5-(3-chloro-4-propoxyphenyl)-1,2,4-oxadiazol-3-yl)-1H-indol-1-yl)methyl)-2,2-dimethyl-1,3-dioxan-5-ylcarbamate When the product of Step E was substituted for 5-(3,4-diethoxyphenyl)-3-(1H-indolin-4-yl)-1,2,4-oxadiazole in Example 34, Step D, the identical process afforded the title compound in 49% yield. $^1$H-NMR (CDCl$_3$) 1.1 (tr, 3H, J=7.37 Hz); 1.41-1.47 (m, 15H); 1.81-1.94 (m, 2H); 3.44 (tr, 2H, J=7.9 Hz), 3.61 (tr, 2H, J=7.96 Hz); 3.63 (s, 2H); 3.8 (s, 2H); 3.98 (s, 2H); 4.08 (tr, 2H, J=6.47 Hz); 5.28 (broad s, 1H); 6.78 (d, 1H, J=7.98 Hz); 7.00 (d, 1H, J=8.71 Hz); 7.21 (tr, 1H, J=7.84 Hz); 7.51 (d, 1H, J=7.75 Hz); 8.04 (dd, 1H, J=2.09, 8.6 Hz); 8.20 (d, 1H, J=2.09 Hz).

Step G: 2-Amino-2-((4-(5-(3-chloro-4-propoxyphenyl)-1,2,4-oxadiazol-3-yl)indolin-1-yl)methyl)propane-1,3-diol When the product of Step F was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 54% yield, as a fluffy white solid. $^1$H-NMR (DMSO-$d_6$) 0.99 (tr, 3H, J=7.4 Hz); 1.74-1.81 (m, 2H); 3.03 (s, 2H); 3.27-3.32 (m, 6H); 3.53 (rt, 2H, J=8.03 Hz); 4.73 (m, 2H); 6.78 (d, 1H, J=7.8 Hz); 7.14 (tr, 1H, J=7.78 Hz); 7.25 (d, 1H, J=7.12 Hz); 7.36 (d, 1H, J=8.72 Hz); 8.0 (d, 1H, J=8.31 Hz); 8.11 (d, 1H, J=3.4 Hz).

Example 51

2-Amino-2-((5-(5-(3-chloro-4-isopropoxyphenyl)-1,2,4-oxadiazol-3-yl)indolin-1-yl)methyl)propane-1,3-diol Step A: 3-Chloro-4-iso-propoxybenzoic acid When the 3-chloro-4-isopropoxybenzaldehyde was substituted for 3-chloro-4-ethoxybenzaldehyde in Example 49, Step A the identical process afforded the title compound in 98% yield, as a colourless solid. $^1$H-NMR (CDCl$_3$) 1.4 (d, 6H, J=5.1 Hz); 4.67 (m, 1H); 6.95 (m, 1H); 7.96 (m, 1H); 8.10 (m, 1H).

Step B: 5-(3-Chloro-4-isopropoxyphenyl)-3-(1H-indol-5-yl)-1,2,4-oxadiazole

A mixture of the product of Step A (0.31 g, 1.44 mmol), the product of Example 34, Step A (0.25 g, 1.44 mmol), EDC (0.36 g, 1.87 mmol) and HOBT (0.01 g) in anhydrous DMF (1 ml) was stirred overnight at 40° C. 1M solution of TBAF in THF (0.25 mL) was added to it and mixture was stirred for 3 h at 120° C. This was diluted to 20 ml with $H_2O$ and extracted with EtOAc (50 ml). The organic layer was separated, dried over $MgSO_4$ and filtered. The filtrate was evaporated to dryness and the residue was purified by FCC ($SiO_2$) and crystallized from MeOH to give the title compound (0.17 g; 33.3%) as creamy crystalline solid. $^1$H-NMR ($CDCl_3$) 1.43 (d, 6H, J=6.06 Hz); 7.65-7.74 (m, 1H); 7.05 (d, 1H, J=8.76 Hz); 7.3-7.38 (m, 3H); 7.55 (d, 1H, J=8.14 Hz); 8.1-8.03 (m, 2H); 8.28 (d, 1H, J=2.13 Hz); 8.4 (broad s, 1H).

Step C: 5-(3-Chloro-4-isopropoxyphenyl)-3-(1H-indolin-5-yl)-1,2,4-oxadiazole When the product of Step B was substituted for 5-(3,4-diethoxyphenyl)-3-(1H-indol-4-yl)-1,2,4-oxadiazole in Example 34, Step C, the identical process afforded the title compound in quantitative yield. $^1$H-NMR ($CDCl_3$) 1.42 (d, 6H, J=6.03 Hz); 3.5 (tr, 2H, J=7.83 Hz); 3.7 (tr, 2H, J=7.92 Hz); 4.75-4.67 (m, 1H); 6.91 (d, 1H, J=7.74 Hz); 7.03 (d, 1H, J=9.09 Hz); 7.2 (tr, 1H, J=7.86 Hz); 7.65 (d, 1H, J=7.71 Hz); 8.01 (dd, 1H, J=2.13, 8.67 Hz); 8.2 (d, 1H, J=2.1 Hz).

Step D: tert-Butyl-5-((5-(5-(3-chloro-4-isopropoxyphenyl)-1,2,4-oxadiazol-3-yl)indolin-1-yl)methyl)-2,2-dimethyl-1,3-dioxan-5-ylcarbamate When the product of Step C was substituted for 5-(3,4-diethoxyphenyl)-3-(1H-indol-4-yl)-1,2,4-oxadiazole in Example 34, Step D, the identical process afforded the title compound in 69% yield. $^1$H-NMR ($CDCl_3$) 1.42-1.55 (m, 21H); 3.42 (s, 2H); 3.46 (tr, 2H, J=6.76 Hz); 3.57 (tr, 2H, J=7.49 Hz); 3.94 (d, 2H, J=11.27 Hz); 4.04 (d, 2H, J=11.74 Hz); 4.67-4.71 (m, 1H); 5.83 (broad s, 1H); 6.73 (d, 1H, J=7.92 Hz); 7.0 (d, 1H, J=8.78 Hz); 7.19 (tr, 1H, J=7.89 Hz); 7.47 (d, 1H, J=7.85 Hz); 8.04 (dd, 1H, J=2.1, 8.57 Hz); 8.20 (d, 1H, J=2.05 Hz).

Step E: 2-Amino-2-((5-(5-(3-chloro-4-isopropoxyphenyl)-1,2,4-oxadiazol-3-yl)indolin-1-yl)methyl)propane-1,3-diol When the product of Step D was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 40% yield, as a fluffy white solid. $^1$H-NMR (DMSO-$d_6$) 1.32 (d, 6H, J=5.54 Hz); 2.99 (s, 2H), 3.29 (m, 6H); 3.53 (m, 2H); 4.58 (m, 2H); 6.77 (d, 1H, J=7.46 Hz), 7.13 (tr, 1H), 7.24 (d, 1H, J=7.47 Hz); 7.39 (d, 1H, J=8.7 Hz); 7.82-7.84 (m, 1H); 8.05 (d, 1H, J=7.75 Hz); 8.12 (s, 1H).

Example 52

2-Amino-2-((5-(5-(4-butoxy-3-chlorophenyl)-1,2,4-oxadiazol-3-yl)indolin-1-yl)methyl)propane-1,3-diol

Step A: 4-Butoxy-3-chlorobenzaldehyde

When the 1-bromobutane and 3-chloro-4-hydroxybenzaldehyde was substituted for 1-bromopropane and 4-hydroxybenzaldehyde in Example 50, Step A, the identical process afforded the title compound in 86% yield, as light yellow oil. $^1$H-NMR ($CDCl_3$) 0.98 (tr, 3H); 1.56-1.58 (m, 2H); 1.78-1.88 (m, 2H); 4.1 (tr, 2H, J=6.3 Hz); 6.98 (d, 1H, J=7.17 Hz); 7.71 (dd, 1H, J=2.1, 8., Hz); 7.87 (d, 1H, J=2.1 Hz); 9.81 (s, 1H).

Step B: 4-Butoxy-3-chlorobenzoic acid

When the product of Step A was substituted for 3-chloro-4-ethoxybenzaldehyde in Example 49, Step A the identical process afforded the title compound in 85% yield. $^1$H-NMR ($CDCl_3$) 0.96 (tr, 3H, J=7.38 Hz); 1.46-1.57 (m, 2H); 1.59-2.77 (m, 2H); 4.1 (tr, 2H, J=6.45 Hz); 6.93 (d, 1H, J=8.67 Hz); 7.96 (dd, 1H, J=8.64, 2.1 Hz); 8.1 (d, 1H, J=2.07 Hz).

Step C: 5-(4-Butoxy-3-chlorophenyl)-3-(1H-indol-5-yl)-1,2,4-oxadiazole

When the product of Step B was substituted for 3-chloro-4-iso-propoxybenzoic acid in Example 51, Step B the similar process afforded the title compound in 19% yield. $^1$H-NMR $CDCl_3$) 1.00 (tr, 3H, J=7.35 Hz); 1.52-1.59 (m, 2H); 1.82-1.89 (m, 2H); 4.13 (tr, 2H, J=6.45 Hz); 7.04 (d, 1H, J=8.67 Hz); 7.29-7.39 (m, 3H); 7.56 (d, 1H, J=8.16 Hz); 8.05 (d, 1H, J=7.41 Hz); 8.1 (dd, 1H, J=2.1, 8.61 Hz); 8.28 (d, 1H, J=2.1 Hz); 8.36 (broad s, 1H).

Step D: 5-(4-Butoxy-3-chlorophenyl)-3-(indolin-5-yl)-1,2,4-oxadiazole

When the product of Step C was substituted for 5-(3,4-diethoxyphenyl)-3-(1H-indol-4-yl)-1,2,4-oxadiazole in Example 34, Step C, the identical process afforded the title compound in 92% yield. $^1$H-NMR $CDCl_3$) 0.97 (tr, 3H, J=8.34 Hz), 1.41-1.6 (m, 2H); 1.76-1.91 (m, 2H); 3.45 (tr, 2H, J=8.16 Hz; 3.63 (tr, 2H); 4.10 (tr, 2H, J=6.45 Hz); 6.75 (d, 1H, J=7.56 Hz); 7.06 (d, 1H, J=7.11 Hz); 7.18 (tr, 1H, J=7.77 Hz); 7.51 (broad d, 1H, J=7.8 Hz); 8.04 (dd, 1H, J=2.07-8.61 Hz); 8.21 (d, 1H, J=2.07 Hz).

Step E: tert-Butyl-5-((5-(5-(4-butoxy-3-chlorophenyl)-1,2,4-oxadiazol-3-yl)indolin-1-yl)methyl)-2,2-dimethyl-1,3-dioxan-5-ylcarbamate When the product of Step D was substituted for 5-(3,4-diethoxyphenyl)-3-(1H-indol-4-yl)-1,2,4-oxadiazole in Example 34, Step D, the identical process afforded the title compound in 83% yield. $^1$H-NMR ($CDCl_3$) 1.00 (tr, 3H, J=7.44 Hz); 1.24-1.26 (m, 17H); 1.81-1.88 (m, 2H); 3.42-4.07 (m, 10H); 4.12 (tr, 2H, J=6.51 Hz); 6.73 (d, 1H, J=7.83 Hz); 7.00 (d, 1H, J=8.76 Hz); 7.19 (tr, 1H, J=7.86 Hz); 7.46 (d, 1H, J=7.44 Hz); 8.04 (dd, 1H, J=2.1, 8.61 Hz); 8.21 (d, 1H, J=2.1 Hz).

Step F: 2-Amino-2-((5-(5-(4-butoxy-3-chlorophenyl)-1,2,4-oxadiazol-3-yl)indolin-1-yl)methyl)propane-1,3-diol When the product of Step E was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 52% yield. $^1$H-NMR (DMSO-$d_6$) 0.92 (tr, 3H, J=7.47 Hz); 1.07-1.48 (m, 2H); 1.71-1.76 (m, 2H); 2.98 (s, 2H); 3.22-3.56 (m, 8H); 4.17 (tr, 2H, J=6.36 Hz); 4.62 (m, 2H); 6.76 (d, 1H, J=7.74 Hz); 7.13 (tr, 1H, J=7.83 Hz); 7.24 (d, 1H, J=7.17 Hz); 7.37 (d, 1H, J=8.79 Hz); 8.07 (dd, 1H, J=2.13, 8.64 Hz); 8.12 (d, 1H, J=2.13 Hz).

Example 53

2-Amino-2-((4-(5-(4-propoxy-3,5-dichlorophenyl)-1,2,4-oxadiazol-3-yl)indolin-1-yl)methyl)propane-1,3-diol Step A: 3,5-Dichloro-4-propoxybenzaldehyde When 3,5-dichloro-4-hydroxybenzaldehyde was substituted for 4-hydroxy-benzaldehyde in Example 50, Step A the similar procedure afforded the title compound in 94% yield, as pale oil. $^1$H-NMR (CDCl$_3$) 1.1 (tr, 3H, J=7.41 Hz); 1.82-1.93 (m, 2H); 4.04 (tr, 2H, J=6.54 Hz); 7.8 (s 2H); 9.84 (s, 1H).

Step B: 3,5-Dichloro-4-propoxybenzoic acid

When the above product was substituted for 3-chloro-4-ethoxybenzaldehyde in Example 49, Step A, the identical process afforded the title compound in 78% yield, as a creamy solid. $^1$H-NMR (DMSO-d$_6$) 0.97 (tr, 3H, J=7.44 Hz); 1.67-1.9 (m, 2H); 3.89 (tr, 2H); 7.76 (s, 2H).

Step C: 5-(3,5-Dichloro-4-propoxyphenyl)-3-(1H-indol-5-yl)-1,2,4-oxadiazole

When the product of Step B was substituted for 3,4-dipropoxy benzoic acid in Example 43, Step C, the similar process afforded the title compound in 44% yield, as a creamy solid $^1$H-NMR (CDCl$_3$) 1.1 (tr, 3H, J=7.38 Hz); 1.97-1.85 (m, 2H); 4.09 (tr, 2H, J=6.57 Hz); 7.33 (tr, 1H, J=7.56 Hz); 7.57 (d, 1H, J=8.1 Hz); 8.04 (d, 1H, J=7.41 Hz); 8.2 (m, 2H); 8.38 (broad s, 1H).

Step D: 2-Amino-2-((5-(5-(3,5-dichloro-4-propoxyphenyl)-1,2,4-oxa diazol-3-yl)indolin-1-yl)methyl)propane-1,3-diol When the product of Step C was substituted for 5-(3,4-diethoxyphenyl)-3-(1H-indol-4-yl)-1,2,4-oxadiazole in Example 34, Step C, followed by Step D and E, the similar process afforded the title compound in 9% overall yield, as off white solid. $^1$H-NMR (DMSO-d$_6$) 1.0 (tr, 2H, J=7.35 Hz); 1.75-1.83 (m, 2H); 2.98 (s, 2H); 3.51 (d, 2H); 3.55 (d, 2H, J=8.73 Hz); 4.04 (tr, 2H, J=6.42 Hz); 4.57 (b, 2H); 6.77 (d, 1H, J=7.83 Hz); 7.13 (tr, 1H, J=7.83 Hz); 7.24 (d, 1H, J=7.35 Hz); 8.17 (s, 2H).

Example 54

2-Amino-2-((5-(5-(3-chloro-4-(pentyloxy)phenyl)-1,2,4-oxadiazol-3-yl)indolin-1-yl)methyl)propane-1,3-diol Step A: 3-Chloro-4-(pentyloxy)benzaldehyde When the 1-bromopentane and 3-chloro-4-hydroxybenzaldehyde was substituted for 1-bromopropane and 4-hydroxybenzaldehyde in Example 50 Step A the identical process afforded the title compound in 96% yield, as light yellow oil. $^1$H-NMR (CDCl$_3$) 0.9 (tr, 3H, J=7.05 Hz); 1.34-1.39 (m, 4H); 1.41-1.45 (m, 2H); 4.07 (tr, 2H, J=3.66 Hz); 6.97 (d, 1H, J=8.49 Hz); 7.7 (dd, 1H, J=2.01, 8.46 Hz); 7.85 (d, 1H, J=2.04 Hz); 9.81 (s, 1H).

Step B: 3-Chloro-4-(pentyloxy)benzoic acid

When the product of Step A was substituted for 3-chloro-4-ethoxybenzaldehyde in Example 49, Step A the identical process afforded the title compound in 72% yield. $^1$H-NMR (CDCl$_3$) 0.92 (tr, 3H); 1.42-1.65 (m, 4H); 1.76-1.9 (m, 2H); 4.08 (tr, 2H, J=6.51 Hz); 6.92 (d, 1H, J=8.7 Hz); 7.95 (dd, 1H, J=2.1, 8.61 Hz); 8.1 (d, 1H, J=2.07 Hz).

Step C: 5-(3-Chloro-4-(pentyloxy)phenyl)-3-(1H-indol-5-yl)-1,2,4-oxadiazole

When the product of Step B was substituted for 3-chloro-4-iso-propoxybenzoic acid in Example 51, Step B the similar process afforded the title compound in 24% yield. $^1$H-NMR (CDCl$_3$) 0.94 (tr, 3H, J=7.14 Hz); 1.39-1.52 (m, 4H); 1.53-1.91 (m, 2H); 4.12 (tr, 2H, J=6.5 Hz); 7.04 (d, 1H, J=8.67 Hz); 7.29-7.39 (m, 3H); 7.56 (d, 1H, J=8.16 Hz); 8.05 (d, 1H, J=7.41 Hz); 8.1 (dd, 1H, J=2.1, 8.61 Hz); 8.28 (d, 1H, J=2.1 Hz); 8.36 (broad s, 1H).

Step D: 5-(3-Chloro-4-(pentyloxy)phenyl)-3-(indolin-5-yl)-1,2,4-oxadiazole

When the product of Step C was substituted for 5-(3,4-diethoxyphenyl)-3-(1H-indol-4-yl)-1,2,4-oxadiazole in Example 34, Step C, the identical process afforded the title compound in 100% yield. $^1$H-NMR (CDCl$_3$) 0.94 (tr, 3H, J=7.11 Hz); 1.44-1.54 (m, 4H); 1.66-2.03 (m, 2H); 3.45 (tr, 2H, J=8.16 Hz); 3.65 (tr, 2H, J=7.83 Hz); 4.11 (tr, 2H, J=6.51 Hz); 6.75 (d, 1H, J=7.68 Hz); 7.00 (d, 1H, J=8.67 Hz); 7.20 (tr, 1H, J=6.24 Hz); 7.51 (broad d, 1H, J=7.77 Hz); 8.04 (dd, 1H, J=2.13, 8.64 Hz); 8.21 (d, 1H, J=2.1 Hz).

Step E: tert-Butyl-5-((5-(5-(3-chloro-4-(pentyloxy)phenyl)-1,2,4-oxadiazol-3-yl) indolin-1-yl)methyl)-2,2-dimethyl-1,3-dioxan-5-ylcarbamate When the product of Step D was substituted for 5-(3,4-diethoxyphenyl)-3-(1H-indolin-4-yl)-1,2,4-oxadiazole in Example 34, Step D, the identical process afforded the title compound in 81% yield. $^1$H-NMR (CDCl$_3$) 1.00 (tr, 3H, J=7.44 Hz), 1.37-1.6 (m, 19H); 1.81-1.88 (m, 2H); 3.42-4.07 (m, 10H); 4.12 (tr, 2H, J=6.39 Hz); 6.72 (d, 1H, J=7.71 Hz); 7.02 (d, 1H, J=8.73 Hz); 7.18 (tr, 1H, J=7.92 Hz); 7.46 (d, 1H, J=7.38 Hz); 8.04 (dd, 1H, J=2.07, 8.61 Hz); 8.2 (d, 1H, J=2.07 Hz).

Step F: 2-Amino-2-((5-(5-(3-chloro-4-(pentyloxy)phenyl)-1,2,4-oxadiazol-3-yl)indolin-1-yl)methyl) propane-1,3-diol When the product of Step E was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 56% yield. $^1$H-NMR (DMSO-d$_6$) 0.87 (tr, 3H, J=5.91 Hz); 1.31-1.4 (m, 4H); 1.72-1.77 (m, 2H); 2.98 (s, 2H); 3.24-3.35 (m, 8H); 4.14 (tr, 2H, J=6.18 Hz); 4.6 (m, 2H); 6.75 (d, 1H, J=7.74 Hz); 7.12 (tr, 1H); 7.23 (d, 1H, J=7.71 Hz); 7.34 (d, 1H, J=8.7 Hz); 8.1 (broad s, 1H); 8.4 (d, 1H, J=8.61 Hz).

Example 55

2-Amino-2-((4-(5-(4-ethoxy-3-methoxyphenyl)-1,2,4-oxadiazol-3-yl)indolin-1-yl)methyl)propane-1,3-diol Step A: 4-Ethoxy-3-methoxybenzaldehyde When the EtI and 3-methoxy-4-hydroxybenzaldehyde was substituted for 1-bromopropane and 4-hydroxybenzaldehyde respectively in Example 49, Step A, the identical process afforded the title compound in 90% yield, as light yellow oil. $^1$H-NMR (CDCl$_3$) 1.49 (tr, 3H, J=6.98 Hz); 3.91 (s, 3H); 4.17 (q, 2H, J=14, 7 Hz); 6.94 (d, 1H, J=8.09 Hz); 7.38-7.43 (m, 2H); 9.02 (s, 1H).

Step B: 4-Ethoxy-3-methoxybenzoic acid

When the product of Step A was substituted for 3-chloro-4-ethoxybenzaldehyde in Example 49 Step A the identical process afforded the title compound in 89% yield. $^1$H-NMR CDCl$_3$) 1.4 (tr, 3H, J=6.95 Hz); 3.83 (s, 3H); 4.07 (q, 2H, J=6.96, 13.9, Hz); 6.79 (d, 1H, J=8.4 Hz); 7.47 (s, 1H); 7.58 (d, 1H, J=8.33 Hz).

Step C: 5-(4-Ethoxy-3-methoxyphenyl)-3-(1H-indol-4-yl)-1,2,4-oxadiazole

When the product of Step B was substituted for 3,4-dipropoxybenzoic acid and DCC was substituted for EDC in Example 43, Step C the similar process afforded the title compound in 38% yield, as creamy solid. $^1$H-NMR CDCl$_3$) 1.49 (tr, 3H, J=7.61 Hz); 4.00 (s, 3H); 4.19 (q, 2H, J=6.98, 13.98 Hz); 7.00 (d, 1H, J=8.44 Hz); 7.37-7.29 (m, 3H); 7.56 (d, 1H, J=8.08 Hz); 7.73 (d, 1H, J=1.81 Hz); 7.84 (dd, 1H, J=8.4, 1.92 Hz); 8.06 (d, 1H, J=7.41 Hz); 8.44 (broad s, 1H).

Step D: 5-(4-Ethoxy-3-methoxyphenyl)-3-(indolin-4-yl)-1,2,4-oxadiazole

When the product of Step C was substituted for 5-(3,4-diethoxyphenyl)-3-(1H-indol-4-yl)-1,2,4-oxadiazole in Example 34, Step C, the identical process afforded the title compound 100% yield. $^1$H-NMR (CDCl$_3$) 1.5 (tr, 3H, J=3.98 Hz); 3.6 (tr, 2H, J=7.79 Hz); 3.8 (tr, 2H, J=8.87 Hz); 3.99 (s, 3H); 4.19 (q, 2H, J=14, 7 Hz); 6.97 (d, 1H, J=8.5 Hz); 7.17 (d, 1H, J=7.79 Hz); 7.32 (tr, 1H, J=7.82 Hz); 7.66 (d, 1H, J=1.92 Hz); 7.67 (dd, 1H, J=1.97, 8.41 Hz), 7.89 (d, 1H, J=7.78 Hz).

Step E: tert-Butyl-5-((4-(5-(4-ethoxy-3-methoxyphenyl)-1,2,4-oxadiazol-3-yl)-1H-indol-1-yl)methyl)-2,2-dimethyl-1,3-dioxan-5-ylcarbamate When the product of Step D was substituted for 5-(3,4-diethoxyphenyl)-3-(1H-indolin-4-yl)-1,2,4-oxadiazole in Example 34, Step D, the identical process afforded the title compound in 52% yield. $^1$H-NMR (CDCl$_3$) 1.41-1.53 (m, 18H); 3.43 (tr, 2H, J=7.73 Hz); 3.58 (tr, 2H, J=7.92 Hz); 3.61 (s, 2H); 3.97 (s, 4H, 4.18 (q, 2H, J=6.98, 14 Hz); 5.3 (broad s, 1H); 6.75 (d, 1H, J=7.97 Hz); 6.97 (d, 1H, J=8.49 Hz); 7.2 (tr, 1H, J=7.85 Hz); 7.5 (d, 1H, J=7.77 Hz); 7.67 (d, 1H, J=1.87 Hz); 7.78 (dd, 1H, J=1.93, 8.41 Hz).

Step F: 2-Amino-2-((4-(5-(4-ethoxy-3-methoxyphenyl)-1,2,4-oxadiazol-3-yl)indolin-1-yl)methyl)propane-1,3-diol When the product of Step E was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 83% yield, as white solid. $^1$H-NMR (CDCl$_3$: CD$_3$OD) 1.43 (tr, 3H, J=6.98 Hz); 3.14 (s, 2H); 3.24-3.5 (m, 4H); 3.58 (d, 2H, J=11.87 Hz); 3.64 (d, 2H, J=11.63 Hz); 3.91 (s, 3H); 4.1 (q, 2H, J=14, 7.02 Hz); 6.75 (d, 1H, J=7.78 Hz); 6.91 (d, 1H, J=8.54 Hz); 7.17 (tr, 1H, J=7.98 Hz); 7.41 (d, 1H, J=7.75 Hz), 7.6 (s, 1H); 7.71 (d, 1H, J=1.86, 8.49 Hz).

Example 56

2-Amino-2-((5-(5-(3-bromo-4-propoxyphenyl)-1,2,4-oxadiazol-3-yl)indolin-1-yl)methyl)propane-1,3-diol Step A: 3-Bromo-4-propoxybenzaldehyde When the NBS was substituted for NCS in Example 49, Step A, the identical process afforded the title compound in 98% yield. $^1$H-NMR (CDCl$_3$) 1.02 (tr, 2H, J=7.38 Hz); 1.76-1.88 (m, 2H); 4.00 (tr, 2H, J=6.42 Hz); 6.9 (d, 1H, J=8.49 Hz); 7.71 (dd, 1H, J=1.98, 8.46 Hz); 7.99 (d, 1H, J=2.01 Hz); 9.74 (s, 1H).

Step B: 3-Bromo-4-propoxybenzoic acid

When the product of Step A was substituted for 3-chloro-4-ethoxybenzaldehyde in Example 49, Step A, the identical process afforded the title compound in 86% yield. $^1$H-NMR (DMSO-d$_6$) 0.98 (tr, 3H, J=7.32 Hz); 1.68-1.79 (m, 2H); 4.06 (tr, 2H, J=6.39 Hz); 7.14 (d, 1H, J=8.7 Hz); 7.87 (dd, 1H, J=2.07, 8.61 Hz); 8.01 (d, 1H, J=2.04 Hz); 11.2 (broad s, 1H).

Step C: 5-(3-Bromo-4-propoxyphenyl)-3-(1H-indol-5-yl)-1,2,4-oxadiazole

When the product of Step B was substituted for 3-chloro-4-iso-propoxybenzoic acid in Example 51 Step B the similar process afforded the title compound in 40% yield, as a colourless solid. $^1$H-NMR (CDCl$_3$) 1.08 (tr, 3H, J=7.38 Hz); 1.52-1.85 (m, 2H); 4.09 (tr, 2H, J=6.45 Hz); 6.99 (d, 1H, J=8.67 Hz); 7.23-7.29 (m, 3H); 7.56 (d, 1H, J=8.16 Hz); 8.05 (broad d, 1H, J=7.41 Hz); 8.14 (dd, 1H, J=2.1, 8.61 Hz); 8.37 (broad s, 1H); 8.45 (d, 1H, J=2.13 Hz).

Step D: 5-(3-Bromo-4-propoxyphenyl)-3-(indolin-5-yl)-1,2,4-oxadiazole

When the product of Step C was substituted for 5-(3,4-diethoxyphenyl)-3-(1H-indol-4-yl)-1,2,4-oxadiazole in Example 34, Step C, the identical process afforded the title compound in 95% yield. $^1$H-NMR (CDCl$_3$) 1.10 (tr, 3H, J=7.38 Hz); 1.85-1.94 (m, 2H); 3.54 (tr, 2H, J=7.92 Hz); 3.75 (tr, 2H, J=8.28 Hz); 4.08 (tr, 2H, J=6.42 Hz); 6.98 (d, 1H, J=8.73 Hz); 7.03 (d, 1H, J=7.77 Hz); 7.26 (tr, 1H, J=7.83 Hz); 7.75 (d, 1H, J=7.17 Hz); 8.09 (dd, 1H, J=2.1, 8.61 Hz); 8.39 (d, 1H, J=2.1 Hz).

Step E: tert-Butyl-5-((5-(5-(3-bromo-4-propoxyphenyl)-1,2,4-oxadiazol-3-yl)indolin-1-yl)methyl)-2,2-dimethyl-1,3-dioxan-5-ylcarbamate When the product of Step D was substituted for 5-(3,4-diethoxyphenyl)-3-(1H-indolin-4-yl)-1,2,4-oxadiazole in Example 34, Step D, the identical process afforded the title compound in 84% yield. $^1$H-NMR (CDCl$_3$) 1.0 (tr, 3H, J=7.44 Hz); 1.42-1.44 (m, 15H); 1.84-1.94 (m, 2H); 3.32-3.44 (m, 2H); 3.8-3.54 (m, 3H); 3.88-4.00 (m, 4H, 4.05 (tr, 2H, J=5.29 Hz); 6.72 (d, 1H, J=7.74 Hz); 6.97 (d, 1H, J=8.7 Hz); 7.18 (tr, 1H, J=7.86 Hz); 7.46 (d, 1H, J=7.53 Hz); 8.08 (dd, 1H, J=2.07, 8.61 Hz); 8.39 (d, 1H, J=2.07 Hz).

Step F: 2-Amino-2-((5-(5-(3-bromo-4-propoxyphenyl)-1,2,4-oxadiazol-3-yl)indolin-1-yl)methyl)propane-1,3-diol When the product of Step E was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 44% yield. $^1$H-NMR (DMSO-d$_6$) 1.0 (tr, 3H, J=7.38 Hz); 1.75-1.79 (m, 2H); 2.99 (5, 2H); 3.2-3.4 (m, 8H); 4.13 (tr, 2H, J=6.30 Hz); 4.61 (broad s, 1H); 6.77 (d, 1H); 7.13 (tr, 1H); 7.24 (d, 1H, J=7.59 Hz), 7.31 (d, 1H, J=8.79 Hz), 8.11 (dd, 1H, J=2.13, 8.64 Hz), 8.27 (d, 1H, J=2.46 Hz).

Example 57

2-Amino-2-((4-(5-(1-adamantyl)-1,2,4-oxadiazol-3-yl)indolin-1-yl)methyl) propane-1,3-diol

Step A: 5-(1-Admantyl)-3-(1H-indol-4-yl)-1,2,4-oxadiazole

The product of Example 34 Step A (0.14 g, 0.8 mmol), admantane-1 carboxylic acid (0.147 g, 0.8 mmol), EDC (0.306 g, 1.6 mmol) and HOBT (0.135 g, 1 mmol) was dissolved in anhydrous DMF (4 ml) and stirred overnight at room temperature. This was diluted to 40 ml with EtOAc and washed with H$_2$O. The organic layer was separated, dried over MgSO$_4$ and filtered. The filtrate was passed through silica gel bead and the filtrate was evaporated to dryness to give the syrup (0.169 g). To this (0.12 g) a solution of 1M TBAF in THF (0.5 mL,) was added and the mixture was heated for 2 h at 120° C. This was diluted to 30 ml with EtOAc and washed with H$_2$O. The organic layer was separated, dried over MgSO$_4$, and filtered. The filtrate was evaporated to dryness and the residue was purified by FCC (SiO$_2$) to give the title compound (0.025 g, 21%). $^1$H-NMR (CDCl$_3$) 1.82 (s, 6H); 2.13 (s, 3H); 2.18 (s, 6H); 7.51 (d, 1H, J=8.1 Hz); 7.95 (d, 1H, J=7.41 Hz); 8.38 (broad s, 1H).

Step B: 5-(1-Admantyl)-3-(1H-indolin-4-yl)-1,2,4-oxadiazole

When the product of Step A was substituted for 5-(3,4-diethoxyphenyl)-3-(1H-indol-4-yl)-1,2,4-oxadiazole in Example 34, Step C, the identical process afforded the title compound in 90% yield. $^1$H-NMR (CDCl$_3$) 1.86 (s, 6H); 2.12 (s, 9H); 3.46 (tr, 2H, J=8.11 Hz); 3.69 (tr, 2H, J=8.33 Hz); 6.9 (d, 1H, J=7.9 Hz); 7.18 (tr, 1H, J=7.7 Hz); 7.59 (d, 1H, J=7.8 Hz).

Step C: tert-Butyl-5-((4-(5-(1-admantyl)-1,2,4-oxadiazol-3-yl)indolin-1-yl)methyl)-2,2-dimethyl-1,3-dioxan-5-ylcarbamate When the product of Step B was substituted for 5-(3,4-diethoxyphenyl)-3-(1H-indolin-4-yl)-1,2,4-oxadiazole in Example 34, Step D, the identical process afforded the title compound in 50% yield. $^1$H-NMR (CDCl$_3$) 1.41-1.58 (m, 15H); 1.8 (s, 6H); 2.12 (s, 9H); 3.38 (tr, 2H, J=8.05 Hz); 3.52 (rt, 2H, J=7.84 Hz); 3.56 (s, 2H); 3.7-3.76 (m, 4H); 5.3 (s, 1H); 6.68 (d, 1H, J=7.61 Hz); 7.14 (tr, 1H, J=8.00 Hz); 7.38 (d, 1H, J=7.7 Hz).

Step D: 2-Amino-2-((4-(5-(1-admantyl)-1,2,4-oxadiazol-3-yl)indolin-1-yl)methyl)propane-1,3-diol When the product of Step C was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 78% yield. $^1$H-NMR (DMSO-d$_6$) 1.75 (s, 6H); 2.07 (s, 9H); 2.97-3.57 (m, 12H); 6.7 (d, 1H, J=7.6 Hz); 7.12 (tr, 1H); 7.34 (d, 1H, J=7.7 Hz).

Example 58

2-Amino-2-((4-(4-(5-(3,4-diethoxyphenyl)-1,2,4-oxadiazol-3-yl)phenyl)-5,6-dihydropyridin-1(2H)-yl)methyl)propane-1,3-diol

Step A: 4-Bromo-N-hydroxybenzimidamide

A mixture of 4-cyano-bromobenzene (0.5 g, 2.75 mmol), HCl×NH$_2$OH (0.476 g, 6.9 mmol) and Na$_2$CO$_3$ (0.731 g, 6.9 mmol) in a mixture of EtOH and H$_2$O (25 ml: 5 ml) was stirred for 7 h at reflux. The solvent was evaporated to dryness and the residue was taken in EtOAc (100 ml) and washed with H$_2$O. The organic layer was separated, dried over MgSO$_4$ and filtered. The filtrate was evaporated to dryness to give the product as colourless solid (0.51 g, 87%). $^1$H-NMR (DMSO-d$_6$) 5.81 (broad s, 2H); 7.53 (d, 2H, J=6.66 Hz); 7.58 (d, 2H, J=6.54 Hz); 9.69 (s, 1H).

Step B: 3-(4-Bromophenyl)-5-(3,4-diethoxyphenyl)-1,2,4-oxadiazole

When the product of Step A was substituted for N-hydroxy-1H-indole-4-carboximidamide and 3,4-diethoxybenzoic acid was substituted for 3,4-dipropoxybenzoic acid in Example 43, Step C the similar process afforded the title compound in 58% yield. $^1$H-NMR (CDCl$_3$) 1.47-1.53 (m, 6H); 4.14-4.24 (m, 4H); 6.97 (d, 1H, J=8.48 Hz); 7.61-7.66 (m, 3H); 7.77 (dd, 1H, J=1.98, 8.42 Hz); 8.00 (d, 2H, J=8.55 Hz).

Step C: 5-(3,4-Diethoxyphenyl)-3-(4-(1,2,3,6-tetrahydropyridin-4-yl)phenyl)-1,2,4-oxadiazole When the product of Step B was substituted for 2-trifluoromethyl-bromobenzene and 3,6-dihydro-2H-pyridine-1-tert-butoxycarbonyl-4-boronic acid was substituted for 4-carbaldehyde boronic acid in Example 36 Step A, the similar process gave the title compound in 57% yield. This (0.085 g) was dissolved in anhydrous CH$_2$Cl$_2$ (2 ml) and CF$_3$CO$_2$H (0.5 ml) was added to it. The mixture was stirred for 3 h, then the solvent was evaporated to dryness. The residue was purified by FCC (SiO$_2$) to give the title compound (0.063 g, 93%), as a colourless solid. $^1$H-NMR (CDCl$_3$) 1.47-1.52 (m, 6H); 2.72 (m, 2H); 3.33-3.29 (m, 2H); 3.75 (m, 2H); 4.14-4.24 (m, 4H); 6.2 (s, 1H); 6.97 (d, 1H, J=8.4 Hz); 7.64-7.68 (m, 3H); 7.78 (d, 1H, J=8.42); 8.24 (d, 2H, J=8.19 Hz).

Step D: 2-Amino-2-((4-(4-(5-(3,4-diethoxyphenyl)-1,2,4-oxadiazol-3-yl)phenyl)-5,6-dihydropyridin-1(2H)-yl)methyl)propane-1,3-diol When the product of Step C was substituted for 5-(3,4-diethoxyphenyl)-3-(1H-indolin-4-yl)-1,2,4-oxadiazole in Example 34, Step D, the identical process afforded the compound which was de-protected as in Example 34, Step E to afford the title compound in 59% yield. $^1$H-NMR (DMSO-d$_6$) 1.32-1.37 (m, 6H); 2.37 (s, 2H); 2.77 (m, 2H); 3.24-3.28 (m, 8H); 4.11-4.16 (m, 4H); 4.51 (broad s, 2H); 6.3 (s, 1H); 7.17 (d, 1H, J=8.39 Hz); 7.6-7.63 (m, 3H); 7.73 (d, 1H, J=9.07); 8.00 (d, 2H, J=8.18 Hz).

Example 59

2-Amino-2-((5-(2-(2'-(trifluoromethyl)biphenyl-4-yl)ethyl)indolin-1-yl)methyl)propane-1,3-diol

Step A: 4'-Ethynyl-2-(trifluoromethyl)biphenyl

To a stirred suspension of the product of Example 36, Step A, (0.21 g, 1 mmol) and $K_2CO_3$ (0.166 g, 1.1 mmol) in anhydrous MeOH (5 mL) was added a solution of dimethyl 1-diazo-2-oxopropylphosphonate (0.212 g, 1.1 mmol) in anhydrous MeOH (1 ml) and the mixture was stirred overnight at room temperature. The solvent was evaporated to dryness and the residue was diluted to 50 ml with EtOAc and washed with $H_2O$. The organic layer was separated, dried over $MgSO_4$, and filtered. The filtrate was passed through silica gel bead. The filtrate was evaporated to dryness to give the product (0.21 g, 85.4%), as creamy paste, which was used as such in next step. $^1$H-NMR ($CDCl_3$) 3.11 (s, 1H); 7.25-7.31 (m, 3H); 7.44-7.55 (m, 4H); 7.73 (d, 1H, J=7.69 Hz).

Step B: 5-((2'-(Trifluoromethyl)biphenyl-4-yl)ethynyl)-1H-indole

When the product of Step A was substituted for 1-octyne and 5-iodoindole was substituted for 5-iodo-2-tritylisoindoline in Example 2, Step D, the similar process afforded the title compound in 86% yield, as a colourless paste. $^1$H-NMR ($CDCl_3$) 7.56 (broad s, 1H); 7.28-7.4 (m, 5H); 7.46 (tr, 1H, J=7.25 Hz); 7.53-7.58 (m, 3H); 7.73 (d, 1H, J=7.85 Hz); 7.87 (s, 1H); 8.23 (broad s, 1H).

Step C: 5-(2-(2'-(Trifluoromethyl)biphenyl-4-yl)ethyl)-1H-indole

A suspension of the product of Step B (0.25 g, 0.7 mmol) and 10% Pd/C (0.1 g) in EtOH (10 ml) was stirred overnight under $H_2$. The mixture was filtered through Celite bead and the filtrate was evaporated to dryness to give the desired product (0.25 g, 98%) as pale paste. $^1$H-NMR ($CDCl_3$) 2.97-3.1 (m, 4H); 6.5 (m, 1H); 7.04 (dd, 1H, J=1.37, 8.3 Hz), 7.15-7.2 (m, 2H); 7.30-7.34 (m, 2H); 7.37-7.44 (m, 2H); 7.51 (d, 1H, J=7.56 Hz); 8.68 (broad s, 1H).

Step D: 5-(2-(2'-(Trifluoromethyl)biphenyl-4-yl)ethyl)indoline

The product of Step C (0.24 g, 0.65 mmol) was dissolved in AcOH (2 ml) and $NaCNBH_3$ (0.082 g, 1.3 mmol) was added in portions. The mixture was stirred for 1 h and then poured into an aqueous solution of $NaHCO_3$ and extracted with EtOAc (50 ml). The organic layer was separated, dried over $MgSO_4$ and filtered. The filtrate was evaporated to dryness and the residue was purified by FCC ($SiO_2$) to give the desired product (0.18 g, 75%), as pale paste. $^1$H-NMR ($CDCl_3$) 2.81-2.94 (m, 4H); 3.0 (tr, 2H, J=7.22 Hz); 3.54 (tr, 2H, J=8.35 Hz); 6.58 (d, 1H, J=7.83 Hz); 6.84 (d, 1H, J=7.82 Hz); 6.9 (b, 1H); 7.17-7.21 (m, 3H); 7.31-7.35 (m, 2H); 7.43 (tr, 1H, J=7.65 Hz); 7.54 (tr, 1H, J=7.37 Hz); 7.72 (d, 1H, J=7.78 Hz).

Step E: tert-Butyl-2,2-dimethyl-5-((5-(2-(2'-(trifluoromethyl)biphenyl-4-yl)ethyl) indolin-1-yl)methyl)-1,3-dioxan-5-ylcarbamate When the product of Step D was substituted for 5-(3,4-diethoxyphenyl)-3-(1H-indolin-4-yl)-1,2,4-oxadiazole in Example 34, Step D, the identical process afforded the title compound in 54% yield. $^1$H-NMR $CDCl_3$) 1.46 (s, 12H), 1.48 (s, 3H), 2.83-2.92 (m, 4H); 2.97 (tr, 2H, J=8.3 Hz); 3.44 (tr, 2H, J=8.41 Hz); 3.5 (s, 2H); 3.91 (d, 2H, J=11.5 Hz); 4.00 (d, 1H, J=11.6 Hz); 4.72 (s, 1H); 6.53 (d, 1H, J=8.1 Hz); 6.91 (d, 1H, J=7.6 Hz); 6.92 (m, 1H); 7.23 (m, 4H); 7.32 (d, 1H, J=7.49 Hz); 7.43 (tr, 1H, J=7.82 Hz); 7.53 (tr, 1H, J=7.38 Hz); 7.73 (d, 1H, J=7.81 Hz).

Step F: 2-Amino-2-((5-(2-(2'-(trifluoromethyl)biphenyl-4-yl)ethyl)indolin-1-yl)methyl)propane-1,3-diol When the product of Step E was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 100%. $^1$H-NMR ($CD_3OD/CDCl_3$) 2.8-2.86 (m, 4H); 2.89 (tr, 2H, J=8.29 Hz); 3.0 (s, 2H); 3.39 (tr, 2H, J=8.29 Hz); 3.48 (d, 2H, J=10.88 Hz); 3.55 (d, 2H, J=10.92 Hz); 6.51 (d, 1H, J=8.6 Hz); 6.86-6.88 (m, 2H); 7.14 (m, 3H); 7.17-7.37 (m, 2H); 7.4 (tr, 1H, J=7.57 Hz); 7.5 (tr, 1H, J=7.01 Hz); 7.68 (d, 1H, J=7.77 Hz).

Example 60

2-Amino-2-(((3-(1-admantyl)-4-isopropoxyphenethyl)(methyl)amino)methyl)propane-1,3-diol

Step A: 3-(1-Admantyl)-4-isopropoxybenzaldehyde

To a stirred suspension of 3-(1-admantyl)-4-hydroxybenzaldehyde (0.5 g, 1.95 mmol) and $K_2CO_3$ (0.276 g, 2 mmol) in anhydrous DMF (5 ml) was added 2-bromopropane (1 ml) and the mixture was reflux for 2 h. The reaction mixture was brought to room temperature and diluted to 50 ml with EtOAc and washed with $H_2O$. The organic layer was separated, dried over $MgSO_4$ and filtered. The filtrate was evaporated to dryness and the residue was crystallized from MeOH to give the title compound (0.25 g, 86%), as a colourless solid. $^1$H-NMR ($CDCl_3$) 1.42 (d, 6H, J=6 Hz); 1.76 (broad s, 6H); 2.07 (broad s, 3H); 2.12 (s, 6H); 4.69-4.78 (m, 1H); 6.91 (d, 1H, J=8.44 Hz); 7.66 (dd, 1H, J=2.13, 8.45 Hz); 7.76 (d, 1H, J=2.11 Hz); 9.84 (s, 1H).

Step B: (E)-2-(1-Admantyl)-1-isopropoxy-4-(2-nitrovinyl)benzene

To a stirred solution of 3-(1-admantyl)-4-isopropoxybenzaldehyde (0.24 g, 0.8 mmol) in $CH_3NO2$ (5 mL) was added $CH_3CO_2NH_4$ (0.125 g, 1.6 mmol) and the mixture was stirred for 3 h at reflux. The solvent was evaporated to dryness and the residue was diluted to 50 ml with EtOAc and washed with 1M HCl and $H_2O$. The organic layer was separated, dried over $MgSO_4$ and filtered. The filtrate was evaporated to dryness to give the title product (0.275 g; 88%) as yellow solid. $^1$H-NMR ($CDCl_3$) 1.41 (d, 6H, J=6 Hz); 1.7-1.76 (m, 6H); 2.08-2.12 (m, 9H); 4.68-4.74 (m, 1H); 6.85 (d, 1H, J=8.45 Hz); 7.33-7.38 (m, 2H); 7.51 (d, 1H, J=13.53 Hz); 7.97 (d, 1H, J=13.54 Hz).

Step C: 2-(3-(1-Admantyl)-4-isopropoxyphenyl)ethanamine

A solution of the product of Step B (0.27 g, 0.8 mmol) in anhydrous $Et_2O$ (10 ml) was added drop wise to the stirred slurry of $LiAlH_4$ (0.040 g) in anhydrous $Et_2O$ (5 ml). After addition the mixture was stirred for 1 h at room temperature and then quenched with a mixture of $Et_2O:EtOAc:MeOH$:

H₂O; 80:15:4:1. The white solid was separated and filtered through Celite bead. The filtrate was evaporated to dryness to give the title compound (0.235 g; 96%). ¹H-NMR CDCl₃) 1.35 (d, 6H, J=5.9 Hz); 1.59 (s, 6H); 1.7 (s, 9H); 1.73 (s, 6H); 2.03-2.12 (m, 9H); 2.69 (m, 2H); 2.93 (m, 2H); 4.55-4.6 (m, 1H); 6.72 (d, 1H, J=8.46 Hz); 6.9-6.99 (m, 2H).

Step D: N-(3-(1Admantyl)-4-isopropoxyphenethyl)-2,2,2-trifluoro-acetamide

To a stirred solution of 2-(3-(1-Admantyl)-4-isopropoxyphenyl)ethanamine (0.28 g, 0.86 mmol) in a mixture of solvents (CH₂Cl₂:Et₃N: 10:0.5 ml) (CF₃CO)₂O (0.157 ml) was added at 0° C. under N₂. The reaction mixture was stirred for 2 h at room temperature, then the solvent was evaporated to dryness. The residue was diluted to 50 ml with EtOAc and washed with 1M HCl. The organic layer was separated, dried over MgSO₄ and filtered. The filtrate was evaporated to dryness to give the title product (0.29 g, 82.4%). ¹H-NMR (CDCl₃) 1.37 (d, 6H, J=6 Hz); 1.67-1.75 (m, 6H); 2.04-2.23 (m, 9H); 2.78 (tr, 2H, J=6.84 Hz); 3.53-3.59 (m, 2H); 4.57-4.63 (m, 1H); 6.77 (d, 1H, J=8.32 Hz); 6.92 (dd, 1H, J=2.21, 8.27 Hz); 6.98 (d, 1H, J=2.21 Hz).

Step E: N-(3-(1-Admantyl)-4-isopropoxyphenethyl)-2,2,2-trifluoro-N-methyl-acetamide To a solution of the product of Step D (0.25 g, 0.61 mmol) in anhydrous THF (5 ml) 60% NaH in mineral oil (0.03 g, 0.75 mmol) was added at 0° C. and the mixture was stirred for 2 h. To it MeI (0.23 ml) was added and the resulting mixture was stirred for additional 3 h. The mixture was passed trough Celite bead and washed with CH₂Cl₂ (10 ml). The combined filtrates were evaporated to dryness to give the title product (0.22 g; 85.3%). ¹H-NMR (CDCl₃) 1.36 (d, 6H, J=6 Hz); 1.75 (s, 6H); 2.04 (s, 3H); 2.09 (s, 6H); 2.8 (tr, 2H, J=7.7 Hz); 2.96 (s, 3H); 3.59 (tr, 2H, J=6.02 Hz); 4.58-4.63 (m, 1H); 6.76 (d, 1H, J=8.32 Hz); 6.91-7.01 (m, 2H).

Step F: 2-(3-(1-Admantyl)-4-isopropoxyphenyl)-N-methylethanamine

To a stirred solution of the product of Step E (0.21 g; 0.5 mmol) in MeOH (10 ml) was added NaOH (0.1 g) and this was stirred for 3 h at room temperature. The solvent was evaporated to dryness and the residue was taken in a mixture of solvents (EtOAc:MeOH:AcOH; 10 ml:2 ml:0.5 ml) and passed through Celite bead, which was washed with EtOAc (10 ml). The combined filtrates were evaporated to dryness to give the title compound (0.145 g, 94%) as pale paste. ¹H-NMR (CDCl₃) 1.36 (d, 6H, J=6 Hz); 1.74 (5, 6H); 2.04 (s, 3H, 2.1 (s, 6H); 2.43 (s, 3H); 2.72-2.81 (m, 4H); 4.55-4.63 (m, 1H); 6.74 (d, 1H, J=8.25 Hz); 6.94 (dd, 1H, J=1.97, 8.18 Hz); 7.01 (d, 1H, J=1.98 Hz).

Step G: tert-Butyl 5-(((3-(1-admantyl)-4-isopropoxyphenethyl)(methyl)amino)methyl)-2,2-dimethyl-1,3-dioxan-5-ylcarbamate When the product of Step F was substituted for 5-(3,4-diethoxyphenyl)-3-(1H-indolin-4-yl)-1,2,4-oxadiazole in Example 34, Step D, the identical process afforded the title compound in 39% yield. ¹H-NMR (CDCl₃) 1.29 (d, 6H, J=5.89 Hz); 1.35 (s, 9H); 1.37 (s, 3H); 1.38 (s, 3H); 1.74 (s, 6H); 2.04 (s, 3H); 2.1 (s, 6H); 2.37 (s, 3H); 2.66 (s, 4H); 2.82 (s, 2H); 3.72 (d, 2H, J=11.61 Hz); 3.96 (d, 2H, J=11.53 Hz); 4.61-4.56 (m, 1H); 4.83 (s, 1H); 6.72 (d, 1H, J=8.3 Hz); 6.91 (dd, 1H, J=2.08, 8.29 Hz); 6.99 (d, 1H, J=2.11 Hz).

Step H: 2-Amino-2-(((3-(1-admantyl)-4-isopropoxyphenethyl)(methyl)amino methyl)propane-1,3-diol When the product of Step G was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 49% yield. ¹H-NMR (CDCl₃) 1.34 (d, 6H, J=6.00 Hz); 1.73 (s, 6H); 2.03 (s, 3H); 2.08 (s, 6H); 2.4 (s, 3H); 2.51 (s, 2H); 2.66 (s, 4H); 3.42 (d, 2H, J=10.87 Hz); 3.47 (d, 2H, J=10.88 Hz); 4.56-4.61 (m, 1H); 6.72 (d, 1H, J=8.34 Hz); 6.98 (dd, 1H, J=2.12, 8.24 Hz); 6.97 (d, 1H, J=2.12 Hz).

Example 61

2-Amino-2-((7-(1-admantyl)-6-isopropoxy-3,4-dihydroisoquinolin-2(1H)-yl)methyl)propane-1,3-diol

Step A: Methyl 4-(1-admantyl)-3-isopropoxybenzoate

When methyl 4-(1-admantyl)-3-hydroxybenzoate was substituted for 3-(1-admantyl)-4-hydroxybenzaldehyde in Example 60, Step A, the identical process afforded the title compound (0.95 g, 75.4%) as a colourless solid. ¹H-NMR (CDCl₃) 1.39 (d, 6H, J=6 Hz); 1.75 (5, 6H); 2.05 (s, 3H); 2.11 (s, 6H); 3.87 (s, 3H); 4.69-4.71 (m, 1H); 7.24 (d, 1H, J=8.1 Hz); 7.47 (b, 1H); 7.51 (dd, 1H, J=1.55, 8.09 Hz).

Step B: (4-(1-Admantyl)-3-isopropoxyphenyl)methanol

When the product of Step A was substituted for (E)-2-(1-Admantyl)-1-isopropoxy-4-(2-nitrovinyl)benzene in Example 60, Step C, the identical process afforded the title compound in 89% yield, as creamy paste. ¹H-NMR (CDCl₃) 1.38 (d, 6H, J=6 Hz); 1.75 (s, 6H); 2.04 (s, 3H); 2.1 (s, 6H); 4.62 (s, 2H); 4.53-4.71 (m, 1H); 6.79-6.9 (m, 2H); 7.20 (d, 1H, J=7.88 Hz).

Step C: 4-(1-Admantyl)-3-isopropoxybenzaldehyde

A mixture of the product of Step B (0.7 g) and MnO₂ (1.5 g) in dioxane (20 ml) was stirred for 6 h at reflux. The mixture was filtered through Celite pad and the filtrate was evaporated to dryness to give the title compound (0.51 g, 73.4%) as creamy solid. ¹H-NMR (CDCl₃) 1.4 (d, 6H, J=6 Hz); 1.76 (s, 6H); 2.07 (s, 3H); 2.11 (s, 6H); 4.7-4.78 (m, 1H); 7.32-7.42 (m, 3H); 9.91 (s, 1H).

Step D: (E)-1-(1-Admantyl)-2-isopropoxy-4-(2-nitrovinyl)benzene

When the product of Step C was substituted for 4-(1-admantyl)-3-isopropoxybenzaldehyde in Example 60, Step B, the identical process afforded the title compound (0.53 g, 93%), as yellow solid. ¹H-NMR (CDCl₃) 1.41 (d, 6H, J=6.02 Hz); 1.75 (s, 6H); 2.06 (s, 3H); 2.09 (s, 6H); 6.91 (d, 1H, J=1.4 Hz); 7.06 (dd, 1H, J=1.48, 8.02 Hz); 7.26 (d, 1H, J=8.10 Hz); 7.53 (d, 1H, J=13.6 Hz); 7.94 (d, 1H, J=13.6 Hz).

Step E: 2-(4-(1-Admantyl)-3-isopropoxyphenyl)ethanamine

When the product of Step D was substituted for (E)-1-(1-Admantyl)-2-isopropoxy-4-(2-nitrovinyl)benzene in Example 60, Step C, the identical process afforded the title compound in 89% yield, as creamy paste. $^1$H-NMR (CDCl$_3$) 1.37 (d, 6H, J=6.02 Hz); 1.74 (s, 6H); 2.04 (s, 3H); 2.1 (5, 6H); 2.68 (t, 2H, J=6.5 Hz); 2.94 (t, 2H, J=6.9 Hz); 7.61-7.68 (m, 1H); 6.66-6.76 (m, 2H); 7.11 (d, 1H, J=7.78 Hz).

Step F: 7-(1-Admantyl)-6-isopropoxy-1,2,3,4-tetrahydroisoquinoline

To a solution of the product of Step E (0.4 g, 0.78 mmol) in HCOOH (3 ml) (CH$_2$O)$_n$ (0.026 g, 0.87 mmol) was added and the mixture was stirred for 18 h at 60° C. This was evaporated to dryness and the residue was purified by FCC (SiO$_2$) to give the desired product (0.17 g, 41%), as light yellow paste. $^1$H-NMR (CDCl$_3$) 1.36 (d, 6H, J=6 Hz); 1.74 (s, 6H); 2.03 (s, 3H); 2.08 (s, 6H); 2.7 (tr, 2H, J=5.91 Hz); 3.10 (tr, 2H, J=5.99 Hz); 3.91 (5, 2H); 4.55-4.64 (m, 1H); 6.53 (s, 1H); 6.82 (s, 1H).

Step G: tert-Butyl-5-((7-(1-admantyl)-6-isopropoxy-3,4-dihydroisoquinolin-2(1H)-yl)methyl)-2,2-dimethyl-1,3-dioxan-5-ylcarbamate When the product of Step F was substituted for 5-(3,4-diethoxyphenyl)-3-(1H-indolin-4-yl)-1,2,4-oxadiazole in Example 34, Step D, the identical process afforded the title compound in 58% yield, as a yellow paste. $^1$H-NMR (CDCl$_3$) 1.33 (d, 6H, J=6 Hz); 1.44 (s, 3H); 1.45 (s, 9H); 1.46 (s, 3H); 1.73 (s, 6H); 2.02 (s, 3H); 2.07 (s, 6H); 2.81 (s, 4H); 2.92 (s, 2H); 3.66 (s, 2H); 3.79 (d, 2H, J=11.6 Hz); 4.11 (d, 2H, J=11.6 Hz); 4.55-4.63 (m, 1H); 4.91 (s, 1H); 6.55 (s, 1H); 6.80 (s, 1H).

Step H: 2-Amino-2-((7-(1-admantyl)-6-isopropoxy-3,4-dihydroisoquinolin-2(1H)-yl)methyl)propane-1,3-diol When the product of Step G was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 77% yield, as pale paste. $^1$H-NMR (CDCl$_3$) 1.26 (d, 6H, J=6.07 Hz); 1.65 (m, 6H); 1.94 (m, 3H); 1.67 (m, 6H); 2.52 (m, 2H); 2.75 (m, 4H); 3.38-3.47 (m, 4H); 3.59 (s, 2H); 4.48-4.52 (m, 1H); 6.46 (s, 1H); 6.72 (s, 1H).

Example 62

2-Amino-2-((octahydroisoquinolin-2(1H)-yl)methyl)propane-1,3-diol

Step A: tert-Butyl 2,2-dimethyl-5-((decahydroisoquinolin-2(1H)-yl)methyl)-1,3-dioxan-5-ylcarbamate When decahydroisoquinoline was substituted for 5-(3,4-diethoxyphenyl)-3-(1H-indolin-4-yl)-1,2,4-oxadiazole in Example 34, Step D, the identical process afforded the title compound in 31% yield, as light yellow paste. $^1$H-NMR (CDCl$_3$) 0.76-0.88 (m, 2H); 1.13-1.28 (m, 4H); 1.39 (s, 9H); 1.4 (s, 3H); 1.42 (s, 3H); 1.53-1.69 (m, 4H); 1.9 (tr, 1H, J=10.73 Hz); 2.24 (tr, 1H, J=11.98 Hz); 2.56-2.75 (m, 4H); 3.7-3.85 (m, 4H); 4.0 (d, 2H, J=11.37 Hz); 4.9 (broad s, 1H).

Step B: 2-Amino-2-((decahydroisoquinolin-2(1H)-yl)methyl)propane-1,3-diol

When the product of Step A was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 79% yield. $^1$H-NMR (CDCl$_3$) 0.74-0.91 (m, 2H); 1.02-1.22 (m, 4H); 1.33-1.63 (m, 6H); 1.83 (tr, 1H, J=11 Hz); 2.11 (tr, 1H, J=11.45 Hz); 2.37 (s, 2H); 2.67 (d, 1H, J=11.09 Hz); 2.83 (d, 1H, J=11.45 Hz); 3.39 (d, 2H, J=10.97 Hz); 3.43 (d, 2H, J=10.91 Hz).

Example 63

2-Amino-2-(3-(1-admantyl)-4-(octyloxy)phenethyl)propane-1,3-diol hydrochloride salt

Step A: 2-(1-Admantyl)-4-iodo-1-(octyloxy)benzene

When 1-bromooctane was substituted for 2-bromopropane and 2-(1-admantyl)-4-iodo-phenol was substituted for 3-(1-admantyl)-4-hydroxybenzaldehyde in Example 60, Step A, the identical process afforded the title compound in 72% yield. $^1$H-NMR (CDCl$_3$) 0.87 (tr, 3H, J=5.22 Hz); 1.26-1.29 (m, 9H); 1.51-1.53 (m, 2H); 1.75 (s, 6H); 1.81-1.86 (m, 2H); 2.07 (5, 9H); 3.91 (tr, 2H, J=6.28 Hz); 6.58-6.6 (d, 1H, J=8.21 Hz); 7.39-7.42r(m, 2H).

Step B: tert-Butyl 5-((3-(1-admantyl)-4-(octyloxy)phenyl)ethynyl)-2,2-dimethyl-1,3-dioxan-5-ylcarbamate When the product of Step A was substituted for 6-iodoindole and tert-butyl 5-ethynyl-2,2-dimethyl-1,3-dioxan-5-ylcarbamate was substituted for 4'-ethynyl-2-(trifluoromethyl)biphenyl in Example 59, Step B the identical process afforded the title compound in 48%, as creamy paste. $^1$H-NMR (CDCl$_3$) 0.85 (tr, 3H, J=8.99 Hz); 1.27-1.47 (m, 23H); 1.73 (s, 6H); 1.8-1.87 (m, 2H); 2.06 (s, 9H); 3.94 (tr, 2H, J=6.34 Hz); 3.99 (d, 2H, J=11.44 Hz); 4.08 (d, 2H, J=11.52 Hz); 5.17 (s, 1H); 6.73 (d, 1H, J=8.41 Hz); 7.19-7.21 (m, 2H).

Step C: 2-Amino-2-(3-(1-admantyl)-4-(octyloxy)phenethyl)propane-1,3-diol

A slurry of the product of Step B (0.04 g, 0.068 mmol) and 10% Pd/C (0.04 g) in a mixture of EtOH: CF$_3$CO$_2$H (10 ml: 2 drops) was stirred for 36 h under H$_2$. The mixture was filtered through Celite bead and washed with EtOH (10 ml). The filtrates were evaporated to dryness and the residue was dissolved in MeOH:CH$_2$Cl$_2$ 1:1 (5 ml) and 5 drops of concentrated HCl was added. The mixture was stirred for 1 h and solvents were evaporated to dryness. The residue was crystallized from CH$_3$CN to give the titled compound (0.025 g, 81%) as colourless powder. $^1$H-NMR (CDCl$_3$) 0.79 (t, 3H, J=6.57 Hz); 1.12-1.21 (m, 7H); 1.37-1.41 (m, 2H); 1.69 (s, 6H); 1.73-1.88 (m, 3H); 2.00 (b, 9H); 2.48-2.52 (m, 2H); 3.61 (d, 2H, J=11.84 Hz); 3.67 (d, 2H, J=12.2 Hz); 3.85 (tr, 2H, J=6.22 Hz); 6.69 (d, 1H, J=8.13 Hz); 6.88-7.93 (m, 2H).

Example 64

2-Amino-2-(2-(3'-(1-admantyl)-4'-hydroxybiphenyl-4-yl)ethyl)propane-1,3-diol hydrochloride salt

Step A: 3-(1-Admantyl)-4'-iodobiphenyl-4-ol

To a mixture of 4'-iodobiphenyl-4-ol (0.332 g, 2 mmol) and 1-admantanol (0.15 g, 0.51 mmol) in AcOH (2 ml) concentrated H$_2$SO$_4$ (0.5 ml) was added and the reaction mixture was stirred for 50 h at room temperature. This was diluted to 100 ml with EtOAc and washed with NaHCO₃ solution, dried over MgSO₄ and filtered. The filtrate was evaporated to dryness and the residue was crystallized from MeOH to give the product (0.195 g; 93%), as a colourless paste. ¹H NMR (CDCl₃) 1.78 (m, 6H); 2.07 (s, 3H); 2.15 (s, 6H); 6.69 (d, 1H, J=8.15 Hz); 7.21-7.28 (m, 3H); 7.37 (d, 1H, J=2.28 Hz); 7.69 (d, 2H, J=8.45 Hz).

Step B: tert-Butyl-5-((3'-(1-admantyl)-4'-hydroxybiphenyl-4-yl)ethynyl)-2,2-dimethyl-1,3-dioxan-5-ylcarbamate When product of Step A was substituted for 2-(1-admantyl)-4-iodo-1-(octyloxy)benzene in Example 63, Step B the identical process afforded the title compound in 71% yield, as light yellow paste. ¹H-NMR (CDCl₃) 1.44 (s, 3H); 1.48 (s, 9H); 1.5 (s, 3H); 1.78 (b, 6H); 2.08 (b, 3H); 2.16 (bs, 6H); 4.03 (d, 2H, J=11.45 Hz); 4.11 (d, 2H, J=11.75 Hz); 5.24 (broad s, 1H); 5.4 (s, 1H); 6.72 (d, 1H, J=8.18 Hz); 7.12 (broad d, 1H, J=7.75 Hz); 7.25-7.44 (m, 5H).

Step C: 2-Amino-2-(2-(3'-(1-admantyl)-4'-hydroxybiphenyl-4-yl)ethyl) propane-1,3-diol When product of Step B was substitute for tert-butyl 5-((3-(1-admantyl)-4-(octyloxy)phenyl)ethynyl)-2,2-dimethyl-1,3-dioxan-5-ylcarbamate in Example 63 Step C, the similar process afforded the title compound in 71% yield, as a colourless solid. ¹H-NMR (CDCl₃) 1.70 (s, 6H); 1.88-1.94 (m, 2H); 2.0 (broad s, 3H); 2.1 (broad s, 6H); 2.58-2.64 (m, 2H); 3.63 (d, 2H, J=12 Hz); 3.69 (d, 2H, J=12.08 Hz); 6.69 (d, 1H, J=8.18 Hz); 7.13-7.16 (m, 3H); 7.3 (d, 1H, J=2.06 Hz); 7.37 (d, 2H, J=8.07 Hz).

Example 65

2-Amino-2-((5-(5-(3,4-diethoxyphenyl)-1,2,4-oxadiazol-3-yl)isoindolin-2-yl)methyl)propane-1,3-diol

Step A: 5-Iodoisoindoline trifluoroacetate

A product of Example 2, Step C (1.32 g; 2.71 mmol) in 60% CF₃CO₂H/CH₂Cl₂ (10 ml) was stirred for 10 min at room temperature under N₂, then diluted to 30 ml with EtOH and stirred for additional 15 min. This was evaporated to dryness under reduced pressure and the residue was dissolved in EtOAc (10 ml) and hexane (20 ml) was added. After standing overnight at room temperature, the precipitate formed was filtered off, washed with hexane and dried to give the title compound (0.77 g; 79%), as off white solid, which was used in the next step without further purification. ¹H-NMR (CDCl₃) 4.47 (5, 2H); 4.51 (s, 2H); 6.7-6.8 (m, 1H); 7.0-7.21 (m, 1H); 7.4-7.7 (m, 1H); 10.6 (broad s, 1H).

Step B: tert-Butyl 5-iodoisoindoline-2-carboxylate

A mixture of the product of Step A (0.77 g; 2.15 mmol) and (BOC)₂O (0.7 g; 3.2 mmol) in anhydrous pyridine (3 ml) was stirred for 1 h at ~70° C. After removing solvents under reduced pressure, the residue was diluted to 20 ml with Et₂O. The insoluble material was filtered off, and filtrate was washed with diluted HCl (5 ml), saturated NaHCO₃ (5 ml), brine and dried over anhydrous MgSO₄ and filtered. The filtrate was evaporated under reduced pressure and the residue was purified by FCC (SiO₂; CH₂Cl₂:hexane 1:1) to give title compound (0.58 g; 78%) as creamy oil. ¹H-NMR (CDCl₃) 1.49 (5, 9H); 4.58-4.63 (m, 4H); 6.9-7.04 (m, 1H); 7.5-7.63 (m, 2H).

Step C: tert-Butyl 5-cyanoisoindoline-2-carboxylate

When the product of Step B was substituted for 5-iodoindole in Example 7, Step A, the similar process afforded the title compound in 85%, as colourless solid, after purification by FCC (SiO₂; CH₂Cl₂). ¹H-NMR (CDCl₃) 1.49 (s, 9H); 4.56-4.72 (m, 4H); 7.32-7.37 (m, 1H); 7.49-7.56 (m, 2H).

Step D: tert-Butyl 5-(N-hydroxycarbamimidoyl)isoindoline-2-carboxylate

A product of Step C (0.22 g; 0.904 mmol), HCl×NH₂OH (0.16 g; 2.3 mmol) and DIPEA (0.48 ml; 5 mmol) in anhydrous EtOH (3.5 ml) was refluxed for 2 h under N₂. The solvents were removed under reduced pressure and the residue was diluted to 30 ml with EtOAc, washed with H₂O (2×5 ml), brine, dried over anhydrous MgSO₄, filtered and the filtrate evaporated to dryness to give the title compound (0.25 g; 100%) as colourless foam, which was used in next step without further purification.

Step E: tert-Butyl 5-(5-(3,4-diethoxyphenyl)-1,2,4-oxadiazol-3-yl)isoindoline-2-carboxylate A mixture of 3,4-diethoxybenzoic acid (0.19 g; 0.904 mmol), a product of Step D (0.25 g; 0.904 mmol) and EDC (0.27 g; 1.4 mmol) in anhydrous DMF (2 ml) was stirred at ~60° C. for 1 h, then cooled to room temperature and diluted to 20 ml with EtOAc. This was washed with H₂O (2×5 ml), brine, dried over anhydrous MgSO₄, filtered and filtrate evaporated to dryness. The residue was diluted to 3 ml with anhydrous diglyme and 1M TBAF in THF (0.5 ml) was added and the resulting mixture was stirred at ~80° C. for 1 h, then solvents were removed in vacuo. The residue was purified by crystallization from MeOH, to give the title compound (0.084 g; 20%) as greyish solid. ¹H-NMR (CDCl₃) 1.4-1.6 (m, 15H+ H₂O); 4.14-4.24 (m, 4H); 4.7-4.76 (m, 4H); 6.97 (d, 1H, J=6 Hz); 7.32-7.4 (m, 1H); 7.66 (d, 1H, J=3 Hz); 7.78 (dd, 1H, J=3, 9 Hz); 8.02-8.08 (m, 2H).

Step F: tert-Butyl 5-((5-(5-(3,4-diethoxyphenyl)-1,2,4-oxadiazol-3-yl)isoindolin-2-yl)methyl)-2,2-dimethyl-1,3-dioxan-5-ylcarbamate A mixture of the product of Step E (0.084 g; 0.186 mmol) in 60% TFA/CH₂Cl₂ (1.5 ml) was stirred for 5 min at room temperature under N₂, then diluted to 4 ml with EtOH, stirred for additional 15 min and evaporated to dryness under reduced pressure. To it, tert-butyl 5-formyl-2,2-dimethyl-1,3-dioxan-5-ylcarbamate (0.05 g; 0.193 mmol) was added followed by NaBH(OAc)₃ (0.13 g; 0.58 mmol) and 1,2-dichloroethane (1.5 ml). The resulting mixture was stirred for 1 h at room temperature, diluted to 15 ml with EtOAc, washed with 10% NaOH (2×5 ml), brine, dried over anhydrous MgSO₄, filtered and filtrate evaporated to dryness. The residue was purified by FCC (SiO₂; CH₂Cl₂:EtOAc 8:2) to give the title compound (0.07 g; 63%) as off white foam. ¹H-NMR (CDCl₃) 1.38-1.61 (m, 21H); 3.21 (s, 2H); 3.82 (d, 2H, J=12 Hz); 4.05-4.24 (m, 10H); 4.98 (broad s, 1H); 6.97 (d, 1H, J=9 Hz); 7.2-7.3 (m, 1H+CDCl₃); 7.66 (d, 1H, J=3 Hz); 7.78 (dd, 1H, J=3, 6 Hz); 7.96-8.02 (m, 2H).

Step G: 2-Amino-2-((5-(5-(3,4-diethoxyphenyl)-1,2,4-oxadiazol-3-yl)isoindolin-2-yl)methyl)propane-1,3-diol When the product of Step F was substituted for tert-butyl 5-((4-(5-(3,4-diethoxyphenyl)-1,2,4-oxadiazol-3-yl)indolin-1-yl)methyl)-2,2-dimethyl-1,3-dioxan-5-ylcarbamate in Example 34, Step E, the identical process afforded the title compound in 57% yield, as a colourless solid. $^1$H-NMR (CDCl$_3$) 1.45-1.56 (m, 6H); 1.97 (broad s, 4H+2H$_2$O); 2.94 (s, 2H); 3.59 (s, 4H); 4.14-4.25 (m, 8H); 6.97 (d, 1H, J=8.5 Hz); 7.3 (d, 1H, J=8 Hz); 7.66 (d, 1H, J=2 Hz); 7.77 (dd, 1H, J=2, 8.5 Hz); 7.9-8.04 (m, 2H).

Example 66

2-Amino-2-((4-(5-(6-propylpyridin-3-yl)-1,2,4-oxadiazol-3-yl)indolin-1-yl)methyl)propane-1,3-diol

Step A: 6-(Prop-1-ynyl)nicotinic acid

When 6-iodonicotinic acid was substituted for the 3-iodo-4-propylbenzoic acid in Example 47, Step B, the similar process afforded the title compound in 45% yield, as yellow solid. $^1$H-NMR (CDCl$_3$) 2.12 (s, 3H); 7.25 (broad s, 1H+H$_2$O); 7.46 (dd, 1H, J=0.6, 7.6 Hz); 8.2 (dd, 1H, J=2.16, 6 Hz); 9.23 (dd, 1H, J=0.8, 1.4 Hz).

Step B: 6-Propylnicotinic acid

A solution of the product of Step A (0.25 g; 1.55 mmol), 10% Pd/C (0.15 g) and triethylamine (0.5 ml) in EtOH (15 ml) was stirred overnight at room temperature under H$_2$ (Parr apparatus; 100 psi). The catalyst was removed by filtration, washed with fresh EtOH (2×10 ml), and combined filtrates were evaporated to dryness to give the title compound (0.25 g; 100%), as greyish solid, which was used in the next Step without further purification. $^1$H-NMR (CDCl$_3$) 0.94 (tr, 3H, J=6 Hz); 1.69-1.81 (m, 2H); 2.83 (tr, 2H, J=6 Hz); 7.2 (d, 1H, J=9 Hz); 8.19 (s, 1H); 8.28 (d, 1H, J=9 Hz); 10.65 (broad s, 1H).

Step C: 3-(1H-indol-4-yl)-5-(6-propylpyridin-3-yl)-1,2,4-oxadiazole

A mixture of the product of Example 34, Step A (0.087 g; 0.5 mmol), 6-propylnicotinic acid (0.082 g; 0.5 mmol) and EDC (0.11 g; 0.57 mmol) in anhydrous DMSO (2 ml) was stirred for 1 h at ~40° C. under N$_2$. To this 1M TBAF in THF (0.5 ml) was added and the resulting mixture was stirred for 1 h at ~110° C. After cooling to room temperature the mixture was diluted to 15 ml with EtOAc, washed with H$_2$O, brine, dried over anhydrous MgSO$_4$, filtered and filtrate evaporated to dryness. The residue was purified by FCC (SiO$_2$, CH$_2$Cl$_2$: EtOAc 9:1) to give the title compound (0.05 g; 33%), as colorless solid. $^1$H-NMR (CDCl$_3$) 1.0 (m, 3H); 1.8 (m, 2H); 2.88 (tr, 2H, J=9 Hz); 7.3-7.4 (m, 4H); 7.57 (d, 1H, J=9 Hz); 8.08 (dd, 1H, J=2, 9 Hz); 8.38-8.43 (m, 2H); 9.39 (d, 1H, J=2 Hz).

Step D: 3-(Indolin-4-yl)-5-(6-propylpyridin-3-yl)-1,2,4-oxadiazole

When the product of Step C was substituted for 5-(3,4-diethoxyphenyl)-3-(1H-indol-4-yl)-1,2,4-oxadiazole in Example 34, Step C, the similar process afforded the title compound in 19% yield, as creamy solid. $^1$H-NMR (CDCl$_3$) 1.01 (m, 3H); 1.7-1.9 (m, 2H); 2.87 (m, 2H); 3.46 (tr, 2H, J=9 Hz); 3.64 (tr, 2H, J=9 Hz); 3.9 (broad s, 1H); 6.76 (d, 1H, J=6 Hz); 7.16 (m, 1H); 7.33 (d, 1H, J=9 Hz); 7.53 (dd, 1H, J=2, 9 Hz); 8.35 (dd, 1H, 3, 9 Hz); 9.33 (d, 1H, J=3 Hz).

Step E: tert-Butyl 2,2-dimethyl-5-((4-(5-(6-propylpyridin-3-yl)-1,2,4-oxadiazol-3-yl)indolin-1-yl)methyl)-1,3-dioxan-5-ylcarbamate When the product of Step D was substituted for 5-(3,4-diethoxyphenyl)-3-(indolin-4-yl)-1,2,4-oxadiazole in Example 34, Step D, the similar process afforded the crude title compound in 100% yield, which was used in next step without further purification. $^1$H-NMR (CDCl$_3$) 0.98 (tr, 3H, J=9 Hz); 1.44 (m, 15H+H2O); 1.81 (m, 2H); 2.86 (tr, 2H, J=9 Hz); 3.42 (tr, 2H, J=9 Hz); 3.57 (tr, 2H, J=9 Hz); 3.6 (s, 2H); 4.0-4.09 (m, 4H); 4.68 (broad s, 2H); 6.74 (d, 1H, J=9 Hz); 7.19 (m, 1H); 7.32 (d, 1H, J=9 Hz); 7.48 (d, 1H, J=6 Hz); 8.34 (dd, 1H, J=3, 9 Hz); 9.32 (d, 1H, 3 Hz).

Step F: 2-Amino-2-((4-(5-(6-propylpyridin-3-yl)-1,2,4-oxadiazol-3-yl)indolin-1-yl)methyl)propane-1,3-diol To a solution of the product of Step E (0.018 g; 0.033 mmol), NaI (0.015 g; 0.0981 mmol) in anhydrous CH$_3$CN (0.6 ml), Me$_3$SiCl (0.08 ml) was added at room temperature with stirring under N$_2$. After stirring for 30 min MeOH (0.5 ml) was added and solvents were removed under reduced pressure. The residue was purified by FCC (SiO$_2$; NH$_4$OH saturated CH$_2$Cl$_2$:MeOH 95:5) to give the title compound (0.0066 g; 49%) as colourless solid. $^1$H-NMR (CDCl$_3$+CD$_3$OD) 0.93 (tr, 3H, J=(Hz); 1.67-1.81 (m, 2H); 2.81 (tr, 2H, J=9 Hz); 2.99 (broad s, CD$_3$OH); 3.07 (s, 2H); 3.26-3.65 (m, 8H); 6.74 (d, 1H, J=9 Hz); 7.15 (m, 1H); 7.31 (d, 1H, J=9 Hz); 7.42 (d, 1H, J=9 Hz); 8.32 (dd, 1H, J=3, 9 Hz); 9.33 (d, 1H, 3 Hz).

Example 67

2-Amino-2-((5-(5-(4-propylphenyl)-1,2,4-oxadiazol-3-yl)-3,4-dihydroquinolin-1(2H)-yl)methyl)propane-1,3-diol

Step A: 5-Cyanoquinoline

A mixture of 5-iodoquinoline (0.56 g; 2.2 mmol) and CuCN (0.51 g; 5.7 mmol) in anhydrous DMF (3 ml) was refluxed for 40 min under N$_2$. After cooling to room temperature, the mixture was diluted to 20 ml with EtOAc and NaCN (0.75 g; 15.3 mmol) was added followed by H$_2$O (10 ml). The resulting mixture was vigorously stirred for 10 min and organic phase was separated, washed with H$_2$O, brine, dried over anhydrous MgSO$_4$, filtered and filtrate evaporated to dryness to give the title compound (0.33 g; 97%) as colourless solid. $^1$H-NMR (CDCl$_3$) 7.59-7.63 (m, 1H); 7.78 (m, 1H); 7.98 (dd, 1H, J=3, 6 Hz); 8.36 (d, 1H, J=9 Hz); 8.54 (m, 1H): 9.05 (dd, 1H, J=3, 6 Hz).

Step B: N-Hydroxyquinoline-5-carboximidamide

When the product of Step A was substituted for tert-butyl 5-cyanoisoindoline-2-carboxylate in Example 65, Step D, the identical process afforded the title compound in 48%, as colourless solid. $^1$H-NMR (DMSO-d$_6$) 7.54 (d, 0.5H, J=4.14

Hz); 7.59 (d, 0.5H, J=4.14 Hz); 7.64 (broad s, 1H); 7.73–7.76 (m, 2H); 8.7-8.75 (m, 1H); 8.9 (dd, 1H, J=2, 4.14 Hz); 8.04-8.1 (m, 2H).

Step C: 5-(4-Propylphenyl)-3-(quinolin-5-yl)-1,2,4-oxadiazole

When the product of Step B was substituted for N-hydroxy-1H-indole-4-carboximidamide and 4-propylbenzoic acid was substituted for 6-propylnicotinic acid in Example 66, Step C, the similar process afforded the title compound in 36% yield, as creamy solid. $^1$H-NMR (CDCl$_3$) 0.97 (tr, 3H, J=9 Hz); 1.7 (m, 2H); 2.69 (tr, 2H, J=9 Hz); 7.38 (d, 2H, J=9 Hz); 7.53 (d, 0.5H, J=6 Hz); 7.56 (d, 0.5H, J=6 Hz); 7.8-7.86 (m, 1H); 8.17 (d, 2H, J=9 Hz); 8.45 (m, 1H); 8.9 (dd, 1H, j=3, 6 Hz); 9.4 (d, 1H, J=9 Hz).

Step D: 5-(4-Propylphenyl)-3-(1,2,3,4-tetrahydroquinolin-5-yl)-1,2,4-oxadiazole

To a solution of the product of Step C (0.069 g; 0.219 mmol) in AcOH (1 ml) and anhydrous THF (1.5 ml) NaBH$_3$CN (3×0.07 g; 3.34 mmol) was added portion wise over a period of 2 h, while the temperature of the reaction mixture was kept <15° C. The solvents were removed in vacuo and the residue was diluted to 15 ml with EtOAc, washed with 5% NaOH, H$_2$O, brine, dried over anhydrous MgSO$_4$, filtered and filtrate evaporated to dryness under reduced pressure. The residue was dissolved in a mixture of CF$_3$CO$_2$H and EtOH (2 ml+2 ml), refluxed for 1 h and re evaporated. The residue was treated with NH$_4$OH saturated CH$_2$Cl$_2$ (5 ml) and evaporated under reduced pressure. The residue was purified by FCC (SiO$_2$, CH$_2$Cl$_2$) to give the title compound (0.034 g; 48%), as colourless solid. $^1$H-NMR (CDCl$_3$) 0.95 (tr, 3H, J=7.4 Hz); 1.61-1.75 (m, 2H); 1.91-2.0 (m, 2H); 2.66 (tr, 2H, J=7.8 Hz); 3.09 (tr, 2H, J=6.5 Hz); 3.29-3.33 (m, 2H); 3.8 (broad s, 1H); 6.6 (dd, 1H, J=1, 8 Hz); 7.07 (tr, 1H, J=7.9 Hz); 7.3-7.35 (m, 3H); 8.1 (d, 2H, J=8.3 Hz).

Step E: tert-Butyl 2,2-dimethyl-5-((5-(5-(4-propylphenyl)-1,2,4-oxadiazol-3-yl)-3,4-dihydroquinolin-1(2H)-yl)methyl)-1,3-dioxan-5-ylcarbamate To a mixture of the product of Step D (0.0334 g; 0.1 mmol), tert-butyl 5-formyl-2,2-dimethyl-1,3-dioxan-5-ylcarbamate (3×0.03 g; 0.33 mmol) and NaBH(OAc)$_3$ (3×0.07 g; 0.93 mmol) in 1,2-dichloroethane (1.5 ml) AcOH (3×0.01 ml) was added portion wise over a period of 3 days with stirring at room temperature. The mixture was then diluted to 15 ml with EtOAc, washed with 10% NaOH, H$_2$O, brine, dried over anhydrous MgSO$_4$, filtered and filtrate evaporated to dryness under reduced pressure. The residue was purified by FCC (SiO$_2$, hexane:EtOAc, 9:1), to give the title compound (0.03 g; 51%) as colourless foam. $^1$H-NMR (CDCl$_3$) 0.95 (tr, 3H, J=7.4 Hz); 1.44 (m, 15H); 1.61-1.72 (m, 2H); 1.89-1.97 (m, 2H); 2.66 (tr, 2H, J=7.8 Hz); 3.06 (tr, 2H; J=6.5 Hz); 3.34 (tr, 2H, J=5.4 Hz); 3.77 (s, 2H); 3.95 (s, 4H); 4.7 (broad s, 1H); 7.02 (d, 1H, J=7.6 Hz); 7.14 (tr, 1H, J=7.6 Hz); 7.22-7.25 (m, 1H+CDCl$_3$); 7.33 (d, 2H, J=8.3 Hz); 8.09 (d, 2H, J=8.3 Hz).

Step F: 2-Amino-2-((5-(5-(4-propylphenyl)-1,2,4-oxadiazol-3-yl)-3,4-dihydroquinolin-1(2H)-yl)methyl)propane-1,3-diol When the product of Step E was substituted for tert-butyl 2,2-dimethyl-5-((4-(5-(6-propylpyridin-3-yl)-1,2,4-oxadiazol-3-yl)indolin-1-yl)methyl)-1,3-dioxan-5-ylcarbamate in Example 66 Step F, the identical process afforded the title compound in 45% yield, as colourless solid. $^1$H-NMR (CDCl$_3$+CD$_3$OD) 0.89 (tr, 3H, J=7.4 Hz); 1.55-1.68 (m, 2H); 1.88 (m, 2H); 2.61 (tr, 2H, J=7.4 Hz); 2.95-3.1 (m, 8H+H$_2$O); 3.31 (m, 4H); 3.35-3.79 (m, 4H); 7.06-7.16 (m, 3H); 7.23-7.29 (m, 2H+CDCl$_3$); 8.02 (d, 2H, J=8 Hz).

Example 68

2-Amino-2-((5-((5-propylbenzofuran-2-yl)methoxy)indolin-1-yl)methyl)propane-1,3-diol Step A: 2-Iodo-4-propylphenol When 4-propylphenol was substituted for 4-hydroxybenzonitrile in Example 42, Step A, a similar process afforded the title compound in 35%, as colourless solid, after purification by FCC (SiO$_2$, CH$_2$Cl$_2$). $^1$H-NMR (CDCl$_3$) 0.9 (m, 3H); 1.5-1.64 (m, 2H); 2.47 (m, 2H); 5.1 (s, 1H); 6.68 (d, 1H, J=6 Hz); 7.03 (dd, 1H, j=3, 9 Hz); 7.45 (d, 1H, 3 Hz).

Step B: (5-Propylbenzofuran-2-yl)methanol

When the product of Step A was substituted for 3,5-dichloro-2-iodophenol in Example 8, Step E, the similar process afforded the title compound in 31%, as off-white oil. $^1$H-NMR (CDCl$_3$) 0.93 (m, 3H); 1.58-1.73 (m, 2H); 1.9 (tr, 1H, J=6 Hz); 2.65 (tr, 2H, J=6 Hz); 4.76 (d, 2H, J=6 Hz); 6.58 (s, 1H); 7.08 (dd, 1H, J=3, 9 Hz); 7.3-7.37 (m, 2H).

Step C: 2-(Chloromethyl)-5-propylbenzofuran

When the product of Step B was substituted for 4,6-dichlorobenzofuran-2-yl)methanol in Example 8, Step F, the identical process afforded the title compound in 100%, as brownish oil. $^1$H-NMR (CDCl$_3$) 0.94 (m, 3H); 1.58-1.7 (m, 2H); 2.66 (tr, 2H, J=6 Hz); 4.68 (s, 2H); 6.67 (s, 1H); 7.12 (dd, 1H, J=3, 9 Hz); 7.3-7.4 (m, 2H).

Step D: tert-Butyl 2,2-dimethyl-5-((5-((5-propylbenzofuran-2-yl)methoxy)indolin-1-yl)methyl)-1,3-dioxan-5-ylcarbamate When the product of Step E was substituted for 2-chloromethyl-4,5-dichlorobenzofuran in Example 8, Step F, the identical process afforded the title compound in 83% yield, as creamy foam. $^1$H-NMR (CDCl$_3$) 0.94 (m, 3H); 1.2-1.3 (m, 15H); 1.56-1.68 (m, 2H); 2.64 (tr, 2H, J=9 Hz); 2.94 (tr, 2H, 2H, J=9 Hz); 3.4 (tr, 2H, J=9 Hz); 3.44 (s, 2H); 3.86-4.08 (m, 4H); 4.68 (broad s, 1H); 5.03 (s, 2H); 6.49 (d, 1H, J=9 Hz); 6.65 (s, 1H); 6.69-6.82 (m, 2H); 7.08 (dd, 1H, J=2, 9 Hz); 7.31-7.39 (m, 2H).

Step E: 2-Amino-2-((5-((5-propylbenzofuran-2-yl)methoxy)indolin-1-yl)methyl)propane-1,3-diol When the product of Step D was substituted for tea-butyl 2,2-dimethyl-5-((4-(5-(6-propylpyridin-3-yl)-1,2,4-oxadiazol-3-yl)indolin-1-yl)methyl)-1,3-dioxan-5-ylcarbamate in Example 66, Step F, the identical process afforded the title compound in 45% yield, as colourless solid. $^1$H-NMR (CDCl$_3$+CD$_3$OD) 0.92 (tr, 3H, J=6 Hz); 1.56-1.67 (m, 2H+H$_2$O); 2.55-2.65 (m, 2H); 2.91 (tr, 2H, J=(Hz); 2.98 (s, 2H); 3.39 (tr, 2H, J=6 Hz); 3.4-3.6 (m, 4H); 5.02 (s, 2H); 6.5 (d, 1H, J=9 Hz); 6.64 (s, 1H); 6.68-6.81 (m, 2H); 7.06 (dd, 1H, J=3, 9 Hz); 7.28-7.37 (m, 2H).

Example 69

2-Amino-2-((4-octylindolin-1-yl)methyl)propane-1,3-diol

Step A:
2,2,2-Trifluoro-1-(4-hydroxyindolin-1-yl)ethanone

To a solution of the product of Example 41, Step A (0.31 g; 2.25 mmol) in anhydrous pyridine, $(CF_3CO)_2O$ (0.35 ml; 2.5 ml) was added drop wise at 0° C. with stirring under $N_2$. After stirring for 30 min at room temperature solvents were removed in vacuo and the residue was diluted to 20 ml with EtOAc, washed with diluted HCl (2×5 ml), brine, dried over anhydrous $MgSO_4$, filtered and filtrate evaporated to dryness under reduced pressure. The residue was purified by FCC ($SiO_2$, $CH_2Cl_2$:EtOAc, 8:2) to give the title compound (0.16 g; 31%), as colourless solid. $^1$H-NMR ($CDCl_3$) 3.19 (tr, 2H, J=8.2 Hz); 4.28 (tr, 2H, 8 Hz); 5.17 (s, 1H); 6.61 (d, 1H, J=8.1 Hz); 7.13 (tr, 1H, J=8.1 Hz); 7.78 (d, 1H, J=8.1 Hz).

Step B: 2,2,2-Trifluoro-1-(4-(oct-1-ynyl)indolin-1-yl)ethanone

To a solution of the product of Step A (0.16 g; 0.75 mmol) in anhydrous THF (1.5 ml) DIPEA (0.14 ml; 0.8 mmol) was added at 0° C. under $N_2$, followed by $(CF_3SO_2)_2O$ (0.13 ml; 0.77 mmol), with stirring. After 1 h of stirring at room temperature, the mixture was diluted to 20 ml with $Et_2O$, washed with $H_2O$ (2×5 ml), brine, dried over anhydrous $MgSO_4$, filtered and filtrate evaporated to dryness to give 1-(2,2,2-trifluoroacetyl)indolin-4-yl trifluoromethanesulfonate (0.3 g; 100%), which was used in the next step without further purification. This was diluted to 2 ml with anhydrous DMF and $Cl_2Pd(PPh_3)_2$ (0.3 g; 0.42 mmol was added, followed by CuI (0.1 g; 0.52 mmol). The resulting suspension was degassed under reduced pressure and saturated with $N_2$. To it, 1-octyne (0.2 ml; 1.35 mmol) was added at room temperature, followed by DIPEA (0.5 ml), under $N_2$. This was stirred for 4 h at room temperature and solvents were removed in vacuo. The residue was treated with hexane (20 ml). The insoluble material was filtered off, washed with fresh hexane (3×10 ml) and combined filtrates were evaporated to dryness. The residue was purified by FCC ($SiO_2$, hexane/$CH_2Cl_2$, 7:3) to give the title compound (0.09 g; 37%) as brownish oil. $^1$H-NMR ($CDCl_3$) 0.89 (tr, 3H, J=7 Hz); 1.24-1.63 (m, 8H+$H_2O$); 2.42 (tr, 2H, J=7 Hz); 3.26 (tr, 2H, J=8.3 Hz); 4.27 (tr, 2H, J=8 Hz); 7.13-7.21 (m, 2H); 8.07-8.13 (m, 1H).

Step C:
2,2,2-Trifluoro-1-(4-octylindolin-1-yl)ethanone

When the product of Step B was substituted for 5-(oct-1-ynyl)-1H-indole in Example 3, Step B, the identical process afforded the title compound in 77% yield, as colourless oil. $^1$H-NMR ($CDCl_3$) 0.86 (m, 3H); 1.28 (m, 10H); 1.57 (m, 2H); 2.54 (tr, 2H, J=8 Hz); 3.17 (tr, 2H, J=8.3 Hz); 4.27 (tr, 2H, J=8 Hz); 6.97 (d, 1H, J=7.6 Hz); 7.2 (tr, 1H, J=7.9 Hz); 8.04 (d, 1H, J=8.1 Hz).

Step D: 4-Octylindoline

A solution of the product of Step C (0.07 g; 0.21 mmol) and $Cs_2CO_3$ (0.07 g; 0.21 mmol) in MeOH (2 ml) was stirred overnight at room temperature under N2. After removing solvent under reduced pressure, the residue was diluted to 15 ml with $Et_2O$, washed with $H_2O$, brine, dried over anhydrous $MgSO_4$, filtered and filtrate evaporated to dryness to give the title compound (0.045 g; 93%), as brownish oil, which was used in the next step without further purification. $^1$H-NMR ($CDCl_3$) 0.86 (m, 3H); 1.28 (m, 10H); 2.47 (m, 2H); 2.95 (m, 2H); 3.52 (m, 2H); 3.7 (broad s, 1H); 6.47-6.54 (m, 2H); 6.89-7.02 (m, 1H).

Step E: tert-Butyl 2,2-dimethyl-5-((4-octylindolin-1-yl)methyl)-1,3-dioxan-5-ylcarbamate When the product of Step D was substituted for 4-octylaniline in Example 1, Step A, the similar process afforded the title compound in 76% yield, as colourless syrup. $^1$H-NMR ($CDCl_3$) 0.86 (m, 3H); 1.24 (m, 10H); 1.44-1.47 (m, 15H); 1.55 (, 2H+$H_2O$); 2.47 (tr, 2H, J=7.6 Hz); 2.93 (tr, 2H, J=8.3 Hz); 3.44 (tr, 2H, J=8.5 Hz); 3.49 (s, 2H); 3.87-4.02 (m, 4H); 4.69 (broad s, 1H); 6.42 (d, 1H, J=7.8 Hz); 6.5 (d, 1H, J=7.5 Hz); 6.99 (tr, 1H, J=7.7 Hz).

Step F: 2-Amino-2-((4-octylindolin-1-yl)methyl)propane-1,3-diol

When the product of Step E was substituted for tert-butyl 2,2-dimethyl-5-((4-(5-(6-propylpyridin-3-yl)-1,2,4-oxadiazol-3-yl)indolin-1-yl)methyl)-1,3-dioxan-5-ylcarbamate in Example 66, Step F, the identical process afforded the title compound in 68% yield, as colourless solid. $^1$H-NMR ($CDCl_3$) 0.86 (m, 3H); 1.28 (m, 10H); 1.53 (m, 2H); 1.8 (broad s, 4H+$H_2O$); 2.48 (tr, 2H, J=7.6 Hz); 2.93 (tr, 2H, J=8.2 Hz); 3.08 (s, 2H); 3.46 (tr, 2H, J=8.7 Hz); 3.58 (m, 4H); 6.46 (d, 1H, J=7.8 Hz); 6.53 (d, 1H, J=7.6 Hz); 7.01 (m, 1H).

Example 70

2-Amino-2-((7-octyl-1,2,4,5-tetrahydrobenzo[d]azepin-3-yl)methyl)-propane-1,3-diol

Step A: 2,2,2-Trifluoro-1-(1,2,4,5-tetrahydrobenzo[d]azepin-3-yl)ethanone

To a stirred solution of 2,3,4,5-tetrahydro-1H-benzo[d]azepine (0.25 g, 1.7 mmol) in anhydrous $CH_2Cl_2$ (5 ml), $Et_3N$ (0.28 ml, 2 mmol) was added at 0° C. and under $N_2$, followed by $(CF_3CO)_2O$ (0.29 ml, 2 mmol) and the resulting mixture was stirred for 1 h, than washed with aqueous $NaHCO_3$ and $H_2O$. The organic layer was dried over $MgSO_4$, filtered and the filtrate was evaporated to dryness to give the title product (0.418 g, 100%), as pale oil. $^1$H-NMR ($CDCl_3$) 3.6-3.97 (m, 8H); 7.11-7.19 (m, 4H).

Step B: 2,2,2-Trifluoro-1-(7-iodo-1,2,4,5-tetrahydrobenzo[d]azepin-3-yl)ethanone To a stirred solution of the product of Step A (0.4 g, 1.65 mmol) and $CF_3SO_3Ag$ (0.46 g, 1.8 mmol) in $CH_2Cl_2$ (15 ml) $I_2$ (0.42 g; 1.65 mmol) was added and the mixture was stirred at 65° C. for 3 h. This was filtered through Celite bead, washed with fresh $CH_2Cl_2$ (20 ml). The combined filtrates were evaporated to dryness to give the title product (0.31 g; 51%), as colourless paste. $^1$H-NMR ($CDCl_3$) 2.8-2.93 (m, 4H); 3.64-3.73 (m, 4H); 6.86 (t, 1H, J=8.04 Hz); 7.39 (b, 1H); 7.61 (d, 1H, J=9.69 Hz).

Step C: 2,2,2-Trifluoro-1-(7-(oct-1-ynyl)-1,2,4,5-tetrahydrobenzo-[d]azepin-3-yl)ethanone When the product of Step B was substituted for 5-iodo-2-tritylisoindoline in Example 2, Step D, the similar process afforded the title compound in 73% yield, as a pale oil. ¹H-NMR (CDCl₃) 0.9 (tr, 3H), 1.28-1.33 (m, 10H); 1.42-1.46 (m, 2H); 2.88-2.96 (m, 4H); 3.64-3.67 (m, 2H); 3.71-3.75 (m, 2H); 7.05 (tr, 1H, J=7.92 Hz), 7.13-7.2 (m, 2H).

Step D: 2,2,2-Trifluoro-1-(7-octyl-1,2,4,5-tetrahydrobenzo[d]azepin-3-yl)ethanone When the product of Step C was substituted for 5-(oct-1-ynyl)-1H-indole in Example 3, Step B, the similar process afforded the title compound in 90%, as pale oil. ¹H-NMR (CDCl₃) 0.87 (tr, 3H, J=6.96 Hz), 1.25-1.28 (m, 10H); 1.4-1.46 (m, 2H); 2.50-2.56 (m, 2H); 2.90-2.95 (m, 4H); 3.64-3.66 (m, 2H); 3.73-3.75 (m, 2H); 6.81-7.07 (m, 3H).

Step E: 7-Octyl-2,3,4,5-tetrahydro-1H-benzo[d]azepine

To a solution of the product of Step D (0.17 g, 0.47 mmol) in a mixture of MeOH and H₂O (10 ml: 1 ml), NaHCO₃ (0.3 g, 3.6 mmol) was added and the reaction mixture was stirred at reflux for 2 h. The solvents were evaporated and the residue was diluted to 20 ml with EtOAc and washed with H₂O, dried over MgSO₄, filtered and the filtrate evaporated to dryness to give the title compound (0.12 g; 100%), as pale oil. ¹H-NMR (CDCl₃) 0.86 (tr, 3H, J=6.93 Hz); 1.25-1.28 (m, 12H), 1.45-1.6 (m, 2H); 2.52 (tr, 2H, J=7.71 Hz); 2.85-2.93 (m, 8H); 6.85-6.92 (m, 2H); 6.97-7.0 (m, 1H).

Step F: tert-Butyl 2,2-dimethyl-5-((7-octyl-1,2,4,5-tetrahydrobenzo-[d]azepin-3-yl)methyl)-1,3-dioxan-5-ylcarbamate When the product of Step E was substituted for 4-n-octylaniline in Example 1, Step A, the identical process afforded the title compound in 30% yield, as the pale paste. ¹H-NMR (CDCl₃) 0.86 (tr, 3H, J=6.66 Hz); 1.24-1.55 (m, 27H); 2.51 (tr, 2H, J=7.95 Hz); 2.75-2.91 (m, 10H); 3.85 (d, 2H, J=11.61 Hz); 4.0 (d, 2H, J=11.49 Hz); 4.88 (s, 1H); 6.81-6.96 (m, 3H).

Step G: 2-Amino-2-((7-octyl-1,2,4,5-tetrahydrobenzo[d]azepin-3-yl)methyl)-propane-1,3-diol When the product of Step F was substituted for tert-butyl 2,2-dimethyl-5-((4-octylphenylamino)methyl)-1,3-dioxan-5-yl-carbamate in Example 1, Step B, the identical process afforded the title compound in 48% yield., as creamy paste. ¹H-NMR (CDCl₃) 0.87 (tr, 3H, J=6.93 Hz); 1.12-1.28 (m, 12H); 2.5 (tr, 2H, J=7.77 Hz); 2.59 (s, 2H); 2.76-2.83 (m, 8H); 3.52 (s, 4H); 6.78-6.94 (m, 3H).

Example 71

2-(4-(5-(3,4-Diethoxyphenyl)-1,2,4-oxadiazol-3-yl)indolin-1-yl)propane-1,3-diol

Step A: 5-(3,4-Diethoxyphenyl)-3-(1-(2,2-dimethyl-1,3-dioxan-5-yl)indolin-4-yl)-1,2,4-oxadiazole When 2,2-dimethyl-1,3-dioxan-5-one was substituted for tert-butyl 5-formyl-2,2-dimethyl-1,3-dioxan-5-ylcarbamate in Example 34, Step D, the identical process afforded the title compound in 43% yield, as a colourless solid. ¹H-NMR (CDCl₃) 1.48-1.59 (m, 12H+H₂O); 3.4 (tr, 2H, J=9 Hz); 3.6-3.8 (m, 3H); 3.9-4.07 (m, 4H); 4.08-4.26 (m, 4H); 6.5 (d, 1H, J=6 Hz); 6.97 (d, 1H, J=9 Hz); 7.14-7.21 (m, 1H); 7.44 (d, 1H, J=6 Hz); 7.6-7.8 (m, 2H).

Step B: 2-(4-(5-(3,4-Diethoxyphenyl)-1,2,4-oxadiazol-3-yl)indolin-1-yl)propane-1,3-diol To a solution of the product of Step A (0.0346 g; 0.0743 mmol) and NaI (0.033 g; 0.22 mmol) in anhydrous CH₃CN (1 ml) Me₃SiCl (0.1 ml) was added at room temperature under N₂. After stirring for 30 min at room temperature MeOH (2 ml) was added and the resulting mixture was evaporated to dryness under reduced pressure. The residue was partitioned between EtOAc (5 ml) and 1% NaHCO₃ (5 ml). The precipitate formed was filtered off, washed with H₂O (5 ml), fresh EtOAc (5 ml) and dried to give the title compound (0.019 g; 61%) as creamy solid. ¹H-NMR (DMSO-d₆) 1.28-1.41 (m, 6H): 3.2-3.4 (m, 2H+H₂O); 3.5-4.02 (m, 7H); 4.07-4.18 (m, 4H); 4.6 (broad s, 2H); 6.52 (d, 1H, J=6 Hz); 7.06-7.19 (m, 3H); 7.58 (d, 1H, J=3 Hz); 7.72 (dd, 1H, J=9 Hz).

Example 72

Cell Viability Assay

In order to measure the apoptotic effect of compounds on the metabolic activity of viable cells, the following assay was performed on Human promyelocytic leukemia cells. The assay utilises the tetrazolium compound (3-(4,5-dimethylthiazol-2-yl)-5-(3-carboxymethoxyphenyl)-2-(4-sulfophenyl)-2H-tetrazolium, inner salt; (MTS) and an electron coupling reagent (phenazine methosulfate; (PMS). MTS is bioreduced by cells into a formazan product the optical absorbance of which is measured directly from 96 well assay plates. The conversion of MTS into aqueous, soluble formazan is accomplished by dehydrogenase enzymes found in metabolically active cells. The quantity of formazan product as measured by the amount of 490 nm absorbance is directly proportional to the number of living cells in culture.

The assay was based on the National Cancer Institute (NCI) protocol, briefly, cells were grown in RPMI 1640 media supplemented with 10% FCS (foetal calf serum) and kept at 37° C. in a humidified environment with 5% CO₂.

For the growth inhibition assay, Human promyelocytic leukemia (HL-60) cells were seeded at a density of 10,000 cells per well in 96 well plates in a volume of 100 μl and allowed to grow for 24 h. Compounds were serially diluted in DMSO at concentrations 100 fold higher than used in the assay (100×). Compounds were freshly prepared for each experiment. The 100× stocks were then diluted to 2× stocks into media and immediately, 100 μl of this 2× stock was added to the cells to create the desired final concentration of drug with a DMSO concentration of 1%. One row of each 96 well plate was treated with DMSO alone as a control. Cells were then incubated for a further 48 hr. Metabolic activity was determined using MTS (Promega) (90% 1.6 mg/ml MTS, 10% 1.6 mg/ml PMS (phenazine methosulfate) made fresh in PBS). 50 μl of this mix was added to all wells of the plates and allowed to incubate for 1.5-2 hr. Plates were shaken gently for about 15 min and absorbance was read on a plate reader at 490 nm. Averages were taken of the readings at each point with standard deviation and plotted using MicroCal Origin. The value that gave a 50% reduction in cell viability of HL-60 cells is taken as the IC₅₀ as shown in Table 8.

Example 73

S1P Receptors Activity Evaluation

Selected Compounds of the Examples were evaluated at Millipore Corporation, USA, using S1P1 receptor; [³⁵S]-GT- PgamaS binding assay. A [$^{35}$S]-GTPgamaS binding assay at Millipore was conducted by GPCR Profiler™ Custom Service Laboratory, Temecula, Calif., Millipore, Inc. to monitor dose-dependent agonist selectivity for selected Examples against the S1P1 receptors. The assay was completed with sample compounds subjected to an eight-point, four-fold dose response curve with starting concentration of 10 μM. Selectivity was determined upon initial addition of compounds followed by a 30 minute incubation at 30° C. Following compound incubation, bounded [$^{35}$S]-GTPgamaS was determined by filtration and scintillation counting. Percentage activation and inhibition values were determined relative to the reference agonist at S1P1 and are shown in Table 8.

Independently, selected compounds were evaluated for S1P1 and S1P3 agonistic activity. The S1P1 assay system was GTPgama-S35 binding in membranes from CHO K1 cells, expressing S1P1 human receptor. The S1P3 assay system was calcium mobilization in CHO K1 cells expressing S1P3 human receptor. There was no significant background response to S1P in the CHO K1 cells with either assay. Compounds were tested initially at a concentration of 10 μM. Those compounds with significant efficacy (Emax>0.15 relative to S1P) at either receptor type were used to generate concentration-effect (dose response) curves at that receptor. These analyses provided efficacy (Emax) and potency (EC$_{50}$) of the compounds relative to S1P, shown in Table 8.

TABLE 8

HL(60) Apoptotic Activity, S1P1 and S1P3 Agonistic Data of selected Examples of Formula (1)

| Entry | Example No | IC$_{50}$(M) HL-60 cells | EC$_{50}$(M) S1P1 | EC$_{50}$S$_1$P$_1$/ EC$_{50}$S$_1$P | Efficacy (% of maximum) | EC$_{50}$(M) S$_1$P$_3$ |
|---|---|---|---|---|---|---|
| 1 | 1 | 5.84. ± 2.33 | >25 | >9259 | * | ND |
| 2 | 2 | 3.48 ± 0.14 | 1.56 | 593 | 91 | ND |
| 3 | 3 | 3.7 ± 1.02 | 2.11 | 709 | 73 | ND |
| 4 | 4 | 3.58 ± 0.04 | ND | ND | ND | ND |
| 5 | 5 | 5.72 ± 2.18 | ND | ND | ND | ND |
| 6 | 9 | 2.46 ± 0.51 | >0.86 | >1000 | * | ND |
| 7 | 8 | 1.93 ± 0.58 | 0.131 | 23 | 85 | ND |
| 8 | 7 | 3.07 ± 0.46 | 0.783 | 278 | 109 | ND |
| 9 | 37 | 26.87 ± 9.16 | ND | ND | ND | ND |
| 10 | 6 | 44.87 ± 8.85 | ND | ND | ND | ND |
| 11 | 13 | 0.44 ± 0.04 | ND | ND | ND | ND |
| 12 | 24 | 1.81 ± 0.74 | ND | ND | ND | ND |
| 13 | 23 | 2.26 ± 0.68 | 1.24 | 419 | 72 | ND |
| 14 | 26 | 2.29 ± 0.57 | ND | ND | ND | ND |
| 16 | 11 | 5.54 ± 2.3 | ND | ND | ND | ND |
| 17 | 18 | 7.07 ± 0.23 | ND | ND | ND | ND |
| 18 | 22 | 10.47 ± 0.4 | ND | ND | ND | ND |
| 19 | 21 | 28.5 ± 3.21 | ND | ND | ND | ND |
| 20 | 33 | 2.91 ± 0.13 | >24 | >1000 | * | NA |
| 21 | 34 | 1.82 ± 0.5 | 0.0068 | 0.4 | 92 | 1.29 |
| 22 | 35 | 1.7 ± 0.1 | 0.054 | 4.75 | 106 | NA |
| 23 | 36 | 1.31 ± 0.35 | 0.501 | 65 | 99 | NA |
| 24 | 37 | 26.87 ± 9.16 | ND | ND | ND | ND |
| 25 | 39 | ND | >3.24 | >1000 | 117 | NA |
| 26 | 40 | 3.1 | 0.344 | 36.41 | 117 | >15.6 |
| 26 | 41(a) | 2.55 ± 0.78 | >1.36 | 144.46 | 42 | NA |
| 27 | 41(b) | ND | >29 | 3066.24 | * | NA |
| 28 | 42 | 1.7 ± 0.1 | 1.42 | 117.8 | 92 | NA |
| 29 | 12 | ND | 1.82 | 557 | 49 | ND |
| 30 | 30 | 3.19 ± 0.26 | >55.4 | >1000 | * | ND |
| 31 | 10 | 1.38 ± 0.17 | >0.51 | >1000 | * | ND |
| 32 | 28 | 1.56 ± 0.37 | ND | ND | ND | ND |
| 33 | 29 | 3.94 ± 0.4 | ND | ND | ND | ND |
| 34 | 31 | >10 | ND | ND | ND | ND |
| 35 | 49 | 10.2 | 0.114 | 9.26 | 112 | NA |
| 36 | 50 | 3 ± 0.17 | 0.0179 | 1.3 | 87 | NA |
| 37 | 55 | ND | 0.0316 | 2.56 | 101 | NA |
| 38 | 57 | 1 | | 268.44 | 82 | NA |
| 39 | 58 | 1.7 | >2.06 | 150 | 60 | NA |
| 40 | 59 | ND | >2.13 | >1000 | * | NA |
| 41 | 60 | 3.3 ± 0.26 | ND | ND | ND | ND |
| 42 | 61 | 3.27 ± 0.12 | ND | ND | ND | ND |
| 43 | 62 | >100 | ND | ND | ND | ND |
| 44 | 63 | 2.4 ± 0.62 | >40 | 3188.66 | * | NA |
| 45 | 64 | 3.44 ± 0.12 | ND | ND | ND | ND |
| 46 | 65 | ND | 0.0074 | 0.16 | 97 | 0.39 |
| 47 | 43 | ND | 0.018 | 2.22 | 89 | 3.1 |
| 48 | 47 | ND | 0.0024 | 0.33 | 94 | 0.965 |
| 49 | 46 | ND | 0.088 | 10.61 | 94 | NA |
| 50 | 44 | ND | 0.0481 | 18.24 | 60 | NA |
| 51 | 48 | ND | 0.0067 | 0.14 | 78 | NA |
| 52 | 52 | ND | 0.0345 | 3.55 | 62 | NA |

TABLE 8-continued

HL(60) Apoptotic Activity, S1P1 and S1P3 Agonistic Data of selected Examples of Formula (1)

| Entry | Example No | IC$_{50}$ (M) HL-60 cells | EC$_{50}$(M) S1P1 | EC$_{50}$S$_1$P$_1$/ EC$_{50}$S$_1$P | Efficacy (% of maximum) | EC$_{50}$(M) S$_1$P$_3$ |
|---|---|---|---|---|---|---|
| 53 | 54 | ND | 0.0438 | 5.93 | 73 | NA |
| 54 | 56 | ND | 0.0029 | 0.29 | 79 | NA |
| 55 | 51 | ND | 0.0035 | 0.38 | 85 | NA |
| standard | FTY 720 | 3.34 ± 0.19 | 2.64 | 891.89 | 99 | ND |

NA = Not Active
ND = Not Determined
* = Efficacy could not be accurately determined for the compounds with EC$_{50}$ values > 25 μM

Example 74

Lymphopenia Assay

The study was performed to determine the ability of the compounds of the invention to induce lymphopenia in female BALB/c mice. On day 0, 27 female BALB/c mice were randomised based on body weight into nine groups of three mice each. Animals received a single i.p. administration of Test compounds and blood was collected by cardiac puncture either 6 or 24 h after administration. Treatment with 3 mg/kg and 30 mg/kg of Example 34 was shown to decrease lymphocyte and total white blood cell counts at both 6 and 24 h, compared to untreated animals (FIGS. 1.1 & 1.2). Changes to other haematological parameters were not observed.

The invention claimed is:

1. A compound having the structure of any one of formulae (8) to (13), or a stereoisomer, isotopic form, or pharmaceutically acceptable salt thereof:

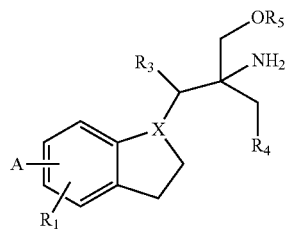
(8)

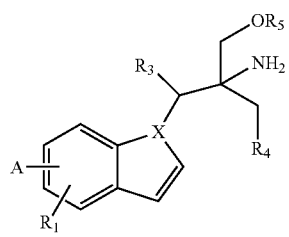
(9)

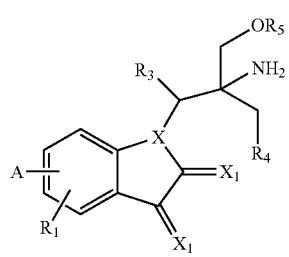
(10)

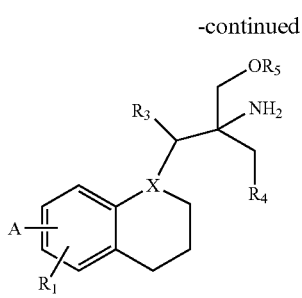
(11)

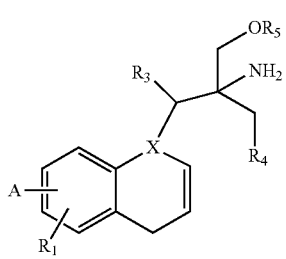
(12)

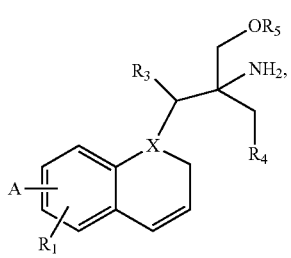
(13)

wherein
X is N;
X$_1$ is O or S;
R$_3$ is hydrogen, deuterium, alkoxy, cyano, amino, hydroxyl, halogen, nitro, carbonyl, carboxy, amido, trifluoromethyl, trihaloalkyl, trifluoroalkoxy or a C$_{1-8}$ substituted or unsubstituted alkyl, alkenyl or alkynyl;
R$_4$ is hydrogen, alkoxy, cyano, amino, hydroxyl, halogen, nitro, carbonyl, carboxy, amido, trifluoromethyl, trihaloalkyl, trifluoroalkoxy or a C$_{1-8}$ substituted or unsubstituted alkyl, alkenyl or alkynyl, R$_5$ is hydrogen or —P(O)(OR$_x$)(OR$_y$) wherein each of R$_x$ and R$_y$ independently is hydrogen, alkoxy, cyano, amino, hydroxyl, halogen, nitro, carbonyl, carboxy, amido, trifluoromethyl, trihaloalkyl, trifluoroalkoxy or a C$_{1-8}$ substituted or unsubstituted alkyl, alkenyl or alkynyl; or R$_4$ and R$_5$ together form —O—(P—)(O)(OR$_7$) wherein R$_7$ is selected from the group consisting of hydrogen, trifluoromethyl, trihaloalkyl or a C$_{1-8}$ substituted or unsubstituted alkyl, alkenyl or alkynyl and salts;

A is hydrogen, deuterium or optionally substituted ($C_1$-$C_{20}$)alkyl, ($C_3$-$C_{20}$)cycloalkyl, ($C_3$-$C_{18}$)cycloalkyl($C_1$-$C_{18}$)alkyl, ($C_6$-$C_{24}$)aryl, ($C_7$-$C_{25}$)aralkyl, ($C_2$-$C_{18}$)alkenyl, ($C_8$-$C_{26}$)aralkenyl, ($C_2$-$C_{18}$)alkynyl, ($C_8$-$C_{26}$)aralkynyl, heterocyclic or optionally substituted sulfonamide;

$R_1$ is hydrogen, deuterium or optionally substituted ($C_1$-$C_{18}$)alkyl, ($C_3$-$C_{18}$)cycloalkyl, ($C_3$-$C_{18}$)cycloalkyl($C_1$-$C_{18}$)alkyl, ($C_6$-$C_{24}$)aryl, ($C_7$-$C_{25}$)aralkyl, ($C_2$-$C_{18}$)alkenyl, ($C_8$-$C_{26}$)aralkenyl, ($C_2$-$C_{18}$)alkynyl, ($C_8$-$C_{26}$)aralkynyl, ($C_8$-$C_{26}$)polycycloalkyl, substituted or unsubstituted heterocyclic, substituted or unsubstituted heteroaryl, substituted $C_{1-20}$alkyl, $C_{3-20}$ cycloalkyl substituted aryl, $C_{3-20}$ cycloalkyl substituted heteroaryl, heteroaryl substituted $C_{2-20}$ alkenyl, heteroaryl substituted $C_{2-20}$ alkynyl, aryl substituted alkoxyl, $C_{3-20}$ cycloalkyl substituted aryl alkoxyl, alkylaryl substituted alkoxyl, substituted or unsubstituted heteroaryl, substituted or unsubstituted heteroaryloxy, fused 4-5, 4-6, 5-5, 5-6 or 6-6 heterobicylic ring system, or a group (a-d),

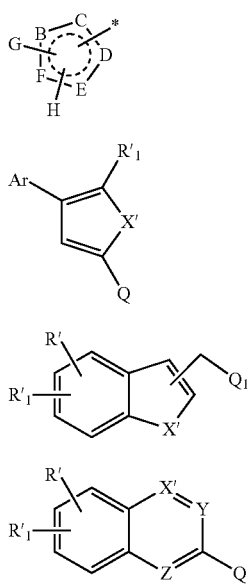

wherein

Ar is an optionally substituted 5-12 atom aromatic or heteroaromatic ring system;

B, C, D, E and F are independently selected from $C(R)_n$, O, $S(O)_n$, and $N(R)_n$;

G and H are independently hydrogen, deuterium or optionally substituted ($C_1$-$C_{20}$)alkyl, ($C_3$-$C_{20}$)cycloalkyl, ($C_3$-$C_{18}$)cycloalkyl($C_1$-$C_{18}$)alkyl, ($C_6$-$C_{24}$)aryl, ($C_7$-$C_{25}$)aralkyl, ($C_7$-$C_{18}$)alkenyl, ($C_8$-$C_{26}$)aralkenyl, ($C_2$-$C_{18}$)alkynyl, ($C_{826}$)aralkynyl, optionally substituted sulfonamide, ($C_8$-$C_{26}$)polycycloalkyl, substituted or unsubstituted heterocyclic, substituted or unsubstituted heteroaryl, $C_{3-20}$ cycloalkyl substituted aryl, $C_{3-20}$ cycloalkyl substituted heteroaryl, heteroaryl substituted $C_{2-20}$ alkenyl, heteroaryl substituted $C_{2-20}$ alkenyl, aryl substituted alkoxyl, $C_{3-20}$ cycloalkyl substituted aryl alkoxyl, alkylaryl substituted alkoxyl, substituted or unsubstituted heteroaryl, substituted or unsubstituted heteroaryloxy, or fused 4-5, 4-6, 5-5, 5-6 or 6-6 heterobicylic ring system;

Q and $Q_1$ are independently represented by —{$C(R)_2$}$_m$—X'—*, the asterisk indicating the bond that is linked to the phenyl ring of any one of formulae (8) to (13), m is 0-5;

X' is $C(R)_n$, $N(R)_n$, O, $S(O)_n$ or C(O) in groups (b) and (c);

X', Y and Z are independently $C(R)_{n''}$ or N in group (d);

R is hydrogen, deuterium, alkoxy, cyano, amino, hydroxyl, halogen, nitro, carbonyl, carboxy, amido, trifluoromethyl, trihaloalkyl, trifluoroalkoxy or a $C_{1-8}$ substituted or unsubstituted alkyl, alkenyl or alkenyl;

R' and R'$_1$ are independently hydrogen, deuterium, alkoxy, cyano, amino, hydroxyl, halogen, nitro, carbonyl, carboxy, amido, trifluoromethyl, trihaloalkyl, trifluoroalkoxy or a $C_{1-8}$ substituted or unsubstituted alkyl, alkenyl or alkynyl;

n is 0-2; and n" is 0-1.

2. A compound according to claim 1 selected from the group consisting of:

2-Amino-2-((4-octylphenylamino)methyl)propane-1,3-diol,

2-Amino-2-((5-octylisoindolin-2-yl)methyl)propane-1,3-diol,

2-Amino-2-((5-octylindolin-1-yl)methyl)propane-1,3-diol,

2-Amino-2-((5-octyl-1H-indol-1-yl)methyl)propane-1,3-diol, 1-(2-Amino-3-hydroxy-2-(hydroxymethyl)propyl)-5-octylindoline-2,3-dione, 2-Amino-2-((6-octyl-3,4-dihydroquinolin-1(2H)-yl)methyl)propane-1,3-diol, 2-Amino-2-((5-((4,6-dichlorobenzofuran-2-yl)methoxy)indolin-1-yl)methyl) propane-1,3-diol, 2-Amino-2-((5-(5-(3-chloro-4-methoxyphenyl)-1,2,4-oxadiazol-3-yl)indolin-1-yl)methyl)propane-1,3-diol, 2-Amino-2-((6-(3-fluorobenzyloxy)-3,4-dihydroisoquinolin-2(1H)-yl)methyl)propane-1,3-diol, 2-Amino-2-((5-(3,4,5-trimethoxyphenethyl)indolin-1-yl)methyl)propane-1,3-diol, 2-Amino-2-((5-(5-3-(1-admantyl)-3-methoxyphenyl)-1,2,4-oxadiazol-3-yl)indolin-1-yl)methyl)propane-1,3-diol, 2-Amino-2-((4-(5-(3,4-diethoxyphenyl)-1,2,4-oxadiazol-3-yl)indolin-1-yl)methyl)propane-1,3-diol, 2-Amino-2-((4-(5-(3,4-diethoxyphenyl)-1,2,4-oxadiazol-3-yl)-1H-indol-1-yl)methyl)propane-1,3-diol, 2-Amino-2-((6-(3-fluorobenzyloxy)-3,4-dihydroisoquinolin-2(1H)-yl)methyl)propane-1,3-diol, 2-Amino-2-((6-((2'-(trifluoromethyl)biphenyl-4-yl)methoxy)-3,4-dihydroisoquinolin-2(1H)-yl)methyl)propane-1,3-diol, 2-Amino-2-((5-(5-(3,4-diethoxyphenyl)-1,2,4-oxadiazol-3-yl)indolin-1-yl)methyl)propane-1,3-diol, 2-Amino-2-((4-((4,6-dichlorobenzofuran-2-yl)methoxy)indolin-1-yl)methyl)propane-1,3-diol, 2-Amino-2-((4-(5-(2-methylbenzofuran-5-yl)-1,2,4-oxadiazol-3-yl)indolin-1-yl)methyl)propane-1,3-diol, 2-Amino-2-((6-octyl-3,4-dihydroisoquinolin-2(1H)-yl)methyl)propane-1,3-diol, 2-Amino-2-((5-(5-3-(1-admantyl)-4-methoxyphenyl)-1,2,4-oxadiazol-3-yl)indolin-1-yl)methyl)propane-1,3-diol, 2-Amino-2-((4-octylbenzylamino)methyl)propane-1,3-diol, 2-Amino-2-((4-(5-(3-chloro-4-ethoxyphenyl)-1,2,4-oxadiazol-3-yl)-1H-indol-1-yl)methyl)propane-1,3-diol, 2-Amino-2-((4-(5-(3-chloro-4-propoxyphenyl)-1,2,4-oxadiazol-3-yl)indolin-1-yl)methyl)propane-1,3-diol, 2-Amino-2-((4-(5-(4-ethoxy-3-methoxyphenyl)-1,2,4-oxadiazol-3-yl)indolin-1-yl)methyl)propane-1,3-diol, 2-Amino-2-((4-(5-(1-adamantyl)-1,2,4-oxadiazol-3-yl)indolin-1-yl)methyl) propane-1,3-diol, 2-Amino-2-((4-(4-(5-(3,4-diethoxyphenyl)-1,2,4-oxadiazol-3-yl)phenyl)-5,6-dihydropyridin-1(2H)-yl)methyl)propane-1,3-diol, 2-Amino-2-((5-(2-(2'-(trifluoromethyl)biphenyl-4-yl)ethyl)indolin-1-yl)methyl)propane-1,3-diol, 2-Amino-2-(((3-(1-adamantyl)-4-isopropoxyphenethyl)(methyl)amino)methyl)propane-1,3-diol, 2-Amino-2-((7-(1-admantyl)-6-isopropoxy-3,4-dihydroisoquinolin-2(1H)-yl)methyl) propane-1,3-diol, 2-Amino-2-((5-(5-(3,4-diethoxyphenyl)-1,2,4-oxadiazol-3-yl)isoindolin-2-yl)methyl)propane-1,3-diol, 2-Amino-2-((4-(5-(3,4-di-propoxyphenyl)-1,2,4-oxadiazol-3-yl)indolin-1-yl)methyl)propane-1,3-diol, 2-Amino-2-((4-(5-(3,4-dipropylphenyl)-1,2,4-oxadiazol-3-yl)indolin-1-yl)methyl)propane-1,3-diol, 2-Amino-2-((4-(5-(3-amino-4-propoxyphenyl)-1,2,4-oxadiazol-3-yl)indolin-1-yl)methyl)propane-1,3-diol, 2-Amino-2-((4-(5-(3-iodo-4-propoxyphenyl)-1,2,4-oxadiazol-3-yl)indolin-1-yl)methyl)propane-1,3-diol, 2-Amino-2-((4-(5-(4-propylphenyl)-1,2,4-oxadiazol-3-yl)indolin-1-yl)methyl)propane-1,3-diol, 2-Amino-2-((5-(5-(4-butoxy-3-chlorophenyl)-1,2,4-oxadiazol-3-yl)indolin-1-yl)methyl)propane-1,3-diol, 2-Amino-2-((5-(5-(3-chloro-4-(pentyloxy)phenyl)-1,2,4-oxadiazol-3-yl)indolin-1-yl)methyl)propane-1,3-diol, 2-Amino-2-((5-(5-(3-bromo-4-propoxyphenyl)-1,2,4-oxadiazol-3-yl)indolin-1-yl)methyl)propane-1,3-diol, 2-Amino-2-((5-(5-(3-chloro-4-isopropoxyphenyl)-1,2,4-oxadiazol-3-yl)indolin-1-yl)methyl)propane-1,3-diol, 2-(4-(5-(3,4-Diethoxyphenyl)-1,2,4-oxadiazol-3-yl)indolin-1-yl)propane-1,3-diol, 2-Amino-2-((7-octyl-1,2,4,5-tetrahydrobenzo[d]azepin-3-yl)methyl)-propane-1,3-diol, 2-Amino-2-((4-octylindolin-1-yl)methyl)propane-1,3-diol, 2-Amino-2-((5-((5-propylbenzofuran-2-yl)methoxy)indolin-1-yl)methyl)propane-1,3-diol, 2-Amino-2-((5-(5-(4-propylphenyl)-1,2,4-oxadiazol-3-yl)-3,4-dihydroquinolin-1(2H)-yl)methyl)propane-1,3-diol, 2-Amino-2-((4-(5-(6-propylpyridin-3-yl)-1,2,4-oxadiazol-3-yl)indolin-1-yl)methyl)propane-1,3-diol, 2-Amino-2-((4-(5-(4-propoxy-3,5-dichlorophenyl)-1,2,4-oxadiazol-3-yl)indolin-1-yl)methyl)propane-1,3-diol, 2-Amino-2-((4-(5-(4-isobutylphenyl)-1,2,4-oxadiazol-3-yl)indolin-1-yl)methyl)propane-1,3-diol, 2-Amino-2-((4-(5-(4-(2-cyclopropylethyl)phenyl)-1,2,4-oxadiazol-3-yl)indolin-1-yl)methyl)propane-1,3-diol, 2-Amino-2-((4-(5-(4-(2,2,2-trifluoroethoxyl)phenyl)-1,2,4-oxadiazol-3-yl)indolin-1-yl)methyl)propane-1,3-diol, 2-Amino-2-((5-(5-(4-propylphenyl)-1,2,4-oxadiazol-3-yl)isoindolin-2-yl)methyl)propane-1,3-diol, 5-(3-(2-(2-Amino-3-hydroxy-2-(hydroxymethyl)propyl)-1,2,3,4-tetrahydroisoquinolin-6-yl)-1,2,4-oxadiazol-5-yl)-2-propylbenzonitrile, and 2-Amino-2-(2-(7-(5-(4-propylphenyl)-1,2,4-oxadiazol-3-yl)-1,2,4,5-tetrahydrobenzo[d]azepin-3-yl)ethyl)propane-1,3-diol.

3. A pharmaceutical composition, comprising at least one compound of claim 1 or 2 or a stereoisomer, isotopic form, or pharmaceutically acceptable salt thereof or mixtures thereof in any ratio together with a pharmaceutically acceptable carrier(s) or excipient(s).

* * * * *

UNITED STATES PATENT AND TRADEMARK OFFICE
CERTIFICATE OF CORRECTION

PATENT NO. : 9,181,182 B2  
APPLICATION NO. : 13/124543  
DATED : November 10, 2015  
INVENTOR(S) : Damian W. Grobelny et al.

Page 1 of 1

It is certified that error appears in the above-identified patent and that said Letters Patent is hereby corrected as shown below:

In the Claims:

At col. 135, line 57, replace

"alkynyl, $(C_{826})$aralkynyl, optionally substituted"

with

--alkynyl, $(C_8-C_{26})$aralkynyl, optionally substituted--

At col. 136, line 19, replace

"2. A compound according to claim 1 selected from the"

with

--2. A compound selected from the--

Signed and Sealed this  
Twenty-third Day of August, 2016

Michelle K. Lee  
*Director of the United States Patent and Trademark Office*